US012799172B2

(12) United States Patent
Sato

(10) Patent No.: US 12,799,172 B2
(45) Date of Patent: Nov. 17, 2026

(54) ARTIFICIAL FUR AND METHOD FOR MANUFACTURING SAME

(71) Applicant: Spiber Inc., Tsuruoka (JP)

(72) Inventor: Akito Sato, Tsuruoka (JP)

(73) Assignee: Spiber Inc., Tsuruoka (JP)

( * ) Notice: Subject to any disclaimer, the term of this patent is extended or adjusted under 35 U.S.C. 154(b) by 794 days.

(21) Appl. No.: 17/622,272

(22) PCT Filed: Jun. 24, 2020

(86) PCT No.: PCT/JP2020/024902
§ 371 (c)(1),
(2) Date: Dec. 23, 2021

(87) PCT Pub. No.: WO2020/262489
PCT Pub. Date: Dec. 30, 2020

(65) Prior Publication Data

US 2022/0251150 A1 Aug. 11, 2022

(30) Foreign Application Priority Data

Jun. 28, 2019 (JP) ................................ 2019-122110
Jun. 28, 2019 (JP) ................................ 2019-122469
(Continued)

(51) Int. Cl.
*C07K 14/435* (2006.01)
*C12N 1/20* (2026.01)
(Continued)

(52) U.S. Cl.
CPC .......... *C07K 14/43518* (2013.01); *C12N 1/20* (2013.01); *C12N 15/70* (2013.01);
(Continued)

(58) Field of Classification Search
CPC ...... D01F 4/02; D06N 2201/06; D06N 3/125; D10B 2211/22; D10B 2501/044;
(Continued)

(56) References Cited

U.S. PATENT DOCUMENTS 2,408,026 A * 9/1946 Atwood .................... D01F 4/00
264/78
2005/0010035 A1 1/2005 Lewis et al.
(Continued)

FOREIGN PATENT DOCUMENTS

CN 103696071 A 4/2014
CN 104762718 A 7/2015
(Continued)

OTHER PUBLICATIONS

International Preliminary Report on Patentability and Written Opinion issued in corresponding International Patent Application No. PCT/JP2020/024902 dated Jan. 6, 2022.
(Continued)

*Primary Examiner* — Lynda Salvatore
(74) *Attorney, Agent, or Firm* — Studebaker Brackett PLLC

(57) ABSTRACT

An object of the present invention is to provide an artificial fur which has a sufficient moisture-absorbing property and reduces energy required for the manufacture. The artificial fur according to this invention includes an artificial protein fiber.

20 Claims, 10 Drawing Sheets

Specification includes a Sequence Listing.

(30) Foreign Application Priority Data

Jun. 28, 2019 (JP) ................................ 2019-122471
Jun. 28, 2019 (JP) ................................ 2019-122504

(51) Int. Cl.
*C12N 15/70* (2006.01)
*C12P 21/02* (2006.01)
*D06N 3/12* (2006.01)

(52) U.S. Cl.
CPC .............. *C12P 21/02* (2013.01); *D06N 3/125* (2013.01); *C12N 2800/101* (2013.01); *D06N 2201/06* (2013.01)

(58) Field of Classification Search
CPC .. D10B 2401/022; D06C 13/00; D06C 13/08; D03D 15/233; D03D 15/47; D03D 27/02; D04B 1/04; D04B 1/025; D04B 1/12; A47G 27/0262; C07K 14/43518; C12N 1/20; C12N 15/70; C12N 2800/101
See application file for complete search history.

(56) References Cited

U.S. PATENT DOCUMENTS

| | | | |
|---|---|---|---|
| 2014/0245923 | A1 | 9/2014 | Sugahara et al. |
| 2019/0135880 | A1 | 5/2019 | Morita et al. |
| 2019/0135881 | A1 | 5/2019 | Morita et al. |
| 2020/0031886 | A1 | 1/2020 | Morinaga et al. |

FOREIGN PATENT DOCUMENTS

| | | | | | |
|---|---|---|---|---|---|
| CN | 107190341 | A | | 9/2017 | |
| CN | 109071619 | A | | 12/2018 | |
| CN | 109311954 | A | | 2/2019 | |
| EP | 1773875 | B1 | | 9/2014 | |
| EP | 2774934 | A1 | | 9/2014 | |
| GB | 801987 | | | 9/1958 | |
| GB | 1175530 | | | 12/1969 | |
| JP | S58-065036 | A | | 4/1983 | |
| JP | S63-006133 | A | | 1/1988 | |
| JP | S63-282379 | A | | 11/1988 | |
| JP | 2018-500470 | A | | 1/2018 | |
| JP | 6337252 | B1 | * | 6/2018 | ........... C07K 14/435 |
| JP | 2018-525541 | A | | 9/2018 | |
| WO | WO-9949125 | A2 | * | 9/1999 | .......... D06M 15/333 |
| WO | 2006/008163 | A2 | | 1/2006 | |
| WO | 2013/065650 | A1 | | 5/2013 | |
| WO | 2016/090055 | A1 | | 6/2016 | |
| WO | WO-2017011679 | A1 | * | 1/2017 | ............ C08J 7/0427 |
| WO | 2017/159565 | A1 | | 9/2017 | |
| WO | 2018/087239 | A1 | | 5/2018 | |
| WO | 2018/164020 | A1 | | 9/2018 | |

OTHER PUBLICATIONS

Extended European Search Report issued in corresponding European Patent Application No. 20832455.8 dated Dec. 8, 2023.
"Press Release of the North Face with regard to "Moon Parka"", 2016.
"QMONOS, Synthetic spider silk, Transmaterial", 2017.
"Press Release of Goldwin with regard to "Goldwin Ski jacket"", 2018.
Third Party Observations filed in European Patent Application No. 20832455.8 dated Dec. 6, 2024.
International Search Report issued in corresponding International Patent Application No. PCT/JP2020/024902 dated Sep. 24, 2020.

* cited by examiner

ARTIFICIAL FUR AND METHOD FOR MANUFACTURING SAME

SEQUENCE LISTING SUBMISSION VIA EFS-WEB

A computer readable text file, entitled "SequenceListing.txt" created on Dec. 21, 2021 with a file size of 249,653 bytes contains the sequence listing for this application and is hereby incorporated by reference in its entirety.

TECHNICAL FIELD

The present invention relates to an artificial fur and a method for manufacturing the same.

BACKGROUND ART

Known artificial furs have been used as alternatives for natural furs. For example, Patent Literature 1 discloses an artificial fur including a synthetic fiber such as an acrylic fiber.

CITATION LIST

Patent Literature

Patent Literature 1: JP 63-6133 A

SUMMARY OF INVENTION

Technical Problem

Unlike natural furs limited in supplied, artificial furs can be mass-produced artificially. In recent years, artificial furs have attained wide use, for example, in clothing, accessories (such as bags), carpets, and stuffed animals. Most artificial furs in the related art are manufactured from acrylic fibers having both lightness and warmness like fluffy wool.

However, artificial furs in the related art include synthetic fibers and have a poor moisture-absorbing property. Furthermore, artificial furs in the related art are derived from petroleum and bound to cause large amount of energy during the manufacture.

In order to solve or alleviate the problems, for example, an artificial fur may be yielded from a protein fiber. However, some protein fibers shrink on contact with water. In artificial furs including such protein fibers, the contact with water may bring the possibility of significant dimensional change.

In addition, artificial furs made from acrylic fibers often used for artificial furs not only put a heavy load on environment but also are sensitive to moisture and water. Particularly, acrylic fibers are elongated by washing or the like.

The present invention has been made in light of the above circumstances. A first object of this invention is to provide an artificial fur which has a sufficient moisture-absorbing property and reduces energy required for the manufacture and to provide a method for manufacturing the artificial fur.

A second object of this invention is to provide an artificial fur which has a sufficient moisture-absorbing property, reduces energy required for the manufacture, and is prevented to the extent possible from being changed in dimension on contact with water.

A third object of this invention is to provide an artificial fur excellent in functionality such as water resistance.

A fourth object of this invention is to provide an artificial fur excellent in water resistance.

A fifth object of this invention is to provide a method for advantageously manufacturing an artificial fur which has a sufficient moisture-absorbing property and reduces energy required for the manufacture.

A sixth object of this invention is to provide a method for advantageously manufacturing an artificial fur which has a sufficient moisture-absorbing property, reduces energy required for the manufacture, and is prevented to the extent possible from being changed in dimension on contact with water.

Solution to Problem

A first aspect of the invention to achieve the first object relates to, for example, the following inventions.

[1-1]

An artificial fur including an artificial protein fiber.

[1-2]

The artificial fur according to [1-1], in which the artificial protein fiber includes an artificial structural protein fiber.

[1-3]

The artificial fur according to [1-2], in which the artificial structural protein fiber includes a modified fibroin fiber.

[1-4]

The artificial fur according to [1-3], in which the modified fibroin fiber includes a modified spider silk fibroin fiber.

[1-5]

The artificial fur according to any one of [1-1] to [1-4] having a limiting oxygen index (LOI) of 26.0 or more.

[1-6]

The artificial fur according to any one of [1-1] to [1-5] having a maximum moisture-absorbing and heat-releasing level over 0.025° C./g determined according to the following Formula A:

maximum moisture-absorbing and heat-releasing level={(maximum sample temperature obtained after sample is transferred to high-humidity environment after being placed in low-humidity environment until sample temperature reaches equilibrium)−(sample temperature when sample is transferred to high-humidity environment after being placed in low-humidity environment until sample temperature reaches equilibrium)} (° C.)/sample weight (g) Formula A:

[In Formula A, the low-humidity environment implies an environment at a temperature of 20° C. and a relative humidity of 40%, while the high-humidity environment implies an environment at a temperature of 20° C. and a relative humidity of 90%].

[1-7]

The artificial fur according to [1-6], in which the maximum moisture-absorbing and heat-releasing level is 0.031° C./g or more.

[1-8]

The artificial fur according to any one of [1-1] to [1-7] having a heat retention index over 0.18 determined according to the following Formula B:

heat retention index=heat retention rate (%)/unit weight of sample ($g/m^2$) Formula B:

[In Formula B, the heat retention rate (%) is measured by dry contact method (temperature: 30° C., wind speed: 30 cm/sec) and calculated by (1−a/b)×100, where "a" is an amount of heat dissipated through a test piece and "b" is an amount of heat dissipated without a test piece].

[1-9]

The artificial fur according to [1-8], in which the heat retention index is 0.22 or more.

A second aspect of the invention to achieve the second object relates to, for example, the following inventions.

[2-1]

An artificial fur including a shrink-proof protein fiber.

[2-2]

The artificial fur according to [2-1], in which the protein fiber in wet condition has a shrinkage rate of 2% or more defined by the following Formula I:

$$\text{shrinkage rate in wet condition}=\{1-(\text{length of protein fiber in wet condition after contact with water}/\text{length of protein fiber after spinning but before contact with water})\}\times 100(\%) \quad \text{(Formula I).}$$

[2-3]

The artificial fur according to [2-1] or [2-2], in which the protein fiber in dry condition has a shrinkage rate over 7% defined by the following Formula II:

$$\text{shrinkage rate in dry condition}=\{1-(\text{length of protein fiber in dry condition}/\text{length of protein fiber after spinning but before contact with water})\}\times 100(\%) \quad \text{(Formula II).}$$

[2-4]

The artificial fur according to any one of [2-1] to [2-3], in which the protein fiber includes a modified fibroin.

[2-5]

The artificial fur according to [2-4], in which the modified fibroin is a modified spider silk fibroin.

[2-6]

The artificial fur according to any one of [2-1] to [2-5] having a limiting oxygen index (LOI) of 26.0 or more.

[2-7]

The artificial fur according to any one of [2-1] to [2-6] having a maximum moisture-absorbing and heat-releasing level over 0.025° C./g determined according to the following Formula A:

$$\text{maximum moisture-absorbing and heat-releasing level}=\{(\text{maximum sample temperature obtained after sample is transferred to high-humidity environment after being placed in low-humidity environment until sample temperature reaches equilibrium})-(\text{sample temperature when sample is transferred to high-humidity environment after being placed in low-humidity environment until sample temperature reaches equilibrium})\}(^\circ\text{ C.})/\text{sample weight (g)} \quad \text{Formula A:}$$

[In Formula A, the low-humidity environment implies an environment at a temperature of 20° C. and a relative humidity of 40%, while the high-humidity environment implies an environment at a temperature of 20° C. and a relative humidity of 90%].

[2-8]

The artificial fur according to [2-7], in which the maximum moisture-absorbing and heat-releasing level is 0.031° C./g or more.

[2-9]

The artificial fur according to any one of [2-1] to [2-8] having a heat retention index over 0.18 determined according to the following Formula B:

$$\text{heat retention index}=\text{heat retention rate (\%)}/\text{unit weight of sample (g/m}^2\text{)} \quad \text{Formula B:}$$

[In Formula B, the heat retention rate (%) is measured by dry contact method (temperature: 30° C., wind speed: 30 cm/sec) and calculated by (1−a/b)×100, where "a" is an amount of heat dissipated through a test piece and "b" is an amount of heat dissipated without a test piece].

[2-10]

The artificial fur according to [2-9], in which the heat retention index is 0.22 or more.

A third aspect of the invention to achieve the third object relates to, for example, the following inventions.

[3-1]

An artificial fur including a fiber and imparted with a functionality.

[3-2]

The artificial fur according to [3-1], in which the fiber includes a protein fiber.

[3-3]

The artificial fur according to [3-2], in which the protein fiber includes a modified fibroin.

[3-4]

The artificial fur according to [3-3], in which the modified fibroin is a modified spider silk fibroin.

[3-5]

The artificial fur according to any one of [3-1 to [3-4] including a protein crosslinking body, in which the protein crosslinking body includes: a plurality of polypeptide skeletons; a plurality of first residues or residues of a first reagent having at least two first reactive groups capable of forming a bond by a reaction with a protein; and a plurality of second residues or residues of a second reagent having one second reactive group capable of forming a bond by a reaction with a first reactive group, at least one of the first residues crosslinks a polypeptide skeleton, and at least one of the first residues is bound to a polypeptide skeleton at one end and to a second residue at the other end.

[3-6]

The artificial fur according to any one of [3-1] to [3-5] including a modified hydroxyl group-containing polymer in which an operative functional group is bound to a hydroxyl group-containing polymer.

[3-7]

The artificial fur according to any one of [3-1] to [3-6] having a limiting oxygen index (LOI) of 26.0 or more.

[3-8]

The artificial fur according to any one of [3-1] to [3-7] having a maximum moisture-absorbing and heat-releasing level over 0.025° C./g determined according to the following Formula A:

$$\text{maximum moisture-absorbing and heat-releasing level}=\{(\text{maximum sample temperature obtained after sample is transferred to high-humidity environment after being placed in low-humidity environment until sample temperature reaches equilibrium})-(\text{sample temperature when sample is transferred to high-humidity environment after being placed in low-humidity environment until sample temperature reaches equilibrium})\}(^\circ\text{ C.})/\text{sample weight (g)} \quad \text{Formula A:}$$

[In Formula A, the low-humidity environment implies an environment at a temperature of 20° C. and a relative humidity of 40%, while the high-humidity environment implies an environment at a temperature of 20° C. and a relative humidity of 90%].

[3-9]

The artificial fur according to [3-8], in which the maximum moisture-absorbing and heat-releasing level is 0.031° C./g or more.

[3-10]

The artificial fur according to any one of [3-1] to [3-9] having a heat retention index over 0.18 determined according to the following Formula B:

heat retention index=heat retention rate (%)/unit weight of sample ($g/m^2$) Formula B:

[In Formula B, the heat retention rate (%) is measured by dry contact method (temperature: 30° C., wind speed: 30 cm/sec) and calculated by (1−a/b)×100, where "a" is an amount of heat dissipated through a test piece and "b" is an amount of heat dissipated without a test piece].

[3-11]

The artificial fur according to [3-10], in which the heat retention index is 0.22 or more.

A fourth aspect of the invention to achieve the fourth object relates to, for example, the following inventions.

[4-1]

An artificial fur including a fiber and a water resistance imparting substance.

[4-2]

The artificial fur according to [4-1], in which the fiber includes a protein fiber.

[4-3]

The artificial fur according to [4-2], in which the protein fiber includes a modified fibroin.

[4-4]

The artificial fur according to [4-3], in which the modified fibroin is a modified spider silk fibroin.

[4-5]

The artificial fur according to any one of [4-2] to [4-4], in which the modified fibroin and the water resistance imparting substance are covalently bound.

[4-6]

The artificial fur according to any one of [4-1] to [4-5], in which the water resistance imparting substance is at least one selected from the group of a silicone-based polymer and a fluorine-based polymer.

[4-7]

The artificial fur according to any one of [4-1] to [4-6] having a limiting oxygen index (LOI) of 26.0 or more.

[4-8]

The artificial fur according to any one of [4-1] to [4-7] having a maximum moisture-absorbing and heat-releasing level over 0.025° C./g determined according to the following Formula A:

maximum moisture-absorbing and heat-releasing level={(maximum sample temperature obtained after sample is transferred to high-humidity environment after being placed in low-humidity environment until sample temperature reaches equilibrium)−(sample temperature when sample is transferred to high-humidity environment after being placed in low-humidity environment until sample temperature reaches equilibrium)} (° C.)/sample weight (g) Formula A:

[In Formula A, the low-humidity environment implies an environment at a temperature of 20° C. and a relative humidity of 40%, while the high-humidity environment implies an environment at a temperature of 20° C. and a relative humidity of 90%].

[4-9]

The artificial fur according to [4-8], in which the maximum moisture-absorbing and heat-releasing level is 0.031° C./g or more.

[4-10]

The artificial fur according to any one of [4-1] to [4-9] having a heat retention index over 0.18 determined according to the following Formula B:

heat retention index=heat retention rate (%)/unit weight of sample ($g/m^2$) Formula B:

[In Formula B, the heat retention rate (%) is measured by dry contact method (temperature: 30° C., wind speed: 30 cm/sec) and calculated by (1−a/b)×100, where "a" is an amount of heat dissipated through a test piece and "b" is an amount of heat dissipated without a test piece].

[4-11]

The artificial fur according to [4-10], in which the heat retention index is 0.22 or more.

A fifth aspect of this invention to achieve the fifth object relates to, for example, the following invention.

[5-1]

A method for manufacturing an artificial fur, the method involving: using a fiber including an artificial protein fiber to obtain a pile fabric having a pile protruded on one surface or both surfaces of the fabric; and cutting a loop of the pile to form a cut pile.

A sixth aspect of the invention to achieve the sixth object relates to, for example, the following inventions.

[6-1]

A method for manufacturing an artificial fur, the method involving: using a shrink-proof protein fiber to obtain a pile fabric having a pile protruded on one surface or both surfaces of the fabric; and cutting a loop of the pile to form a cut pile.

[6-2]

A method for manufacturing an artificial fur, the method involving: using a fiber including a protein fiber to obtain a pile fabric having a pile protruded on one surface or both surfaces of the fabric; cutting a loop of the pile to form a cut pile; and shrink-proofing the pile fabric.

Advantageous Effects of Invention

According to the first aspect of the invention, it is possible to provide an artificial fur which has a sufficient moisture-absorbing property and reduces energy required for the manufacture.

According to the second aspect of the invention, it is possible to provide an artificial fur which has a sufficient moisture-absorbing property, reduces energy required for the manufacture, and is prevented to the extent possible from being changed in dimension on contact with water.

According to the third aspect of the invention, it is possible to provide an artificial fur excellent in functionality such as water resistance.

According to the fourth aspect of the invention, it is possible to provide an artificial fur excellent in water resistance.

According to the fifth aspect of this invention, it is possible to provide a method for advantageously manufacturing an artificial fur which has a sufficient moisture-absorbing property and reduces energy required for the manufacture.

According to the sixth aspect of the invention, it is possible to provide a method for advantageously manufacturing an artificial fur which has a sufficient moisture-absorbing property, reduces energy required for the manufacture, and is prevented to the extent possible from being changed in dimension on contact with water.

DESCRIPTION OF EMBODIMENTS

Figure 1:
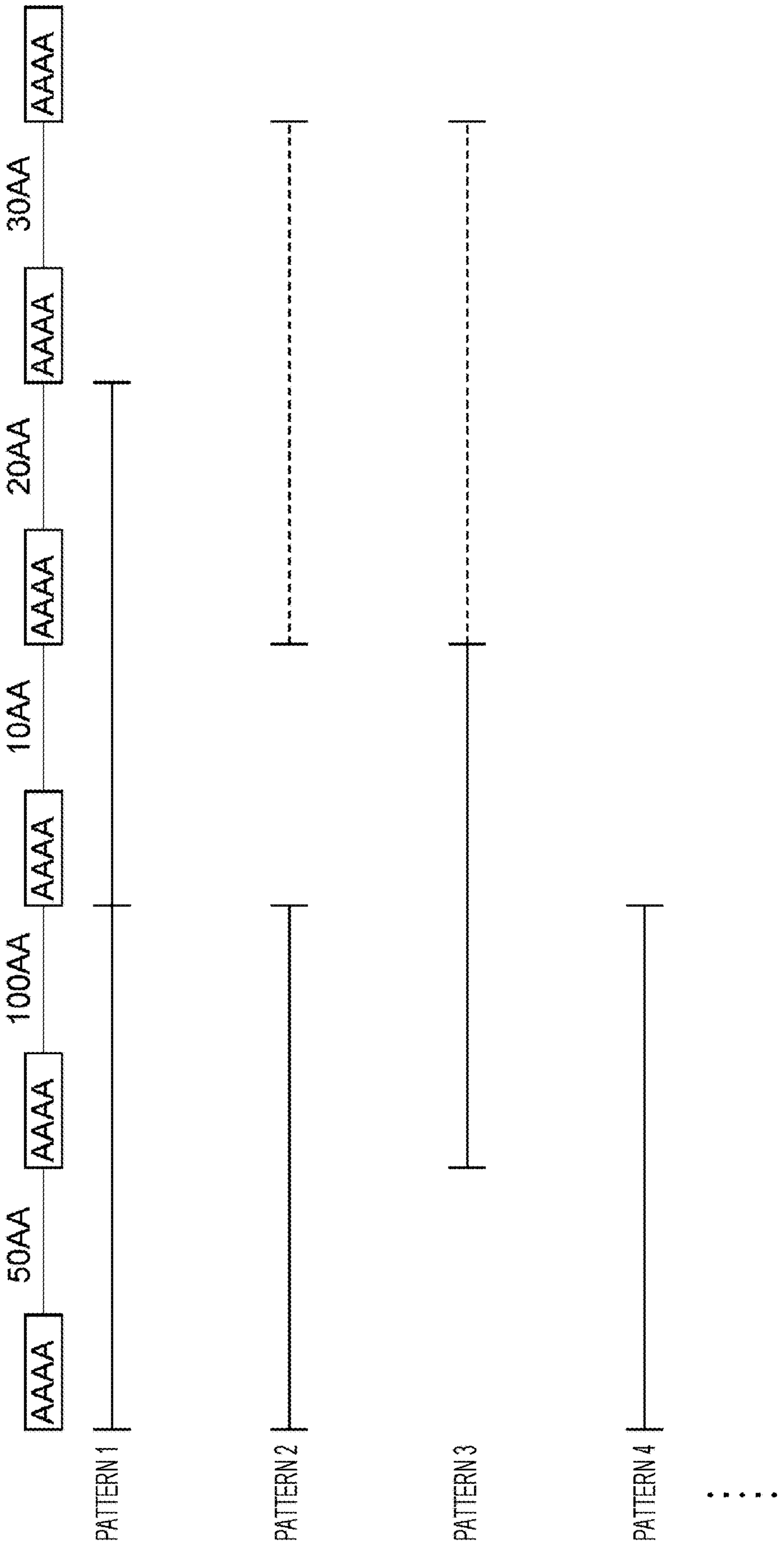
FIG. 1 is a schematic view illustrating an example of a domain sequence of a modified fibroin.

Hereinafter, embodiments of the present invention will be described in detail. However, this invention is not limited to the following embodiments.

First Embodiment

An artificial fur according to a first embodiment of the first aspect of the invention includes an artificial protein fiber.

The artificial protein fiber is a spun fiber using a protein as the main raw material. Examples of the protein include natural proteins and recombinant proteins (artificial proteins). The recombinant proteins may be any protein that can be manufactured at an industrial scale such as proteins used for industrial purposes, proteins used for medical purposes, and structural proteins. Specific examples of the proteins used for industrial purposes or medical purposes include enzymes, regulatory proteins, receptors, peptide hormones, cytokines, membrane or transport proteins, antigens used for vaccination, vaccines, antigen-binding proteins, immunostimulatory proteins, allergens, full length antibodies, antibody fragments, and antibody derivatives. Specific examples of the structural proteins include spider silk, silkworm silk, keratin, collagen, elastin, resilin, and proteins derived from these examples. The protein to be used herein is preferably a modified fibroin, and more preferably a modified spider silk fibroin, from viewpoints of excellent heat retainability, moisture-absorbing and heat-releasing properties, and/or flame retardancy. Employing a modified fibroin (preferably, modified spider silk fibroin) as the protein makes it possible to impart properties such as heat retainability, moisture-absorbing and heat-releasing properties, and/or flame retardancy to the artificial fur according to this embodiment, thereby enhancing the value of the artificial fur.

Herein, fibers obtained by spinning a structural protein, a modified fibroin, and a modified spider silk fibroin are referred to as "artificial structural protein fiber", "modified fibroin fiber", and "modified spider silk fibroin fiber", respectively.

The modified fibroin according to this embodiment is a protein having a domain sequence represented by Formula 1: $[(A)_n$ motif-REP$]_m$ or Formula 2: $[(A)_n$ motif-REP$]_m$-$(A)_n$ motif. To either or both of the N-terminus and the C-terminus of the domain sequence of the modified fibroin, another amino acid sequence (N-terminal sequence and C-terminal sequence) may be added. The N-terminal sequence and the C-terminal sequence are typically, but not limited to, regions with no repetitions of amino acid motifs specific in fibroin, and each sequence has approximately 100 amino acid residues.

The "modified fibroin" herein implies an anthropogenically manufactured fibroin (artificial fibroin). The domain sequence of the modified fibroin may be different from an amino acid sequence of a naturally derived fibroin or may be the same as the amino acid sequence of the naturally derived fibroin. The "naturally derived fibroin" herein is also a protein having a domain sequence represented by Formula 1: $[(A)_n$ motif-REP$]_m$ or Formula 2: $[(A)_n$ motif-REP$]_m$-$(A)_n$ motif.

The "modified fibroin" may be a fibroin having the amino acid sequence of the naturally derived fibroin as it is, a fibroin having an amino acid sequence modified based on the amino acid sequence of the naturally derived fibroin (for example, a fibroin having an amino acid sequence modified by modification of a cloned gene sequence of the naturally derived fibroin), or a fibroin artificially designed and synthesized independently of the naturally derived fibroin (for example, a fibroin having a desired amino acid sequence by chemical synthesis of a nucleic acid that encodes the designed amino acid sequence).

The "domain sequence" herein is a fibroin-specific amino acid sequence that produces a crystal region (typically corresponding to a $(A)_n$ motif of the amino acid sequence) and an amorphous region (typically corresponding to an REP of the amino acid sequence), represented by Formula 1: $[(A)_n$ motif-REP$]_m$ or Formula 2: $[(A)_n$ motif-REP$]_m$-$(A)_n$ motif. Herein, the "$(A)_n$ motif" is an amino acid sequence that principally includes alanine residues and has 2 to 27 amino acid residues. The number of the amino acid residues in an $(A)_n$ motif may be an integer of 2 to 20, 4 to 27, 4 to 20, 8 to 20, 10 to 20, 4 to 16, 8 to 16, or 10 to 16. In addition, a proportion of alanine residues to the total number of the amino acid residues in the $(A)_n$ motif may be 40% or more, or may also be 60% or more, 70% or more, 80% or more, 83% or more, 85% or more, 86% or more, 90% or more, 95% or more, or 100% (that is, the $(A)_n$ motif consists of alanine residues). In a plurality of $(A)_n$ motifs in the domain sequence, at least seven $(A)_n$ motifs may consist of alanine residues. The "REP" represents an amino acid sequence having 2 to 200 amino acid residues. The "REP" may be an amino acid sequence having 10 to 200 amino acid residues. The symbol "m" represents an integer of 2 to 300 and may be an integer of 10 to 300. The plurality of $(A)_n$ motifs may be the same or different amino acid sequences. In a plurality of REPs, the REPs may be the same or different amino acid sequences.

The modified fibroin according to this embodiment can be obtained by, for example, modifying an amino acid sequence that corresponds to a cloned gene sequence of the naturally derived fibroin having at least one amino acid residue substituted, deleted, inserted, and/or added. The substitution, deletion, insertion, and/or addition of amino acid residues can be performed by methods known to those skilled in the art such as site-directed mutagenesis. Specifically, it is possible to perform with reference to methods described in literatures such as Nucleic Acid Res. 10, 6487 (1982) and Methods in Enzymology, 100, 448 (1983).

The "naturally derived fibroin" is a protein having a domain sequence represented by Formula 1: $[(A)_n$ motif-REP$]_m$ or Formula 2: $[(A)_n$ motif-REP$]_m$-$(A)_n$ motif, and a specific example thereof includes those produced by insects or arachnids.

Examples of the fibroin produced by insects include silk proteins produced by silkworms (such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama*) and hornet silk proteins secreted by larvae of *Vespa simillima xanthoptera*.

More specific examples of the fibroin produced by insects include the silkworm fibroin L chain (GenBank Accession No. M76430 (nucleotide sequence) and Accession No. AAA27840.1 (amino acid sequence)).

Examples of the fibroin produced by arachnids include spider silk proteins produced by spiders belonging to Araneae. Specific examples of the spider silk proteins include those produced by spiders belonging to the genus *Araneus* such as *Araneus ventricosus, Araneus diadematus, Araneus pinguis, Araneus pentagrammicus*, and *Araneus nojimai*, spiders belonging to the genus *Neoscona* such as *Neoscona scylla, Neoscona nautica, Neoscona adianta*, and *Neoscona scylloides*, spiders belonging to the genus *Pronus* such as *Pronous minutus*, spiders belonging to the genus *Cyrtarachne* such as *Cyrtarachne bufo* and *Cyrtarachne inaequalis*, spiders belonging to the genus *Gasteracantha* such as *Gasteracantha kuhlii* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena, Argiope minuta*, and *Argiope bruennichi*, spiders belonging to the genus *Arachnura* such as *Arachnura logic*, spiders belonging to the genus *Acusilas* such as *Acusilas coccineus*, spiders belonging to the genus *Cytophora* such as *Cyrtophora moluccensis, Cyrtophora exanthematica*, and *Cyrtophora unicolor*, spiders belonging to the genus *Poltys* such as *Poltys illepidus*, spiders belonging to the genus *Cyclosa such as Cyclosa octotuberculata, Cyclosa sedeculata, Cyclosa vallata*, and *Cyclosa atrata*, and spiders belonging to the genus *Chorizopes* such as *Chorizopes nipponicus*. Furthermore, specific examples of the spider silk proteins include those produced by spiders in the family Tetragnathidae, that is, for example, spiders belonging to the genus *Tetragnatha* such as *Tetragnatha praedonia, Tetragnatha maxillosa, Tetragnatha extensa*, and *Tetragnatha squamata*, spiders belonging to the genus *Leucauge* such as *Leucauge magnifica, Leucauge blanda*, and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus*, and *Latrodectus tredecimguttatus*, and spiders belonging to the genus *Euprosthenops*. Examples of the spider silk proteins include dragline silk proteins such as MaSp (MaSp1 and MaSp2) and ADF (ADF3 and ADF4), MiSp (MiSp1 and MiSp2), AcSp, PySp, and Flag.

Specific examples of the spider silk protein produced by arachnids include fibroin-3 (adf-3) [derived from *Araneus diadematus*] (GenBank Accession No. AAC47010 (amino acid sequence), U47855 (nucleotide sequence)), fibroin-4 (adf-4) [derived from *Araneus diadematus*] (GenBank Accession No. AAC47011 (amino acid sequence), U47856 (nucleotide sequence)), dragline silk protein spidroin 1 [derived from *Nephila clavipes*] (GenBank Accession No. AAC04504 (amino acid sequence), U37520 (nucleotide sequence)), major ampullate spidroin 1 [derived from *Latrodectus hesperus*] (GenBank Accession No. ABR68856 (amino acid sequence), EF595246 (nucleotide sequence)), dragline silk protein spidroin 2 [derived from *Nephila clavata*] (GenBank Accession No. AAL32472 (amino acid sequence), AF441245 (nucleotide sequence)), major ampullate spidroin 1 [derived from *Euprosthenops australis*] (GenBank Accession No. CAJ00428 (amino acid sequence), AJ973155 (nucleotide sequence)), major ampullate spidroin 2 [*Euprosthenops australis*] (GenBank Accession No. CAM32249.1 (amino acid sequence), AM490169 (nucleotide sequence)), minor ampullate silk protein 1 [*Nephila clavipes*] (GenBank Accession No. AAC14589.1 (amino acid sequence)), minor ampullate silk protein 2 [*Nephila clavipes*] (GenBank Accession No. AAC14591.1 (amino acid sequence)), and minor ampullate spidroin-like protein [*Nephilengys cruentata*] (GenBank Accession No. ABR37278.1 (amino acid sequence).

More specific examples of the naturally derived fibroin include those having sequence information deposited in NCBI GenBank. Those examples can be found in sequence information of NCBI GenBank. For example, from sequences described as "INV" in "DIVISION", extract sequences with keywords such as "spidroin", "ampullate", "fibroin", "silk and polypeptide", and "silk and protein" in "DEFINITION" or extract sequences having character strings of a specific product in "CDS" and specific character strings in "SOURCE" to "TISSUE TYPE".

The modified fibroin according to this embodiment may be a modified silk fibroin (or a modified amino acid sequence of silk protein produced by a silkworm) or may be a modified spider silk fibroin (or a modified amino acid sequence of a spider silk protein produced by an arachnid).

Specific examples of the modified fibroin include one derived from a major dragline silk protein produced in the major ampullate silk gland of a spider (first modified fibroin), one having a domain sequence with the glycine residue content reduced (second modified fibroin), one having a domain sequence with the $(A)_n$ motif content reduced (third modified fibroin), one having the glycine residue content and the $(A)_n$ motif content reduced (fourth modified fibroin), one having a domain sequence including a region locally having a high hydropathy index (fifth modified fibroin), and one having a domain sequence with the glutamine residue content reduced (sixth modified fibroin).

An example of the first modified fibroin include a protein having a domain sequence represented by Formula 1: $[(A)_n$ motif-REP$]_m$. In the first modified fibroin, the number of amino acid residues in the $(A)_n$ motif is preferably an integer of 3 to 20, more preferably an integer of 4 to 20, still more preferably an integer of 8 to 20, still more preferably an integer of 10 to 20, still more preferably an integer of 4 to 16, particularly preferably an integer of 8 to 16, and most preferably an integer of 10 to 16. In the first modified fibroin, the number of amino acid residues included in an REP in Formula 1 is preferably 10 to 200, more preferably 10 to 150, still more preferably 20 to 100, and still more preferably 20 to 75. In the first modified fibroin, the total number of glycine residues, serine residues, and alanine residues included in the amino acid sequence represented by Formula 1: $[(A)_n$ motif-REP$]_m$ is preferably 40% or more, more preferably 60% or more, and still more preferably 70% or more with respect to the total number of amino acid residues.

The first modified fibroin may be a polypeptide having a unit of amino acid sequence represented by Formula 1: $[(A)_n$ motif-REP$]_m$ and having the C-terminal sequence corresponding to the amino acid sequence of any one of SEQ ID NO: 1 to SEQ ID NO: 3 or corresponding to an amino acid sequence having 90% or more homology to the amino acid sequence of any one of SEQ ID NO: 1 to SEQ ID NO: 3.

The amino acid sequence of SEQ ID NO: 1 is identical to an amino acid sequence having of 50 amino acid residues included in the C-terminus of the amino acid sequence of ADF3 (GI: 1263287, NCBI). The amino acid sequence of SEQ ID NO: 2 is identical to the amino acid sequence of SEQ ID NO: 1 except that 20 amino acid residues are removed from the C-terminus. The amino acid sequence of SEQ ID NO: 3 is identical to the amino acid sequence of SEQ ID NO: 1 except that 29 amino acid residues are removed from the C-terminus.

More specific examples of the first modified fibroin include (1-i) a modified fibroin having the amino acid sequence of SEQ ID NO: 4 (recombinant spider silk protein ADF3KaiLargeNRSH1) and (1-ii) a modified fibroin having an amino acid sequence having 90% or more sequence identity to the amino acid sequence of SEQ ID NO: 4. The sequence identity is preferably 95% or more.

The amino acid sequence of SEQ ID NO: 4 is obtained by the following mutation. That is, in the amino acid sequence of ADF3 having the N-terminus to which an amino acid sequence including a start codon, His 10 tag, and HRV3C protease (human rhinovirus 3C protease) recognition site (SEQ ID NO: 5) are added, the first to thirteenth repeat regions are roughly doubled and the translation ends at the 1154th amino acid residue. The C-terminal amino acid sequence in the amino acid sequence of SEQ ID NO: 4 is identical to the amino acid sequence of SEQ ID NO: 3.

The modified fibroin (1-i) may have the amino acid sequence of SEQ ID NO: 4.

The domain sequence of the second modified fibroin has the amino acid sequence of the naturally derived fibroin except that the glycine residue content is reduced. In other words, the second modified fibroin has the amino acid sequence of the naturally derived fibroin except that at least one glycine residue in an REP is substituted by another amino acid residue.

The domain sequence of the second modified fibroin may have the amino acid sequence of the naturally derived fibroin except that one glycine residue in at least one motif sequence selected from GGX and GPGXX in an REP is substituted by another amino acid residue (where G is glycine residue, P is proline residue, and X is amino acid residue other than glycine).

In the second modified fibroin, a proportion of motif sequences where the glycine residue is substituted by another amino acid residue may be 10% or more of the entire motif sequence.

The second modified fibroin may have a domain sequence represented by Formula 1: $[(A)_n \text{ motif-REP}]_m$ and have an amino acid sequence in which z/w is 30% or more, 40% or more, 50% or more, or 50.9% or more where "z" represents the total number of amino acid residues in an amino acid sequence having XGX (X is an amino acid residue other than glycine) and included in all REPs of the domain sequence excluding a range from the $(A)_n$ motif closest to the C-terminus of the domain sequence to the C-terminus, and "w" represents the total number of amino acid residues included in the domain sequence excluding the range from the $(A)_n$ motif closest to the C-terminus of the domain sequence to the C-terminus. A proportion of alanine residues to the total number of the amino acid residues in an $(A)_n$ motif is 83% or more, preferably 86% or more, more preferably 90% or more, still more preferably 95% or more, and still more preferably 100% (that is, the $(A)_n$ motif consists of alanine residues).

In the second modified fibroin, a proportion of amino acid sequences having XGX is preferably increased by substituting one glycine residue of a GGX motif by another amino acid residue. In the second modified fibroin, a proportion of amino acid sequences having GGX in the domain sequence is preferably 30% or less, more preferably 20% or less, still more preferably 10% or less, still more preferably 6% or less, still more preferably 4% or less, and particularly preferably 2% or less. A proportion of amino acid sequences having GGX in the domain sequence can be calculated by a method similar to the following method for calculating a proportion of amino acid sequences having XGX (z/w).

The calculation method of z/w will be described in more detail. First, in a fibroin (modified fibroin or naturally derived fibroin) having a domain sequence represented by Formula 1: $[(A)_n \text{ motif-REP}]_m$, an amino acid sequence having XGX is extracted from all REPs of the domain sequence excluding a range from the $(A)_n$ motif closest to the C-terminus of the domain sequence to the C-terminus. The total number of amino acid residues included in XGX is represented by "z". For example, when 50 amino acid sequences having XGX are extracted (no overlap), "z" is $50 \times 3 = 150$. For example, in an amino acid sequence having XGXGX, one X (X in the center) is included in two XGXs, and the overlapping portion is subtracted to calculate "z" (that is, there are 5 amino acid residues in XGXGX). The symbol "w" represents the total number of amino acid residues included in the domain sequence excluding the range from the $(A)_n$ motif closest to the C-terminus of the domain sequence to the C-terminus. For example, in the domain sequence shown in FIG. 1, "w" is $4+50+4+100+4+10+4+20+4+30=230$ (excluding the $(A)_n$ motif closest to the C-terminus). Next, "z" is divided by "w" to calculate z/w (%).

Figure 2:
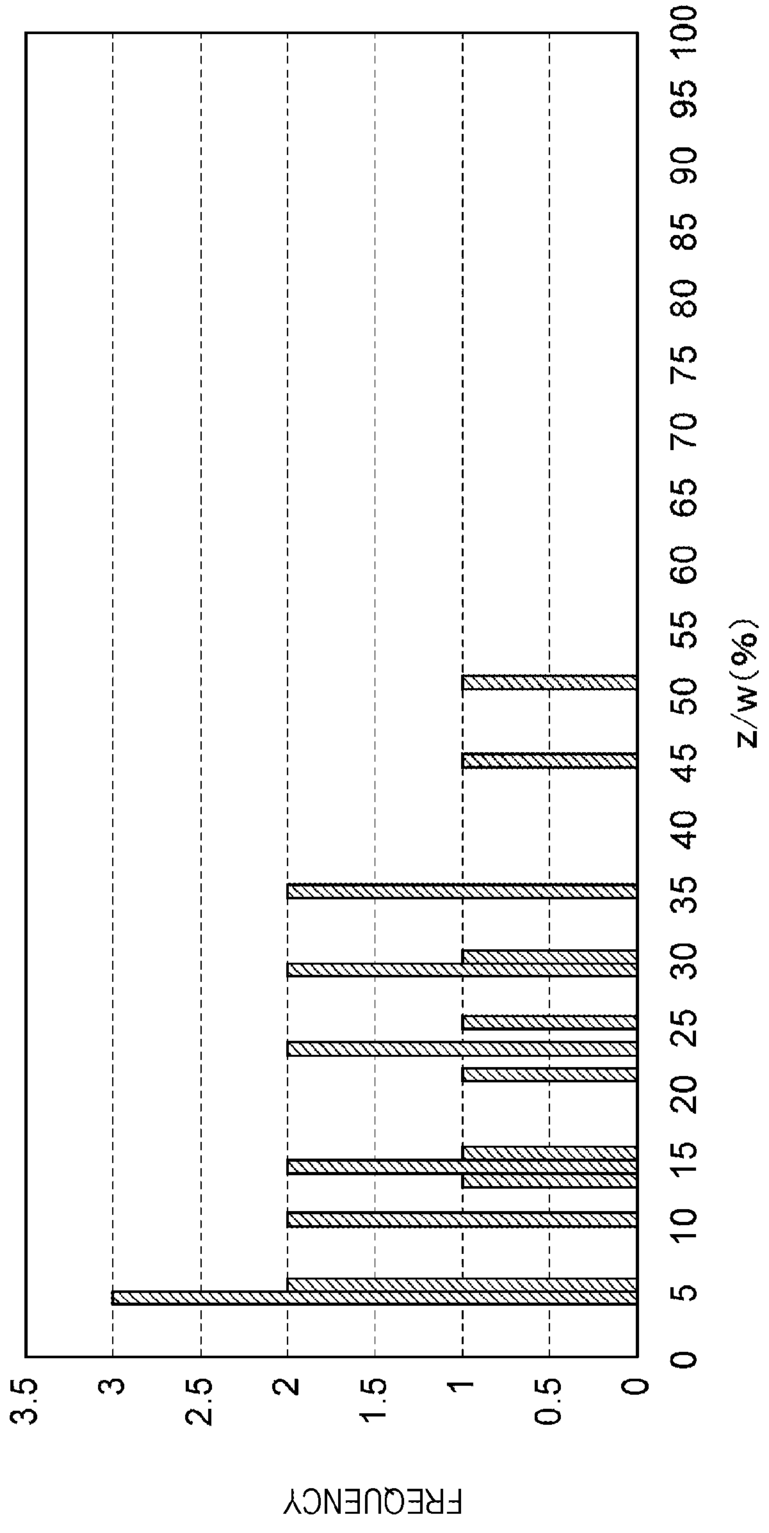
FIG. 2 is a view illustrating a distribution of values of z/w (%) in a naturally derived fibroin.

Now, z/w in the naturally derived fibroin will be described. First, examining the amino acid sequence information deposited in NCBI GenBank by the aforementioned manner, 663 types of fibroins are found (415 types of fibroins are derived from arachnids). Among all the extracted fibroins, z/w is calculated by the aforementioned calculation method from the amino acid sequence of the naturally derived fibroin having a domain sequence represented by Formula 1: $[(A)_n \text{ motif-REP}]_m$ in which a proportion of amino acid sequences having GGX is 6% or less. FIG. 2 shows the results. In FIG. 2, z/w (%) is taken along the abscissa, and the frequency is taken along the ordinate. As is clear from FIG. 2, the values of z/w in the naturally derived fibroin are all smaller than 50.9% (the largest value is 50.86%).

In the second modified fibroin, z/w is preferably 50.9% or more, more preferably 56.1% or more, still more preferably 58.7% or more, still more preferably 70% or more, and still more preferably 80% or more. The upper limit of z/w is not particularly limited but may be, for example, 95% or less.

The second modified fibroin can be obtained, for example, by modifying a cloned gene sequence of the naturally derived fibroin in such a manner that at least part of a nucleotide sequence encoding a glycine residue is substituted so as to encode another amino acid residue. In this case, as the glycine residue to be modified, one glycine residue in a GGX motif or a GPGXX motif may be selected or may be substituted so that z/w becomes 50.9% or more. Alternatively, the second modified fibroin can be obtained by, for example, designing an amino acid sequence satisfying each of the above aspects from the amino acid sequence of the naturally derived fibroin and by chemically synthesizing a nucleic acid that encodes the designed amino acid sequence. In any case, the amino acid sequence of the naturally derived fibroin may be modified not only by substituting a glycine residue in an REP of the amino acid sequence by another amino acid residue but also by substituting, deleting, inserting, and/or adding at least one amino acid residue.

The other amino acid residue is not particularly limited as long as it is an amino acid residue other than glycine residue but is preferably a hydrophobic amino acid residue such as valine (V) residue, leucine (L) residue, isoleucine (I) residue, methionine (M) residue, proline (P) residue, phenylalanine (F) residue, and tryptophan (W) residue or a hydrophilic amino acid residue such as glutamine (Q) residue, asparagine (N) residue, serine (S) residue, lysine (K) residue, or glutamic acid (E) residue. Among these examples, valine (V) residue, leucine (L) residue, isoleucine (I) residue, phenylalanine (F) residue, and glutamine (Q) residue are more preferable, and glutamine (Q) residue is still more preferable.

More specific examples of the second modified fibroin include (2-i) a modified fibroin having the amino acid sequence of SEQ ID NO: 6 (Met-PRT380), SEQ ID NO: 7 (Met-PRT410), SEQ ID NO: 8 (Met-PRT525), or SEQ ID NO: 9 (Met-PRT799) and (2-ii) a modified fibroin having an amino acid sequence having 90% or more sequence identity to the amino acid sequence of SEQ ID NO: 6, SEQ ID NO: 7, SEQ ID NO: 8, or SEQ ID NO: 9.

The modified fibroin (2-i) will be described. The amino acid sequence of SEQ ID NO: 6 is the same as the amino acid sequence of SEQ ID NO: 10 (Met-PRT313) corresponding to the naturally derived fibroin except that all GGXs in REPs are substituted by GQX. The amino acid sequence of SEQ ID NO: 7 is the same as the amino acid sequence of SEQ ID NO: 6 except that every two $(A)_n$ motifs are deleted from the N-terminus to the C-terminus and one $[(A)_n$ motif-REP$]$ is inserted before the C-terminal sequence. The amino acid sequence of SEQ ID NO: 8 is the same as the amino acid sequence of SEQ ID NO: 7 except that two alanine residues are inserted into the side of each $(A)_n$ motif close to the C-terminus and some glutamine (Q) residues are substituted by a serine (S) residue and that some amino acids close to the C-terminus are deleted so as to be substantially equal to the amino acid sequence of SEQ ID NO: 7 in molecular weight. In the amino acid sequence of SEQ ID NO: 9, a predetermined hinge sequence and a His tag sequence are added to the C-terminus of a sequence obtained by repeating a 20-domain-sequence region present in the amino acid sequence of SEQ ID NO: 7 (where several amino acid residues close to the C-terminus of the region are substituted) four times.

A value of z/w in the amino acid sequence of SEQ ID NO: 10 (corresponding to the naturally derived fibroin) is 46.8%. The values of z/w in the amino acid sequences of SEQ ID NO: 6, SEQ ID NO: 7, SEQ ID NO: 8, and SEQ ID NO: 9 are 58.7%, 70.1%, 66.1%, and 70.0%, respectively. In addition, with a GISA ratio (to be described) of 1:1.8 to 11.3, the values of x/y in the amino acid sequences of SEQ ID NO: 10, SEQ ID NO: 6, SEQ ID NO: 7, SEQ ID NO: 8, and SEQ ID NO: 9 are 15.0%, 15.0%, 93.4%, 92.7%, and 89.8%, respectively.

The modified fibroin (2-i) may have the amino acid sequence of SEQ ID NO: 6, SEQ ID NO: 7, SEQ ID NO: 8, or SEQ ID NO: 9.

The modified fibroin (2-ii) has an amino acid sequence having 90% or more sequence identity to the amino acid sequence of SEQ ID NO: 6, SEQ ID NO: 7, SEQ ID NO: 8, or SEQ ID NO: 9. The modified fibroin (2-ii) is also a protein having a domain sequence represented by Formula 1: $[(A)_n$ motif-REP$]_m$. The sequence identity is preferably 95% or more.

The modified fibroin (2-ii) preferably has 90% or more sequence identity to the amino acid sequence of SEQ ID NO: 6, SEQ ID NO: 7, SEQ ID NO: 8, or SEQ ID NO: 9 and has an amino acid sequence in which z/w is 50.9% or more where "z" represents the total number of amino acid residues in an amino acid sequence having XGX (X is an amino acid residue other than glycine) and included in REPs, and "w" represents the total number of amino acid residues in the REPs in the domain sequence.

The second modified fibroin may include a tag sequence at either or both of the N-terminus and the C-terminus. This enables isolation, immobilization, detection, and visualization of the modified fibroin.

The tag sequence may be, for example, an affinity tag utilizing specific affinity (binding property) for another molecule. A specific example of the affinity tag includes a histidine tag (His tag). The His tag is a short peptide which has about 4 to 10 histidine residues aligned and specifically binds to a metal ion such as nickel. Accordingly, the His tag can be used for isolation of a modified fibroin by chelating metal chromatography. A specific example of the tag sequence includes the amino acid sequence of SEQ ID NO: 11 (amino acid sequence having a His tag sequence and a hinge sequence).

In addition, it is possible to employ a tag sequence such as glutathione-S-transferase (GST) that specifically binds to glutathione or a maltose binding protein (MBP) that specifically binds to maltose.

An "epitope tag" utilizing an antigen-antibody reaction can also be employed. Adding a peptide (epitope) exhibiting antigenicity as a tag sequence allows binding of an antibody to the epitope. Examples of the epitope tag include HA (peptide sequence of influenza virus hemagglutinin) tag, myc tag, and FLAG tag. With the epitope tag, the modified fibroin can be purified easily with high specificity.

Furthermore, it is possible to use a tag sequence which can be cleaved with a specific protease. A modified fibroin cleaved from such a tag sequence can be recovered by treating a protein adsorbed through the tag sequence with protease.

More specific examples of the modified fibroin having a tag sequence include (2-iii) a modified fibroin having the amino acid sequence of SEQ ID NO: 12 (PRT380), SEQ ID NO: 13 (PRT410), SEQ ID NO: 14 (PRT525), or SEQ ID NO: 15 (PRT799) and (2-iv) a modified fibroin having an amino acid sequence having 90% or more sequence identity to the amino acid sequence of SEQ ID NO: 12, SEQ ID NO: 13, SEQ ID NO: 14, or SEQ ID NO: 15.

The amino acid sequences of SEQ ID NO: 16 (PRT313), SEQ ID NO: 12, SEQ ID NO: 13, SEQ ID NO: 14, and SEQ ID NO: 15 are obtained by adding the amino acid sequence of SEQ ID NO: 11 (having a His tag sequence and a hinge sequence) to the N-termini of the amino acid sequences of SEQ ID NO: 10, SEQ ID NO: 6, SEQ ID NO: 7, SEQ ID NO: 8, and SEQ ID NO: 9, respectively.

The modified fibroin (2-iii) may have the amino acid sequence of SEQ ID NO: 12, SEQ ID NO: 13, SEQ ID NO: 14, or SEQ ID NO: 15.

The modified fibroin (2-iv) has an amino acid sequence having 90% or more sequence identity to the amino acid sequence of SEQ ID NO: 12, SEQ ID NO: 13, SEQ ID NO: 14, or SEQ ID NO: 15. The modified fibroin (2-iv) is also a protein having a domain sequence represented by Formula 1: $[(A)_n$ motif-REP$]_m$. The sequence identity is preferably 95% or more.

The modified fibroin (2-iv) preferably has 90% or more sequence identity to the amino acid sequence of SEQ ID NO: 12, SEQ ID NO: 13, SEQ ID NO: 14, or SEQ ID NO: 15 and has an amino acid sequence in which z/w is 50.9% or more where "z" represents the total number of amino acid residues in an amino acid sequence having XGX (X is an amino acid residue other than glycine) and included in REPs, and "w" represents the total number of amino acid residues in the REPs in the domain sequence.

The second modified fibroin may include a secretory signal for releasing a protein produced in the recombinant protein production system to the outside of a host. A sequence of the secretory signal can be designed appropriately depending on the type of the host.

The domain sequence of the third modified fibroin has the amino acid sequence of the naturally derived fibroin except that the $(A)_n$ motif content is reduced. In other words, the domain sequence of the third modified fibroin has the amino acid sequence of the naturally derived fibroin except that at least one $(A)_n$ motif is deleted.

The third modified fibroin may have the amino acid sequence of the naturally derived fibroin except that 10 to 40% of $(A)_n$ motifs are deleted.

The domain sequence of the third modified fibroin may have the amino acid sequence of the naturally derived fibroin except that at least one $(A)_n$ motif is deleted per one to three $(A)_n$ motifs from the N-terminus to the C-terminus.

The domain sequence of the third modified fibroin may have the amino acid sequence of the naturally derived fibroin except that deletion of at least two consecutive $(A)_n$ motifs and deletion of one $(A)_n$ motif are repeated in this order from the N-terminus to the C-terminus.

The domain sequence of the third modified fibroin may have an amino acid sequence in which at least every two $(A)_n$ motifs are deleted from the N-terminus to the C-terminus.

The third modified fibroin has a domain sequence represented by Formula 1: $[(A)_n$ motif-REP$]_m$ and may have an amino acid sequence in which x/y is 20% or more, 30% or more, 40% or more, or 50% or more where, when comparing the number of amino acid residues in REPs of two adjacent $[(A)_n$ motif-REP] units sequentially from the N-terminus to the C-terminus, "x" represents the maximum total number of amino acid residues in two adjacent $[(A)_n$ motif-REP] units in which a ratio of amino acid residues in one REP to amino acid residues in the other REP (having fewer amino acid residues and defined as 1) is 1.8 to 11.3, and "y" represents the total number of amino acid residues in the domain sequence. A proportion of alanine residues to the total number of the amino acid residues in an $(A)_n$ motif is 83% or more, preferably 86% or more, more preferably 90% or more, still more preferably 95% or more, and still more preferably 100% (that is, the $(A)_n$ motif consists of alanine residues).

A method of calculating x/y will be described in more detail with reference to FIG. 1. FIG. 1 illustrates a domain sequence excluding the N-terminal sequence and the C-terminal sequence from the modified fibroin. This domain sequence has a sequence of "$(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif" in this order from the N-terminus (left side).

Two adjacent $[(A)_n$ motif-REP] units are sequentially selected from the N-terminus to the C-terminus with no overlap. At this time, there may be $[(A)_n$ motif-REP] units that are not selected. FIG. 1 shows Pattern 1 (a comparison between the first REP and the second REP, and a comparison between the third REP and the fourth REP), Pattern 2 (a comparison between the first REP and the second REP, and a comparison between the fourth REP and the fifth REP), Pattern 3 (a comparison between the second REP and the third REP, and a comparison between the fourth REP and the fifth REP), and Pattern 4 (a comparison between the first REP and the second REP). Note that $[(A)_n$ motif-REP] units may be selected in other ways.

Next, for each pattern, the number of amino acid residues is compared between REPs of the selected two adjacent $[(A)_n$ motif-REP] units. Those units are compared by defining one REP having fewer amino acid residues as 1 and by determining a ratio of amino acid residues in the other REP to amino acid residues in the one having fewer amino acid residues. For example, comparing the first REP (50 amino acid residues) and the second REP (100 amino acid residues), a ratio of amino acid residues in the second REP is 100/50=2, defining the first REP having fewer amino acid residues as 1. Similarly, comparing the fourth REP (20 amino acid residues) and the fifth REP (30 amino acid residues), a ratio of amino acid residues in the fifth REP is 30/20=1.5, defining the fourth REP having fewer amino acid residues as 1.

In FIG. 1, solid lines indicate sets of $[(A)_n$ motif-REP] units in which a ratio of amino acid residues in one REP to amino acid residues in the other REP having fewer amino acid residues (defined as 1) is 1.8 to 11.3. Herein, this ratio is referred to as "GISA ratio". Dashed lines indicate sets of $[(A)_n$ motif-REP] units in which a ratio of amino acid residues in one REP to amino acid residues in the other REP having fewer amino acid residues (defined as 1) is less than 1.8 or over 11.3.

In each pattern, all amino acid residues in two adjacent $[(A)_n$ motif-REP] units indicated by solid lines are added up (including not only the number of amino acid residues in the REPs but also the number of amino acid residues in the $(A)_n$ motifs). The total values of the patterns are compared, and one that has the highest value (the maximum total value) is defined as "x". In the example shown in FIG. 1, the total value of Pattern 1 is the maximum.

Then, "x" is divided by the total number of amino acid residues "y" of the domain sequence to calculate x/y (%).

In the third modified fibroin, x/y is preferably 50% or more, more preferably 60% or more, still more preferably 65% or more, even still more preferably 70% or more, still further preferably 75% or more, and particularly preferably 80% or more. The upper limit of x/y is not particularly limited but may be, for example, 100% or less. With a GISA ratio of 1:1.9 to 11.3, x/y is preferably 89.6% or more. With a GISA ratio of 1:1.8 to 3.4, x/y is preferably 77.1% or more. With a GISA ratio of 1:1.9 to 8.4, x/y is preferably 75.9% or more. With a GISA ratio of 1:1.9 to 4.1, x/y is preferably 64.2% or more.

In a case where the third modified fibroin is a modified fibroin in which at least seven of a plurality of $(A)_n$ motifs in the domain sequence consists of alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited as long as it is 100% or less.

Herein, x/y in the naturally derived fibroin will now be described. First, examining the amino acid sequence information deposited in NCBI GenBank by the aforementioned manner, 663 types of fibroins are found (415 types of fibroins are derived from arachnids). Among all the extracted fibroins, x/y is calculated by the aforementioned calculation method from the amino acid sequence of the naturally derived fibroin having a domain sequence represented by Formula 1: $[(A)_n$ motif-REP$]_m$. Results with a GISA ratio of 1:1.9 to 4.1 are shown in FIG. 3.

Figure 3:
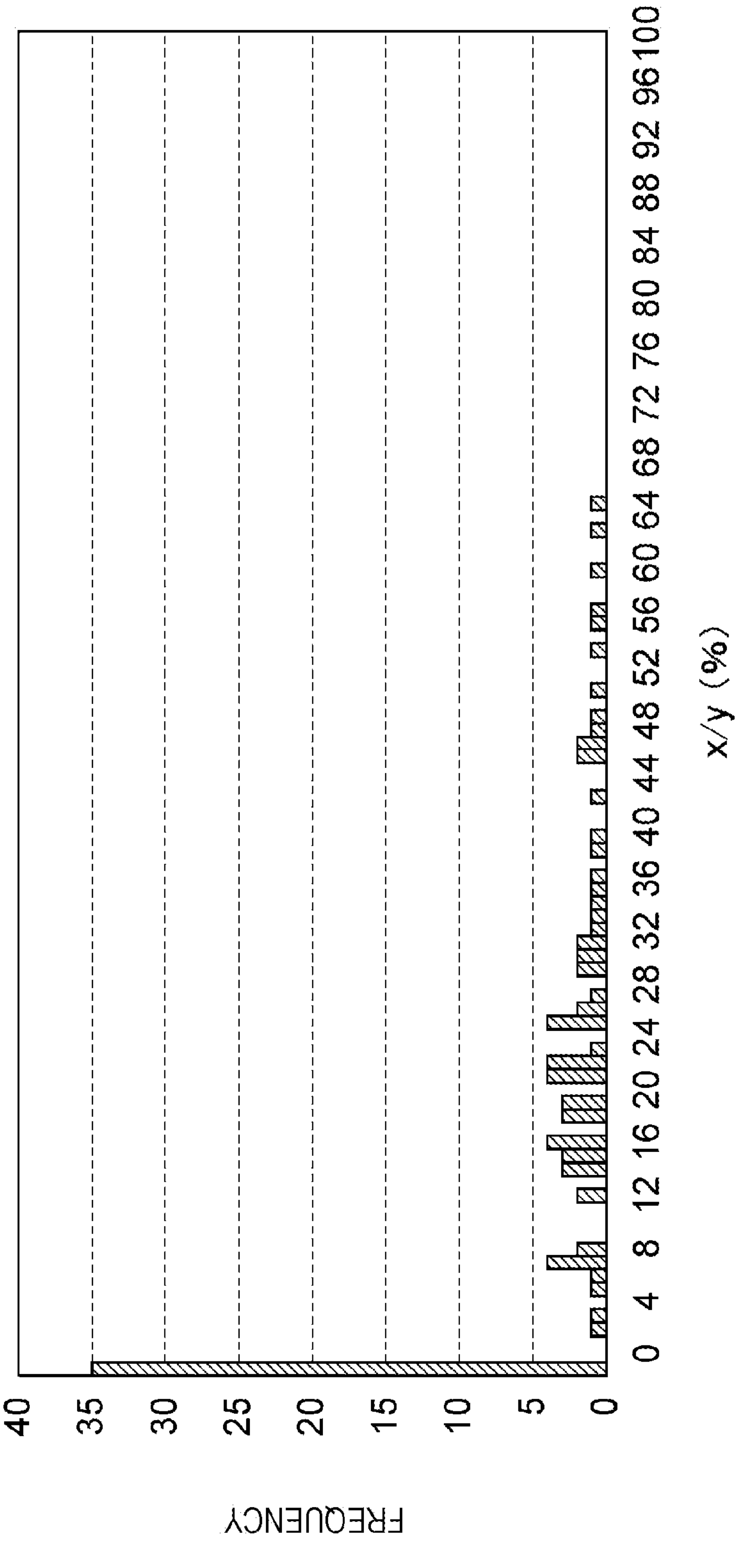
FIG. 3 is a view illustrating a distribution of values of x/y (%) in the naturally derived fibroin.

In FIG. 3, x/y (%) is taken along the abscissa, and the frequency is taken along the ordinate. As is clear from FIG. 3, values of x/y in the naturally derived fibroin are all smaller than 64.2% (the largest value is 64.14%).

The third modified fibroin can be obtained, for example, by deleting at least one sequence encoding an $(A)_n$ motif from a cloned gene sequence of the naturally derived fibroin so that x/y becomes 64.2% or more. In addition, the third modified fibroin can be obtained by, for example, designing the amino acid sequence of the naturally derived fibroin except that at least one $(A)_n$ motif is deleted so that x/y becomes 64.2% or more and by chemically synthesizing a nucleic acid encoding the designed amino acid sequence. In any case, the amino acid sequence of the naturally derived fibroin may be modified not only by deleting an $(A)_n$ motif from the amino acid sequence but also by substituting, deleting, inserting, and/or adding at least one amino acid residue.

More specific examples of the third modified fibroin include (3-i) a modified fibroin having the amino acid sequence of SEQ ID NO: 17 (Met-PRT399), SEQ ID NO: 7 (Met-PRT410), SEQ ID NO: 8 (Met-PRT525), or SEQ ID NO: 9 (Met-PRT799) and (3-ii) a modified fibroin having an amino acid sequence having 90% or more sequence identity to the amino acid sequence of SEQ ID NO: 17, SEQ ID NO: 7, SEQ ID NO: 8, or SEQ ID NO: 9.

The modified fibroin (3-i) will be described. The amino acid sequence of SEQ ID NO: 17 is obtained by deleting every two $(A)_n$ motifs, from the N-terminus to the C-terminus, from the amino acid sequence of SEQ ID NO: 10 (Met-PRT313) corresponding to the naturally derived fibroin and by inserting one $[(A)_n$ motif-REP$]$ before the C-terminal sequence. The amino acid sequence of SEQ ID NO: 7, SEQ ID NO: 8, or SEQ ID NO: 9 is as described in the second modified fibroin.

With a GISA ratio of 1:1.8 to 11.3, the value of x/y in the amino acid sequence of SEQ ID NO: 10 (corresponding to the naturally derived fibroin) is 15.0%. Both values of x/y in the amino acid sequences of SEQ ID NO: 17 and SEQ ID NO: 7 are 93.4%. In the amino acid sequence of SEQ ID NO: 8, the value of x/y is 92.7%. In the amino acid sequence of SEQ ID NO: 9, the value of x/y is 89.8%. In the amino acid sequences of SEQ ID NO: 10, SEQ ID NO: 17, SEQ ID NO: 7, SEQ ID NO: 8, and SEQ ID NO: 9, z/w values are 46.8%, 56.2%, 70.1%, 66.1%, and 70.0%, respectively.

The modified fibroin (3-i) may have the amino acid sequence of SEQ ID NO: 17, SEQ ID NO: 7, SEQ ID NO: 8, or SEQ ID NO: 9.

The modified fibroin (3-ii) has an amino acid sequence having 90% or more sequence identity to the amino acid sequence of SEQ ID NO: 17, SEQ ID NO: 7, SEQ ID NO: 8, or SEQ ID NO: 9. The modified fibroin (3-ii) is also a protein having a domain sequence represented by Formula 1: $[(A)_n$ motif-REP$]_m$. The sequence identity is preferably 95% or more.

The modified fibroin (3-ii) preferably has 90% or more sequence identity to the amino acid sequence of SEQ ID NO: 17, SEQ ID NO: 7, SEQ ID NO: 8, or SEQ ID NO: 9 and has an amino acid sequence in which x/y is 64.2% or more where, when comparing the number of amino acid residues in REPs of two adjacent $[(A)_n$ motif-REP$]$ units sequentially from the N-terminus to the C-terminus, "x" represents the maximum total number of amino acid residues in two adjacent $[(A)_n$ motif-REP$]$ units in which a ratio of amino acid residues in one REP to amino acid residues in the other REP (having fewer amino acid residues and defined as 1) is 1.8 to 11.3 (GISA ratio of 1:1.8 to 11.3), and "y" represents the total number of amino acid residues in the domain sequence.

The third modified fibroin may include the aforementioned tag sequence at either or both of the N-terminus and the C-terminus.

More specific examples of the modified fibroin having a tag sequence include (3-iii) a modified fibroin having the amino acid sequence of SEQ ID NO: 18 (PRT399), SEQ ID NO: 13 (PRT410), SEQ ID NO: 14 (PRT525), or SEQ ID NO: 15 (PRT799) and (3-iv) a modified fibroin having an amino acid sequence having 90% or more sequence identity to the amino acid sequence of SEQ ID NO: 18, SEQ ID NO: 13, SEQ ID NO: 14, or SEQ ID NO: 15.

The amino acid sequences of SEQ ID NO: 18, SEQ ID NO: 13, SEQ ID NO: 14, and SEQ ID NO: 15 are obtained by adding the amino acid sequence of SEQ ID NO: 11 (having a His tag sequence and a hinge sequence) to the N-termini of the amino acid sequences of SEQ ID NO: 17, SEQ ID NO: 7, SEQ ID NO: 8, and SEQ ID NO: 9, respectively.

The modified fibroin (3-iii) may have the amino acid sequence of SEQ ID NO: 18, SEQ ID NO: 13, SEQ ID NO: 14, or SEQ ID NO: 15.

The modified fibroin (3-iv) has an amino acid sequence having 90% or more sequence identity to the amino acid sequence of SEQ ID NO: 18, SEQ ID NO: 13, SEQ ID NO: 14, or SEQ ID NO: 15. The modified fibroin (3-iv) is also a protein having a domain sequence represented by Formula 1: $[(A)_n$ motif-REP$]_m$. The sequence identity is preferably 95% or more.

The modified fibroin (3-iv) preferably has 90% or more sequence identity to the amino acid sequence of SEQ ID NO: 18, SEQ ID NO: 13, SEQ ID NO: 14, or SEQ ID NO: 15 and has an amino acid sequence in which x/y is 64.2% or more where, when comparing the number of amino acid residues in REPs of two adjacent $[(A)_n$ motif-REP$]$ units sequentially from the N-terminus to the C-terminus, "x" represents the maximum total number of amino acid residues in two adjacent $[(A)_n$ motif-REP$]$ units in which a ratio of amino acid residues in one REP to amino acid residues in the other REP (having fewer amino acid residues and defined as 1) is 1.8 to 11.3, and "y" represents the total number of amino acid residues in the domain sequence.

The third modified fibroin may include a secretory signal for releasing a protein produced in the recombinant protein production system to the outside of a host. A sequence of the secretory signal can be designed appropriately depending on the type of the host.

The domain sequence of the fourth modified fibroin has the amino acid sequence of the naturally derived fibroin except that the $(A)_n$ motif content and the glycine residue content are reduced. In other words, the fourth modified fibroin has a domain sequence having the amino acid sequence of the naturally derived fibroin except that not only at least one $(A)_n$ motif is deleted but also one glycine residue in at least an REP is substituted by another amino acid residue. That is, the fourth modified fibroin is a modified fibroin having the properties of the second modified fibroin and the third modified fibroin. Specific aspects of the fourth modified fibroin are as in the descriptions of the second modified fibroin and the third modified fibroin.

More specific examples of the fourth modified fibroin include (4-i) a modified fibroin having the amino acid sequence of SEQ ID NO: 7 (Met-PRT410), SEQ ID NO: 8 (Met-PRT525), SEQ ID NO: 9 (Met-PRT799), SEQ ID NO: 13 (PRT410), SEQ ID NO: 14 (PRT525), or SEQ ID NO: 15 (PRT799) and (4-ii) a modified fibroin having an amino acid sequence having 90% or more sequence identity to the amino acid sequence of SEQ ID NO: 7, SEQ ID NO: 8, SEQ ID NO: 9, SEQ ID NO: 13, SEQ ID NO: 14, or SEQ ID NO: 15. Specific aspects of the modified fibroin having the amino acid sequence of SEQ ID NO: 7, SEQ ID NO: 8, SEQ ID NO: 9, SEQ ID NO: 13, SEQ ID NO: 14, or SEQ ID NO: 15 are as described above.

The domain sequence of the fifth modified fibroin may have an amino acid sequence including a region locally having a high hydropathy index which corresponds to the amino acid sequence of the naturally derived fibroin except that at least one amino acid residue in an REP is substituted by an amino acid residue having a high hydropathy index and/or at least one amino acid residue having a high hydropathy index is inserted into an REP.

The region locally having a high hydropathy index preferably includes two to four consecutive amino acid residues.

The amino acid residue having a high hydropathy index is more preferably an amino acid residue selected from isoleucine (I), valine (V), leucine (L), phenylalanine (F), cysteine (C), methionine (M), and alanine (A).

The fifth modified fibroin may be modified not only by substituting at least one amino acid residue in an REP of the amino acid sequence of the naturally derived fibroin by another amino acid residue having a high hydropathy index and/or inserting at least one amino acid residue having a high hydropathy index into an REP but also by substituting, deleting, inserting, and/or adding at least one amino acid residue.

The fifth modified fibroin can be obtained by, for example, substituting at least one hydrophilic amino acid residue in an REP (for example, an amino acid residue having a negative hydropathy index) by a hydrophobic amino acid residue (for example, an amino acid residue having a positive hydropathy index) in a cloned gene sequence of the naturally derived fibroin and/or by inserting at least one hydrophobic amino acid residue into an REP. In addition, the fifth modified fibroin can be obtained by, for example, designing the amino acid sequence of the naturally derived fibroin except that at least one hydrophilic amino acid residue in an REP is substituted by a hydrophobic amino acid residue and/or at least one hydrophobic amino acid residue is inserted into an REP and by chemically synthesizing a nucleic acid encoding the designed amino acid sequence. In any case, the amino acid sequence of the naturally derived fibroin may be modified not only by substituting at least one hydrophilic amino acid residue by a hydrophobic amino acid residue in an REP of the amino acid sequence and/or inserting at least one hydrophobic amino acid residue into an REP of the amino acid sequence but also by substituting, deleting, inserting, and/or adding at least one amino acid residue.

The fifth modified fibroin may have a domain sequence represented by Formula 1: $[(A)_n \text{ motif-REP}]_m$ and have an amino acid sequence in which p/q is 6.2% or more where "p" represents the total number of amino acid residues included in a region where four consecutive amino acid residues have an average hydropathy index of 2.6 or more in all REPs included in a sequence of the domain sequence excluding a range from the $(A)_n$ motif closest to the C-terminus of the domain sequence to the C-terminus, and "q" represents the total number of amino acid residues included in the sequence of the domain sequence excluding the range from the $(A)_n$ motif closest to the C-terminus of the domain sequence to the C-terminus.

As the hydropathy index of an amino acid residue, a known index is used herein (Hydropathy index: Kyte J, & Doolittle R (1982) "A simple method for displaying the hydropathic character of a protein", J. Mol. Biol., 157, pp. 105-132). Specifically, the following Table 1 shows the hydropathy index (hereinafter also referred to as "HI") of each amino acid.

TABLE 1

| Amino Acid | HI |
|---|---|
| Isoleucine (Ile) | 4.5 |
| Valine (Val) | 4.2 |
| Leucine (Leu) | 3.8 |
| Phenylalanine (Phe) | 2.8 |
| Cysteine (Cys) | 2.5 |
| Methionine (Met) | 1.9 |
| Alanine (Ala) | 1.8 |
| Glycine (Gly) | −0.4 |
| Threonine (Thr) | −0.7 |
| Serine (Ser) | −0.8 |
| Tryptophan (Trp) | −0.9 |
| Tyrosine (Tyr) | −1.3 |
| Proline (Pro) | −1.6 |
| Histidine (His) | −3.2 |
| Asparagine (Asn) | −3.5 |
| Asparatic Acid (Asp) | −3.5 |
| Glutamine (Gln) | −3.5 |
| Glutamic Acid (Glu) | −3.5 |
| Lysine (Lys) | −3.9 |
| Arginine (Arg) | −4.5 |

The calculation method of p/q will be described in more detail. The calculation employs the domain sequence represented by Formula 1: $[(A)_n \text{ motif-REP}]_m$ excluding the range from the $(A)_n$ motif closest to the C-terminus of the domain sequence to the C-terminus (hereinafter also referred to as "sequence A"). First, in all REPs included in the sequence A, the average hydropathy index of four consecutive amino acid residues is calculated. The average hydropathy index is determined by dividing a sum of HI of each amino acid residue in four consecutive amino acid residues by 4 (the number of amino acid residues). The average hydropathy index is determined for all four consecutive amino acid residues (each amino acid residue is used for calculating the average one to four times). Then, a region where four consecutive amino acid residues have an average hydropathy index of 2.6 or more is determined. Even when a certain amino acid residue corresponds to a plurality of "four consecutive amino acid residues having an average hydropathy index of 2.6 or more", the region is regarded as including one amino acid residue. The total number of amino acid residues included in the region is "p". The total number of amino acid residues included in the sequence A is "q".

Figure 4:
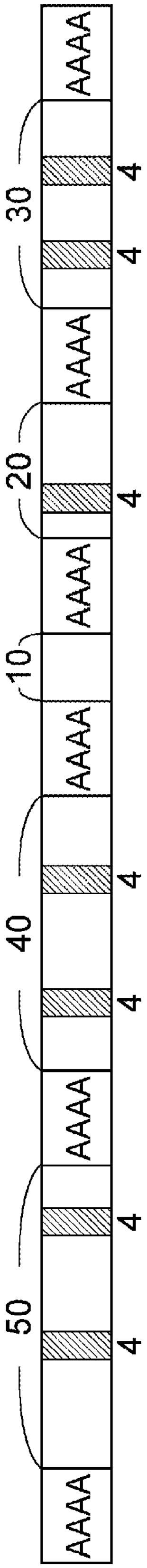
FIG. 4 is a schematic view illustrating an example of a domain sequence of a modified fibroin.

For example, in a case where "four consecutive amino acid residues having an average hydropathy index of 2.6 or more" are extracted from 20 places (no overlap), there are 20 sets of four consecutive amino acid residues (no overlap) in a region where four consecutive amino acid residues have an average hydropathy index of 2.6 or more, and thus, "p" is 20×4=80. Furthermore, for example, in a case where one amino acid residue overlaps within two sets of "four consecutive amino acid residues having an average hydropathy index of 2.6 or more", a region where four consecutive amino acid residues have an average hydropathy index of 2.6 or more is regarded as including seven amino acid residues (p=2×4-1=7. The overlapping amino acid residue is deducted, being indicated by "−1"). For example, the domain sequence shown in FIG. 4 includes seven sets of "four consecutive amino acid residues having an average hydropathy index of 2.6 or more" with no overlap, and thus, "p" is 7×4=28. Furthermore, for example, in the domain sequence shown in FIG. 4, "q" is 4+50+4+40+4+10+4+20+4+30=170 (excluding the $(A)_n$ motif at the end of the C-terminus). Next, "p" is divided by "q" to calculate p/q (%). In an example illustrated in FIG. 4, 28/170=16.47%.

In the fifth modified fibroin, p/q is preferably 6.2% or more, more preferably 7% or more, still more preferably 10% or more, even still more preferably 20% or more, and still further preferably 30% or more. The upper limit of p/q is not particularly limited but may be, for example, 45% or less.

The fifth modified fibroin can be obtained by, for example, modifying a cloned amino acid sequence of the naturally derived fibroin into an amino acid sequence including a region locally having a high hydropathy index by the following manner. That is, at least one hydrophilic amino acid residue in an REP (for example, an amino acid residue having a negative hydropathy index) is substituted by a hydrophobic amino acid residue (for example, an amino acid residue having a positive hydropathy index) and/or at least one hydrophobic amino acid residue is inserted into an REP, thereby satisfying the aforementioned condition of p/q. Alternatively, the fifth modified fibroin can be obtained by, for example, designing an amino acid sequence satisfying the condition of p/q from the amino acid sequence of the naturally derived fibroin and by chemically synthesizing a nucleic acid encoding the designed amino acid sequence. In any case, the amino acid sequence of the naturally derived fibroin may be modified not only by substituting at least one amino acid residue in an REP of the amino acid sequence by another amino acid residue having a high hydropathy index and/or inserting at least one amino acid residue having a high hydropathy index into an REP of the amino acid sequence but also by substituting, deleting, inserting, and/or adding at least one amino acid residue.

The amino acid residue with a high hydropathy index is not particularly limited but is preferably isoleucine (I), valine (V), leucine (L), phenylalanine (F), cysteine (C), methionine (M), and alanine (A). Among these examples, valine (V), leucine (L), and isoleucine (I) are more preferable.

More specific examples of the fifth modified fibroin include (5-i) a modified fibroin having the amino acid sequence of SEQ ID NO: 19 (Met-PRT720), SEQ ID NO: 20 (Met-PRT665), or SEQ ID NO: 21 (Met-PRT666) and (5-ii) a modified fibroin having an amino acid sequence having 90% or more sequence identity to the amino acid sequence of SEQ ID NO: 19, SEQ ID NO: 20, or SEQ ID NO: 21.

The modified fibroin (5-i) will be described. The amino acid sequence of SEQ ID NO: 19 is obtained by inserting two sites of amino acid sequence having three amino acid residues (VLI) into every other REP of the amino acid sequence of SEQ ID NO: 7 (Met-PRT410) except for the domain sequence at the end of the C-terminus, and then, substituting a part of glutamine (Q) residues by serine (S) residues and deleting a part of amino acids in the C-terminus. The amino acid sequence of SEQ ID NO: 20 is obtained by inserting one site of amino acid sequence having three amino acid residues (VLI) into every other REP of the amino acid sequence of SEQ ID NO: 8 (Met-PRT525). The amino acid sequence of SEQ ID NO: 21 is obtained by inserting two sites of amino acid sequence having three amino acid residues (VLI) into every other REP of the amino acid sequence of SEQ ID NO: 8.

The modified fibroin (5-i) may have the amino acid sequence of SEQ ID NO: 19, SEQ ID NO: 20, or SEQ ID NO: 21.

The modified fibroin (5-ii) has an amino acid sequence having 90% or more sequence identity to the amino acid sequence of SEQ ID NO: 19, SEQ ID NO: 20, or SEQ ID NO: 21. The modified fibroin (5-ii) is also a protein having a domain sequence represented by Formula 1: $[(A)_n\text{ motif-REP}]_m$. The sequence identity is preferably 95% or more.

The modified fibroin (5-ii) preferably has 90% or more sequence identity to the amino acid sequence of SEQ ID NO: 19, SEQ ID NO: 20, or SEQ ID NO: 21 and has an amino acid sequence in which p/q is 6.2% or more where "p" represents the total number of amino acid residues included in a region where four consecutive amino acid residues have an average hydropathy index of 2.6 or more in all REPs included in a sequence of the domain sequence excluding a range from the $(A)_n$ motif closest to the C-terminus of the domain sequence to the C-terminus, and "q" represents the total number of amino acid residues included in the sequence of the domain sequence excluding the range from the $(A)_n$ motif closest to the C-terminus of the domain sequence to the C-terminus.

The fifth modified fibroin may include a tag sequence at either or both of the N-terminus and the C-terminus.

More specific examples of the modified fibroin having a tag sequence include (5-iii) a modified fibroin having the amino acid sequence of SEQ ID NO: 22 (PRT720), SEQ ID NO: 23 (PRT665), or SEQ ID NO: 24 (PRT666) and (5-iv) a modified fibroin having an amino acid sequence having 90% or more sequence identity to the amino acid sequence of SEQ ID NO: 22, SEQ ID NO: 23, or SEQ ID NO: 24.

The amino acid sequences of SEQ ID NO: 22, SEQ ID NO: 23, and SEQ ID NO: 24 are obtained by adding the amino acid sequence of SEQ ID NO: 11 (having a His tag sequence and a hinge sequence) to the N-termini of the amino acid sequences of SEQ ID NO: 19, SEQ ID NO: 20, and SEQ ID NO: 21, respectively.

The modified fibroin (5-iii) may have the amino acid sequence of SEQ ID NO: 22, SEQ ID NO: 23, or SEQ ID NO: 24.

The modified fibroin (5-iv) has an amino acid sequence having 90% or more sequence identity to the amino acid sequence of SEQ ID NO: 22, SEQ ID NO: 23, or SEQ ID NO: 24. The modified fibroin (5-iv) is also a protein having a domain sequence represented by Formula 1: $[(A)_n\text{ motif-REP}]_m$. The sequence identity is preferably 95% or more.

The modified fibroin (5-iv) preferably has 90% or more sequence identity to the amino acid sequence of SEQ ID NO: 22, SEQ ID NO: 23, or SEQ ID NO: 24 and has an amino acid sequence in which p/q is 6.2% or more where "p" represents the total number of amino acid residues included in a region where four consecutive amino acid residues have an average hydropathy index of 2.6 or more in all REPs included in a sequence of the domain sequence excluding a range from the $(A)_n$ motif closest to the C-terminus of the domain sequence to the C-terminus, and "q" represents the total number of amino acid residues included in the sequence of the domain sequence excluding the range from the $(A)_n$ motif closest to the C-terminus of the domain sequence to the C-terminus.

The fifth modified fibroin may include a secretory signal for releasing a protein produced in the recombinant protein production system to the outside of a host. A sequence of the secretory signal can be designed appropriately depending on the type of the host.

The sixth modified fibroin has the amino acid sequence of the naturally derived fibroin except that the glutamine residue content is reduced.

In the sixth modified fibroin, at least one motif selected from GGX motif and GPGXX motif is preferably included in the amino acid sequence of REP.

In a case where the sixth modified fibroin includes a GPGXX motif in an REP, the GPGXX motif content is usually 1% or more, may also be 5% or more, and is preferably 10% or more. The GPGXX motif content is not particularly limited in upper value and may be 50% or less or 30% or less.

The "GPGXX motif content" herein is a value calculated by the following method.

In a fibroin having a domain sequence represented by Formula 1: $[(A)_n$ motif-REP$]_m$ or Formula 2: $[(A)_n$ motif-REP$]_m$-$(A)_n$ motif (modified fibroin or naturally derived fibroin), the GPGXX motif content is calculated as s/t where "s" represents the number obtained by tripling the total number of GPGXX motifs in all REPs included in a sequence of the domain sequence excluding a range from the $(A)_n$ motif closest to the C-terminus of the domain sequence to the C-terminus (that is, the total number of G and P in the GPGXX motifs), and "t" represents the total number of amino acid residues in all REPs included in the sequence of the domain sequence excluding the range from the $(A)_n$ motif closest to the C-terminus of the domain sequence to the C-terminus and further excluding the $(A)_n$ motifs.

In calculating the GPGXX motif content, "the sequence of the domain sequence excluding the range from the $(A)_n$ motif closest to the C-terminus of the domain sequence to the C-terminus" is used to eliminate influence on calculation results of the GPGXX motif content when "m" is small (that is, when the domain sequence is short). This is because "the range from the $(A)_n$ motif closest to the C-terminus of the domain sequence to the C-terminus" (sequence corresponding to an REP) may include a sequence that has low correlation with a specific sequence of fibroin. In a case where the "GPGXX motif" is located at the C-terminus of an REP, even when "XX" is "AA", for example, it is regarded as the "GPGXX motif".

Figure 5:
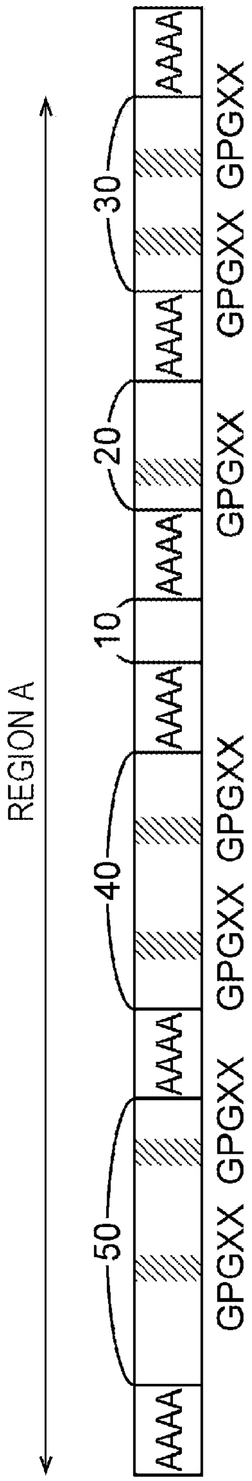
FIG. 5 is a schematic view illustrating an example of a domain sequence of a modified fibroin.

FIG. 5 is a schematic view illustrating the domain sequence of the modified fibroin. A method for calculating the GPGXX motif content will be specifically described referring to FIG. 5. First, in the domain sequence of the modified fibroin shown in FIG. 5 ("$[(A)_n$ motif-REP$]_m$-$(A)_n$ motif" type), all REPs are included in "the sequence of the domain sequence excluding the range from the $(A)_n$ motif closest to the C-terminus of the domain sequence to the C-terminus" (shown as "region A" in FIG. 5). The number of GPGXX motifs for calculating "s" is 7, and "s" is 7×3=21. Similarly, since all REPs are included in "the sequence of the domain sequence excluding the range from the $(A)_n$ motif closest to the C-terminus of the domain sequence to the C-terminus" (shown as "region A" in FIG. 5), the total number "t" of amino acid residues in all REPs when the $(A)_n$ motifs are further excluded from the sequence is 50+40+10+20+30=150. Next, "s" is divided by "t" to calculate s/t (%). In the modified fibroin shown in FIG. 5, s/t is 21/150=14.0%.

In the sixth modified fibroin, the glutamine residue content is preferably 9% or less, more preferably 7% or less, still more preferably 4% or less, and particularly preferably 0%.

The "glutamine residue content" herein is a value calculated by the following method.

In a fibroin having a domain sequence represented by Formula 1: $[(A)_n$ motif-REP$]_m$ or Formula 2: $[(A)_n$ motif-REP$]_m$-$(A)_n$ motif (modified fibroin or naturally derived fibroin), the glutamine residue content is calculated as u/t where "u" represents the total number of glutamine residues in all REPs included in a sequence of the domain sequence excluding a range from the $(A)_n$ motif closest to the C-terminus of the domain sequence to the C-terminus (corresponding to "region A" in FIG. 5), and "t" represents the total number of amino acid residues in all REPs included in the sequence of the domain sequence excluding the range from the $(A)_n$ motif closest to the C-terminus of the domain sequence to the C-terminus and further excluding the $(A)_n$ motifs. In calculating the glutamine residue content, "the sequence of the domain sequence excluding the range from the $(A)_n$ motif closest to the C-terminus of the domain sequence to the C-terminus" is used for the same reason as descried above.

The domain sequence of the sixth modified fibroin may have the amino acid sequence of the naturally derived fibroin except that at least one glutamine residue in an REP is deleted or at least one glutamine residue is substituted by another amino acid residue.

The "another amino acid residue" may be an amino acid residue other than the glutamine residue but is preferably an amino acid residue having a higher hydropathy index than that of the glutamine residue. The hydropathy index of each amino acid residue is shown in Table 1.

As shown in Table 1, an example of the amino acid residue having a higher hydropathy index than that of the glutamine residue includes one selected from isoleucine (I), valine (V), leucine (L), phenylalanine (F), cysteine (C), methionine (M), alanine (A), glycine (G), threonine (T), serine (S), tryptophan (W), tyrosine (Y), proline (P), and histidine (H). Among these examples, the amino acid residue is more preferably one selected from isoleucine (I), valine (V), leucine (L), phenylalanine (F), cysteine (C), methionine (M), and alanine (A), and still more preferably one selected from isoleucine (I), valine (V), leucine (L), and phenylalanine (F).

In the sixth modified fibroin, each REP preferably has a hydropathy level of −0.8 or more, more preferably −0.7 or more, still more preferably 0 or more, still more preferably 0.3 or more, and particularly preferably 0.4 or more. The upper limit of the hydropathy level of each REP is not particularly limited but may be 1.0 or less or 0.7 or less.

The "hydropathy level of each REP" herein is a value calculated by the following method.

In a fibroin having a domain sequence represented by Formula 1: $[(A)_n$ motif-REP$]_m$ or Formula 2: $[(A)_n$ motif-REP$]_m$-$(A)_n$ motif (modified fibroin or naturally derived fibroin), the hydropathy level of each REP is calculated as v/t where "v" represents a sum of hydropathy index of all amino acid residues in all REPs included in a sequence of the domain sequence excluding a range from the $(A)_n$ motif closest to the C-terminus of the domain sequence to the C-terminus (corresponding to "region A" in FIG. 5), and "t" represents the total number of amino acid residues in all REPs included in the sequence of the domain sequence excluding the range from the $(A)_n$ motif closest to the C-terminus of the domain sequence to the C-terminus and further excluding the $(A)_n$ motifs. In calculating the hydropathy level of each REP, "the sequence of the domain sequence excluding the range from the $(A)_n$ motif closest to the C-terminus of the domain sequence to the C-terminus" is used for the same reason as descried above.

The domain sequence of the sixth modified fibroin may be modified not only by deleting at least one glutamine residue in an REP of the amino acid sequence of the naturally derived fibroin and/or substituting at least one glutamine residue in an REP by another amino acid residue but also by substituting, deleting, inserting, and/or adding at least one amino acid residue.

The sixth modified fibroin can be obtained by, for example, deleting at least one glutamine residue in an REP from a cloned gene sequence of the naturally derived fibroin and/or by substituting at least one glutamine residue in an REP by another amino acid residue. In addition, the sixth modified fibroin can be obtained by, for example, designing the amino acid sequence of the naturally derived fibroin except that at least one glutamine residue in an REP is deleted and/or at least one glutamine residue in an REP is substituted by another amino acid residue and by chemically synthesizing a nucleic acid encoding the designed amino acid sequence.

More specific examples of the sixth modified fibroin include (6-i) a modified fibroin having the amino acid sequence of SEQ ID NO: 25 (Met-PRT888), SEQ ID NO: 26 (Met-PRT965), SEQ ID NO: 27 (Met-PRT889), SEQ ID NO: 28 (Met-PRT916), SEQ ID NO: 29 (Met-PRT918), SEQ ID NO: 30 (Met-PRT699), SEQ ID NO: 31 (Met-PRT698), SEQ ID NO: 32 (Met-PRT966), SEQ ID NO: 41 (Met-PRT917), or SEQ ID NO: 42 (Met-PRT1028) and (6-ii) a modified fibroin having an amino acid sequence having 90% or more sequence identity to the amino acid sequence of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin (6-i) will be described. The amino acid sequence of SEQ ID NO: 25 is obtained by substituting all QQs in the amino acid sequence of SEQ ID NO: 7 (Met-PRT410) by VL. The amino acid sequence of SEQ ID NO: 26 is obtained by substituting all QQs in the amino acid sequence of SEQ ID NO: 7 by TS and substituting the remaining Q by A. The amino acid sequence of SEQ ID NO: 27 is obtained by substituting all QQs in the amino acid sequence of SEQ ID NO: 7 by VL and substituting the remaining Q by I. The amino acid sequence of SEQ ID NO: 28 is obtained by substituting all QQs in the amino acid sequence of SEQ ID NO: 7 by VI and substituting the remaining Q by L. The amino acid sequence of SEQ ID NO: 29 is obtained by substituting all QQs in the amino acid sequence of SEQ ID NO: 7 by VF and substituting the remaining Q by I.

The amino acid sequence of SEQ ID NO: 30 is obtained by substituting all QQs in the amino acid sequence of SEQ ID NO: 8 (Met-PRT525) by VL. The amino acid sequence of SEQ ID NO: 31 is obtained by substituting all QQs in the amino acid sequence of SEQ ID NO: 8 by VL and substituting the remaining Q by I.

The amino acid sequence of SEQ ID NO: 32 is obtained by substituting all QQs by VF in a sequence obtained by repeating a 20-domain-sequence region present in the amino acid sequence of SEQ ID NO: 7 (Met-PRT410) two times, and then, substituting the remaining Q by I.

The amino acid sequence of SEQ ID NO: 41 (Met-PRT917) is obtained by substituting all QQs in the amino acid sequence of SEQ ID NO: 7 by LI and substituting the remaining Q by V. The amino acid sequence of SEQ ID NO: 42 (Met-PRT1028) is obtained by substituting all QQs in the amino acid sequence of SEQ ID NO: 7 by IF and substituting the remaining Q by T.

The amino acid sequences of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42 each have the glutamine residue content of 9% or less (Table 2).

TABLE 2

| Modified Fibroin | Glutamine Residue Content | GPGXX Motif Content | Hydropathy of REP |
|---|---|---|---|
| Met-PRT410 (SEQ ID NO: 7) | 17.7% | 27.9% | −1.52 |
| Met-PRT888 (SEQ ID NO: 25) | 6.3% | 27.9% | −0.07 |
| Met-PRT965 (SEQ ID NO: 26) | 0.0% | 27.9% | −0.65 |
| Met-PRT889 (SEQ ID NO: 27) | 0.0% | 27.9% | 0.35 |
| Met-PRT916 (SEQ ID NO: 28) | 0.0% | 27.9% | 0.47 |
| Met-PRT918 (SEQ ID NO: 29) | 0.0% | 27.9% | 0.45 |
| Met-PRT699 (SEQ ID NO: 30) | 3.6% | 26.4% | −0.78 |
| Met-PRT698 (SEQ ID NO: 31) | 0.0% | 26.4% | −0.03 |
| Met-PRT966 (SEQ ID NO: 32) | 0.0% | 28.0% | 0.35 |
| Met-PRT917 (SEQ ID NO: 41) | 0.0% | 27.9% | 0.46 |
| Met-PRT1028 (SEQ ID NO: 42) | 0.0% | 28.1% | 0.05 |

The modified fibroin (6-i) may have the amino acid sequence of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin (6-ii) has an amino acid sequence having 90% or more sequence identity to the amino acid sequence of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42. The modified fibroin (6-ii) is also a protein having a domain sequence represented by Formula 1: $[(A)_n \text{ motif-REP}]_m$ or Formula 2: $[(A)_n \text{ motif-REP}]_m\text{-}(A)_n$ motif. The sequence identity is preferably 95% or more.

In the modified fibroin (6-ii), the glutamine residue content is preferably 9% or less. In the modified fibroin (6-ii), the GPGXX motif content is preferably 10% or more.

The sixth modified fibroin may include a tag sequence at either or both of the N-terminus and the C-terminus. This enables isolation, immobilization, detection, and visualization of the modified fibroin.

More specific examples of the modified fibroin having a tag sequence include (6-iii) a modified fibroin having the amino acid sequence of SEQ ID NO: 33 (PRT888), SEQ ID NO: 34 (PRT965), SEQ ID NO: 35 (PRT889), SEQ ID NO: 36 (PRT916), SEQ ID NO: 37 (PRT918), SEQ ID NO: 38 (PRT699), SEQ ID NO: 39 (PRT698), SEQ ID NO: 40 (PRT966), SEQ ID NO: 43 (PRT917), or SEQ ID NO: 44 (PRT1028) and (6-iv) a modified fibroin having an amino acid sequence having 90% or more sequence identity to the amino acid sequence of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

The amino acid sequences of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, and SEQ ID NO: 44 are obtained by adding the amino acid sequence of SEQ ID NO: 11 (having a His tag sequence and a hinge sequence) to the N-termini of the amino acid sequences of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42, respectively. Only the tag sequence is added to each N-terminus, which does not change the glutamine residue content. Accordingly, the amino acid sequences of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, and SEQ ID NO: 44 all have the glutamine residue content of 9% or less (Table 3).

TABLE 3

| Modified Fibroin | Glutamine Residue Content | GPGXX Motif Content | Hydropathy of REP |
|---|---|---|---|
| PRT888 (SEQ ID NO: 33) | 6.3% | 27.9% | −0.07 |
| PRT965 (SEQ ID NO: 34) | 0.0% | 27.9% | −0.65 |
| PRT889 (SEQ ID NO: 35) | 0.0% | 27.9% | 0.35 |
| PRT916 (SEQ ID NO: 36) | 0.0% | 27.9% | 0.47 |
| PRT918 (SEQ ID NO: 37) | 0.0% | 27.9% | 0.45 |
| PRT699 (SEQ ID NO: 38) | 3.6% | 26.4% | −0.78 |
| PRT698 (SEQ ID NO: 39) | 0.0% | 26.4% | −0.03 |
| PRT966 (SEQ ID NO: 40) | 0.0% | 28.0% | 0.35 |
| PRT917 (SEQ ID NO: 43) | 0.0% | 27.9% | 0.46 |
| PRT1028 (SEQ ID NO: 44) | 0.0% | 28.1% | 0.05 |

The modified fibroin (6-iii) may have the amino acid sequence of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

The modified fibroin (6-iv) has an amino acid sequence having 90% or more sequence identity to the amino acid sequence of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44. The modified fibroin (6-iv) is also a protein having a domain sequence represented by Formula 1: $[(A)_n \text{ motif-REP}]_m$ or Formula 2: $[(A)_n \text{ motif-REP}]_m\text{-}(A)_n$ motif. The sequence identity is preferably 95% or more.

In the modified fibroin (6-iv), the glutamine residue content is preferably 9% or less. In the modified fibroin (6-iv), the GPGXX motif content is preferably 10% or more.

The sixth modified fibroin may include a secretory signal for releasing a protein produced in the recombinant protein production system to the outside of a host. A sequence of the secretory signal can be designed appropriately depending on the type of the host.

The modified fibroin may also be a modified fibroin having at least two or more properties among the properties of the first modified fibroin, the second modified fibroin, the third modified fibroin, the fourth modified fibroin, the fifth modified fibroin, and the sixth modified fibroin.

The modified fibroin may be a hydrophilic modified fibroin or a hydrophobic modified fibroin. The "hydrophilic modified fibroin" herein has an average hydropathy index (HI) of zero or less which is obtained in the following manner. That is, a sum of HI of all amino acid residues included in the modified fibroin is obtained, and then, the sum is divided by the total number of the amino acid residues, thereby obtaining an average HI. The hydropathy index is shown in Table 1. In addition, the "hydrophobic modified fibroin" has an average HI over zero. The hydrophilic modified fibroin particularly has excellent flame retardancy. The hydrophobic modified fibroin particularly has excellent moisture-absorbing and heat-releasing properties and heat retainability.

Examples of the hydrophilic modified fibroin include modified fibroins having the amino acid sequence of SEQ ID NO: 4, the amino acid sequence of SEQ ID NO: 6, SEQ ID NO: 7, SEQ ID NO: 8, or SEQ ID NO: 9, the amino acid sequence of SEQ ID NO: 13, SEQ ID NO: 11, SEQ ID NO: 14, or SEQ ID NO: 15, the amino acid sequence of SEQ ID NO: 18, SEQ ID NO: 7, SEQ ID NO: 8, or SEQ ID NO: 9, the amino acid sequence of SEQ ID NO: 17, SEQ ID NO: 11, SEQ ID NO: 14, or SEQ ID NO: 15, and the amino acid sequence of SEQ ID NO: 19, SEQ ID NO: 20, or SEQ ID NO: 21.

Examples of the hydrophobic modified fibroin include modified fibroins having the amino acid sequence of SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43 and the amino acid sequence of SEQ ID NO: 35, SEQ ID NO: 37, SEQ ID NO: 38, SEQ ID NO: 39, SEQ ID NO: 40, SEQ ID NO: 41, or SEQ ID NO: 44.

The modified fibroin according to this embodiment can be manufactured by a commonly-used technique using a nucleic acid encoding the modified fibroin. The nucleic acid encoding the modified fibroin may be chemically synthesized based on nucleotide sequence information or may be synthesized by, for example, PCR.

For example, a protein is dissolved in a protein-dissolving solvent to prepare a dope solution, and the dope solution is spun by a known fiber-spinning method such as wet spinning, dry spinning, dry-wet spinning, and melt spinning, thereby obtaining an artificial protein fiber. Examples of the protein-dissolving solvent include dimethyl sulfoxide (DMSO), N,N-dimethylformamide (DMF), formic acid, and hexafluoroisopropanol (HFIP). An inorganic salt may be added to the solvent as a dissolution promoter.

(Artificial Fur)

The artificial fur according to this embodiment may include fibers other than the artificial protein fiber as long as the effects of this invention are not impaired. Examples of other fibers include synthetic fibers such as nylon, polyamide, polyester, polyacrylonitrile, polyolefin, polyvinyl alcohol, polyethylene terephthalate, polytetrafluoroethylene, and acrylic resin, regenerated fibers such as cupra, rayon, and lyocell, and natural fibers such as cotton, cotton linen, silk, wool, and cashmere.

The artificial fur according to this embodiment may further include components other than fibers. Examples of other components include colorants, lubricants, antioxidants, ultraviolet absorbers, dyes, fillers, crosslinkers, delustrants, and leveling agents.

The artificial fur according to this embodiment may have a maximum moisture-absorbing and heat-releasing level over 0.025° C./g determined according to the following Formula A:

maximum moisture-absorbing and heat-releasing level={(maximum sample temperature obtained after sample is transferred to high-humidity environment after being placed in low-humidity environment until sample temperature reaches equilibrium)−(sample temperature when sample is transferred to high-humidity environment after being placed in low-humidity environment until sample temperature reaches equilibrium)} (° C.)/sample weight (g) Formula A:

In Formula A, note that the low-humidity environment implies an environment at a temperature of 20° C. and a relative humidity of 40%, while the high-humidity environment implies an environment at a temperature of 20° C. and a relative humidity of 90%.

The artificial fur according to this embodiment may have a maximum moisture-absorbing and heat-releasing level of 0.026° C./g or more, 0.027° C./g or more, 0.028° C./g or more, 0.029° C./g or more, 0.030° C./g or more, 0.031° C./g or more, 0.035° C./g or more, or 0.040° C./g or more. The upper limit of the maximum moisture-absorbing and heat-releasing level is not particularly limited but is usually 0.060° C./g or less.

The artificial fur according to this embodiment may have a limiting oxygen index (LOI) of 18.0 or more, 20.0 or more, 22.0 or more, 24.0 or more, 26.0 or more, 28.0 or more, 29.0 or more, and 30.0 or more. Herein, LOI is a value measured in accordance with the test method for granular materials or synthetic resin having a low melting point prescribed in Notice No. 50 issued on May 31, 1995 by Chief of Dangerous Goods Regulation Division, Fire and Disaster Management Agency.

The artificial fur according to this embodiment may have a heat retention index over 0.18 determined according to the following Formula B.

$$\text{heat retention index} = \text{heat retention rate (\%)}/\text{unit weight of sample (g/m}^2\text{)} \quad \text{Formula B:}$$

Herein, the heat retention rate is measured by dry contact method using Thermo Labo II (at a wind speed of 30 cm/sec) and measured by a method to be described in Examples.

The artificial fur according to this embodiment may have a heat retention index of, for example, 0.20 or more, 0.22 or more, 0.24 or more, 0.26 or more, 0.28 or more, 0.30 or more, or 0.32 or more. The upper limit of the heat retention index is not particularly limited and may be, for example, 0.60 or less or 0.40 or less.

(Method for Manufacturing Artificial Fur)

The artificial fur according to this embodiment can be obtained, for example, by a method involving: pile fabric manufacturing in which the aforementioned fiber (fiber including an artificial protein fiber) is used to obtain a pile fabric having large numbers of piles protruded on one surface or both surfaces of the fabric; shearing to cut (shear) a loop of each pile to form a cut pile; and, as needed, combing to comb the cut pile and/or washing to wash a woven fabric on which the cut pile is formed.

The pile fabric manufacturing can be performed, for example, according to pile weaving and pile knitting which are known as methods for manufacturing a pile woven fabric or a pile knitted fabric. In manufacturing a pile woven fabric, piles may be formed by warp yarn (warp pile weaving) or weft yarn (weft pile weaving). The size of each pile (loop) can be appropriately set according to the application of the artificial fur and may be, for example, 5 mm or more and 50 mm or less.

The shearing can be performed, for example, according to a commonly-used technique in manufacturing a cut pile.

Note that the fiber used for manufacturing the artificial leather according to this embodiment may include an artificial protein fiber, and the aspect of the fiber as a yarn is not particularly limited. In other words, the yarn may be, for example, a bundle of filaments, a twist yarn obtained by twisting such a bundle of filaments, or a spun yarn including staples. The spun yarn may be a twist yarn as long as it is spun. These examples of the yarn are manufactured according to a known method. For example, a spun yarn can be obtained by a method involving: fiber-spinning to spin a fiber raw material according to a commonly-used technique to obtain a fiber; crimping to crimp the obtained fiber as needed; cutting to cut the fiber to obtain a staple (short fiber); water treatment to treat the staple with water as needed; opening to open and/or defibrate the staple as needed; and spinning to spin the staple.

The fiber-spinning can be performed according to a commonly-used technique. A method for the fiber-spinning may be any of wet spinning, dry spinning, dry-wet spinning, and melt spinning.

The crimping may be performed as needed, for example, by mechanical crimping such as pressing or by bringing the staple into contact with an aqueous medium (hereinafter referred to as "water crimping").

The aqueous medium is a liquid or a gas (steam) medium containing water (including water vapor). The aqueous medium may be water or a liquid mixture of water and a hydrophilic solvent. Examples of the hydrophilic solvent include volatile solvents such as ethanol and methanol or vapor of those examples. The aqueous medium may be a liquid mixture of water and a volatile solvent such as ethanol and methanol and is preferably water or a liquid mixture of water and ethanol. Using the aqueous medium containing a volatile solvent or vapor thereof increases the drying speed after the water crimping, which may impart a soft feeling to the resulting crimped staple. A ratio between the water and the volatile solvent or vapor thereof is not particularly limited. For example, water:volatile solvent or vapor thereof may be 10:90 to 90:10 in mass ratio. A proportion of the water is preferably 30 mass % or more and may be 40 mass % or 50 mass % or more.

The aqueous medium is preferably a liquid or a gas at a temperature of 10 to 230° C. including water (or water vapor). The aqueous medium may have a temperature of 10° C. or higher, 25° C. or higher, 40° C. or higher, 60° C. or higher, or 100° C. or higher, and may be 230° C. or lower, 120° C. or lower, or 100° C. or lower.

The time in contact with the aqueous medium is not particularly limited and may be 30 seconds or more, one minute or more, or two minutes or more. From a viewpoint of productivity, the time is preferably 10 minutes or less. The contact with the aqueous medium may be performed under normal pressure or under reduced pressure (for example, in vacuum).

As a method for bringing the staple into contact with the aqueous medium, the staple may be immersed in the aqueous medium, or the aqueous medium may be sprayed onto the staple. Alternatively, the staple may be exposed to an environment filled with steam of the aqueous medium. In a case where the aqueous medium is steam, the aqueous medium is brought into contact with the staple by a typical steam setting device. Specific examples of the steam setting device include FMSA-type steam setter (available from Fukushin Kougyo. Co., Ltd) and EPS-400 (available from Tsujii Senki Kogyo). As a specific method for crimping the staple using the steam of the aqueous medium, for example, the staple is stored in a predetermined storage chamber, and the steam of the aqueous medium is introduced into the storage chamber and allowed to contact to the staple while the temperature inside the storage chamber is adjusted to a predetermined temperature (for example, 100° C. to 230° C.).

The staple in contact with the aqueous medium may be dried. A method of drying is not particularly limited and may be natural drying or drying by hot wind or with a hot roller. A temperature of drying is not particularly limited and may be, for example, 20 to 150° C., preferably 40 to 120° C., and more preferably 60 to 100° C.

The cutting can be performed with any device capable of cutting a fiber. An example of the device includes a desktop fiber cutting machine (s/NO. IT-160201-NP-300). The staple is not particularly limited in length and has a length of, for example, 20 mm or more. The staple may have a length of 20 to 140 mm, 70 to 140 mm, or 20 to 70 mm.

The water treatment may be performed as needed in a similar manner to the water crimping or the like.

The opening may be performed as needed and can be performed, for example, by opening or defibrating the staple with an opening machine (opener) or a defibrating machine (breaker).

The spinning can be performed by a known spinning method. Examples of a spinning method include cotton spinning, worsted spinning, and woolen spinning. These examples of the spinning method are not particularly limited in device and may employ a typically used device. The spun yarn may be a one-ply yarn or a blended yarn such as two-ply yarn (for example, a blended yarn of an artificial protein fiber and the aforementioned other fibers).

Second Embodiment

An artificial fur according to a second embodiment of the second aspect of the invention includes a shrink-proof protein fiber.

The protein fiber is a spun fiber using a protein as the main raw material. For example, the protein is dissolved in a dissolving solvent to prepare a dope solution, and the dope solution is spun by a known fiber-spinning method such as wet spinning, dry spinning, dry-wet spinning, and melt spinning, thereby obtaining the protein fiber. Examples of the protein-dissolving solvent include dimethyl sulfoxide (DMSO), N,N-dimethylformamide (DMF), formic acid, and hexafluoroisopropanol (HFIP). An inorganic salt may be added to the solvent as a dissolution promoter.

Figure 6:
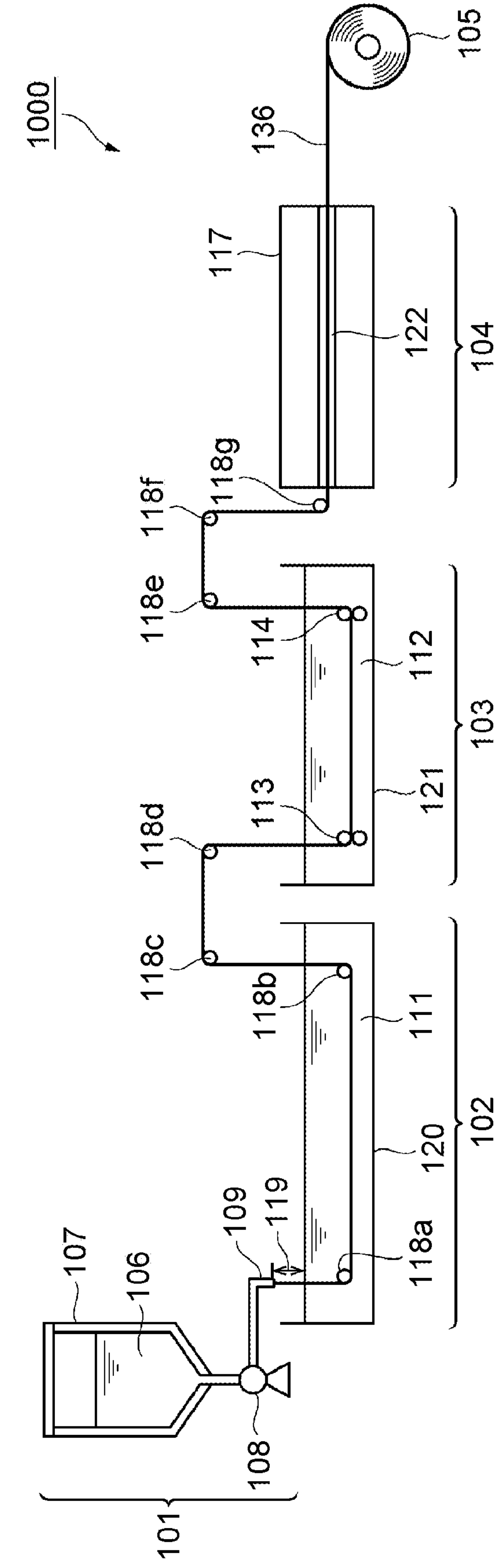
FIG. 6 is a schematic view for explaining an example of a spinning device for manufacturing a protein fiber (filament).

FIG. 6 is a schematic view for explaining an example of a spinning device for manufacturing a protein fiber. A spinning device 1000 illustrated in FIG. 6 is an example of a spinning device for dry-wet spinning, including an extruder 101, an undrawn yarn manufacturing device 102, a wet heat drawing device 103, and a drying device 104.

A fiber-spinning method using the spinning device 1000 will now be described. First, a dope solution 106 stored in a reservoir 107 is extruded from a spinneret 109 by a gear pump 108. In a laboratory, the dope solution may be charged in a cylinder, and then, extruded from a nozzle with a syringe pump. Next, the extruded dope solution 106 is fed into a coagulating liquid 111 in a coagulating liquid tank 120 through an air gap 119 so as to remove a solvent and to coagulate a protein, thereby forming a fibrous coagulate. The fibrous coagulate is then fed into warm water 112 in a drawing bath 121 and drawn. An elongation rate is determined by a speed ratio between a let-off nip roller 113 and a take-up nip roller 114. Thereafter, the drawn fibrous coagulate is fed into the drying device 104 and dried in a yarn passage 122 to yield a protein fiber 136, followed by winding the protein fiber 136 to obtain a wound yarn 105. The symbols 118*a* to 118*g* are yarn guides.

(Shrink-Proofing Treatment)

Examples of a method for preventing shrinkage of a protein fiber include a water shrinkage method in which a protein fiber after spinning but before contact with water is brought into contact with water so as to be irreversibly shrunk, and a dry heat shrinkage method in which a protein fiber after spinning but before contact with water is heated, and then, relaxed so as to be irreversibly shrunk. Both the water shrinkage method and the dry heat shrinkage method may be performed on a protein fiber before knitting an artificial fur or may be performed on a knitted artificial fur (before or after cutting the loop of each pile).

The irreversible shrinkage of the protein fiber is considered to occur, for example, for the following reasons. One possible cause is a secondary structure or a tertiary structure of the protein fiber, and another possible cause is relaxation of the residual stress in the protein fiber, for example, by drawing in the manufacturing process.

The water shrinkage method involves shrinking in which a protein fiber after spinning but before contact with water is brought into contact with water so as to be irreversibly shrunk. In the shrinking, the protein fiber shrinks on contact with water regardless of external force. The water to be brought into contact may be water in either a liquid state or a gas state. A method for bringing the protein fiber into contact with water is not particularly limited. For example, the protein fiber may be immersed in water, or water at normal temperature or water in a heated state such as steam may be sprayed onto the protein fiber. Alternatively, the protein fiber may be exposed to a high-humidity environment filled with water vapor. Among these examples, the method for immersing the protein fiber in water is preferable because it is possible to effectively shorten the shrinking time and to simplify the processing equipment. As a specific example of the method for immersing the protein fiber in water, the protein fiber (or artificial fur) is put into a container filled with water at a predetermined temperature and brought into contact with the water.

The temperature of the water to be brought into contact with the protein fiber is not particularly limited but is preferably, for example, lower than the boiling point. Such a temperature enhances handleability and workability in the shrinking. The upper limit of the water temperature is preferably 90° C. or lower, and more preferably 80° C. or lower. The lower limit of the water temperature is preferably 10° C. or higher, more preferably 40° C. or higher, and still more preferably 70° C. or higher. The temperature of the water to be brought into contact with the protein fiber can be adjusted according to the fiber included in the protein fiber. In addition, while the protein fiber is brought into contact with moisture, the water temperature may be constant or may be varied to reach a predetermined temperature.

The time for bringing the protein fiber into contact with water is not particularly limited and may be, for example, one minute or more. The time may be 10 minutes or more, 20 minutes or more, or 30 minutes or more. The upper limit of the time is not particularly limited, but may be, for example, 120 minutes or less, 90 minutes or less, or 60 minutes or less from viewpoints of shortening the time of the manufacturing process and eliminating the possibility of hydrolysis of the protein fiber.

Subsequent to the shrinking, the water shrinkage method may further involve drying to dry the protein fiber after contact with the water.

The drying is not particularly limited in method and may employ, for example, natural drying or forced drying using a drying facility. The drying temperature is not limited as long as it is lower than the temperature at which the protein is thermally damaged. Typically, the drying temperature is within a range of 20 to 150° C., preferably within a range of 40 to 120° C., and more preferably within a range of 60 to 100° C. Within these temperature ranges, it is possible to quickly and efficiently dry the protein fiber without causing a thermal damage or the like of the protein. The drying time is appropriately selected according to the drying temperature and the like.

For example, the drying time may be set to eliminate the influence on the quality, physical properties, and the like of a knitted or woven fabric due to excessive drying of the protein fiber.

The dry heat shrinkage method involves heating to heat the protein fiber after spinning but before contact with water; and relaxing and shrinking to relax and irreversibly shrink the heated protein fiber.

In the heating, the heating temperature is preferably equal to or higher than a softening temperature of the protein used in the protein fiber. Herein, the softening temperature of the protein is a temperature at which shrinkage is initiated due to stress relaxation of the protein fiber. In relaxing and shrinking by heating at a temperature equal to or higher than the softening temperature of the protein, the fiber shrinks to such an extent that it cannot be obtained only by simply removing moisture in the fiber. Accordingly, the obtained protein fiber is sufficiently prevented from being shrunk or changed in dimension due to contact with water. The heating temperature is preferably 80° C. or higher, more preferably 180° C. to 280° C., still more preferably 200° C. to 240° C., and still more preferably 220° C. to 240° C.

The heating time in the heating is preferably 60 seconds or less, more preferably 30 seconds or less, and still more preferably 5 seconds or less from a viewpoint of elongation of the fiber after the heat treatment. It is considered that the length of the heating time does not significantly affect the stress.

In the relaxing and shrinking, a relaxation rate preferably exceeds 1-fold, more preferably 1.4-fold or more, still more preferably 1.7-fold or more, and particularly preferably 2-fold or more. The relaxation rate is understood as, for example, a ratio of the let-off speed to the take-up speed of the protein fiber.

(Protein Fiber and Protein)

In the artificial fur according to the second embodiment, the protein fiber is prevented from being shrunk by the shrink-proofing treatment and is prevented from being changed in dimension due to contact with water. Therefore, the protein fiber (and protein) used for the artificial fur may be one that inherently changed in dimension (significantly) due to the contact with water.

For example, the protein fiber in wet condition may have a shrinkage rate of 2% or more. The shrinkage rate in wet condition may be 4% or more, 6% or more, 8% or more, 10% or more, 15% or more, 20% or more, 25% or more, or 30% or more. The upper limit of the shrinkage rate in wet condition is usually 80% or less. The shrinkage rate in wet condition is defined by the following Formula I:

shrinkage rate in wet condition={1−(length of protein fiber in wet condition after contact with water/length of protein fiber after spinning but before contact with water)}×100(%) (Formula I).

Furthermore, the protein fiber in dry condition may have, for example, a shrinkage rate over 7%. The shrinkage rate in dry condition may be 15% or more, 25% or more, 32% or more, 40% or more, 48% or more, 56% or more, 64% or more, or 72% or more. The upper limit of the shrinkage rate in dry condition is usually 80% or less. The shrinkage rate in dry condition is defined by the following Formula II:

shrinkage rate in dry condition={1−(length of protein fiber in dry condition/length of protein fiber after spinning but before contact with water)}×100(%) (Formula II).

The protein as a raw material of the protein fiber is not particularly limited and may be any protein. Examples of the protein include natural proteins and recombinant proteins (artificial proteins). The recombinant proteins may be any protein that can be manufactured at an industrial scale such as proteins used for industrial purposes, proteins used for medical purposes, and structural proteins. Specific examples of the proteins used for industrial purposes or medical purposes include enzymes, regulatory proteins, receptors, peptide hormones, cytokines, membrane or transport proteins, antigens used for vaccination, vaccines, antigen-binding proteins, immunostimulatory proteins, allergens, full length antibodies, antibody fragments, and antibody derivatives. Specific examples of the structural proteins include spider silk, silkworm silk, keratin, collagen, elastin, resilin, and proteins derived from these examples. The protein to be used herein is preferably a modified fibroin, and more preferably a modified spider silk fibroin, from viewpoints of excellent heat retainability, moisture-absorbing and heat-releasing properties, and/or flame retardancy. Employing a modified fibroin (preferably, modified spider silk fibroin) as the protein makes it possible to impart properties such as heat retainability, moisture-absorbing and heat-releasing properties and/or flame retardancy to the artificial fur according to this embodiment, thereby enhancing the value of the artificial fur.

The artificial fur according to this embodiment (second embodiment) may employ a modified fibroin similar to the modified fibroin used in the artificial fur according to the first embodiment.

(Artificial Fur)

The artificial fur according to this embodiment may include fibers other than the protein fiber as long as the effects of this invention are not impaired. Examples of the other fibers include those similar to the fiber included in the artificial fur according to the first embodiment.

The artificial fur according to this embodiment may further include components other than fibers. Examples of other components include those similar to other components included in the artificial fur according to the first embodiment.

The artificial fur according to this embodiment may also have a maximum moisture-absorbing and heat-releasing level, limiting oxygen index (LOI), and heat retention index similar to those of the artificial fur according to the first embodiment.

(Method for Manufacturing Artificial Fur)

The artificial fur according to this embodiment can be obtained by a method involving: pile fabric manufacturing in which the aforementioned fiber (fiber including a protein fiber) is used to obtain a pile fabric having a pile protruded on one surface or both surfaces of the fabric; shearing to cut (shear) a loop of the pile to form a cut pile; shrink-proofing to prevent shrinkage; and, as needed, combing to comb the cut pile and/or washing to wash a woven fabric on which the cut pile is formed. The aspect of the fiber used in the pile fabric manufacturing is not particularly limited as long as the fiber includes a protein fiber. In other words, the pile fabric manufacturing may employ, for example, a twist yarn obtained by twisting a bundle of filaments or a spun yarn including staples.

Specifically, for example, a manufacturing method according to one embodiment involves shrink-proofing to prevent shrinkage of a protein fiber. Here, the protein fiber may be subjected to shrink-proofing treatment before being bundled, before being twisted, or before being spun (in a filament state or staple state) or may be subjected to shrink-proofing treatment after being bundled, after being twisted, or after being spun. In addition, the method according to this embodiment involves: pile fabric manufacturing in which a shrink-proof protein fiber is used to obtain a pile fabric having a pile protruded on one surface or both surfaces of the fabric; and shearing to cut (shear) a loop of the pile to form a cut pile. The method may further involve combing and/or washing as needed.

For example, a manufacturing method according to another embodiment involves: pile fabric manufacturing in which a fiber including a protein fiber is used to obtain a pile fabric having a pile protruded on one surface or both surfaces of the fabric by pile weaving or pile knitting; shearing to cut a loop of the pile to form a cut pile; and shrink-proofing to prevent shrinkage of the pile fabric. The method may further involve combing and/or washing as needed. The shrink-proofing may be performed before the shearing or after the shearing.

The aspect described in the shrink-proofing treatment can be applied to the shrink-proofing.

The pile fabric manufacturing and the shearing may be similar to, for example, the pile fabric manufacturing and the shearing employed in manufacturing the artificial leather according to the first embodiment.

The spun yarn may be a twist yarn as long as it is spun. The spun yarn can be obtained by, for example, a method involving: fiber-spinning to spin a fiber raw material according to a commonly-used technique to obtain a fiber; crimping to crimp the obtained fiber as needed; cutting to cut the fiber to obtain a staple (short fiber); opening to open and/or defibrate the staple as needed; and spinning to spin the staple.

The fiber-spinning can be performed according to a commonly-used technique. A method for the fiber-spinning may be any of wet spinning, dry spinning, dry-wet spinning, and melt spinning.

The crimping may be performed as needed and can be performed by, for example, mechanical crimping such as pressing.

The cutting, opening, and spinning also employ, for example, steps similar to the cutting, opening, and spinning employed in manufacturing the artificial leather according to the first embodiment. The length of the staple obtained by the cutting is not particularly limited and is, for example, 20 mm or more, or may be 20 to 140 mm, 70 to 140 mm, or 20 to 70 mm.

Third Embodiment

An artificial fur according to a third embodiment of the third aspect of the invention includes a fiber, having functionalities.

Examples of the fiber included in the artificial leather according to this embodiment (third embodiment) include synthetic fibers such as nylon, polyamide, polyester, polyacrylonitrile, polyolefin, polyvinyl alcohol, polyethylene terephthalate, polytetrafluoroethylene, and acrylic resin, regenerated fibers such as cupra, rayon, and lyocell, natural fibers such as cotton, cotton linen, silk, wool, and cashmere, artificial fibers such as protein fibers, and composite fibers thereof.

The fiber preferably includes a modified fibroin, more preferably, a modified spider silk fibroin. Containing the modified fibroin (preferably, modified spider silk fibroin) makes it possible to impart the artificial fur with functionalities such as heat retainability, moisture-absorbing and heat-releasing properties, and/or flame retardancy. The modified fibroin may be included in the artificial fur as a modified fibroin fiber (protein fiber) or a conjugate fiber of the modified fibroin fiber and another fiber. The fiber that provides the artificial fur according to this embodiment (third embodiment) may employ a modified fibroin similar to one preferably used in the artificial fur according to the first and second embodiments.

The artificial fur according to this embodiment may be one imparted with functionalities by containing a functionality imparting substance (for example, a predetermined protein crosslinking body and a modified hydroxyl group-containing polymer in a second method and a third method which are to be described) in addition to a normal fiber or may be one imparted with functionality by containing a fiber imparted with functionalities (for example, a modified fibroin-containing fiber in a first method described later, and a fiber containing the predetermined protein crosslinking body and the modified hydroxyl group-containing polymer in the second method and the third method which are to be described).

Examples of a method for imparting functionalities to the artificial fur include letting the artificial fur contain a modified fibroin (first method), letting the artificial fur contain a predetermined protein crosslinking body (second method), or letting the artificial fur contain a modified hydroxyl group-containing polymer in which an operative functional group is bound to a hydroxyl group-containing polymer (third method).

(First Method)

The first method employs, for example, a modified fibroin-containing fiber (protein fiber or conjugate fiber) as a raw material to achieve the artificial fur imparted with functionalities. The modified fibroin-containing fiber can be obtained by spinning the raw material containing the modified fibroin according to a commonly-used technique. Letting the fiber contain the modified fibroin makes it possible to impart the fiber with functionalities such as heat retainability, moisture-absorbing and heat-releasing properties, and/or flame retardancy, thereby imparting the artificial fur according to this embodiment with the functionalities (heat retainability, moisture-absorbing and heat-releasing properties, and/or flame retardancy). The modified fibroin is preferably a modified spider silk fibroin due to its advantage in the above functionalities. The details of the modified fibroin are as described above.

(Second Method)

The predetermined protein crosslinking body in the second method includes a plurality of polypeptide skeletons, a plurality of first residues, and a plurality of second residues. The first residues are residues of a first reagent having at least two first reactive groups capable of forming a bond by a reaction with a protein. The second residues are residues of a second reagent having one second reactive group capable of forming a bond by a reaction with a first reactive group. At least one of the first residues crosslinks a polypeptide skeleton, and at least one of the first residues is bound to a polypeptide skeleton at one end and to a second residue at the other end.

The second method employs, for example, the fiber containing the predetermined protein crosslinking body as a raw material to achieve the artificial fur imparted with functionalities. The fiber containing the predetermined protein crosslinking body can be obtained, for example, by spinning the raw material containing the predetermined protein crosslinking body according to a commonly-used technique. The fiber containing the predetermined protein crosslinking body can also be obtained by spinning the raw material containing a protein according to a commonly-used technique to obtain a protein raw fiber or a composite raw fiber (precursor), and then, by reacting the raw fiber (precursor) with a first reagent and a second reagent to crosslink the protein in the raw fiber. Furthermore, in the second method, for example, using a mixture of a normal fiber and the predetermined protein crosslinking body as the raw material, it is possible to achieve the artificial fur imparted with functionalities.

More specifically, the second method involves: a first step in which a body precursor containing a protein is reacted with the first reagent having at least two first reactive groups capable of forming a bond by a reaction with the protein, thereby obtaining an intermediate; and a second step in which the intermediate is reacted with the second reagent having one second reactive group capable of forming a bond by a reaction with the first reactive group, thereby obtaining a body. Examples of the "body" in this method include a predetermined protein crosslinking body itself (a body precursor is a protein itself) and a protein fiber or a multicomponent fiber containing a protein (a body precursor is a protein filament or a composite filament containing a protein).

The first step is to react the body precursor containing a protein with the first reagent. The first reagent is a polyfunctional reagent having at least two first reactive groups capable of forming a bond by a reaction with the protein. In the first step, the protein may be crosslinked by the first reagent.

The protein has at least one reactive functional group selected from the group consisting of amide group, hydroxyl group, phenolic hydroxyl group, amino group, carboxyl group, thiol group, selenol group, imidazolyl group, indolyl group, and guanidino group. The first reactive groups of the first reagent may be groups that react with the reactive functional group to form a bond.

The first reactive groups are preferably electrophilic groups. In a case where the first reactive groups are electrophilic groups, a bond is easily formed by an addition reaction with the reactive functional group of the protein.

Preferred examples of the first reactive groups, or the electrophilic groups, include groups represented by the following Formulae (A-1), (A-2), (A-3), (A-4), (A-5), and (A-6). The wavy line in each Formula represents a bond of each group.

[Formula 1]

(A-1)

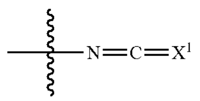

(A-2)

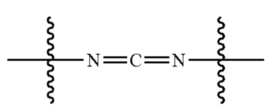

(A-3)

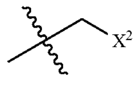

(A-4)

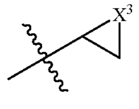

-continued (A-5)

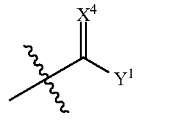

(A-6)

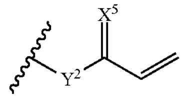

In Formula (A-1), $X^1$ is an oxygen atom (0) or a sulfur atom (S). $X^1$ is more preferably an oxygen atom.

In Formula (A-3), $X^2$ is a leaving group. The leaving group is not particularly limited as long as it enables a nucleophilic substitution reaction by the reactive functional group of the protein. Examples of the leaving group include a halogen atom (fluorine atom (F), chlorine atom (Cl), bromine atom (Br), and iodine atom (I)), a sulfonic ester group ($-OSO_2R^1$), a carboxylic acid ester group ($-OCOR^2$), and a quaternary ammonium group ($-NR^3_3$). $R^1$ may be, for example, a fluorine atom, an alkyl group, an aryl group, a halogenated alkyl group, or a halogenated aryl group. $R^2$ may be, for example, an alkyl group, an aryl group, a halogenated alkyl group, or a halogenated aryl group. $R^3$ may be, for example, an alkyl group, an aryl group, a halogenated alkyl group, or a halogenated aryl group. $R^1$, $R^2$, and $R^3$ may have a substituent. Examples of the substituent include alkyl group, alkenyl group, aryl group, and a halogen atom.

More preferable examples of $X^2$ include chlorine atom, bromine atom, iodine atom, ester group, and sulfonic ester group. Among these examples, bromine atom, iodine atom, and sulfonic ester group are still more preferable. More preferable examples of $R^1$ include fluorine atom, alkyl group (particularly, methyl group, ethyl group, benzyl group, and allyl group), perfluoroalkyl group (particularly, trifluoromethyl group and pentafluoroethyl group), and aryl group (particularly, phenyl group, tolyl group, naphthyl group, and fluorophenyl group). More preferable examples of $R^2$ include alkyl group (particularly, methyl group, ethyl group, benzyl group, and allyl group), perfluoroalkyl group (particularly, trifluoromethyl group and pentafluoroethyl group), and aryl group (particularly, phenyl group, tolyl group, naphthyl group, and fluorophenyl group). More preferable examples of $R^3$ include alkyl group (particularly, methyl group, ethyl group, benzyl group, and allyl group), and aryl group (particularly, phenyl group, tolyl group, naphthyl group, and fluorophenyl group).

In Formula (A-4), $X^3$ is an oxygen atom (O), a sulfur atom (S), a group represented by $-NR^4-$, or a group represented by $-C(R^5)_2-$. $R^4$ may be, for example, a hydrogen atom, an alkyl group, an aryl group, a halogenated alkyl group, a halogenated aryl group, an arylsulfonyl group, an alkylsulfonyl group, an acyl group, or a carbamate group. $R^5$ is an electron-withdrawing group. Examples of the electron-withdrawing group include carbonyl group, cyano group, aryl group, alkenyl group, and alkynyl group. The two $R^5$s may be the same or different. $R^4$ and $R^5$ may have a substituent. Examples of the substituent include alkyl group, alkenyl group, aryl group, and a halogen atom.

$X^3$ is more preferably an oxygen atom. More preferable examples of $R^4$ include arylsulfonyl group, alkylsulfonyl group, acyl group, and carbamate group.

In Formula (A-5), $X^4$ is an oxygen atom (O) or a sulfur atom (S), and Y' is a halogen atom, a hydroxyl group, a group represented by —$R^6$, a group represented by —$OR^6$, or a group represented by —$OCOR^6$. $R^6$ may be, for example, an alkyl group, an aryl group, a halogenated alkyl group, or a halogenated aryl group. $R^6$ may have a substituent. Examples of the substituent include alkyl group, alkenyl group, aryl group, and a halogen atom.

$X^4$ is more preferably an oxygen atom. Y' is more preferably a halogen atom, a group represented by —$OR^6$, a group represented by —$OCOR^6$ or the like. More preferable examples of $R^6$ include alkyl group and aryl group.

In Formula (A-6), $X^5$ is an oxygen atom (0) or a sulfur atom (S), and $Y^2$ is an oxygen atom (O), a sulfur atom (S), or a group represented by $NR^7$. $R^7$ may be, for example, an alkylsulfonyl group, an arylsulfonyl group, an acyl group, a carbamate group, an alkyl group, an aryl group, a halogenated alkyl group, or a halogenated aryl group. $R^7$ may have a substituent. Examples of the substituent include alkyl group, alkenyl group, aryl group, and a halogen atom.

$X^5$ is more preferably an oxygen atom. $Y^2$ is more preferably an oxygen atom. More preferable examples of $R^7$ include alkylsulfonyl group, arylsulfonyl group, acyl group, and carbamate group.

The first reagent may be a compound having two or more first reactive groups. The number of the first reactive groups of the first reagent is not particularly limited and may be, for example, 2 to 10000, preferably, 2 to 1000.

The first step may be performed by, for example, bringing a first reaction solution containing the first reagent into contact with the body precursor and by heating the body precursor.

The first reaction solution may be solvent-free or may further contain a solvent. The solvent of the first reaction solution is not particularly limited as long as it can dissolve the first reagent and does not inhibit the reaction between the reactive functional group of the protein and a first reactive group. In a case where the first reactive groups are electrophilic groups, preferable examples of the solvent of the first reaction solution include N,N-dimethylacetamide, N,N-dimethylformamide, N-methylpyrrolidone, benzene, toluene, xylene, mesitylene, tetrahydrofuran, dimethyl sulfoxide, ethyl acetate, butyl acetate, and propylene glycol monomethyl ether acetate.

Reaction conditions in the first step are not particularly limited as long as the reactive functional group of the protein reacts with a first reactive group.

In the first step, it is preferable that at least a part of the first reagent crosslinks the protein and at least a part of the first reactive groups remains in the intermediate. That is, in the first step, it is preferable to obtain the intermediate that includes the protein crosslinked by the first reagent and has the first reactive groups.

For example, in a case where the first reagent is a compound having two first reactive groups, a part of the first reagent may crosslink the protein (that is, both of the first reactive groups may react with the protein). In addition, in another part of the first reactive groups, only one of the first reactive groups may react with the protein, while the other first reactive group may remain unreacted in the intermediate.

Alternatively, for example, in a case where the first reagent is a compound having three or more first reactive groups, in a part of the first reagent, all of the first reactive groups may crosslink the protein (that is, all of the first reactive groups may react with the protein), and in another part of the first reagent, a part of the first reactive groups may react with the protein, and the other part or other parts of the first reactive groups may remain unreacted in the intermediate.

The reaction in the first step can also be referred to as a reaction to form side chains having first reactive groups or crosslinked structures by the first reagent, regarding the reactive functional group of the protein as a starting point. The number of crosslinked structures and side chains can be adjusted by an amount of the first reagent used in the reaction. Decreasing the amount of the first reagent used tends to form a small number of side chains and a large number of crosslinked structures, and increasing the amount of the first reagent used tends to form a small number of crosslinked structures and a large number of side chains.

The number of crosslinked structures and side chains can also be adjusted, for example, by a preliminary step toward the first step in which a part of the first reactive groups of the first reagent is reacted with the second reactive group of the second reagent. The number of first reactive groups remaining without reaction with the second reactive group in the preliminary step can be controlled by appropriately adjusting, for example, an amount of the second reagent relative to the first reagent used in the preliminary step. Accordingly, in the first step, the number of bonds between the first reactive groups and the protein can be easily adjusted, which easily enables controlling of the number of crosslinked structures and side chains of the protein.

In other words, before the first step, the second method may further involve: the preliminary step in which a part of the first reagent is reacted with a part of the second reagent so as to react a part of the first reactive groups of the first reagent with a part of the second reactive group of the second reagent.

Forming many crosslinked structures tends to enhance, for example, water resistance (for example, a property of controlling an amount of shrinkage due to contact with moisture and a property of controlling an amount of shrinkage during drying after contact with moisture), mechanical strength, and heat resistance of the body. Furthermore, forming many side chains tends to enhance functionalities (for example, texture to be described) imparted to the body. In the second method, proportions of crosslinked structures and side chains may be appropriately adjusted according to the desired properties.

In the first step, the intermediate containing a reactant of the protein and the first reagent is obtained. In the reactant, the protein is crosslinked by the first reagent, and an unreacted first reactive group may remain. In other words, the reactant may contain a protein-derived polypeptide skeleton, a crosslinking part that crosslinks the polypeptide skeleton, and a side chain that is bound to the polypeptide skeleton and has a first reactive group at the end.

The second step is to react the intermediate obtained in the first step with the second reagent. The second reagent has one second reactive group capable of forming a bond by reacting with a first reactive group. The second step can also be referred to as a step to react a first reactive group remaining in the intermediate with the second reagent.

The second reactive group of the second reagent is not particularly limited and may be appropriately changed according to the type of the first reactive groups. For example, when the first reactive groups are electrophilic groups, the second reactive group is preferably a nucleophilic group.

Examples of the second reactive group, or the nucleophilic group, include hydroxyl group, thiol group, amino group, and one represented by the following Formula (B-1).

[Formula 2]

(B-1)

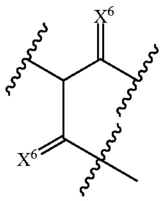

In Formula (B-1), $X^6$ is an oxygen atom (0) or a sulfur atom (S).

Examples of the group represented by Formula (B-1) include a group represented by the following Formula (B-1-1).

[Formula 3]

(B-1-1)

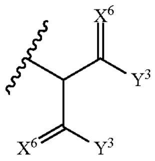

In Formula (B-1-1), $Y^3$ is a monovalent group. Examples of $Y^3$ include alkyl group, alkenyl group, alkynyl group, aryl group, alkoxy group, alkyl sulfide group, aryl sulfide group, monosubstituted amino group, and disubstituted amino group. Among these examples, alkyl group, aryl group, alkoxy group, and monosubstituted amino group are preferable. $Y^3$ may have a substituent. Examples of the substituent include alkyl group, alkenyl group, aryl group, and a halogen atom.

The second reagent may be a compound having one second reactive group and may further have an operative group inert to the reaction in the second step (reaction between a first reactive group and the second reactive group). With such a second reagent, the operative group can be easily introduced into the body, starting from an unreacted first reactive group in the intermediate.

The operative group is not particularly limited and may be a group that directly imparts functionality to the body or may be a group that imparts the body with reactivity to another reagent.

Examples of the operative group include hydrocarbon groups such as alkyl group, alkenyl group, and alkynyl group; groups having a ring structure such as aryl group and heterocyclic group; reactive groups protected by a protecting group (such as hydroxyl group, amino group, and thiol group); groups having a carbonyl group (—C(═O)—) or having a structure such as ether bond (—O—), amide bond (>NC(═O)—), urethane bond (>NC(═O)O—), urea bond (>N(C═O)N<), and carbonate bond (—OC(═O)O—). Examples of the operative group also include alkoxysilyl group, sulfonyl group (—S(═O)—), carboxyl group (—C(═O)OH), sulfonic acid group (—S(═O)$_2$OH), and quaternary ammonium group.

For example, when the operative group is an alkyl group, the texture of the body is improved. Therefore, for example, in a case where the body is fibrous, the second reagent having an alkyl group as the operative group makes it possible to obtain a material having excellent texture and good feeling.

With regard to a protein material in the related art, although crosslinking improves the water resistance and strength of the material, the texture is deteriorated, which may cause difficulty when the protein material directly touches human skin. However, according to the second method, it is possible to obtain excellent texture and feeling by the operative group while maintaining the water resistance and mechanical strength by crosslinking. Accordingly, it is possible to achieve a material that can be preferably used for items that directly touch human skin.

The second step may be performed by, for example, bringing a second reaction solution containing the second reagent into contact with the intermediate and by heating the intermediate.

The second reaction solution may be solvent-free and may further contain a solvent. The solvent of the second reaction solution is not particularly limited and may be, for example, any solvent that can dissolve the second reagent and does not inhibit a reaction between a first reactive group and the second reactive group. When the first reactive groups are electrophilic groups and the second reactive group is a nucleophilic group, preferred examples of the solvent of the second reaction solution include N,N-dimethylacetamide, N,N-dimethylformamide, N-methylpyrrolidone, benzene, toluene, xylene, mesitylene, tetrahydrofuran, dimethyl sulfoxide, ethyl acetate, butyl acetate, and propylene glycol monomethyl ether acetate.

In the second step, an amount of the second reagent used is not particularly limited. For example, the amount of the second reagent used may exceed the amount of the first reactive group in the intermediate.

In the second step, a part or all of the first reactive groups in the intermediate is consumed by reacting with the second reactive group. It is desirable that the first reactive groups do not remain in the body to the extent possible. Accordingly, in the second method, it is preferable that all of the first reactive groups are consumed by a reaction with the second reactive group or another side reaction.

In the second step, the body containing the protein crosslinking body is obtained.

In the second method, the first residue indicates a structure of the first reagent excluding the first reactive groups. In addition, the second residue indicates a structure of the second reagent excluding the second reactive group.

A polypeptide skeleton and a first residue are bound by a bond (by a urea bond when the reactive functional group is an amino group and the first reactive groups are isocyanate groups) formed by a reaction of the reactive functional group of the protein and a first reactive group. The first residue and the second residue are bound by a bond (a urethane bond in a case where, for example, the first reactive groups are isocyanate groups and the second reactive group is a hydroxyl group) formed by the reaction between a first reactive group and the second reactive group.

In the second method, the protein is crosslinked by the first reagent, thereby obtaining a body excellent in water resistance, mechanical strength, and heat resistance. In the second method, since the operative group can be imparted by the second reagent starting from a first reactive group remaining in the intermediate, it is possible to easily obtain a body with various functionalities.

(Third Method)

The modified hydroxyl group-containing polymer in the third method is a polymer in which an operative functional group is bound to a hydroxyl group-containing polymer. The modified hydroxyl group-containing polymer can be obtained, for example, by reacting a hydroxyl group-containing polymer with a reagent having an operative functional group.

The hydroxyl group-containing polymer can be used without particular limitation as long as it is a polymer compound having a hydroxyl group. Specific examples of the hydroxyl group-containing polymer include a polysaccharide such as starch, glycogen, cellulose, chitin, agarose, hyaluronic acid, chondroitin sulfate, pectin, and carrageenan; and a synthetic polymer such as polyvinyl alcohol (PVA) and phenol resin.

From a viewpoint of biodegradability, the hydroxyl group-containing polymer is preferably a polysaccharide. Furthermore, from a viewpoint of high solubility in addition to biodegradability, the hydroxyl group-containing polymer is preferably starch.

The operative functional group is a functional group having a property (such as hydrophobic property and hydrophilic property) corresponding to the functionality to be imparted (for example, water resistance, hydrophilicity, lipophilicity, and oil resistance) and is appropriately selected according to the functionality to be imparted.

For example, in order to improve water resistance, it is possible to use, as the operative functional group, an alkyl group such as methyl group, ethyl group, n-propyl group, and isopropyl group, an aromatic group such as phenyl group and naphthyl group, and a hydrophobic functional group or an acyl group such as acetyl group, propanoyl group, and benzoyl group.

The reagent having an operative functional group is a compound having a functional group and further having a bonding functional group bound to a hydroxyl group-containing polymer. The bonding functional group may be a functional group that can be bound to the hydroxyl group-containing polymer by a hydrogen bond or a covalent bond, but is preferably a functional group that can be covalently bound to the hydroxyl group-containing polymer, more preferably, a functional group that can be covalently bound to the hydroxyl group in the hydroxyl group-containing polymer.

Examples of the reagent having an operative functional group include isocyanates having an operative functional group (R—N═C═O, where R is an operative functional group), acid anhydrides (R—C(═O)—O—C(═O)—R, where R is a functional group), epoxides, aziridines, and alkyl halides. Preferable examples of the reagent having an operative functional group include an isocyanate having an operative functional group and acetic anhydride because those examples can be covalently bound to the hydroxyl group in the hydroxyl group-containing polymer. An isocyanate having an operative functional group is more preferable because any functional group can be introduced.

The third method employs, for example, a fiber containing a modified hydroxyl group-containing polymer as a raw material to achieve the artificial fur imparted with functionalities. The fiber containing the modified hydroxyl group-containing polymer can be obtained, for example, by spinning the raw material mixed with the modified hydroxyl group-containing polymer according to a commonly-used technique. Furthermore, in the third method, for example, using a mixture of a normal fiber and the modified hydroxyl group-containing polymer as the raw material, it is possible to achieve the artificial fur imparted with functionalities.

The modified hydroxyl group-containing polymer content in the raw material is not particularly limited and may be appropriately set according to functionalities or the like to be imparted. The modified hydroxyl group-containing polymer content may be, for example, 0.001 to 70 mass %, 0.01 to 65 mass %, or 0.1 to 60 mass % of the total amount of the artificial fur.

The modified hydroxyl group-containing polymer is preferably bound to the fiber by a hydrogen bond. This further improves the functionalities. The hydrogen bond can be formed, for example, between the functional group in the modified hydroxyl group-containing polymer (for example, the functional group may be a hydroxyl group, an operative functional group, or a bonding functional group) and the functional group in the fiber (for example, an amino group and a carboxyl group in a protein fiber).

In the third method, the artificial fur may further contain a hydroxyl group-containing polymer. The hydroxyl group-containing polymer is preferably the same kind of polymer as the hydroxyl group-containing polymer which is the raw material of the modified hydroxyl group-containing polymer. When the artificial fur includes the hydroxyl group-containing polymer, the hydroxyl group-containing polymer content may be 50 mass % or more, 60 mass % or more, 70 mass % or more, or 80 mass % or more with respect to 100 mass % of the total amount of the modified hydroxyl group-containing polymer and the hydroxyl group-containing polymer. The upper limit may be 90 mass % or less.

The artificial fur obtained by the second method or the third method may or may not contain a modified fibroin.

The artificial fur according to this embodiment may further include components other than fibers. Examples of other components include colorants, lubricants, antioxidants, ultraviolet absorbers, dyes, fillers, crosslinkers, delustrants, and leveling agents in addition to the predetermined protein crosslinking body and the modified hydroxyl group-containing polymer.

Even in the artificial fur according to this embodiment, when a modified fibroin-containing fiber is used, the artificial fur may have a maximum moisture-absorbing and heat-releasing level, limiting oxygen index (LOI), and heat retention index similar to those of the artificial fur according to the first embodiment.

(Method for Manufacturing Artificial Fur)

Using the aforementioned fiber (fiber containing an artificial protein fiber), the artificial fur according to this embodiment can be manufactured similarly to, for example, the method for manufacturing the artificial fur according to the first embodiment.

Fourth Example

An artificial fur according to a fourth embodiment of the fourth aspect of the invention includes a fiber and a water resistance imparting substance.

Examples of the fiber included in the artificial leather according to this embodiment (fourth embodiment) include synthetic fibers such as nylon, polyamide, polyester, polyacrylonitrile, polyolefin, polyvinyl alcohol, polyethylene terephthalate, polytetrafluoroethylene, and acrylic resin, regenerated fibers such as cupra, rayon, and lyocell, natural fibers such as cotton, cotton linen, silk, wool, and cashmere, artificial fibers such as protein fibers, and composite fibers thereof.

The fiber preferably includes a modified fibroin, more preferably, a modified spider silk fibroin. Containing the modified fibroin (preferably, modified spider silk fibroin) makes it possible to impart the artificial fur with functionalities such as heat retainability, moisture-absorbing and heat-releasing properties, and/or flame retardancy. The modified fibroin may be included in the artificial fur as a modified fibroin fiber (protein fiber) or a conjugate fiber of the modified fibroin fiber and another fiber. The fiber that provides the artificial fur according to this embodiment (fourth embodiment) may employ a modified fibroin similar to one preferably used in the artificial furs according to the first to third embodiments.

For example, the protein is dissolved in a dissolving solvent to prepare a dope solution, and the dope solution is spun by a known fiber-spinning method such as wet spinning, dry spinning, dry-wet spinning, and melt spinning, thereby obtaining the protein fiber. Examples of the protein-dissolving solvent include dimethyl sulfoxide (DMSO), N,N-dimethylformamide (DMF), formic acid, and hexafluoroisopropanol (HFIP). An inorganic salt may be added to the solvent as a dissolution promoter.

The protein fiber containing a modified fibroin may contain another protein other than the modified fibroin. Other protein is not particularly limited and may be any protein.

(Water Resistance Imparting Substance)

The water resistance imparting substance is a substance capable of improving the water resistance of the artificial fur. With the water resistance imparting substance, the artificial fur exhibits, for example, effects of improving water repellency and preventing shrinkage when the artificial fur is brought into contact with water. Accordingly, the artificial fur further enhances in waterproof property. The artificial fur may contain one kind of water resistance imparting substance or may contain two or more kinds thereof.

Specific examples of the water resistance imparting substance include a hydrophobic polymer such as fluorine-based polymer and silicone-based polymer and also includes a modified hydroxyl group-containing polymer in which a hydrophobic functional group is bound to a hydroxyl group-containing polymer. When the artificial fur includes a protein, specific examples of the water resistance imparting substance also include a protein binder such as a polyfunctional reagent having at least two first reactive groups capable of forming a bond by a reaction with a protein (first reagent), and a reagent having at least one first reactive group capable of forming a bond by a reaction with a protein and having an operative group.

The fluorine-based polymer is not particularly limited as long as it is a polymer containing fluorine. The fluorine-based polymer may be, for example, a polymer obtained by polymerizing an olefin containing fluorine. Examples of the fluorine-based polymer include polytetrafluoroethylene, polytrifluoroethylene, polychlorotrifluoroethylene, polyvinyl fluoride, polyvinylidene fluoride, polyperfluoroalkyl vinyl ether, polyperfluoropropylene, a polytetrafluoroethylene-perfluoropropylene copolymer, a tetrafluoroethylene-ethylene copolymer, and a polyvinyl fluoride-ethylene copolymer. The fluorine-based polymer may be a copolymer (a random copolymer, a block copolymer, or an alternating copolymer) obtained by polymerizing two or more monomers included in the aforementioned polymers.

The silicone-based polymer is not particularly limited as long as it is a polymer having a polysiloxane structure in the main chain. The silicone-based polymer may be, for example, a homopolymer or copolymer (a random copolymer, a block copolymer, or an alternating copolymer) obtained by polymerizing one kind or at least two kinds of monomers having a siloxane structural unit. The silicone-based polymer may be a copolymer (a random copolymer, a block copolymer, or an alternating copolymer) obtained by polymerizing one kind or at least two kinds of monomers having a siloxane structural unit and one kind or at least two kinds of monomers not having a siloxane structural unit.

The modified hydroxyl group-containing polymer is a polymer in which a hydrophobic functional group is bound to a hydroxyl group-containing polymer. The modified hydroxyl group-containing polymer can be obtained, for example, by reacting a hydroxyl group-containing polymer with a reagent having a hydrophobic functional group.

The hydroxyl group-containing polymer can be used without particular limitation as long as it is a polymer compound having a hydroxyl group. Specific examples of the hydroxyl group-containing polymer include a polysaccharide such as starch, glycogen, cellulose, chitin, agarose, hyaluronic acid, chondroitin sulfate, pectin, and carrageenan; and a synthetic polymer such as polyvinyl alcohol (PVA) and phenol resin. From a viewpoint of biodegradability, the hydroxyl group-containing polymer is preferably a polysaccharide. Furthermore, from a viewpoint of high solubility in addition to biodegradability, the hydroxyl group-containing polymer is preferably starch.

The reagent having a hydrophobic functional group is a compound having a hydrophobic functional group and further having a bonding functional group bound to a hydroxyl group-containing polymer. The bonding functional group may be a functional group that can be bound to the hydroxyl group-containing polymer by a hydrogen bond or a covalent bond, but is preferably a functional group that can be covalently bound to the hydroxyl group-containing polymer, more preferably, a functional group that can be covalently bound to the hydroxyl group in the hydroxyl group-containing polymer. Examples of the hydrophobic functional group include alkyl groups such as methyl group, ethyl group, n-propyl group, and isopropyl group; aromatic groups such as phenyl group and naphthyl group; and acyl groups such as acetyl group, propanoyl group, and benzoyl group. Examples of the reagent having a hydrophobic functional group include isocyanates having a hydrophobic functional group (R—N═C═O, where R is a hydrophobic functional group), acid anhydrides (R—C(═O)—O—C(═O)—R, where R is a hydrophobic functional group), epoxides, aziridines, and alkyl halides.

The hydrophobic polymer content in the artificial fur according to this embodiment may be 0.001 to 70 mass %, 0.01 to 65 mass %, 0.1 to 60 mass %, 1 to 50 mass %, 1 to 40 mass %, 1 to 30 mass %, 1 to 20 mass %, 1 to 10 mass %, or 1 to 5 mass % of the total amount of the artificial fur.

Examples of the protein binder include a polyfunctional reagent having at least two first reactive groups capable of forming a bond by a reaction with a protein (first reagent), and a reagent having at least one first reactive group capable of forming a bond by a reaction with a protein and having an operative group (functional reagent).

The first reagent has the first reactive groups capable of forming a bond by reacting with at least one reactive functional group selected from the group consisting of amide group, hydroxyl group, phenolic hydroxyl group, amino group, carboxyl group, thiol group, selenol group, imidazolyl group, indolyl group, and guanidino group included in the protein.

Examples of the first reactive groups include groups represented by the following Formulas (A-1), (A-2), (A-3), (A-4), (A-5), and (A-6). A wavy line in each Formula represents a bond of each group.

[Formula 1]

(A-1)

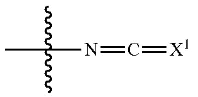

(A-2)

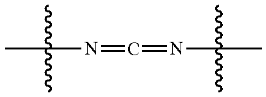

(A-3)

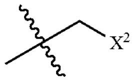

(A-4)

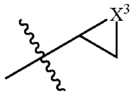

(A-5)

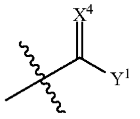

(A-6)

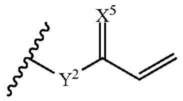

In Formula (A-1), $X^1$ is an oxygen atom (0) or a sulfur atom (S). In Formula (A-3), $X^2$ is a leaving group. In Formula (A-4), $X^3$ is an oxygen atom (O), a sulfur atom (S), a group represented by —$NR^4$—, or a group represented by —$C(R^5)_2$—. $R^4$ may be, for example, a hydrogen atom, an alkyl group, an aryl group, a halogenated alkyl group, a halogenated aryl group, an arylsulfonyl group, an alkylsulfonyl group, an acyl group, or a carbamate group. $R^5$ is an electron-withdrawing group. In Formula (A-5), $X^4$ is an oxygen atom (0) or a sulfur atom (S), and Y' is a halogen atom, a hydroxyl group, a group represented by —$R^6$, a group represented by —$OR^6$, or a group represented by —$OCOR^6$. $R^6$ may be, for example, an alkyl group, an aryl group, a halogenated alkyl group, or a halogenated aryl group. In Formula (A-6), $X^5$ is an oxygen atom (0) or a sulfur atom (S), and $Y^2$ is an oxygen atom (O), a sulfur atom (S), or a group represented by $NR^7$. $R^7$ may be, for example, an alkylsulfonyl group, an arylsulfonyl group, an acyl group, a carbamate group, an alkyl group, an aryl group, a halogenated alkyl group, or a halogenated aryl group.

The functional reagent can be obtained by reacting the first reagent with a reagent (second reagent) which has a (one) second reactive group capable of forming a bond by a reaction with a first reactive group and has an operative group.

Examples of the second reactive group include hydroxyl group, thiol group, amino group, and one represented by the following Formula (B-1).

[Formula 2]

(B-1)

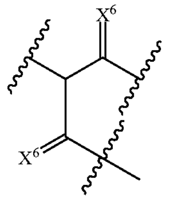

In Formula (B-1), $X^6$ is an oxygen atom (0) or a sulfur atom (S).

Examples of the operative group include hydrocarbon groups such as alkyl group, alkenyl group, and alkynyl group; groups having a ring structure such as aryl group and heterocyclic group; reactive groups protected by a protecting group (such as hydroxyl group, amino group, and thiol group); groups having a carbonyl group (—C(═O)—) or having a structure such as ether bond (—O—), amide bond (>NC(═O)—), urethane bond (>NC(═O)O—), urea bond (>N(C═O)N<), and carbonate bond (—OC(═O)O—). Examples of the operative group also include alkoxysilyl group, sulfonyl group (—S(═O)—), carboxyl group (—C(═O)OH), sulfonic acid group (—$S(=O)_2OH$), and quaternary ammonium group.

Specific examples of the first reagent include hexane diisocyanate (HDI). Specific examples of the second reagent include butanol (BuOH).

The water resistance imparting substance is preferably a fluorine-based polymer or a silicone-based polymer from viewpoints of improving the water repellency of the artificial fur and preventing shrinkage on contact with water.

Examples of the method for adding a water resistance imparting substance to an artificial fur include: the method according to the first embodiment in which an artificial fur is manufactured according to a commonly-used technique using a fiber containing a water resistance imparting substance (for example, a fiber mixed with a water resistance imparting substance or a fiber bound with a water resistance imparting substance); the method according to the second embodiment in which a water resistance imparting substance is mixed with an artificial fur manufactured from a fiber that does not contain a water resistance imparting substance; and the method according to the third embodiment in which a water resistance imparting substance is bound to an artificial fur manufactured from a fiber that does not contain a water resistance imparting substance. In the method according to the second embodiment, the artificial fur and the water resistance imparting substance do not necessarily need to be bound.

The method according to the third embodiment involves binding the water resistance imparting substance to the artificial fur. The binding can be performed by, for example, by techniques such as coating or dipping to bring the water resistance imparting substance into contact with the artificial fur, by heating or plasma irradiation as needed, thereby binding the artificial fur and the water resistance imparting substance. When the water resistance imparting substance is, for example, a hydrophobic polymer such as a silicon-based polymer and a fluorine-based polymer, the binding may be a step to covalently bind the artificial fur and the water resistance imparting substance by, for example, irradiating the artificial fur with plasma while the artificial fur is brought into contact with the water resistance imparting substance or a precursor (monomer) of the water resistance imparting substance. Even when the precursor (monomer) of the water resistance imparting substance is used, the precursor (monomer) of the water resistance imparting substance is polymerized by plasma irradiation to form the water resistance imparting substance (hydrophobic polymer such as silicon-based polymer and fluorine-based polymer). Accordingly, it is possible to obtain the artificial fur containing the water resistance imparting substance. The method according to the third embodiment may be performed not only on the artificial fur but also on the pile fabric before the shearing.

The plasma to be used for the irradiation may be appropriately set according to, for example, the types of the artificial fur (fiber to be used) and water resistance imparting substance (or precursor thereof). The discharge gas may flow at a rate of, for example, 0.1 L/min or more and 10 L/min or less. The plasma density of the plasma to be generated may be, for example, in a range of $1\times10^{13}$ $cm^{-3}$ or more and $1\times10^{15}$ $cm^{-3}$ or less. The discharge gas may be, for example, a rare gas such as helium, neon, and argon or may be oxygen or nitrogen. Air can also be used as the discharge gas.

The plasma irradiation can be performed with a known plasma irradiation device. An example of the plasma irradiation device includes plasma treatment equipment available from Europlasma.

(Artificial Fur)

The artificial fur according to this embodiment may further contain components other than the fiber and the water resistance imparting substance. Examples of other components include colorants, lubricants, antioxidants, ultraviolet absorbers, dyes, fillers, crosslinkers, delustrants, and leveling agents.

Even in the artificial fur according to this embodiment, when a modified fibroin-containing fiber is used, the artificial fur may have a maximum moisture-absorbing and heat-releasing level, limiting oxygen index (LOI), and heat retention index similar to those of the artificial fur according to the first embodiment.

(Method for Manufacturing Artificial Fur)

Using the aforementioned fiber (fiber containing an artificial protein fiber), the artificial fur according to this embodiment can be manufactured similarly to, for example, the method for manufacturing the artificial fur according to the first embodiment.

(Application of Artificial Fur)

The artificial fur according to this embodiment (first to fourth embodiments) can be used in any application that employs a known artificial fur (an artificial fur using a synthetic fiber) (for example, clothing, accessories such as bags, carpets, and stuffed animals).

EXAMPLES

Hereinafter, the present invention will be described in more detail based on Test Examples. However, this invention is not limited to the following Test Examples.

Test Example 1: Manufacture of Modified Fibroin

Designed were a modified spider silk fibroin having the amino acid sequence of SEQ ID NO: 18 (PRT399), a modified spider silk fibroin having the amino acid sequence of SEQ ID NO: 12 (PRT380), a modified spider silk fibroin having the amino acid sequence of SEQ ID NO: 13 (PRT410), a modified fibroin having the amino acid sequence of SEQ ID NO: 37 (PRT918), a modified fibroin having the amino acid sequence of SEQ ID NO: 40 (PRT966), and a modified fibroin having the amino acid sequence of SEQ ID NO: 15 (PRT799). Nucleic acids encoding the designed modified fibroins were synthesized. To the 5'-end of each nucleic acid, an NdeI site was added, and an EcoRI site was placed downstream of a stop codon. The nucleic acids were cloned into cloning vectors (pUC118). Thereafter, the nucleic acids were subjected to restriction enzyme fragmentation using NdeI and EcoRI, and then, recombined and changed into protein expression vectors pET-22b(+), thereby obtaining expression vectors.

The obtained expression vectors were used to transform *Escherichia coli* BLR (DE3). The transformed *Escherichia coli* was cultured for 15 hours in 2 mL of an LB culture medium containing ampicillin. The broth was added to a 100 mL seed culture medium containing ampicillin (Table 4) in such a manner that $OD_{600}$ reached 0.005. The broth was maintained at a temperature of 30° C. and subjected to flask culture (for about 15 hours) until $OD_{600}$ reached 5, thereby obtaining a seed broth.

TABLE 4

Seed Culture Medium

| Reagent | Concentration (g/L) |
|---|---|
| Glucose | 5.0 |
| $KH_2PO_4$ | 4.0 |
| $K_2HPO_4$ | 9.3 |
| Yeast Extract | 6.0 |
| Ampicillin | 0.1 |

A 500 mL growing medium (Table 5) was added to a jar fermenter, and the seed broth was added to the jar fermenter in such a manner that $OD_{600}$ reached 0.05. Being maintained at a temperature of 37° C., the broth was cultured and controlled to have pH 6.9 constantly. Furthermore, the broth was maintained to have a 20% dissolved oxygen concentration of the dissolved oxygen saturated concentration.

TABLE 5

Growing Medium

| Reagent | Concentration (g/L) |
|---|---|
| Glucose | 12.0 |
| $KH_2PO_4$ | 9.0 |
| $MgSO_4•7H_2O$ | 2.4 |
| Yeast Extract | 15 |
| $FeSO_4•7H_2O$ | 0.04 |
| $MnSO_4•5H_2O$ | 0.04 |
| $CaCl_2•2H_2O$ | 0.04 |
| Adeka Nol (Adeka, LG-295S) | 0.1 (mL/L) |

Immediately after glucose in the growing medium was completely consumed, a feed solution (455 g/1 L of glucose, 120 g/1 L of Yeast Extract) was added at a rate of 1 mL/min. Being maintained at a temperature of 37° C., the broth was cultured and controlled to have pH 6.9 constantly. Furthermore, the broth was cultured for 20 hours, being maintained to have a 20% dissolved oxygen concentration of the dissolved oxygen saturated concentration. Thereafter, 1 M of isopropyl-R-thiogalactopyranoside (IPTG) was added to the broth to obtain a final concentration of 1 mM, thereby inducing the expression of modified fibroins. Twenty hours after the addition of IPTG, the broth was centrifuged to recover bacterial cells. SDS-PAGE was conducted using bacterial cells prepared from the broth before the addition of IPTG and the broth after the addition of IPTG. Due to the appearance of a band having a size of a target modified fibroin depending on the addition of IPTG, the expression of the target modified fibroin was determined.

Bacterial cells recovered two hours after the addition of IPTG were washed with 20 mM Tris-HCl buffer solution (pH 7.4). The washed bacterial cells were suspended in 20 mM Tris-HCl buffer (pH 7.4) containing about 1 mM PMSF, and the cells were disrupted with a high pressure homogenizer (available from GEA Niro Soavi). The disrupted cells were centrifuged to obtain a precipitate. The obtained precipitate was washed with 20 mM Tris-HCl buffer (pH 7.4) until the precipitate reached a high level of purity. The washed precipitate was suspended in 8 M guanidine buffer (8 M guanidine hydrochloride, 10 mM sodium dihydrogen phosphate, 20 mM NaCl, 1 mM Tris-HCl, pH 7.0) at a concentration of 100 mg/mL, and then, dissolved by being stirred with a stirrer at 60° C. for 30 minutes. After the dissolution, the resultant was dialyzed with water using a dialysis tube (cellulose tube 36/32, available from Sanko Junyaku Co., Ltd.). White aggregated proteins obtained after the dialysis were collected by centrifugation, followed by removing moisture with a lyophilizer and collecting lyophilized powders, thereby obtaining modified fibroins (PRT399, PRT380, PRT410, PRT918, PRT966, and PRT799).

PRT 918 and PRT 966 are hydrophobic modified fibroins having an average HI over zero. PRT410, PRT399, and PRT799 are hydrophilic modified fibroins having an average HI of zero or less.

Test Example 2: Manufacture of Modified Fibroin Fiber and Evaluation of Shrinkability (1)

LiCl was dissolved in dimethyl sulfoxide (DMSO) at a concentration of 4.0 mass % to prepare a solvent. To the solvent, lyophilized powder of the modified fibroin (PRT399, PRT380, PRT410, or PRT799) was added at a concentration of 18 mass % or 24 mass %, followed by dissolving the mixture for three hours with a shaker. Thereafter, insoluble matters and foams were removed to obtain a modified fibroin solution.

The obtained modified fibroin solution was used as a dope solution (spinning dope) to manufacture a modified spider silk fibroin fiber spun and drawn by dry-wet spinning with a spinning device based on the spinning device 1000 illustrated in FIG. 6. The spinning device used in this Example is the same as the spinning device 1000 illustrated in FIG. 6 except that the spinning device includes a second undrawn yarn manufacturing device (second bath) between the undrawn yarn manufacturing device 102 (first bath) and the wet heat drawing device 103 (third bath). The dry-wet spinning was conducted under the following conditions.

Diameter of extruder nozzle: 0.2 mm

Coagulation bath temperature: 2 to 15° C.

Overall elongation rate: 1 to 4-fold

Drying temperature: 60° C.

(Evaluation of Shrinkability)

A shrinkage rate of each of the obtained modified fibroin fibers (Manufacture Examples 1 to 19) was evaluated. In other words, shrinking was conducted to bring each modified fibroin fiber (fiber after spinning but before contact with water) into contact with water to be in wet condition (contacting step) and dry the wetted fiber (drying step), thereby obtaining a shrinkage rate of each modified fibroin fiber in wet condition and a shrinkage rate of each modified fibroin fiber in dry condition after being wetted.

<Contacting Step>

From the wound body of each of the modified fibroin fibers, a plurality of modified fibroin fibers (30 cm-length) for testing was cut out. The plurality of modified fibroin fibers was bundled to obtain modified fibroin fiber bundles having a fineness of 150 denier. A lead weight (0.8 gram) was attached to each modified fibroin fiber bundle, and each modified fibroin fiber bundle was immersed in water for 10 minutes at a temperature shown in Tables 6 to 9. Thereafter, a length of each modified fibroin fiber bundle was measured in water. The measurement was performed while the lead weight (0.8 gram) was attached to each modified fibroin fiber bundle so that the modified fibroin fiber bundles would not shrink. Next, shrinkage rates of the modified fibroin fibers in wet condition were calculated according to the following Formula V. In the Formula V, L0 is a length (30 cm) of each modified fibroin fiber bundle before being immersed in water, and Lw is a length of each modified fibroin fiber bundle in wet condition after being immersed in water.

$$\text{Shrinkage rate in wet condition (\%)}=\{1-(Lw/L0)\}\times 100 \qquad \text{(Formula V)}$$

<Drying Step>

After the contacting step, the modified fibroin fiber bundles were removed from the water. The modified fibroin fiber bundles taken out from the water were left to dry at room temperature for two hours with the 0.8-gram lead weight still attached thereto. After drying, a length of each modified fibroin fiber bundle was measured. Next, according to the following Formula VI, shrinkage rates of the modified fibroin fibers dried after being in wet condition (shrinkage rate in dry condition) were calculated. In Formula VI, L0 is a length (30 cm) of each modified fibroin fiber bundle before being immersed in water, and Lwd is a length of each modified fibroin fiber bundle in dry condition after being immersed in water.

$$\text{Shrinkage rate in dry condition (\%)}=\{1-(Lwd/L0)\}\times 100(\%) \qquad \text{(Formula VI)}$$

Results are shown in Tables 6 to 9. In Tables 6 to 9, values in "overall elongation rate" are values during the fiber-spinning.

TABLE 6

| | Modified Spider Silk Fibroin | Overall Elongation Rate (fold) | Water Temperature (° C.) | Shrinkage Rate in Wet Condition (%) | Shrinkage Rate in Dry Condition (%) |
|---|---|---|---|---|---|
| Manufacture Example 1 | 24 wt % PRT799 | 1 | 20 | 0.0 | 7.8 |
| Manufacture Example 2 | 24 wt % PRT799 | 2 | | −1.2 | 10.3 |
| Manufacture Example 3 | 24 wt % PRT799 | 3 | | 7.2 | 21.2 |
| Manufacture Example 4 | 24 wt % PRT799 | 4 | | 13.5 | 26.3 |
| Manufacture Example 6 | 18 wt % PRT799 | 2 | | −2.3 | 9.5 |
| Manufacture Example 7 | 18 wt % PRT799 | 3 | | 6.0 | 19.7 |
| Manufacture Example 8 | 18 wt % PRT799 | 4 | | 14.3 | 27.5 |
| Manufacture Example 2 | 24 wt % PRT799 | 2 | 40 | −5.3 | 7.2 |
| Manufacture Example 3 | 24 wt % PRT799 | 3 | | 8.7 | 21.3 |
| Manufacture Example 4 | 24 wt % PRT799 | 4 | | 14.5 | 26.0 |

TABLE 6-continued

| | Modified Spider Silk Fibroin | Overall Elongation Rate (fold) | Water Temperature (° C.) | Shrinkage Rate in Wet Condition (%) | Shrinkage Rate in Dry Condition (%) |
|---|---|---|---|---|---|
| Manufacture Example 6 | 18 wt % PRT799 | 2 | | −4.3 | 7.3 |
| Manufacture Example 7 | 18 wt % PRT799 | 3 | | 6.2 | 18.3 |
| Manufacture Example 8 | 18 wt % PRT799 | 4 | | 16.0 | 28.7 |
| Manufacture Example 3 | 24 wt % PRT799 | 3 | 60 | 6.8 | 21.0 |
| Manufacture Example 4 | 24 wt % PRT799 | 4 | | 15.0 | 27.5 |
| Manufacture Example 6 | 18 wt % PRT799 | 2 | | −1.5 | 10.7 |
| Manufacture Example 7 | 18 wt % PRT799 | 3 | | 3.3 | 18.2 |
| Manufacture Example 8 | 18 wt % PRT799 | 4 | | 16.2 | 29.0 |

TABLE 7

| | Modified Fibroin | Overall Elongation Rate (fold) | Water Temperature (° C.) | Shrinkage Rate in Wet Condition (%) | Shrinkage Rate in Dry Condition (%) |
|---|---|---|---|---|---|
| Manufacture Example 10 | 24 wt % PRT410 | 2 | 20 | −2.3 | 8.7 |
| Manufacture Example 11 | 24 wt % PRT410 | 3 | | 4.7 | 16.7 |
| Manufacture Example 12 | 24 wt % PRT410 | 4 | | 10.3 | 22.3 |
| Manufacture Example 11 | 24 wt % PRT410 | 3 | 40 | 4.7 | 17.5 |
| Manufacture Example 12 | 24 wt % PRT410 | 4 | | 11.5 | 24.0 |
| Manufacture Example 11 | 24 wt % PRT410 | 3 | 60 | 2.0 | 16.5 |
| Manufacture Example 12 | 24 wt % PRT410 | 4 | | 10.8 | 25.0 |

TABLE 8

| | Modified Fibroin | Overall Elongation Rate (fold) | Water Temperature (° C.) | Shrinkage Rate in Wet Condition (%) | Shrinkage Rate in Dry Condition (%) |
|---|---|---|---|---|---|
| Manufacture Example 13 | 24 wt % PRT399 | 1 | 20 | −3.5 | 7.6 |
| Manufacture Example 14 | 24 wt % PRT399 | 2 | | 3.7 | 12.5 |
| Manufacture Example 15 | 24 wt % PRT399 | 3 | | 7.0 | 16.8 |
| Manufacture Example 14 | 24 wt % PRT399 | 2 | 40 | 3.0 | 12.7 |
| Manufacture Example 15 | 24 wt % PRT399 | 3 | | 7.3 | 16.7 |
| Manufacture Example 14 | 24 wt % PRT399 | 2 | 60 | 3.3 | 9.3 |
| Manufacture Example 15 | 24 wt % PRT399 | 3 | | 6.8 | 14.2 |

TABLE 9

| | Modified Fibroin | Overall Elongation Rate (fold) | Water Temperature (° C.) | Shrinkage Rate in Wet Condition (%) | Shrinkage Rate in Dry Condition (%) |
|---|---|---|---|---|---|
| Manufacture Example 16 | 24 wt % PRT380 | 1 | 20 | −1.1 | 9.4 |
| Manufacture Example 17 | 24 wt % PRT380 | 2 | | 2.7 | 13.3 |
| Manufacture Example 18 | 24 wt % PRT380 | 3 | | 7.0 | 17.7 |
| Manufacture Example 19 | 24 wt % PRT380 | 4 | | 10.0 | 20.2 |
| Manufacture Example 17 | 24 wt % PRT380 | 2 | 40 | 3.3 | 14.2 |
| Manufacture Example 18 | 24 wt % PRT380 | 3 | | 7.7 | 19.0 |
| Manufacture Example 19 | 24 wt % PRT380 | 4 | | 12.0 | 22.0 |
| Manufacture Example 17 | 24 wt % PRT380 | 2 | 60 | 2.7 | 14.3 |
| Manufacture Example 18 | 24 wt % PRT380 | 3 | | 8.2 | 20.3 |
| Manufacture Example 19 | 24 wt % PRT380 | 4 | | 12.0 | 23.2 |

Both in wet condition and in dry condition, the modified fibroin fibers had high shrinkage rates. On the other hand, the modified fibroin fibers subjected to the evaluation of shrinkability (subjected to the shrinking) sufficiently reduced in shrinkage rate when the modified fibroin fibers were brought into contact with water again. The possible reason of this fact is that the shrinking relaxed the residual stress caused by drawing or the like during the spinning.

Test Example 3: Manufacture of Modified Fibroin Fiber and Evaluation of Shrinkability (2)

The modified fibroin (PRT799) was added to formic acid at a concentration of 24 mass %. The mixture was then dissolved by being stirred at room temperature for one hour. Thereafter, insoluble matters and foams were removed to obtain a modified fibroin solution.

The obtained modified fibroin solution was used as a dope solution (spinning dope) to yield a modified fibroin fiber by dry-wet spinning with a spinning device based on the spinning device 1000 illustrated in FIG. 6. The dry-wet spinning was conducted under the following conditions.

Temperature of coagulating liquid (methanol): 5 to 10° C.

Overall elongation rate: 6-fold

Drying temperature: 80° C.

The obtained modified fibroin fiber was used to perform heat relaxation shrinkage treatment. The modified fibroin fiber was brought into contact with a dry heat plate heated to a predetermined temperature and allowed to pass over the dry heat plate. The let-off speed was increased relative to the take-up speed to relax the modified fibroin fiber. The slack was shrunk by heat to perform dry relaxation treatment. A value obtained by dividing the let-off speed by the take-up speed was regarded as "relaxation rate". In this test, the relaxation rate was adjusted so that the slack of the modified fibroin fiber caused by excessive letting-off was the maximum shrinkage rate that can be offset by relaxation. The relaxation rate was adjusted by adjusting at least one of a let-off roller and a take-up roller.

The water shrinkage evaluation was performed by the following procedure. The fiber after the heat relaxation shrinkage treatment was cut into a 300-mm piece (test piece) and immersed in water at 40° C. for 10 minutes without a load. Immediately after that, a length of the test piece (length in wet condition) was measured, and the test piece was dried at room temperature for two hours. Thereafter, a length of the test piece (fiber length after drying) was measured to measure a water shrinkage rate. The water shrinkage rate is a numerical value calculated by the following Formula (1):

$$\text{water shrinkage rate}=(1-\text{fiber length after drying}/\text{fiber length before immersion})\times 100 \quad (1)$$

Test Example 3-1

The relation between the heating temperature and the relaxation rate was examined. In Test Example 3-1, Test Example 3-1-1 to Test Example 3-1-7 were performed under different conditions except that lengths before water immersion were all set to 300 mm. Specifically, tests were performed with different heating temperatures, different relaxation rates, and different staying times. Table 10 shows temperature and relaxation conditions, and results of the shrinkage rate measurement. As shown in Table 10, the higher the heating temperature and the higher the relaxation rate, the lower the water shrinkage rate. As shown in the results of Test Example 3-1-3 to Test Example 3-1-5, heating at a temperature of 220° C. or higher enables a water shrinkage rate of 4% or less. Note that, in Example 5 which employed a heating temperature of 280° C., the fiber was stained. As a result of the tests, the optimum heating temperature was considered to be 240° C.

TABLE 10

| | Temperature and Relaxation Conditions | | | | | Results of Shrinkage Rate Measurement (Length Before Immersion: 300 mm) | | |
|---|---|---|---|---|---|---|---|---|
| | Heating Temperature | Relaxation Rate | Let-off Speed (m/min) | Take-up Speed (m/min) | Staying Time (sec) | Length in Wet Condition (mm) | Length After Drying (mm) | Water Shrinkage Rate |
| Test Example 3-1-1 | 180° C. | 1.05 | 1.05 | 1 | 60 | 210 | 190 | 37% |
| Test Example 3-1-2 | 200° C. | 1.38 | 0.69 | 0.5 | 60 | 269 | 257 | 14% |
| Test Example 3-1-3 | 220° C. | 1.64 | 0.82 | 0.5 | 60 | 299 | 288 | 4% |
| Test Example 3-1-4 | 240° C. | 2.00 | 2 | 1 | 60 | 330 | 294 | 2% |
| Test Example 3-1-5 | 280° C. | 2.00 | 2 | 1 | 5 | 335 | 297 | 1% |
| Test Example 3-1-6 | Room Temperature | 1.00 | 1 | 1 | 60 | 192 | 167 | 44% |
| Test Example 3-1-7 | 40° C. | 1.00 | 1 | 1 | 60 | 189 | 159 | 47% |

Test Example 3-2

Next, the relation between the relaxation rate and the water shrinkage rate was examined. In Test Example 3-2, Test Example 3-2-1 to Test Example 3-2-6 were performed under different conditions except that lengths before water immersion were all set to 300 mm, heating temperatures were set to 240° C., and staying times were set to one minute (60 sec). Specifically, tests were performed with different relaxation rates (let-off speeds). Table 11 shows relaxation conditions and results of the shrinkage rate measurement. As shown in Table 11, the water shrinkage rate decreased along with an increase in relaxation rate. As shown in the results of Test Example 3-2-3 to Test Example 3-2-5, a relaxation rate from 1.4-fold to 2.0-fold enables a water shrinkage rate of 16% or less.

TABLE 11

| | Relaxation Conditions | | | Results of Shrinkage Rate Measurement (Length Before Immersion: 300 mm) | | |
|---|---|---|---|---|---|---|
| | Relaxation Rate | Let-off Speed (m/min) | Take-up Speed (m/min) | Length in Wet Condition (mm) | Length After Drying (mm) | Water Shrinkage Rate |
| Test Example 3-2-1 | 1.1 | 1.1 | 1.0 | 245 | 213 | 29% |
| Test Example 3-2-2 | 1.3 | 1.3 | 1.0 | 265 | 232 | 23% |
| Test Example 3-2-3 | 1.4 | 1.4 | 1.0 | 283 | 251 | 16% |
| Test Example 3-2-4 | 1.7 | 1.7 | 1.0 | 320 | 279 | 7% |
| Test Example 3-2-5 | 2.0 | 2.0 | 1.0 | 330 | 294 | 2% |
| Test Example 3-2-6 | 1.0 | 1.0 | 1.0 | 210 | 184 | 39% |

Test Example 3-3

The relation between the water shrinkage rate and various heating temperatures, heating times, and relaxation rates was examined. In Test Example 3-3, Test Example 3-3-1 to Test Example 3-3-10 were performed under different conditions except that lengths before water immersion were all set to 300 mm. Specifically, the tests were performed with different heating temperatures, heating times (staying times), and relaxation rates (let-off speed/take-up speed). Table 12 shows temperature and relaxation conditions, and results of the shrinkage rate measurement. In Test Example 3-3-10, the test piece was immersed in water and dried but not relaxed and heated. As shown in the results of Test Example 3-3-4 to Test Example 3-3-9, heating at a temperature of 200° C. or higher enables a water shrinkage rate less than 15%. Setting a heating temperature to 220° C. or higher reduces a water shrinkage rate to a low level such as 4% or less. With regard to the staying time, five seconds were enough for shrinkage. Extension of the staying time had little effect on the shrinkage rate.

TABLE 12

| | Temperature and Relaxation Conditions | | | | Results of Shrinkage Rate Measurement (Length Before Immersion: 300 mm) | | |
|---|---|---|---|---|---|---|---|
| | Heating Temperature (° C.) Staying Time (sec) | Relaxation Rate | Let-off Speed (m/min) | Take-up Speed (m/min) | Length in Wet Condition (mm) | Length After Drying (mm) | Water Shrinkage Rate (%) |
| Test Example 3-3-1 | 180° C./180 s | 1.42 | 0.47 | 0.33 | 265 | 257 | 14.3 |
| Test Example 3-3-2 | 180° C./60 s | 1.38 | 0.69 | 0.5 | 270 | 261 | 13.0 |
| Test Example 3-3-3 | 180° C./5 s | 1.41 | 8.45 | 6 | 265 | 253 | 15.7 |
| Test Example 3-3-4 | 200° C./60 s | 1.38 | 0.69 | 0.5 | 269 | 257 | 14.3 |
| Test Example 3-3-5 | 200° C./5 s | 1.38 | 8.25 | 6 | 270 | 258 | 14.0 |
| Test Example 3-3-6 | 220° C./60 s | 1.64 | 0.82 | 0.5 | 299 | 288 | 4.0 |
| Test Example 3-3-7 | 220° C./5 s | 1.64 | 9.85 | 6 | 300 | 288 | 4.0 |

TABLE 12-continued

| | Temperature and Relaxation Conditions | | | | Results of Shrinkage Rate Measurement (Length Before Immersion: 300 mm) | | |
|---|---|---|---|---|---|---|---|
| | Heating Temperature (° C.) Staying Time (sec) | Relaxation Rate | Let-off Speed (m/min) | Take-up Speed (m/min) | Length in Wet Condition (mm) | Length After Drying (mm) | Water Shrinkage Rate (%) |
| Test Example 3-3-8 | 240° C./60 s | 1.76 | 0.86 | 0.5 | 304 | 292 | 2.7 |
| Test Example 3-3-9 | 240° C./5 s | 1.72 | 10.35 | 6 | 305 | 292 | 2.7 |
| Test Example 3-3-10 | — | — | — | — | 175 | 167 | 44.3 |

Test Example 4: Shrink-proofing Treatment and Evaluation of Knitted or Woven Fabric Using Modified Fibroin Fiber

Manufacture, Shrink-proofing Treatment, and Evaluation of Knitted Fabric

Test Example 4-1

A knitted fabric was formed by circular knitting with a seamless knitting machine using a modified fibroin fiber obtained in a similar manner to Test Example 2 except that the overall elongation rate during the fiber-spinning was set to 4.55-fold. Here, the yarn count of the modified fibroin fiber was 58.1 Nm, and the gauge of the seamless knitting machine was 18.

The obtained knitted fabric was marked with a square having a side length of 1 cm in both wale and course directions. Thereafter, the knitted fabric was immersed in water at 20° C. for 10 minutes. After immersion in water, the knitted fabric was subjected to shrink-proofing treatment by drying.

<Measurement of Rate of Dimensional Change>

A rate of dimensional change (%) in both wale and course directions of the knitted fabric subjected to the shrink-proofing treatment was calculated according to the following Formula. In the Formula, L0f is the length of one side of the square marked on the knitted fabric before contact with water, and Lwf is the length of one side of the square marked on the knitted fabric after the shrink-proofing treatment. Results are shown in Table 13.

$$\text{rate of dimensional change}=\{(Lwf/L0f)-1\}\times 100(\%) \quad \text{Formula:}$$

<Measurement of Rate of Increase in Number of Loops>

With regard to the obtained knitted fabric and the knitted fabric subjected to the shrink-proofing treatment, the number of loops per 1 cm in both wale and course directions was counted, thereby calculating the rate of increase in number of loops according to the following Formula. In the Formula, NO is the number of loops of the knitted fabric before contact with water, and Nw is the number of loops of the knitted fabric after the shrink-proofing treatment. Results are shown in Table 13.

$$\text{rate of increase in number of loops}=\{(Nw/N0)-1\}\times 100(\%) \quad \text{Formula:}$$

<Measurement of Rate of Increase in Knitting Density>

With regard to the obtained knitted fabric and the knitted fabric subjected to the shrink-proofing treatment, the number of loops per 1 $cm^2$ was counted, thereby calculating the rate of increase in knitting density according to the following Formula. In the Formula, M0 is the knitting density of the knitted fabric before contact with water, and Mw is the knitting density of the knitted fabric after the shrink-proofing treatment. Results are shown in Table 13.

$$\text{rate of increase in knitting density}=\{(Mw/M0)-1\}\times 100(\%) \quad \text{Formula:}$$

<Measurement of Rate of Increase in Bursting Strength>

With regard to the obtained knitted fabric and the knitted fabric subjected to the shrink-proofing treatment, the bursting strength was measured according to the method in prescribed in JIS L 1096B, thereby calculating the rate of increase in bursting strength according to the following Formula. In Formula, R0 is the bursting strength of the knitted fabric before contact with water, and Rw is the bursting strength of the knitted fabric after the shrink-proofing treatment. Results are shown in Table 13.

$$\text{rate of increase in bursting strength}=\{(Rw/R0)-1\}\times 100(\%) \quad \text{Formula:}$$

Test Example 4-2

A knitted fabric was formed by weft knitting with a seamless knitting machine using a natural silk fibroin fiber (natural silk yarn) instead of a modified fibroin fiber. The natural silk fibroin fiber herein was obtained by bundling two yarns (29 Nm yarn count). The gauge of the seamless knitting machine was 18. The obtained knitted fabric subjected to shrink-proofing treatment in a similar manner to Test Example 4-1. With regard to the obtained knitted fabric and the knitted fabric subjected to the shrink-proofing treatment, the rate of dimensional change, the rate of increase in number of loops, and the rate of increase in knitting density were calculated. Results are shown in Table 13.

Test Example 4-3

A knitted fabric was obtained in a similar manner to Test Example 4-1 except that a polyethylene terephthalate (PET) fiber was used instead of a modified fibroin fiber. The obtained knitted fabric was subjected to shrink-proofing treatment under conditions similar to those in Test Example 4-1. With regard to the obtained knitted fabric and the knitted fabric subjected to the shrink-proofing treatment, the rate of dimensional change, the rate of increase in number of loops, the rate of increase in knitting density, and the bursting strength were calculated. Results are shown in Table 13.

Test Example 4-4

A knitted fabric was obtained in a similar manner to Test Example 4-1 except that a polyethylene terephthalate (PET) fiber was used instead of a modified fibroin fiber and that flat knitting was employed instead of circular knitting. The obtained knitted fabric was subjected to shrink-proofing treatment under conditions similar to those in Test Example 4-1. With regard to the obtained knitted fabric and the knitted fabric subjected to the shrink-proofing treatment, the rate of dimensional change, the rate of increase in number of loops, the rate of increase in knitting density, and the bursting strength were calculated. Results are shown in Table 13.

TABLE 13

| | | | Test Example 4-1 | Test Example 4-2 | Test Example 4-3 | Test Example 4-4 |
|---|---|---|---|---|---|---|
| Fiber Contained in Knitted Fabric | | | Modified Fibroin Fiber | Silk Fibroin Fiber | PET | PET |
| Knitting Method | | | Circular | Weft | Circular | Flat |
| Rate of Dimensional Change [%] | After Shrink-proofing Treatment | Wale Direction | −45 | −13.9 | −1.3 | −4.1 |
| | | Course Direction | −30.9 | 2.8 | −1.7 | 0 |
| Number of Loops [per cm] | Before Shrink-proofing Treatment | Wale Direction | 10 | 8 | 13 | 8.5 |
| | | Course Direction | 7.5 | 8.5 | 8.5 | 8 |
| | After Shrink-proofing Treatment | Wale Direction | 16.5 | 9.5 | 13 | 9 |
| | | Course Direction | 12 | 7.5 | 8.5 | 8 |
| Rate of Increase in Number of Loops (%) | | Wale Direction | 65 | 18.8 | 0 | 5.9 |
| | | Course Direction | 60 | −11.7 | 0 | 0 |
| Knitting Density [Number of Loops/$cm^2$] | Before Shrink-proofing Treatment | | 75 | 68 | 110.5 | 68 |
| | After Shrink-proofing Treatment | | 198 | 71.25 | 110.5 | 72 |
| Rate of Increase in Knitting Density (%) | | | 164 | 4.8 | 0 | 5.9 |
| Bursting Strength [N] | Before Shrink-proofing Treatment | | 300.3 | — | 659.4 | 585.1 |
| | After Shrink-proofing Treatment | | 364.5 | — | 677.6 | 540.5 |
| Rate of Increase in Bursting Strength (%) | | | 21.4 | — | 2.8 | −7.7 |

[Manufacture, Shrink-proofing Treatment, and Evaluation of Woven Fabric]

Using a twist yarn including a modified fibroin fiber, four types of woven fabrics having different weaving densities as shown in the following Table 14 were woven by plain weave with a rapier loom (available from Evergreen Automatic Sampling Loom: CCI) (Test Example 4-5 to Test Example 4-8). Here, the fineness of the twist yarn including the modified fibroin fiber was 190d, and the twists per meter was 450 T/m.

Each of the four woven fabrics obtained was immersed in water at 40° C. for 10 minutes and subjected to shrink-proofing treatment by drying. Thereafter, densities of the woven fabrics of Test Example 4-5 to Test Example 4-8 were inspected. The following Table 14 shows the results. In Table 14, the weaving density is shown by "warp density multiplied by weft density". For example, the weaving density "26×26" represents "warp density of 26 (yarns/in) and the weft density of 26 (yarns/in)".

Four types of woven fabrics having different densities as shown in Table 14 below were woven fabric in a manner similar to the aforementioned manner except that a twist yarn including a polyamide fiber was used instead of the twist yarn including a modified fibroin fiber (Test Example 4-9 to Test Example 4-12). Here, the fineness of the twist yarn including the polyamide fiber was 150d, and the twists per meter was 150 T/m.

The woven fabrics of Test Example 4-9 to Test Example 4-12 were subjected to shrink-proofing treatment similarly to the aforementioned manner. Thereafter, densities of the woven fabrics of Test Example 4-9 to Test Example 4-12 were inspected. Results are also shown in Table 14.

TABLE 14

| | Weaving Density Before Immersion | Weaving Density After Immersion | Rate of Increase in Weaving Density |
|---|---|---|---|
| Test Example 4-5 | 26 × 26 | 60 × 74 | 2.57 |
| Test Example 4-6 | 51 × 39 | 92 × 88 | 2 |
| Test Example 4-7 | 51 × 65 | 92 × 107 | 1.71 |
| Test Example 4-8 | 102 × 78 | 119 × 93 | 1.17 |
| Test Example 4-9 | 26 × 26 | 26 × 26 | 1 |
| Test Example 4-10 | 51 × 39 | 51 × 39 | 1 |
| Test Example 4-11 | 51 × 65 | 51 × 65 | 1 |
| Test Example 4-12 | 110 × 87 | 110 × 87 | 1 |

Test Example 5: Manufacture and Evaluation of Protein Fiber Having Functionality

Test Example 5-1

<Preparation of Spinning Dope (Dope Solution)>

In 11400 mg of a solvent (dimethyl sulfoxide (DMSO) containing 4 wt % of LiCl), 200 mg of starch (available from Wako Pure Chemical Industries, Ltd.) was dissolved, and 400 mg of phenyl isocyanate (available from Tokyo Chemical Industry Co., Ltd.) was added thereto, followed by stirring the mixture at 90° C. for four hours so as to react the materials. Accordingly, the hydroxyl group of the starch and the isocyanate group of the phenyl isocyanate were reacted, thereby obtaining a modified starch (modified hydroxyl group-containing polymer) in which a phenyl group (operative functional group) was bound via a urethane bond. Calculating from proportions of charged materials, the modified starch was 100% modified (percentage at which a hydroxyl group was converted into an operative functional group).

After cooling the reaction solution to room temperature, 300 mg of powder of the modified fibroin (PRT799) was added to the reaction solution, and the mixture was stirred at 90° C. for 12 hours for dissolution, thereby obtaining a transparent spinning dope. The modified starch content in the spinning dope was 17 mass % based on the total amount of the modified starch and the starch.

<Manufacture of Protein Fiber>

The prepared spinning dope was heated to 60° C. and filtrated with a metallic filter having a mesh opening of 5 μm. Thereafter, the filtrate was allowed to stand in a 30 mL stainless steel syringe to remove foams. The resultant was discharged from a solid nozzle having a needle diameter of 0.2 mm into 100 mass % of methanol coagulation bath, using a nitrogen gas. The discharging temperature was 60° C., and the discharging pressure was 0.3 MPa. After the coagulation, the obtained original yarn was wound at a take-up speed of 3.00 m/min and naturally dried to obtain a protein fiber (modified fibroin fiber).

<Water Shrinkage Test>

The obtained protein fiber was cut to a length of about 10 cm, and before immersion in water, the length (cm) of the yarn was measured. The yarn was then immersed in a water bath at 40° C. for one minute. Thereafter, the yarn was taken out from the water bath, vacuum-dried at room temperature for 15 minutes, followed by measuring the length of the dried yarn. The water shrinkage rate of the protein fiber was calculated according to the following Formula:

$$\text{water shrinkage rate (\%)}=\{(\text{length before immersion}/\text{length after immersion and drying})-1\}\times 100$$

Test Example 5-2

<Preparation of Spinning Dope (Dope Solution)>

In 7600 mg of a solvent (dimethyl sulfoxide (DMSO) containing 4 wt % of LiCl), 253 mg of starch (available from Wako Pure Chemical Industries, Ltd.) was dissolved, and 147 mg of acetic anhydride (available from Wako Pure Chemical Industries, Ltd.) was added thereto, followed by stirring the mixture at 90° C. for four hours so as to react the materials. Accordingly, the hydroxyl group of the starch and the acetic anhydride were reacted, thereby obtaining a modified starch (modified hydroxyl group-containing polymer) to which an acetyl group (operative functional group) was bound. Calculating from proportions of charged materials, the modified starch was 100% modified (percentage at which a hydroxyl group was converted into an operative functional group).

After cooling the reaction solution to room temperature, 2000 mg of powder of the modified fibroin (PRT799) was added to the reaction solution, and the mixture was stirred at 90° C. for 12 hours for dissolution, thereby obtaining a transparent spinning dope. The modified starch content in the spinning dope was 17 mass % based on the total amount of the modified starch and the starch.

<Manufacture of Protein Fiber and Water Shrinkage Test>

Using the prepared spinning dope, a protein fiber was manufactured and a water shrinkage test was performed in a similar manner to Test Example 5-1.

Test Example 5-3

<Preparation of Spinning Dope (Dope Solution)>

In 7600 mg of a solvent (dimethyl sulfoxide (DMSO) containing 4 wt % of LiCl), 215 mg of starch (available from Wako Pure Chemical Industries, Ltd.) was dissolved, and 185 mg of acetic anhydride (available from Wako Pure Chemical Industries, Ltd.) was added thereto, followed by stirring the mixture at 90° C. for four hours so as to react the materials. Accordingly, the hydroxyl group of the starch and the acetic anhydride were reacted, thereby obtaining a modified starch (modified hydroxyl group-containing polymer) to which an acetyl group (operative functional group) was bound. Calculating from proportions of charged materials, the modified starch was 50% modified (percentage at which a hydroxyl group was converted into an operative functional group).

After cooling the reaction solution to room temperature, 2000 mg of powder of the modified fibroin (PRT799) was added to the reaction solution, and the mixture was stirred at 90° C. for 12 hours for dissolution, thereby obtaining a transparent spinning dope. The modified starch content in the spinning dope was 17 mass % based on the total amount of the modified starch and the starch.

<Manufacture of Protein Fiber and Water Shrinkage Test>

Using the prepared spinning dope, a protein fiber was manufactured and a water shrinkage test was performed in a similar manner to Test Example 5-1.

Test Example 5-4

<Preparation of Spinning Dope (Dope Solution)>

In 7600 mg of a solvent (dimethyl sulfoxide (DMSO) containing 4 wt % of LiCl), 128 mg of polyvinyl alcohol (PVA) (available from Wako Pure Chemical Industries, Ltd.) was dissolved, and 272 mg of phenyl isocyanate (available from Tokyo Chemical Industry Co., Ltd.) was added thereto, followed by stirring the mixture at 90° C. for four hours so as to react the materials. Accordingly, the hydroxyl group of the PVA and the phenyl isocyanate were reacted, thereby obtaining modified PVA (modified hydroxyl group-containing polymer) in which a phenyl group (operative functional group) was bound via a urethane bond. Calculating from proportions of charged materials, the modified PVA was 100% modified (percentage at which a hydroxyl group was converted into an operative functional group).

After cooling the reaction solution to room temperature, 2000 mg of powder of the modified fibroin (PRT799) was added to the reaction solution, and the mixture was stirred at 90° C. for 12 hours for dissolution, thereby obtaining a transparent spinning dope. The modified PVA content in the spinning dope was 17 mass % based on the total amount of the modified PVA and the PVA.

<Manufacture of Protein Fiber and Water Shrinkage Test>

Using the prepared spinning dope, a protein fiber was manufactured and a water shrinkage test was performed in a similar manner to Test Example 5-1.

Test Example 5-5

<Preparation of Spinning Dope (Dope Solution)>

In 7600 mg of a solvent (dimethyl sulfoxide (DMSO) containing 4 wt % of LiCl), 193 mg of polyvinyl alcohol (PVA) (available from Wako Pure Chemical Industries, Ltd.) was dissolved, and 207 mg of phenyl isocyanate (available from Tokyo Chemical Industry Co., Ltd.) was added thereto, followed by stirring the mixture at 90° C. for four hours so as to react the materials. Accordingly, the hydroxyl group of the PVA and the phenyl isocyanate were reacted, thereby obtaining modified PVA (modified hydroxyl group-containing polymer) in which a phenyl group (operative functional group) was bound via a urethane bond. Calculating from proportions of charged materials, the modified PVA was 50% modified (percentage at which a hydroxyl group was converted into an operative functional group).

After cooling the reaction solution to room temperature, 2000 mg of powder of the modified fibroin (PRT799) was added to the reaction solution, and the mixture was stirred at 90° C. for 12 hours for dissolution, thereby obtaining a transparent spinning dope. The modified PVA content in the spinning dope was 17 mass % based on the total amount of the modified PVA and the PVA.

<Manufacture of Protein Fiber and Water Shrinkage Test>

Using the prepared spinning dope, a protein fiber was manufactured and a water shrinkage test was performed in a similar manner to Test Example 5-1.

Test Example 5-6

<Preparation of Spinning Dope (Dope Solution)>

To a solvent (dimethyl sulfoxide (DMSO) containing 4 wt % of LiCl), 1200 mg of powder of the modified fibroin (PRT799) was added, and the mixture was stirred at 90° C. for 12 hours for dissolution, thereby obtaining a transparent spinning dope.

<Manufacture of Protein Fiber and Water Shrinkage Test>

Using the prepared spinning dope, a protein fiber was manufactured and a water shrinkage test was performed in a similar manner to Test Example 5-1.

Test Example 5-7

<Preparation of Spinning Dope (Dope Solution)>

To a solvent (dimethyl sulfoxide (DMSO) containing 4 wt % of LiCl), 3000 mg of powder of the modified fibroin (PRT799) and 600 mg of starch (available from Wako Pure Chemical Industries, Ltd.) were added, and the mixture was stirred at 90° C. for 12 hours for dissolution, thereby obtaining a transparent spinning dope.

<Manufacture of Protein Fiber and Water Shrinkage Test>

Using the prepared spinning dope, a protein fiber was manufactured and a water shrinkage test was performed in a similar manner to Test Example 5-1.

Figure 7:
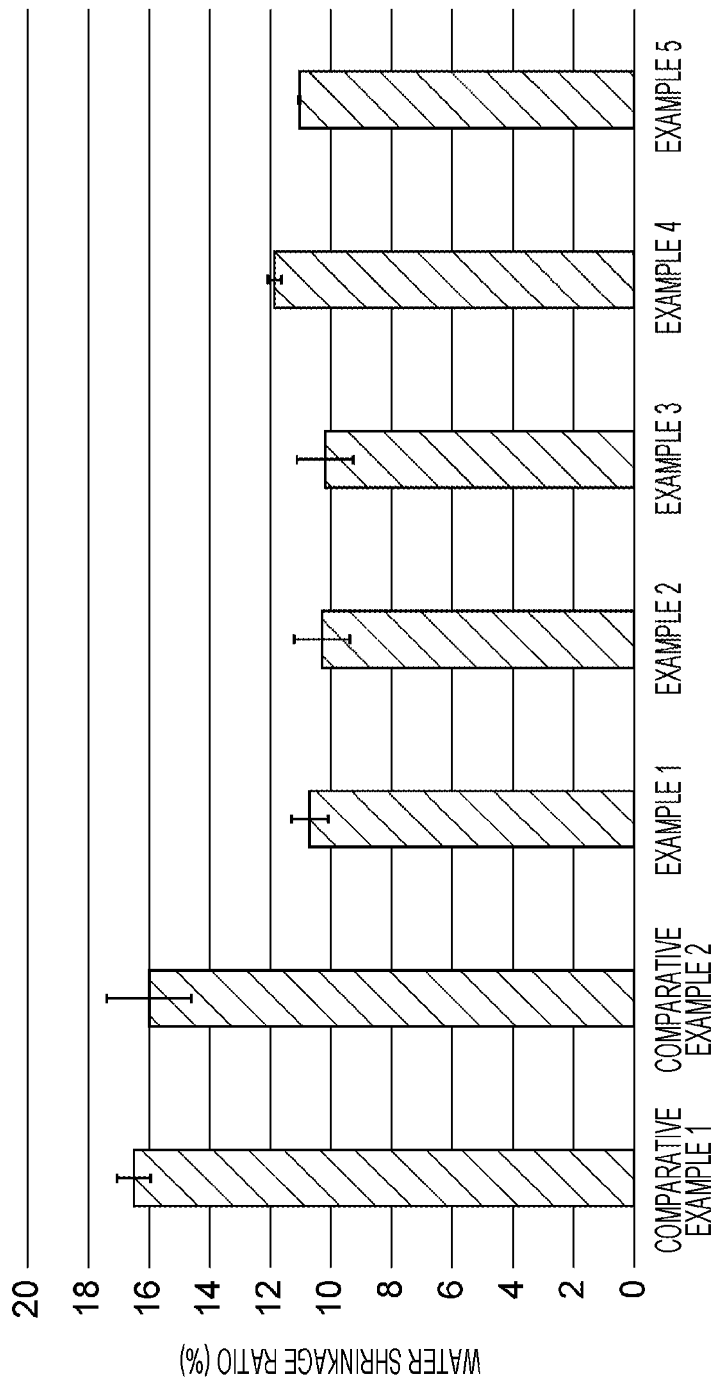
FIG. 7 is a graph showing evaluation results of water shrinkage rate of a manufactured protein fiber.

Results are shown in FIG. 7 and Table 15. In Table 15, Test Example 3-1 shows Test Example 5-1, Test Example 3-2 shows Test Example 5-2, Test Example 3-3 shows Test Example 5-3, Test Example 3-4 shows Test Example 5-4, Test Example 3-5 shows Test Example 5-5, Test Example 3-6 shows Test Example 5-6, and Test Example 3-7 shows Test Example 5-7.

TABLE 15

| | Hydroxyl Group-containing Polymer | Operative Functional Group | Percentage of Modification (%) | Proportion of Modified Hydroxyl Group-containing Polymer *1 (%) | Water Shrinkage Rate |
|---|---|---|---|---|---|
| Test Example 3-1 | Starch | Phenyl Group | 100 | 17 | 10.8 |
| Test Example 3-2 | Starch | Acetyl Group | 100 | 17 | 10.2 |
| Test Example 3-3 | Starch | Acetyl Group | 50 | 17 | 10.1 |
| Test Example 3-4 | PVA | Phenyl Group | 100 | 17 | 11.8 |
| Test Example 3-5 | PVA | Phenyl Group | 50 | 17 | 11.0 |
| Test Example 3-6 | — | — | — | — | 16.3 |
| Test Example 3-7 | Starch | — | — | 0 | 16.0 |

*1 (Modified hydroxyl group-containing polymer content/total amount of modified hydroxyl group-containing polymer and hydroxyl group-containing polymer) × 100

Manufacturing a protein fiber from a spinning dope containing a modified hydroxyl group-containing polymer (modified starch or modified PVA) to which a hydrophobic functional group (phenyl group or acetyl group) was bound as an operative functional group and containing a protein (modified fibroin) (Test Examples 5-1 to 5-5 (Test Examples 3-1 to 3-5 in Table 15)) enabled a protein fiber having water resistance with a reduced water shrinkage rate as compared with a spinning dope manufactured only from a protein (Test Example 5-6 (Test Example 3-6 in Table 15)) and a spinning dope manufactured from a protein and an unmodified hydroxyl group-containing polymer (Test Example 5-7 (Test Example 3-7 in Table 15)). Forming a knitted or woven fabric from such a protein fiber imparts a functionality (water resistance) to the knitted or woven fabric.

Test Example 6: Manufacture and Evaluation of Functional Protein Fiber

Manufacture Example 1

To dimethyl sulfoxide (DMSO), the aforementioned spider silk fibroin protein (PRT799) was added at a concentration of 24 mass %. To the mixture, LiCl was added as a dissolution promoter at a concentration of 4.0 mass %. Next, the spider silk fibroin was dissolved over three hours using a shaker to obtain a DMSO solution. Dust and bubbles in the obtained DMSO solution were removed to prepare a dope solution. The dope solution had a solution viscosity of 5000 cP (centipoise) at 90° C.

Dry-wet spinning was performed using the dope solution obtained as described above and a known spinning device, thereby obtaining a monofilament including a spider silk fibroin. Note that the dry-wet spinning herein was performed under the following conditions.

Temperature of coagulating liquid (methanol): 5 to 10° C.

Overall elongation rate: 6-fold

Drying temperature: 80° C.

A spun yarn was manufactured by a known method from the modified spider silk fibroin fiber obtained in the aforementioned manner. Using the spun yarn including the modified spider silk fibroin fiber, a 5-cm square knitted fabric (knitted or woven fabric) was knitted by weft knitting with a known knitting machine. The yarn count of the spun yarn including the modified spider silk fibroin fiber was 58.1 Nm, and the gauge of the knitting machine was 18.

Test Example 6-1

The knitted or woven fabric (5-cm square knitted fabric) obtained in Manufacture Example 1 was immersed in 20 mL of hexane diisoanate (HDI). Then, the knitted or woven fabric impregnated with HDI was sandwiched between aluminum foils and heated at 130° C. for 30 minutes. The heated knitted or woven fabric was taken out, immersed in 20 mL of butanol (BuOH), and reacted at 100° C. for 240 minutes. The test sample after the reaction was washed with THE to obtain a knitted or woven fabric imparted with a functionality (to which water resistance imparting substances (first reagent and second reagent) were bound).

Test Example 6-2

The knitted or woven fabric obtained in Manufacture Example 1 was evaluated as a knitted or woven fabric of Test Example 6-2.

Test Example 6-3

The knitted or woven fabric obtained in Manufacture Example 1 was immersed in 20 mL of hexane diisocyanate (HDI, first reagent). Then, the knitted or woven fabric impregnated with HDI was sandwiched between aluminum foils and heated at 130° C. for 30 minutes. Thereafter, the knitted or woven fabric was washed with THE to obtain a knitted or woven fabric of Test Example 6-3 to which only the first reagent was bound.

With regard to the knitted or woven fabrics of Test Example 6-1 to Test Example 6-3, the water resistance (shrinkability) and texture were evaluated by the following test method.

<Evaluation of Water Resistance (Shrinkability)>

Each knitted or woven fabric was marked with a 3-cm square with a pencil to obtain an evaluation sample. The evaluation samples were washed in a washing mode "ouchi cleaning (professional-grade cleaning at home)" with a washing machine (Na-VG 1100L) available from Panasonic Corporation. Next, the samples were dehydrated for 15 minutes in the same washing machine and naturally dried for 120 minutes. The longitudinal and lateral lengths of each square before and after washing were measured to obtain shrinkage rates in the longitudinal and lateral directions. The same test was performed three times, and an average of the three tests was used as the evaluation result. Each result is shown in Table 16. In Table 16, Test Example 4-1 represents Test Example 6-1, Test Example 4-2 represents Test Example 6-2, and Test Example 4-3 represents Test Example 6-3.

<Evaluation of Texture>

The texture of each knitted or woven fabric was evaluated in three stages. Regarding the texture of the knitted or woven fabric of Test Example 6-2 as a standard (B), one with better feeling was rated "A", and one with rough texture and poor feeling was rated "C". Each result is shown in Table 16.

TABLE 16

| | Shrinkage Rate (%) | | |
|---|---|---|---|
| | Longitudinal Direction | Lateral Direction | Texture |
| Test Example 4-1 | 16 | 32 | A |
| Test Example 4-2 | 32 | 50 | B |
| Test Example 4-3 | 18 | 31 | C |

Test Example 7: Manufacture and Evaluation of Woven Fabric Using Modified Fibroin Fiber (1) Preparation of Spinning Dope (Dope Solution)

Lithium chloride was dissolved in DMSO at a concentration of 4 mass % to prepare a solvent. To the solvent, lyophilized powder of the modified fibroin (PRT799) was added at a concentration of 24 mass %. The resultant was dissolved in an aluminum block heater at 90° C. for one hour, followed by removing insoluble matters and bubbles, thereby obtaining a spinning dope (dope solution).

(2) Spinning

The spinning dope was charged in a reserve tank and discharged into a 100 mass % of methanol coagulation bath through a mono-hole nozzle having a diameter of 0.1 or 0.2 mm, using a gear pump. The discharge amount was adjusted to 0.01 to 0.08 mL/min. After coagulation, washing and drawing were performed in a 100 mass % of methanol washing bath. After washing and drawing, drying was performed using a dry heat plate, and the obtained original yarn (modified fibroin fiber) was wound up.

(3) Manufacture of Woven Fabric

From the obtained modified fibroin fiber, organzine was prepared. The prepared organzine was woven by plain weave, thereby obtaining a woven fabric.

(4) Binding of Water Resistance Imparting Substance to Woven Fabric

Fluorine-based coating monomers were applied to the obtained woven fabric, and plasma treatment was performed with a plasma treatment device (available from Europlasma). The plasma treatment was performed to obtain a woven fabric having covalently bound fluorine-based polymers in which the fluorine-based coating monomers (water resistance imparting substance) were polymerized. Nanofics 110 (Test Example 7-2) and Nanofics 120 (Test Example 7-3) (both available from Europlasma) were used as the fluorine-based coating monomers.

(5) Evaluation of Water Repellency

A water repellency test (spray test) was performed on the plasma-treated woven fabrics (Test Example 7-2 and Test Example 7-3) and the woven fabric not subjected to the plasma treatment (Test Example 7-1). The water repellency test (spray test) was performed according to ISO 4920: 2012. The test samples were visually assessed according to the following 6-step evaluation (on a scale of 0 to 5).

Score 5: Dry surface with no water droplet.

Score 4: Dry surface with some water droplets.

Score 3: Slightly wet surface.

Score 2: Wet surface from place to place with some wet regions connected to each other.

Score 1: Part brought into contact with water is completely wetted.

Score 0: Thoroughly wet surface.

Results are shown in Table 17. The woven fabric not subjected to the plasma treatment (Test Example 7-1) was rated 0, while the woven fabrics subjected to the plasma treatment (Test Example 7-2 and Test Example 7-3) were rated 4, showing water resistance (water repellency). In Tables 17, 18, and 19, Test Example 2-1 shows Test Example 7-1, Test Example 2-2 shows Test Example 7-2, and Test Example 2-3 shows Test Example 7-3.

TABLE 17

| | Score |
|---|---|
| Test Example 2-1 | 0 |
| Test Example 2-2 | 4 |
| Test Example 2-3 | 4 |

(6) Evaluation of Texture and Shrinkability

A 5-cm square test piece was cut out from each of the woven fabrics of Test Example 7-1 to Test Example 7-3. One surface of each test piece was marked with vertexes (four points) of a 30-mm square using a pencil. Each test piece was immersed in water at 40° C. for 10 minutes and vacuum-dried at room temperature. This procedure was repeated five times. The vacuum drying was performed with a vacuum dry oven (VOS-310C, available from Tokyo Rikakikai Co., Ltd.) at a pressure of −0.1 MPa for 30 minutes. At the end of each cycle, the texture was sensory rated, and distances between the marked four points was measured to evaluate a shrinkage rate.

The texture was determined according to the following criteria. Results are shown in Table 18. Both the plasma-treated woven fabrics of Test Example 7-2 and Test Example 7-3 were prevented from degrading in texture as compared with the woven fabric of Test Example 7-1 which was not subjected to the plasma treatment.

Score 5: Good as the original.

Score 4: Good, but slightly inferior to the original.

Score 3: Fair, but slightly rough.

Score 2: Poor and rough, but bendable.

Score 1: Very bad, rough, non-bendable.

TABLE 18

| | Score | | | | | |
|---|---|---|---|---|---|---|
| | Original | After 1 Cycle | After 2 Cycles | After 3 Cycles | After 4 Cycles | After 5 Cycles |
| Test Example 2-1 | 5 | 2 | 2 | 2 | 2 | 2 |
| Test Example 2-2 | 5 | 3 | 3 | 3 | 3 | 3 |
| Test Example 2-3 | 5 | 4 | 4 | 4 | 4 | 4 |

The shrinkage rate was calculated according to the following Formula. Note that "average length of all sides" is a value obtained by diving the total length of all sides of the square (marked by the four points) by 4.

$$\text{Shrinkage rate }(\%)=\{1-(\text{average length of all sides }(\text{mm})/30\text{ mm})\}\times 100$$

Results are shown in Table 19. Both the plasma-treated woven fabrics of Test Example 2-2 and Test Example 7-3 had a shrinkage rate smaller than that of the woven fabric of Test Example 7-1 which was not subjected to the plasma treatment.

TABLE 19

| | Shrinkage rate (%) | | | | |
|---|---|---|---|---|---|
| | After 1 Cycle | After 2 Cycles | After 3 Cycles | After 4 Cycles | After 5 Cycles |
| Test Example 2-1 | 25.0 | 24.5 | 25.3 | 25.6 | 25.6 |
| Test Example 2-2 | 3.8 | 5.4 | 10.5 | 17.4 | 17.8 |
| Test Example 2-3 | 9.4 | 9.5 | 9.9 | 14.7 | 15.0 |

Test Example 8: Production and Evaluation of Knitted Fabric Using Modified Fibroin Fiber (1) Preparation of Spinning Dope (Dope Solution)

Lithium chloride was dissolved in DMSO at a concentration of 4 mass % to prepare a solvent. To the solvent, lyophilized powder of the modified fibroin (PRT918) was added at a concentration of 24 mass %. The resultant was dissolved in an aluminum block heater at 90° C. for one hour, followed by removing insoluble matters and bubbles, thereby obtaining a spinning dope (dope solution).

(2) Spinning

The spinning dope was filled in a reserve tank and discharged into a 100 mass % of methanol coagulation bath through a mono-hole nozzle having a diameter of 0.1 or 0.2 mm, using a gear pump. The discharge amount was adjusted to 0.01 to 0.08 mL/min. After coagulation, washing and drawing were performed in a 100 mass % of methanol washing bath. After washing and drawing, drying was performed using a dry heat plate, and the obtained original yarn (modified fibroin fiber) was wound up.

(3) Manufacture of Knitted Fabric for Evaluation

The obtained modified fibroin fiber was cut to prepare a modified fibroin staple. The prepared modified fibroin staple was opened and spun by a known spinning device to obtain a spun yarn. The obtained spun yarn was knitted using a whole garment knitting machine (MACH2XS, available from Shima Seiki MFG., Ltd.) to obtain a knitted fabric.

(4) Binding of Water Resistance Imparting Substance to Knitted Fabric

Fluorine-based coating monomers were applied to the obtained knitted fabric, and plasma treatment was performed with a plasma treatment device (available from Europlasma). The plasma treatment was performed to obtain a knitted fabric having covalently bound fluorine-based polymers in which the fluorine-based coating monomers (water resistance imparting substance) were polymerized (Test Example 3-2). Nanofics 120 (available from Europlasma) was used as the fluorine-based coating monomers.

(5) Evaluation of Water Repellency

A water repellency test (spray test) was performed in a similar manner to Test Example 7 on the plasma-treated knitted fabric (Test Example 8-2) and the knitted fabric not subjected to the plasma treatment (Test Example 8-1). Results are shown in Table 20. The knitted fabric not subjected to the plasma treatment (Test Example 8-1) was rated 0, while the knitted fabric subjected to the plasma treatment (Test Example 8-2) was rated 5, showing water resistance (water repellency). Hereinafter, in Tables 20, 21, and 22, Test Example 3-1 shows Test Example 8-1, and Test Example 3-2 shows Test Example 8-2.

TABLE 20

| | Score |
|---|---|
| Test Example 3-1 | 0 |
| Test Example 3-2 | 5 |

(6) Evaluation of Texture and Shrinkability

A 5-cm square test piece was cut out from each of the knitted fabrics of Test Example 8-1 and Test Example 8-2. One surface of each test piece was marked with vertexes (four points) of a 30-mm square using a pencil. As a preliminary treatment, each test piece was immersed in water at 40° C. for 10 minutes and vacuum-dried at room temperature. This procedure was repeated five times. The vacuum drying was performed with a vacuum dry oven (VOS-310C, available from Tokyo Rikakikai Co., Ltd.) at a pressure of −0.1 MPa for 30 minutes.

Next, washing, drying, immersing, and drying were repeated in this order five times for each test piece subjected to the preliminary treatment. In the washing, the test piece was washed for five minutes using a washing machine (NA-VG 1100L) available from Panasonic Corporation and a detergent (Top Clear Liquid) available from Lion Corporation and was rinsed twice, and then, dehydrated for one minute. In the drying, the test piece was dried at room temperature at a set pressure of −0.1 MPa for 30 minutes using a vacuum constant temperature dryer (VOS-310C, available from Tokyo Rikakikai Co., Ltd.). In the immersing, the test piece was immersed in water at 40° C. for 10 minutes. At the end of each cycle, the texture was sensory rated according to a criteria similar to Test Example 7, and distances between the marked four points was measured to evaluate a shrinkage rate.

Sensory rating results of the texture are shown in Table 21. The "beginning" shows the evaluation result after the preliminary treatment and before the cycle was started. The knitted fabric of Test Example 8-2 (in Table 21, Test Example 2-2) subjected to the plasma treatment was prevented from degrading in texture as compared with the knitted fabric of Test Example 8-1 (in Table 21, Test Example 2-1) not subjected to the plasma treatment.

TABLE 21

| | Score | | | | | |
|---|---|---|---|---|---|---|
| | Beginning | After 1 Cycle | After 2 Cycles | After 3 Cycles | After 4 Cycles | After 5 Cycles |
| Test Example 3-1 | 5 | 4 | 4 | 4 | 4 | 4 |
| Test Example 3-2 | 5 | 5 | 5 | 5 | 5 | 5 |

The evaluation results of the shrinkage rate are shown in Table 22. The knitted fabric of Test Example 8-2 (in Table 22, Test Example 2-2) subjected to the plasma treatment had a smaller shrinkage rate than the knitted fabric of Test Example 8-1 (in Table 22, Test Example 2-1) not subjected to the plasma treatment.

TABLE 22

| | Shrinkage Rate (%) | | | | |
|---|---|---|---|---|---|
| | After 1 Cycle | After 2 Cycles | After 3 Cycles | After 4 Cycles | After 5 Cycles |
| Test Example 3-1 | 19.5 | 22.0 | 24.3 | 25.3 | 27.1 |
| Test Example 3-2 | 10.7 | 15.0 | 17.0 | 17.0 | 18.9 |

Test Example 9: Production and Evaluation of Modified Fibroin Fiber

Test Example 9-1

(1) Preparation of Spinning Dope (Dope Solution)

In 11400 mg of a solvent (dimethyl sulfoxide (DMSO) containing 4 wt % of LiCl), 200 mg of starch (available from Wako Pure Chemical Industries, Ltd.) was dissolved, and 400 mg of phenyl isocyanate (available from Tokyo Chemical Industry Co., Ltd.) was added thereto, followed by stirring the mixture at 90° C. for four hours so as to react the materials. Accordingly, the hydroxyl group of the starch and the isocyanate group of the phenyl isocyanate were reacted, thereby obtaining a modified starch (modified hydroxyl group-containing polymer) in which a phenyl group (operative functional group) was bound via a urethane bond. Calculating from proportions of charged materials, the modified starch was 100% modified (percentage at which a hydroxyl group was converted into an operative functional group).

After cooling the reaction solution to room temperature, 300 mg of lyophilized powder of the modified fibroin (PRT799) was added to the reaction solution, and the mixture was stirred at 90° C. for 12 hours for dissolution, thereby obtaining a transparent spinning dope (dope solution). The modified starch content in the spinning dope was 17 mass % based on the total amount of the modified starch and the starch.

(2) Manufacture of Fiber Containing Modified Fibroin and Water Resistance Imparting Substance The prepared spinning dope was heated to 60° C. and filtrated with a metallic filter having a mesh opening of 5 μm. Thereafter, the filtrate was allowed to stand in a 30 mL stainless steel syringe to remove foams. The resultant was discharged from a solid nozzle having a needle diameter of 0.2 mm into 100 mass % of methanol coagulation bath, using a nitrogen gas. The discharging temperature was 60° C., and the discharging pressure was 0.3 MPa. After the coagulation, the obtained original yarn was wound at a take-up speed of 3.00 m/min and naturally dried to obtain a fiber containing the modified fibroin and a water resistance imparting substance (modified starch).

(3) Evaluation of Shrinkability

The obtained fiber was cut to a length of about 10 cm, and the length (cm) of the yarn before immersion in water was measured. The yarn was then immersed in a water bath at 40° C. for one minute. Thereafter, the yarn was taken out from the water bath, vacuum-dried at room temperature for 15 minutes, followed by measuring the length of the dried yarn. The shrinkage rate of the fiber was calculated according to the following Formula. Results are shown in Table 23.

$$\text{Shrinkage rate (\%)}=\{(\text{length before immersion}/\text{length after immersion and drying})-1\}\times 100$$

In Table 23, Test Example 5-1 shows Test Example 9-1, Test Example 5-2 shows Test Example 9-2 to be described later, Test Example 5-3 shows Test Example 9-3 to be described later, Test Example 5-4 shows Test Example 9-4 to be described later, Test Example 5-5 shows Test Example 9-5 to be described later, Test Example 5-6 shows Test Example 9-6 to be described later, and Test Example 5-7 shows Test Example 9-7 to be described later.

Test Example 9-2

(1) Preparation of Spinning Dope (Dope Solution)

In 7600 mg of a solvent (dimethyl sulfoxide (DMSO) containing 4 wt % of LiCl), 253 mg of starch (available from Wako Pure Chemical Industries, Ltd.) was dissolved, and 147 mg of acetic anhydride (available from Wako Pure Chemical Industries, Ltd.) was added thereto, followed by stirring the mixture at 90° C. for four hours so as to react the materials. Accordingly, the hydroxyl group of the starch and the acetic anhydride were reacted, thereby obtaining a modified starch (modified hydroxyl group-containing polymer) to which an acetyl group (operative functional group) was bound. Calculating from proportions of charged materials, the modified starch was 100% modified (percentage at which a hydroxyl group was converted into an operative functional group).

After cooling the reaction solution to room temperature, 2000 mg of lyophilized powder of the modified fibroin (PRT799) was added to the reaction solution, and the mixture was stirred at 90° C. for 12 hours for dissolution, thereby obtaining a transparent spinning dope (dope solution). The modified starch content in the spinning dope was 17 mass % based on the total amount of the modified starch and the starch.

(2) Manufacture of Fiber Containing Modified Fibroin and Water Resistance Imparting Substance Using the prepared spinning dope, a fiber containing a modified fibroin and a water resistance imparting substance (modified starch) were obtained in a similar manner to Test Example 9-1.

(3) Evaluation of Shrinkability

The shrinkability of the obtained fiber was evaluated in a similar manner to Test Example 9-1. Results are shown in Table 23.

Test Example 9-3

(1) Preparation of Spinning Dope (Dope Solution)

In 7600 mg of a solvent (dimethyl sulfoxide (DMSO) containing 4 wt % of LiCl), 215 mg of starch (available from Wako Pure Chemical Industries, Ltd.) was dissolved, and 185 mg of acetic anhydride (available from Wako Pure Chemical Industries, Ltd.) was added thereto, followed by stirring the mixture at 90° C. for four hours so as to react the materials. Accordingly, the hydroxyl group of the starch and the acetic anhydride were reacted, thereby obtaining a modified starch (modified hydroxyl group-containing polymer) to which an acetyl group (operative functional group) was bound. Calculating from proportions of charged materials, the modified starch was 50% modified (percentage at which a hydroxyl group was converted into an operative functional group).

After cooling the reaction solution to room temperature, 2000 mg of lyophilized powder of the modified fibroin (PRT799) was added to the reaction solution, and the mixture was stirred at 90° C. for 12 hours for dissolution, thereby obtaining a transparent spinning dope (dope solution). The modified starch content in the spinning dope was 17 mass % based on the total amount of the modified starch and the starch.

(2) Manufacture of Fiber Containing Modified Fibroin and Water Resistance Imparting Substance Using the prepared spinning dope, a fiber containing a modified fibroin and a water resistance imparting substance (modified starch) were obtained in a manner similar to in Test Example 5-1.

(3) Evaluation of Shrinkability

The shrinkability of the obtained fiber was evaluated in a similar manner to Test Example 9-1. Results are shown in Table 23.

Test Example 9-4

(1) Preparation of Spinning Dope (Dope Solution)

In 7600 mg of a solvent (dimethyl sulfoxide (DMSO) containing 4 wt % of LiCl), 128 mg of polyvinyl alcohol (PVA) (available from Wako Pure Chemical Industries, Ltd.) was dissolved, and 272 mg of phenyl isocyanate (available from Tokyo Chemical Industry Co., Ltd.) was added thereto, followed by stirring the mixture at 90° C. for four hours so as to react the materials. Accordingly, the hydroxyl group of the PVA and the phenyl isocyanate were reacted, thereby obtaining modified PVA (modified hydroxyl group-containing polymer) in which a phenyl group (operative functional group) was bound via a urethane bond. Calculating from proportions of charged materials, the modified PVA was 100% modified (percentage at which a hydroxyl group was converted into an operative functional group).

After cooling the reaction solution to room temperature, 2000 mg of lyophilized powder of the modified fibroin (PRT799) was added to the reaction solution, and the mixture was stirred at 90° C. for 12 hours for dissolution, thereby obtaining a transparent spinning dope (dope solution). The modified PVA content in the spinning dope was 17 mass % based on the total amount of the modified PVA and the PVA.

(2) Manufacture of Fiber Containing Modified Fibroin and Water Resistance Imparting Substance Using the prepared spinning dope, a fiber containing a modified fibroin and a water resistance imparting substance (modified PVA) were obtained in a similar manner to Test Example 9-1.

(3) Evaluation of Shrinkability

The shrinkability of the obtained fiber was evaluated in a similar manner to Test Example 9-1. Results are shown in Table 23.

Test Example 9-5

(1) Preparation of Spinning Dope (Dope Solution)

In 7600 mg of a solvent (dimethyl sulfoxide (DMSO) containing 4 wt % of LiCl), 193 mg of polyvinyl alcohol (PVA) (available from Wako Pure Chemical Industries, Ltd.) was dissolved, and 207 mg of phenyl isocyanate (available from Tokyo Chemical Industry Co., Ltd.) was added thereto, followed by stirring the mixture at 90° C. for four hours so as to react the materials. Accordingly, the hydroxyl group of the PVA and the phenyl isocyanate were reacted, thereby obtaining modified PVA (modified hydroxyl group-containing polymer) in which a phenyl group (operative functional group) was bound via a urethane bond. Calculating from proportions of charged materials, the modified PVA was 50% modified (percentage at which a hydroxyl group was converted into an operative functional group).

After cooling the reaction solution to room temperature, 2000 mg of lyophilized powder of the modified fibroin (PRT799) was added to the reaction solution, and the mixture was stirred at 90° C. for 12 hours for dissolution, thereby obtaining a transparent spinning dope (dope solution). The modified PVA content in the spinning dope was 17 mass % based on the total amount of the modified PVA and the PVA.

(2) Manufacture of Fiber Containing Modified Fibroin and Water Resistance Imparting Substance Using the prepared spinning dope, a fiber containing a modified fibroin and a water resistance imparting substance (modified PVA) were obtained in a similar manner to Test Example 9-1.

(3) Evaluation of Shrinkability

The shrinkability of the obtained fiber was evaluated in a similar manner to Test Example 9-1. Results are shown in Table 23.

Test Example 9-6

(1) Preparation of Spinning Dope (Dope Solution)

To a solvent (dimethyl sulfoxide (DMSO) containing 4 wt % of LiCl), 1200 mg of lyophilized powder of the modified fibroin (PRT799) were added, and the mixture was stirred at 90° C. for 12 hours for dissolution, thereby obtaining a transparent spinning dope (dope solution).

(2) Manufacture of Fiber

Using the prepared spinning dope, a fiber was obtained in a similar manner to Test Example 9-1.

(3) Evaluation of Shrinkability

The shrinkability of the obtained fiber was evaluated in a similar manner to Test Example 9-1. Results are shown in Table 23.

Test Example 9-7

(1) Preparation of Spinning Dope (Dope Solution)

To a solvent (dimethyl sulfoxide (DMSO) containing 4 wt % of LiCl), 3000 mg of lyophilized powder of the modified fibroin (PRT799) and 600 mg of starch (available from Wako Pure Chemical Industries, Ltd.) were added, and the mixture was stirred at 90° C. for 12 hours for dissolution, thereby obtaining a transparent spinning dope (dope solution).

(2) Manufacture of Fiber

Using the prepared spinning dope, a fiber was obtained in a similar manner to Test Example 9-1.

(3) Evaluation of Shrinkability

The shrinkability of the obtained fiber was evaluated in a similar manner to Test Example 9-1. Results are shown in Table 23.

TABLE 23

| | Hydroxyl Group-containing Polymer | Operative Functional Group | Percentage of Modification (%) | Proportion of Modified Hydroxyl Group-containing Polymer *1 (%) | Water Shrinkage Rate |
|---|---|---|---|---|---|
| Test Example 5-1 | Starch | Phenyl Group | 100 | 17 | 10.8 |
| Test Example 5-2 | Starch | Acetyl Group | 100 | 17 | 10.2 |
| Test Example 5-3 | Starch | Acetyl Group | 50 | 17 | 10.1 |
| Test Example 5-4 | PVA | Phenyl Group | 100 | 17 | 11.8 |
| Test Example 5-5 | PVA | Phenyl Group | 50 | 17 | 11.0 |
| Test Example 5-6 | — | — | — | — | 16.3 |
| Test Example 5-7 | Starch | — | — | 0 | 16.0 |

*1 (Modified hydroxyl group-containing polymer content/total amount of modified hydroxyl group-containing polymer and hydroxyl group-containing polymer) × 100

The fiber containing the modified fibroin and the water resistance imparting substance (hydroxyl group-containing polymer (modified starch or modified PVA)) had a reduced shrinkage rate as compared with the fiber not containing the water resistance imparting substance.

Test Example 10: Evaluation of Flame Retardancy of Modified Fibroin Fiber

LiCl was dissolved in dimethyl sulfoxide (DMSO) at a concentration of 4.0 mass % to prepare a solvent. To the solvent, lyophilized powder of the modified fibroin (PRT799) was added at a concentration of 24 mass %, followed by dissolving the mixture for three hours with a shaker. Thereafter, insoluble matters and foams were removed to obtain a modified fibroin solution (spinning dope).

The prepared spinning dope was heated to 90° C. and filtrated with a metallic filter having a mesh opening of 5 μm. Thereafter, the filtrate was allowed to stand in a 30 mL stainless steel syringe to remove foams. The resultant was discharged from a solid nozzle having a needle diameter of 0.2 mm into 100 mass % of methanol coagulation bath. The discharge temperature was 90° C. On completion of the coagulation, the obtained original yarn was wound up and naturally dried to obtain a modified fibroin fiber (raw material fiber).

Using the obtained modified fibroin fiber (twisted filament), a knitted fabric for evaluation was manufactured by circular knitting using a circular knitting machine. The knitted fabric had a thickness of 180 denier and a gauge of 18. To obtain a test piece, 20 gram of the obtained knitted fabric was cut out.

The flammability test was conducted in accordance with the test method for granular materials or synthetic resin having a low melting point prescribed in Notice No. 50 issued on May 31, 1995 by Chief of Dangerous Goods Regulation Division, Fire and Disaster Management Agency. The test was performed at a temperature of 22° C., a relative humidity of 45%, and an atmospheric pressure of 1021 hPa. Table 24 shows measurement results (oxygen concentration (%), combustion rate (%), and converted combustion rate (%)).

TABLE 24

| Oxygen Concentration (%) | Combustion Rate (%) | Converted Combustion Rate (%) |
|---|---|---|
| 20.0 | 39.1 | 40.1 |
| 27.0 | 48.1 | 49.3 |
| 28.0 | 51.9 | 53.2 |
| 30.0 | 53.6 | 54.9 |
| 50.0 | 61.2 | 62.7 |
| 70.0 | 91.1 | 93.3 |
| 100.0 | 97.6 | 100.0 |

As a result of the flame retardancy test, the limiting oxygen index (LOI) of the modified fibroin (PRT799) fibers was 27.2. Typically, when a fabric has LOI of 26 or more, it is regarded as flame-retardant fabric. The result shows that the modified fibroin fiber is excellent in flame retardancy.

Test Example 11: Evaluation of Moisture-absorbing and Heat-releasing Properties of Modified Fibroin Fiber LiCl was dissolved in dimethyl sulfoxide (DMSO) at a concentration of 4.0 mass % to prepare a solvent. To the solvent, lyophilized powder of the modified fibroin was added at a concentration of 24 mass %, followed by dissolving the mixture for three hours with a shaker. Thereafter, insoluble matters and foams were removed to obtain a modified fibroin solution (spinning dope).

The prepared spinning dope was heated to 60° C. and filtrated with a metallic filter having a mesh opening of 5 μm. Thereafter, the filtrate was allowed to stand in a 30 mL stainless steel syringe to remove foams. The resultant was discharged from a solid nozzle having a needle diameter of 0.2 mm into 100 mass % of methanol coagulation bath. The discharge temperature was 60° C. On completion of the coagulation, the obtained original yarn was wound up and naturally dried to obtain a modified fibroin fiber (raw material fiber).

For comparison, a commercially available wool fiber, cotton fiber, tencel fiber, rayon fiber, and polyester fiber were prepared.

Using each fiber, a knitted fabric for evaluation was manufactured by weft knitting using a weft knitting machine. The knitted fabric including the modified fibroin (PRT 918) fiber had a thickness of 1/30 N (yarn count of one-ply yarn), and the gauge was set to 18. The knitted fabric including the modified fibroin (PRT799) fiber had a thickness of 1/30 N (yarn count of one-ply yarn), and the gauge was set to 16. The thickness and gauge of the knitted fabric using other fibers were adjusted to obtain substantially the same cover factor as the knitted fabric using the PRT918 fiber and the PRT799 fiber. Details are as follows.

Wool thickness: 2/30 N (two-ply yarn), gauge: 14

Cotton thickness: 2/34 N (two-ply yarn), gauge: 14

Tencel thickness: 2/30 N (two-ply yarn), gauge: 15

Rayon thickness: 1/38 N (one-ply yarn), gauge: 14

Polyester thickness: 1/60N (one-ply yarn), gauge: 14

Two pieces of knitted fabrics cut into a size of 10 cm×10 cm were combined, and four sides of the combined fabric were sewn to prepare a test piece (sample). The test piece was left to stand in a low-humidity environment (temperature: 20+2° C., relative humidity: 40+5%) for four hours or more, and then, transferred to a high-humidity environment (temperature: 20+2° C., relative humidity: 90±5%). Temperatures of the test piece were measured for 30 minutes at one minute intervals using a temperature sensor attached to the center of inside of the test piece.

Figure 8:
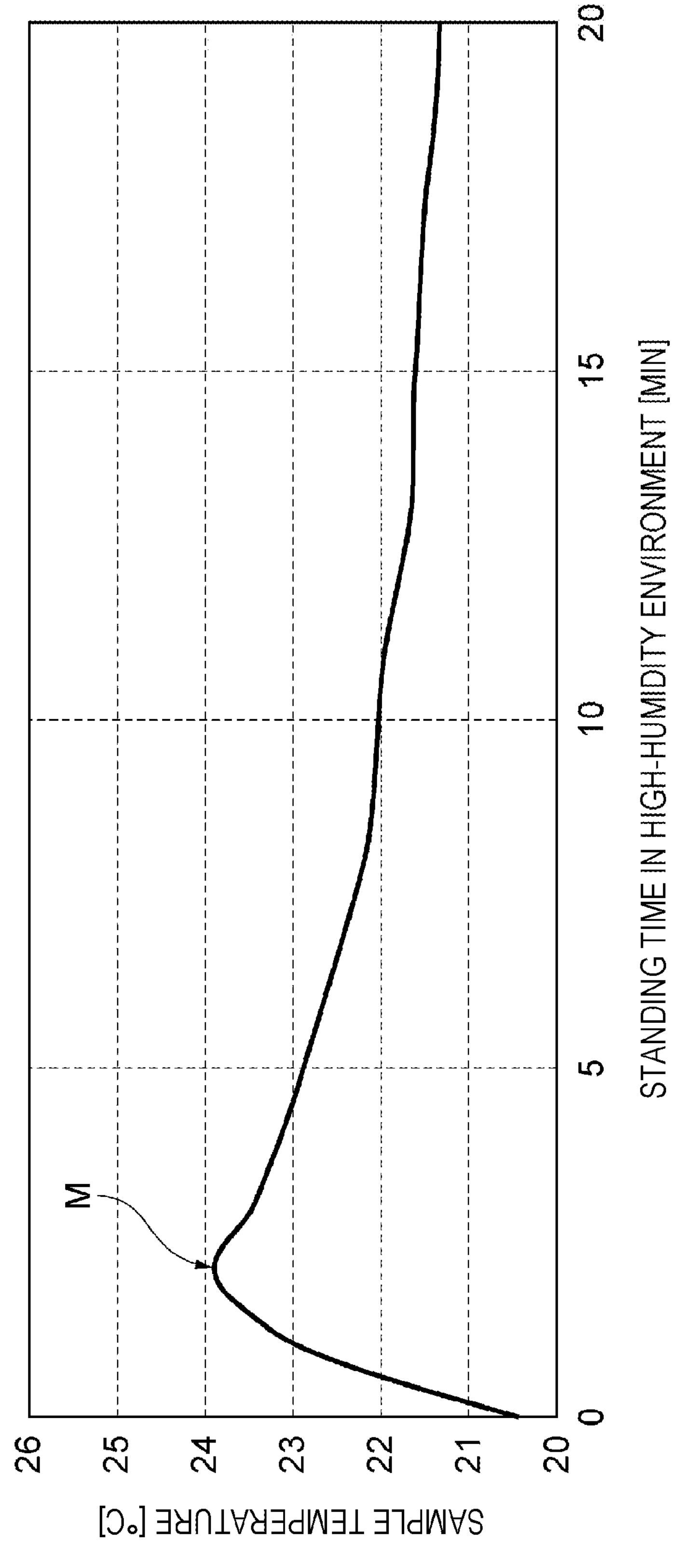
FIG. 8 is a graph showing an example of test results of moisture-absorbing and heat-releasing properties.

From the measurement results, a maximum moisture-absorbing and heat-releasing level was determined according to the following Formula A.

maximum moisture-absorbing and heat-releasing level={(maximum sample temperature obtained after sample is transferred to high-humidity environment after being placed in low-humidity environment until sample temperature reaches equilibrium)−(sample temperature when sample is transferred to high-humidity environment after being placed in low-humidity environment until sample temperature reaches equilibrium)} (° C.)/sample weight (g)    Formula A:

FIG. 8 is a graph showing an example of test results of moisture-absorbing and heat-releasing properties. In the graph, zero indicates the time point at which the sample is transferred from a low-humidity environment to a high-humidity environment, and the time (min) during which the sample is left to stand in a high-humidity environment is taken along the abscissa. The temperature measured with a temperature sensor (sample temperature) is taken along the ordinate. In the graph shown in FIG. 8, the point indicated by "M" corresponds to the maximum sample temperature. Table 25 shows calculation results of the maximum moisture-absorbing and heat-releasing level.

TABLE 25

| Raw Fiber | Maximum Moisture-absorbing and Heat-releasing Level (° C./g) |
|---|---|
| PRT918 | 0.040 |
| PRT799 | 0.031 |
| Wool | 0.020 |
| Cotton | 0.021 |
| Tencel | 0.018 |
| Rayon | 0.025 |
| Polyester | 0.010 |

Table 25 shows that the modified fibroin fibers (PRT918 fiber and PRT799 fiber) have a high maximum moisture-absorbing and heat-releasing level and excellent moisture-absorbing and heat-releasing properties compared to existing fibers.

Test Example 12: Evaluation of Heat Retainability of Modified Fibroin Fiber

LiCl was dissolved in dimethyl sulfoxide (DMSO) at a concentration of 4.0 mass % to prepare a solvent. To the solvent, lyophilized powder of the modified fibroin was added at a concentration of 24 mass %, followed by dissolving the mixture for three hours with a shaker. Thereafter, insoluble matters and foams were removed to obtain a modified fibroin solution (spinning dope).

The prepared spinning dope was heated to 60° C. and filtrated with a metallic filter having a mesh opening of 5 μm. Thereafter, the filtrate was allowed to stand in a 30 mL stainless steel syringe to remove foams. The resultant was discharged from a solid nozzle having a needle diameter of 0.2 mm into 100 mass % of methanol coagulation bath. The discharge temperature was 60° C. On completion of the coagulation, the obtained original yarn was wound up and naturally dried to obtain a modified fibroin fiber (raw material fiber).

For comparison, a commercially available wool fiber, silk fiber, cotton fiber, rayon fiber, and polyester fiber were prepared.

Using each fiber, a knitted fabric for evaluation was manufactured by weft knitting using a weft knitting machine. The yarn count of the knitted fabric including the modified fibroin (PRT966) fiber was 30 Nm, the number of twists was 1, the gauge was 18 GG, and the unit weight was 90.1 g/$m^2$. The yarn count of the knitted fabric including the modified fibroin (PRT799) fiber was 30 Nm, the number of twists was 1, the gauge was 16 GG, and the unit weight was 111.0 g/$m^2$. The thickness and gauge of the knitted fabric using other fibers were adjusted so as to obtain substantially the same cover factor as the knitted fabric using the PRT966 fiber and the PRT799 fiber. Details are as follows.

Wool yarn count: 30 Nm, number of twists: 2, gauge: 14 GG, unit weight: 242.6 g/$m^2$ Silk yarn count: 60 Nm, number of twists: 2, gauge: 14 GG, unit weight: 225.2 g/$m^2$ Cotton yarn count: 34 Nm, number of twists: 2, gauge: 14 GG, unit weight: 194.1 g/$m^2$ Rayon yarn count: 38 Nm, number of twists: 1, gauge: 14 GG, unit weight: 181.8 g/$m^2$ Polyester yarn count: 60 Nm, number of twists: 1, gauge: 14 GG, unit weight: 184.7 g/$m^2$ The heat retainability was evaluated using KES-F7 Thermo Labo II, available from Kato Tech Co., Ltd., according to dry contact method (method based on an assumption that the skin and clothing are in direct contact to each other in a dry state). A knitted fabric cut into a size of 20 cm×20 cm was used as a test piece (sample). The test piece was placed on a hot plate set at a predetermined temperature (30° C.), and an amount of heat dissipated through the test piece (a) was measured at a wind speed of 30 cm/sec in a wind tunnel. An amount of heat dissipated without setting a test piece (b) was determined under condition similar to the above, thereby calculating a heat retention rate (%) according to the following Formula:

$$\text{heat retention rate (\%)}=(1-a/b)\times 100$$

From the measurement result, the heat retention index was determined according to the following Formula B.

$$\text{heat retention index}=\text{heat retention rate (\%)}/\text{unit weight of sample (g/m}^2\text{)} \qquad \text{Formula B:}$$

The calculation result of the heat retention index is shown in Table 26. Materials with a higher heat retention index are rated excellent in heat retainability.

TABLE 26

| Raw Fiber | Heat Retention Index |
|---|---|
| PRT966 | 0.33 |
| PRT799 | 0.22 |
| Wool | 0.16 |
| Silk | 0.11 |
| Cotton | 0.13 |
| Rayon | 0.02 |
| Polyester | 0.18 |

Table 26 shows that the modified fibroin fibers (PRT966 fiber and PRT799 fiber) have a high heat retention index and excellent heat retainability compared to existing fibers.

Test Example 13: Manufacture of Artificial Fur

Figure 9:
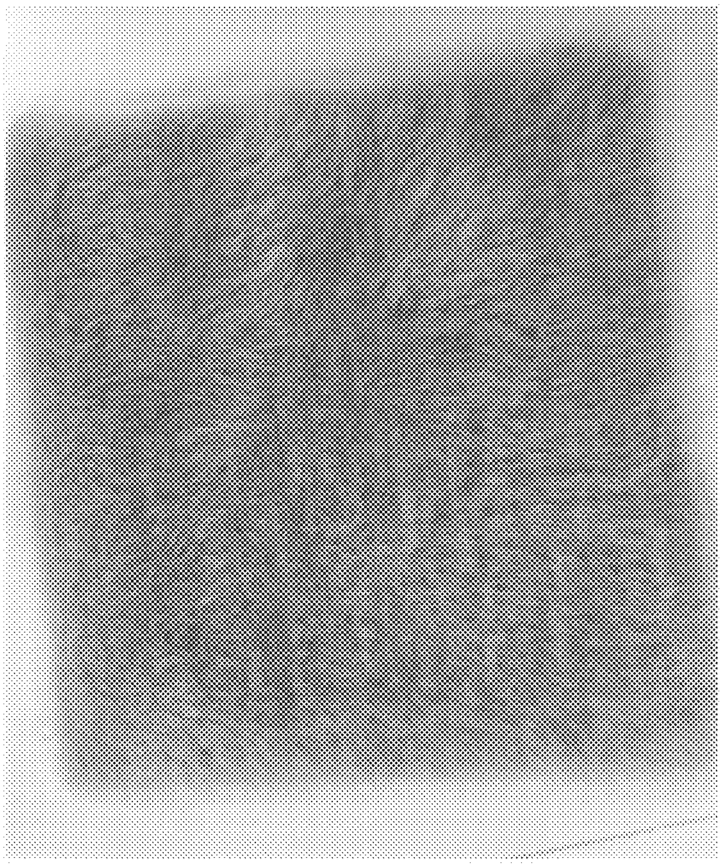
FIG. 9 is a photograph showing a surface of an artificial fur manufactured in Test Example 13.
Figure 10:
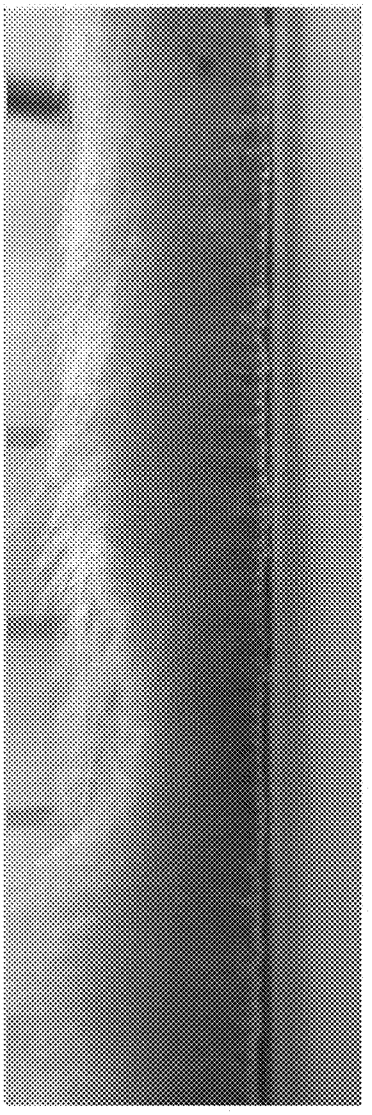
FIG. 10 is a photograph showing a side surface of the artificial fur produced in Test Example 13.

Lyophilized powder of the modified fibroin (PRT 966) was added to formic acid at a concentration of 30 mass %, followed by dissolving the mixture for 1.5 hours using a dissolution tank with stirring blades. Thereafter, insoluble matters and foams were removed to obtain a modified fibroin solution (spinning dope). The obtained modified spider silk fibroin solution was used as a dope solution (spinning dope), and a modified spider silk fibroin fiber (filament) was manufactured by dry-wet spinning using a known dry-wet spinning device. Next, the obtained modified fibroin fiber was mechanically crimped with a known crimping device, and then, cut into a length of 110 to 150 mm to obtain a staple. Using the obtained staple, a spun yarn was obtained according to a commonly-used technique. Next, the obtained spun yarn was used to yield a pile knitted fabric having piles protruded on one surface by pile knitting. Thereafter, the loop of each pile was cut, and the piles were combed. Accordingly, an artificial fur including the modified fibroin fiber was obtained. The photographs of the obtained artificial fur are shown in FIGS. 9 and 10.

[Sequence Listing]

The invention claimed is:

1. An artificial fur comprising an artificial protein fiber, wherein the artificial protein fiber comprises a spun fiber of a manufactured protein, the manufactured protein comprising a modified fibroin having an amino acid sequence of a naturally derived fibroin that includes at least one of a plurality of glycine residues or a plurality of $(A)_n$ motifs, except that at least one glycine residue of the plurality of glycine residues is substituted by another amino acid residue, or at least one $(A)_n$ motif of the plurality of $(A)_n$ motifs is deleted, wherein the artificial protein fiber in wet condition has a shrinkage rate of 2% or more defined by the following Formula I:

Shrinkage rate in wet condition={1−(length of protein fiber in wet condition after contact with water/length of protein fiber after spinning but before contact with water)}×100(%) (Formula I).

2. The artificial fur according to claim 1, wherein the modified fibroin fiber includes a modified spider silk fibroin fiber.

3. The artificial fur according to claim 1, wherein the artificial protein fiber is a shrink-proof artificial protein fiber.

4. The artificial fur according to claim 3, wherein the artificial protein fiber in dry condition has a shrinkage rate over 7% defined by the following Formula II:

Shrinkage rate in dry condition={1−(length of protein fiber in dry condition/length of protein fiber after spinning but before contact with water)}×100(%) (Formula II).

5. The artificial fur according to claim 1, imparted with a functionality.

6. The artificial fur according to claim 5, further comprising a protein crosslinking body, wherein the protein crosslinking body includes: a plurality of polypeptide skeletons; a plurality of first residues or residues of a first reagent having at least two first reactive groups capable of forming a bond by a reaction with a protein; and a plurality of second residues or residues of a second reagent having one second reactive group capable of forming a bond by a reaction with a first reactive group, at least one of the first residues crosslinks a polypeptide skeleton, and at least one of the first residues is bound to a polypeptide skeleton at one end and to a second residue at the other end.

7. The artificial fur according to claim 5, further comprising a modified hydroxyl group-containing polymer in which an operative functional group is bound to a hydroxyl group-containing polymer.

8. The artificial fur according to claim 1, further comprising a water resistance imparting substance.

9. The artificial fur according to claim 8, wherein the artificial protein fiber comprises a modified fibroin, and wherein the modified fibroin and the water resistance imparting substance are covalently bound.

10. The artificial fur according to claim 8, wherein the water resistance imparting substance is at least one selected from the group of a silicone-based polymer and a fluorine-based polymer.

11. The artificial fur according to claim 1, having a limiting oxygen index (LOI) of 26.0 or more.

12. The artificial fur according to claim 1, having a maximum moisture-absorbing and heat-releasing level over 0.025° C./g determined according to the following Formula A:

maximum moisture-absorbing and heat-releasing level={(maximum sample temperature obtained after sample is transferred to high-humidity environment after being placed in low-humidity environment until sample temperature reaches equilibrium)−(sample temperature when sample is transferred to high-humidity environment after being placed in low-humidity environment until sample temperature reaches equilibrium)}(° C.)/sample weight (g) Formula A:

[In Formula A, the low-humidity environment implies an environment at a temperature of 20° C. and a relative humidity of 40%, while the high-humidity environment implies an environment at a temperature of 20° C. and a relative humidity of 90%].

13. The artificial fur according to claim 1, having a heat retention index over 0.18 determined according to the following Formula B:

heat retention index=heat retention rate (%)/unit weight of sample ($g/m^2$)  Formula B:

[In Formula B, the heat retention rate (%) is measured by dry contact method (temperature: 30° C., wind speed: 30 cm/sec) and calculated by (1−a/b)×100, where "a" is an amount of heat dissipated through a test piece and "b" is an amount of heat dissipated without a test piece].

14. A method for manufacturing the artificial fur of claim 1, the method comprising:

using a fiber including an artificial protein fiber to obtain a pile fabric having a pile protruded on one surface or both surfaces of the fabric; and cutting a loop of the pile to form a cut pile.

15. The method for manufacturing an artificial fur according to claim 14, wherein the artificial protein fiber is a shrink-proof artificial protein fiber.

16. The method for manufacturing an artificial fur according to claim 14, the method further comprising:

shrink-proofing the pile fabric.

17. The artificial fur according to claim 1, the artificial fur is comprised of the artificial protein fiber woven or knitted together.

18. The artificial fur according to claim 1, wherein one glycine residue in at least one motif sequence selected from GGX and GPGXX in an REP is substituted by another amino acid residue, where G is glycine residue, P is proline residue, and X is amino acid residue other than glycine.

19. The artificial fur according to claim 1, wherein a proportion of motif sequences where the glycine residue is substituted by another amino acid residue may be 10% or more of an entire motif sequence.

20. The artificial fur according to claim 1, wherein 10 to 40% of $(A)_n$ motifs from among the plurality of $(A)_n$ motifs are deleted.

* * * * *

SEQUENCE LISTING

```
<160> NUMBER OF SEQ ID NOS: 44

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50


<210> SEQ ID NO 2
<211> LENGTH: 30
<212> TYPE: PRT
```

-continued

<213> ORGANISM: Araneus diadematus

<400> SEQUENCE: 2

Ser Gly Cys Asp Val Leu Val Gln Ala Leu Leu Glu Val Val Ser Ala
1 5 10 15

Leu Val Ser Ile Leu Gly Ser Ser Ser Ile Gly Gln Ile Asn
20 25 30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1 5 10 15

Leu Val Ser Ile Leu
20

<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
ADF3KaiLargeNRSH1

<400> SEQUENCE: 4

Met His His His His His His His His His His Ser Ser Gly Ser Ser
1 5 10 15

Leu Glu Val Leu Phe Gln Gly Pro Ala Arg Ala Gly Ser Gly Gln Gln
20 25 30

Gly Pro Gly Gln Gln Gly Pro Gly Gln Gln Gly Pro Gly Gln Gln Gly
35 40 45

Pro Tyr Gly Pro Gly Ala Ser Ala Ala Ala Ala Ala Ala Gly Gly Tyr
50 55 60

Gly Pro Gly Ser Gly Gln Gln Gly Pro Ser Gln Gln Gly Pro Gly Gln
65 70 75 80

Gln Gly Pro Gly Gly Gln Gly Pro Tyr Gly Pro Gly Ala Ser Ala Ala
85 90 95

Ala Ala Ala Ala Gly Gly Tyr Gly Pro Gly Ser Gly Gln Gln Gly Pro
100 105 110

Gly Gly Gln Gly Pro Tyr Gly Pro Gly Ser Ser Ala Ala Ala Ala Ala
115 120 125

Ala Gly Gly Asn Gly Pro Gly Ser Gly Gln Gln Gly Ala Gly Gln Gln
130 135 140

Gly Pro Gly Gln Gln Gly Pro Gly Ala Ser Ala Ala Ala Ala Ala Ala
145 150 155 160

Gly Gly Tyr Gly Pro Gly Ser Gly Gln Gln Gly Pro Gly Gln Gln Gly
165 170 175

Pro Gly Gly Gln Gly Pro Tyr Gly Pro Gly Ala Ser Ala Ala Ala Ala
180 185 190

Ala Ala Gly Gly Tyr Gly Pro Gly Ser Gly Gln Gly Pro Gly Gln Gln
195 200 205

Gly Pro Gly Gly Gln Gly Pro Tyr Gly Pro Gly Ala Ser Ala Ala Ala
210 215 220

Ala Ala Ala Gly Gly Tyr Gly Pro Gly Ser Gly Gln Gln Gly Pro Gly
225 230 235 240

-continued

Gln Gln Gly Pro Gly Gln Gln Gly Pro Gly Gly Gln Gly Pro Tyr Gly
245 250 255

Pro Gly Ala Ser Ala Ala Ala Ala Ala Ala Gly Gly Tyr Gly Pro Gly
260 265 270

Tyr Gly Gln Gln Gly Pro Gly Gln Gln Gly Pro Gly Gly Gln Gly Pro
275 280 285

Tyr Gly Pro Gly Ala Ser Ala Ala Ser Ala Ala Ser Gly Gly Tyr Gly
290 295 300

Pro Gly Ser Gly Gln Gln Gly Pro Gly Gln Gln Gly Pro Gly Gly Gln
305 310 315 320

Gly Pro Tyr Gly Pro Gly Ala Ser Ala Ala Ala Ala Ala Ala Gly Gly
325 330 335

Tyr Gly Pro Gly Ser Gly Gln Gln Gly Pro Gly Gln Gln Gly Pro Gly
340 345 350

Gln Gln Gly Pro Gly Gln Gln Gly Pro Gly Gly Gln Gly Pro Tyr Gly
355 360 365

Pro Gly Ala Ser Ala Ala Ala Ala Ala Ala Gly Gly Tyr Gly Pro Gly
370 375 380

Ser Gly Gln Gln Gly Pro Gly Gln Gln Gly Pro Gly Gln Gln Gly Pro
385 390 395 400

Gly Gln Gln Gly Pro Gly Gln Gln Gly Pro Gly Gln Gln Gly Pro Gly
405 410 415

Gln Gln Gly Pro Gly Gln Gln Gly Pro Gly Gln Gln Gly Pro Gly Gly
420 425 430

Gln Gly Ala Tyr Gly Pro Gly Ala Ser Ala Ala Ala Gly Ala Ala Gly
435 440 445

Gly Tyr Gly Pro Gly Ser Gly Gln Gln Gly Pro Gly Gln Gln Gly Pro
450 455 460

Gly Gln Gln Gly Pro Gly Gln Gln Gly Pro Gly Gln Gln Gly Pro Gly
465 470 475 480

Gln Gln Gly Pro Gly Gln Gln Gly Pro Gly Gln Gln Gly Pro Tyr Gly
485 490 495

Pro Gly Ala Ser Ala Ala Ala Ala Ala Ala Gly Gly Tyr Gly Pro Gly
500 505 510

Ser Gly Gln Gln Gly Pro Gly Gln Gln Gly Pro Gly Gln Gln Gly Pro
515 520 525

Gly Gly Gln Gly Pro Tyr Gly Pro Gly Ala Ala Ser Ala Ala Val Ser
530 535 540

Val Ser Arg Ala Arg Ala Gly Ser Gly Gln Gln Gly Pro Gly Gln Gln
545 550 555 560

Gly Pro Gly Gln Gln Gly Pro Gly Gln Gln Gly Pro Tyr Gly Pro Gly
565 570 575

Ala Ser Ala Ala Ala Ala Ala Ala Gly Gly Tyr Gly Pro Gly Ser Gly
580 585 590

Gln Gln Gly Pro Ser Gln Gln Gly Pro Gly Gln Gln Gly Pro Gly Gly
595 600 605

Gln Gly Pro Tyr Gly Pro Gly Ala Ser Ala Ala Ala Ala Ala Ala Gly
610 615 620

Gly Tyr Gly Pro Gly Ser Gly Gln Gln Gly Pro Gly Gly Gln Gly Pro
625 630 635 640

Tyr Gly Pro Gly Ser Ser Ala Ala Ala Ala Ala Ala Gly Gly Asn Gly
645 650 655

-continued

```
Pro Gly Ser Gly Gln Gln Gly Ala Gly Gln Gln Gly Pro Gly Gln Gln
            660                 665                 670

Gly Pro Gly Ala Ser Ala Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780

Ala Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
        835                 840                 845

Gly Ala Ser Ala Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln  Gly Pro Gly Gln Gln  Gly Pro Gly
        995                 1000                1005

Gln Gln  Gly Pro Gly Gln Gln  Gly Pro Tyr Gly Pro  Gly Ala Ser
    1010                1015                1020

Ala Ala  Ala Ala Ala Ala Gly  Gly Tyr Gly Pro Gly  Ser Gly Gln
    1025                1030                1035

Gln Gly  Pro Gly Gln Gln Gly  Pro Gly Gln Gln Gly  Pro Gly Gly
    1040                1045                1050

Gln Gly  Pro Tyr Gly Pro Gly  Ala Ala Ser Ala Ala  Val Ser Val
    1055                1060                1065

Gly Gly  Tyr Gly Pro Gln Ser  Ser Ser Val Pro Val  Ala Ser Ala
```

```
    1070                1075                1080

Val Ala  Ser Arg Leu Ser Ser  Pro Ala Ala Ser Ser  Arg Val Ser
    1085                1090                1095

Ser Ala  Val Ser Ser Leu Val  Ser Ser Gly Pro Thr  Lys His Ala
    1100                1105                1110

Ala Leu  Ser Asn Thr Ile Ser  Ser Val Val Ser Gln  Val Ser Ala
    1115                1120                1125

Ser Asn  Pro Gly Leu Ser Gly  Cys Asp Val Leu Val  Gln Ala Leu
    1130                1135                1140

Leu Glu  Val Val Ser Ala Leu  Val Ser Ile Leu
    1145                1150
```

<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

```
Met His His His His His His His His His His Ser Ser Gly Ser Ser
1               5                   10                  15

Leu Glu Val Leu Phe Gln Gly Pro
            20
```

<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Ala Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Ala Gly Pro
    50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
            100                 105                 110

Gly Pro Gly Ser Ser Ala Ala Ala Ala Ala Gly Gln Tyr Gly Ser Gly
        115                 120                 125

Pro Gly Gln Gln Gly Pro Tyr Gly Ser Ala Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Ala Gly Ser Gly Gln Gln Gly Pro Gly
            180                 185                 190
```

-continued

```
Gln Tyr Gly Pro Tyr Ala Ser Ala Ala Ala Ala Ala Gly Gln Tyr Gly
        195                 200                 205

Ser Gly Pro Gly Gln Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gln Gln Gly Pro Tyr Gly
                245                 250                 255

Pro Gly Ser Ser Ala Ala Ala Ala Ala Gly Gln Tyr Gly Tyr Gly Pro
            260                 265                 270

Gly Gln Gln Gly Pro Tyr Gly Pro Gly Ala Ser Ala Ala Ala Ala Ala
        275                 280                 285

Gly Gln Asn Gly Pro Gly Ser Gly Gln Tyr Gly Pro Gly Gln Gln Gly
    290                 295                 300

Pro Gly Gln Ser Ala Ala Ala Ala Ala Gly Pro Gly Gln Gln Gly Pro
305                 310                 315                 320

Tyr Gly Pro Gly Ala Ser Ala Ala Ala Ala Ala Gly Gln Tyr Gly Pro
                325                 330                 335

Gly Gln Gln Gly Pro Gly Gln Tyr Gly Pro Gly Ser Ser Ala Ala Ala
            340                 345                 350

Ala Ala Gly Pro Gly Gln Gln Gly Pro Tyr Gly Pro Gly Ser Ser Ala
        355                 360                 365

Ala Ala Ala Ala Gly Gln Tyr Gly Pro Gly Gln Gln Gly Pro Tyr Gly
    370                 375                 380

Pro Gly Gln Ser Ala Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala Ala
                405                 410                 415

Gly Pro Gly Gln Gln Gly Pro Tyr Gly Pro Gly Ala Ser Ala Ala Ala
            420                 425                 430

Ala Ala Gly Pro Gly Gln Tyr Gly Pro Gly Gln Gln Gly Pro Ser Ala
        435                 440                 445

Ser Ala Ala Ala Ala Ala Gly Gln Tyr Gly Ser Gly Pro Gly Gln Tyr
    450                 455                 460

Gly Pro Tyr Gly Pro Gly Gln Ser Ala Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gln Tyr Gly Pro Gly Gln Gln Gly Pro Tyr Gly Pro
            500                 505                 510

Gly Gln Ser Ala Ala Ala Ala Ala Gly Pro Gly Ser Gly Gln Tyr Gly
        515                 520                 525

Pro Gly Ala Ser Ala Ala Ala Ala Ala Gly Gln Asn Gly Pro Gly Ser
    530                 535                 540

Gly Gln Tyr Gly Pro Gly Gln Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
                565                 570                 575

Pro Gly Ala Ser Ala Ala Ala Ala Ala Gly Pro Gly Ser Gly Gln Gln
            580                 585                 590

Gly Pro Gly Ala Ser
        595
```

<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175

Gly Gln Tyr Gly Pro Tyr Ala Ser Ala Ala Ala Ala Ala Gly Gln Tyr
            180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Ala Gly Gln Tyr Gln Gln
        355                 360                 365

Gly Pro Gly Gln Gln Gly Pro Tyr Gly Pro Gly Ala Ser Gly Pro Gly
```

```
    370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Ala Gly Gln Tyr Gly Pro
    450                 455                 460

Gly Gln Gln Gly Pro Tyr Gly Pro Gly Gln Ser Ala Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590


<210> SEQ ID NO 8
<211> LENGTH: 565
<212> TYPE: PRT
<213> ORGANISM: Artificial Sequence
<220> FEATURE:
<223> OTHER INFORMATION: Met-PRT525

<400> SEQUENCE: 8

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Ala Ala Gly Ser Tyr Gly Ser Gly Pro Gly
        115                 120                 125

Gln Gln Gly Pro Tyr Gly Ser Ala Ala Ala Ala Ala Ala Ala Gly Pro
    130                 135                 140

Gly Ser Gly Gln Tyr Gly Gln Gly Pro Tyr Gly Pro Gly Ala Ser Gly
```

-continued

```
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Ala Gly Ser Tyr Gly Ser
        195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
        275                 280                 285

Gly Gln Tyr Gly Pro Gly Gln Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Ala Gly Ser Tyr Gly Pro Gly Gln Gln
                325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Ala Ala Gly Ser
        355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Ala Gly Pro Gly Gln Tyr
            420                 425                 430

Gly Pro Gly Gln Gln Gly Pro Ser Ala Ser Ala Ala Ala Ala Ala Ala
        435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Ala Gly Ser Tyr Gly Pro
                485                 490                 495

Gly Gln Gln Gly Pro Tyr Gly Pro Gly Pro Ser Ala Ala Ala Ala Ala
            500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
    530                 535                 540

Pro Ser Ala Ala Ala Ala Ala Ala Ala Gly Pro Gly Ser Gly Gln Gln
545                 550                 555                 560

Gly Pro Gly Ala Ser
                565
```

<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175

Gly Gln Tyr Gly Pro Tyr Ala Ser Ala Ala Ala Ala Ala Gly Gln Tyr
            180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Ala Gly Gln Tyr Gln Gln
        355                 360                 365
```

```
Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Ala Gly Gln Tyr Gly Pro
    450                 455                 460

Gly Gln Gln Gly Pro Tyr Gly Pro Gly Gln Ser Ala Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser Gly Gln
            580                 585                 590

Gln Gly Pro Tyr Gly Pro Gly Ala Ser Ala Ala Ala Ala Ala Gly Gln
        595                 600                 605

Asn Gly Pro Gly Ser Gly Gln Gln Gly Pro Gly Gln Ser Gly Gln Tyr
    610                 615                 620

Gly Pro Gly Gln Gln Gly Pro Gly Gln Gln Gly Pro Gly Ser Ser Ala
625                 630                 635                 640

Ala Ala Ala Ala Gly Pro Gly Gln Tyr Gly Pro Gly Gln Gln Gly Pro
                645                 650                 655

Ser Ala Ser Ala Ala Ala Ala Ala Gly Pro Gly Ser Gly Gln Gln Gly
            660                 665                 670

Pro Gly Ala Ser Gly Gln Tyr Gly Pro Gly Gln Gln Gly Pro Gly Gln
        675                 680                 685

Gln Gly Pro Gly Ser Ser Ala Ala Ala Ala Ala Gly Gln Tyr Gly Ser
    690                 695                 700

Gly Pro Gly Gln Gln Gly Pro Tyr Gly Ser Ala Ala Ala Ala Ala Gly
705                 710                 715                 720

Pro Gly Ser Gly Gln Tyr Gly Gln Gly Pro Tyr Gly Pro Gly Ala Ser
                725                 730                 735

Gly Pro Gly Gln Tyr Gly Pro Gly Gln Gln Gly Pro Ser Ala Ser Ala
            740                 745                 750

Ala Ala Ala Ala Gly Ser Gly Gln Gln Gly Pro Gly Gln Tyr Gly Pro
        755                 760                 765

Tyr Ala Ser Ala Ala Ala Ala Ala Gly Gln Tyr Gly Ser Gly Pro Gly
    770                 775                 780
```

-continued

```
Gln Gln Gly Pro Tyr Gly Pro Gly Gln Ser Gly Ser Gly Gln Gln Gly
785                 790                 795                 800

Pro Gly Gln Gln Gly Pro Tyr Ala Ser Ala Ala Ala Ala Ala Gly Pro
                805                 810                 815

Gly Gln Gln Gly Pro Tyr Gly Pro Gly Ser Ser Ala Ala Ala Ala Ala
            820                 825                 830

Gly Gln Tyr Gly Tyr Gly Pro Gly Gln Gln Gly Pro Tyr Gly Pro Gly
        835                 840                 845

Ala Ser Gly Gln Asn Gly Pro Gly Ser Gly Gln Tyr Gly Pro Gly Gln
    850                 855                 860

Gln Gly Pro Gly Gln Ser Ala Ala Ala Ala Ala Gly Pro Gly Gln Gln
865                 870                 875                 880

Gly Pro Tyr Gly Pro Gly Ala Ser Ala Ala Ala Ala Ala Gly Gln Tyr
                885                 890                 895

Gly Pro Gly Gln Gln Gly Pro Gly Gln Tyr Gly Pro Gly Ser Ser Gly
            900                 905                 910

Pro Gly Gln Gln Gly Pro Tyr Gly Pro Gly Ser Ser Ala Ala Ala Ala
        915                 920                 925

Ala Gly Gln Tyr Gly Pro Gly Gln Gln Gly Pro Tyr Gly Pro Gly Gln
    930                 935                 940

Ser Ala Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Gly Pro Tyr
                965                 970                 975

Gly Pro Gly Ala Ser Ala Ala Ala Ala Ala Gly Pro Gly Gln Tyr Gly
            980                 985                 990

Pro Gly Gln Gln Gly Pro Ser Ala  Ser Ala Ala Ala Ala  Ala Gly Gln
        995                 1000                1005

Tyr Gly  Ser Gly Pro Gly Gln  Tyr Gly Pro Tyr Gly  Pro Gly Gln
    1010                 1015                 1020

Ser Gly  Pro Gly Ser Gly Gln  Gln Gly Gln Gly Pro  Tyr Gly Pro
    1025                 1030                 1035

Gly Ala  Ser Ala Ala Ala Ala  Ala Gly Gln Tyr Gly  Pro Gly Gln
    1040                 1045                 1050

Gln Gly  Pro Tyr Gly Pro Gly  Gln Ser Ala Ala Ala  Ala Ala Gly
    1055                 1060                 1065

Pro Gly  Ser Gly Gln Tyr Gly  Pro Gly Ala Ser Gly  Gln Asn Gly
    1070                 1075                 1080

Pro Gly  Ser Gly Gln Tyr Gly  Pro Gly Gln Gln Gly  Pro Gly Gln
    1085                 1090                 1095

Ser Ala  Ala Ala Ala Ala Gly  Gln Tyr Gln Gln Gly  Pro Gly Gln
    1100                 1105                 1110

Gln Gly  Pro Tyr Gly Pro Gly  Ala Ser Ala Ala Ala  Ala Ala Gly
    1115                 1120                 1125

Gln Tyr  Gly Ser Gly Pro Gly  Gln Gln Gly Pro Tyr  Gly Pro Gly
    1130                 1135                 1140

Gln Ser  Gly Ser Gly Gln Gln  Gly Pro Gly Gln Gln  Gly Pro Tyr
    1145                 1150                 1155

Ala Ser  Ala Ala Ala Ala Ala  Gly Pro Gly Ser Gly  Gln Gln Gly
    1160                 1165                 1170

Pro Gly  Ala Ser Gly Gln Gln  Gly Pro Tyr Gly Pro  Gly Ala Ser
    1175                 1180                 1185

Ala Ala  Ala Ala Ala Gly Gln  Asn Gly Pro Gly Ser  Gly Gln Gln
```

-continued

```
    1190                1195                1200

Gly Pro  Gly Gln Ser Gly Gln  Tyr Gly Pro Gly Gln  Gln Gly Pro
    1205                1210                1215

Gly Gln  Gln Gly Pro Gly Ser  Ser Ala Ala Ala Ala  Ala Gly Pro
    1220                1225                1230

Gly Gln  Tyr Gly Pro Gly Gln  Gln Gly Pro Ser Ala  Ser Ala Ala
    1235                1240                1245

Ala Ala  Ala Gly Pro Gly Ser  Gly Gln Gln Gly Pro  Gly Ala Ser
    1250                1255                1260

Gly Gln  Tyr Gly Pro Gly Gln  Gln Gly Pro Gly Gln  Gln Gly Pro
    1265                1270                1275

Gly Ser  Ser Ala Ala Ala Ala  Ala Gly Gln Tyr Gly  Ser Gly Pro
    1280                1285                1290

Gly Gln  Gln Gly Pro Tyr Gly  Ser Ala Ala Ala Ala  Ala Gly Pro
    1295                1300                1305

Gly Ser  Gly Gln Tyr Gly Gln  Gly Pro Tyr Gly Pro  Gly Ala Ser
    1310                1315                1320

Gly Pro  Gly Gln Tyr Gly Pro  Gly Gln Gln Gly Pro  Ser Ala Ser
    1325                1330                1335

Ala Ala  Ala Ala Ala Gly Ser  Gly Gln Gln Gly Pro  Gly Gln Tyr
    1340                1345                1350

Gly Pro  Tyr Ala Ser Ala Ala  Ala Ala Ala Gly Gln  Tyr Gly Ser
    1355                1360                1365

Gly Pro  Gly Gln Gln Gly Pro  Tyr Gly Pro Gly Gln  Ser Gly Ser
    1370                1375                1380

Gly Gln  Gln Gly Pro Gly Gln  Gln Gly Pro Tyr Ala  Ser Ala Ala
    1385                1390                1395

Ala Ala  Ala Gly Pro Gly Gln  Gln Gly Pro Tyr Gly  Pro Gly Ser
    1400                1405                1410

Ser Ala  Ala Ala Ala Ala Gly  Gln Tyr Gly Tyr Gly  Pro Gly Gln
    1415                1420                1425

Gln Gly  Pro Tyr Gly Pro Gly  Ala Ser Gly Gln Asn  Gly Pro Gly
    1430                1435                1440

Ser Gly  Gln Tyr Gly Pro Gly  Gln Gln Gly Pro Gly  Gln Ser Ala
    1445                1450                1455

Ala Ala  Ala Ala Gly Pro Gly  Gln Gln Gly Pro Tyr  Gly Pro Gly
    1460                1465                1470

Ala Ser  Ala Ala Ala Ala Ala  Gly Gln Tyr Gly Pro  Gly Gln Gln
    1475                1480                1485

Gly Pro  Gly Gln Tyr Gly Pro  Gly Ser Ser Gly Pro  Gly Gln Gln
    1490                1495                1500

Gly Pro  Tyr Gly Pro Gly Ser  Ser Ala Ala Ala Ala  Ala Gly Gln
    1505                1510                1515

Tyr Gly  Pro Gly Gln Gln Gly  Pro Tyr Gly Pro Gly  Gln Ser Ala
    1520                1525                1530

Ala Ala  Ala Ala Gly Gln Tyr  Gln Gln Gly Pro Gly  Gln Gln Gly
    1535                1540                1545

Pro Tyr  Gly Pro Gly Ala Ser  Gly Pro Gly Gln Gln  Gly Pro Tyr
    1550                1555                1560

Gly Pro  Gly Ala Ser Ala Ala  Ala Ala Ala Gly Pro  Gly Gln Tyr
    1565                1570                1575

Gly Pro  Gly Gln Gln Gly Pro  Ser Ala Ser Ala Ala  Ala Ala Ala
    1580                1585                1590
```

```
Gly Gln  Tyr Gly Ser Gly Pro  Gly Gln Tyr Gly Pro  Tyr Gly Pro
    1595                 1600                 1605

Gly Gln  Ser Gly Pro Gly Ser  Gly Gln Gln Gly Gln  Gly Pro Tyr
    1610                 1615                 1620

Gly Pro  Gly Ala Ser Ala Ala  Ala Ala Ala Gly Gln  Tyr Gly Pro
    1625                 1630                 1635

Gly Gln  Gln Gly Pro Tyr Gly  Pro Gly Gln Ser Ala  Ala Ala Ala
    1640                 1645                 1650

Ala Gly  Pro Gly Ser Gly Gln  Tyr Gly Pro Gly Ala  Ser Gly Gln
    1655                 1660                 1665

Asn Gly  Pro Gly Ser Gly Gln  Tyr Gly Pro Gly Gln  Gln Gly Pro
    1670                 1675                 1680

Gly Gln  Ser Ala Ala Ala Ala  Ala Gly Gln Tyr Gln  Gln Gly Pro
    1685                 1690                 1695

Gly Gln  Gln Gly Pro Tyr Gly  Pro Gly Ala Ser Ala  Ala Ala Ala
    1700                 1705                 1710

Ala Gly  Gln Tyr Gly Ser Gly  Pro Gly Gln Gln Gly  Pro Tyr Gly
    1715                 1720                 1725

Pro Gly  Gln Ser Gly Ser Gly  Gln Gln Gly Pro Gly  Gln Gln Gly
    1730                 1735                 1740

Pro Tyr  Ala Ser Ala Ala Ala  Ala Ala Gly Pro Gly  Ser Gly Gln
    1745                 1750                 1755

Gln Gly  Pro Gly Ala Ser Gly  Gln Gln Gly Pro Tyr  Gly Pro Gly
    1760                 1765                 1770

Ala Ser  Ala Ala Ala Ala Ala  Gly Gln Asn Gly Pro  Gly Ser Gly
    1775                 1780                 1785

Gln Gln  Gly Pro Gly Gln Ser  Gly Gln Tyr Gly Pro  Gly Gln Gln
    1790                 1795                 1800

Gly Pro  Gly Gln Gln Gly Pro  Gly Ser Ser Ala Ala  Ala Ala Ala
    1805                 1810                 1815

Gly Pro  Gly Gln Tyr Gly Pro  Gly Gln Gln Gly Pro  Ser Ala Ser
    1820                 1825                 1830

Ala Ala  Ala Ala Ala Gly Pro  Gly Ser Gly Gln Gln  Gly Pro Gly
    1835                 1840                 1845

Ala Ser  Gly Gln Tyr Gly Pro  Gly Gln Gln Gly Pro  Gly Gln Gln
    1850                 1855                 1860

Gly Pro  Gly Ser Ser Ala Ala  Ala Ala Ala Gly Gln  Tyr Gly Ser
    1865                 1870                 1875

Gly Pro  Gly Gln Gln Gly Pro  Tyr Gly Ser Ala Ala  Ala Ala Ala
    1880                 1885                 1890

Gly Pro  Gly Ser Gly Gln Tyr  Gly Gln Gly Pro Tyr  Gly Pro Gly
    1895                 1900                 1905

Ala Ser  Gly Pro Gly Gln Tyr  Gly Pro Gly Gln Gln  Gly Pro Ser
    1910                 1915                 1920

Ala Ser  Ala Ala Ala Ala Ala  Gly Ser Gly Gln Gln  Gly Pro Gly
    1925                 1930                 1935

Gln Tyr  Gly Pro Tyr Ala Ser  Ala Ala Ala Ala Ala  Gly Gln Tyr
    1940                 1945                 1950

Gly Ser  Gly Pro Gly Gln Gln  Gly Pro Tyr Gly Pro  Gly Gln Ser
    1955                 1960                 1965

Gly Ser  Gly Gln Gln Gly Pro  Gly Gln Gln Gly Pro  Tyr Ala Ser
    1970                 1975                 1980
```

```
Ala Ala  Ala Ala Ala Gly Pro  Gly Gln Gln Gly Pro  Tyr Gly Pro
    1985                 1990                 1995

Gly Ser  Ser Ala Ala Ala Ala  Ala Gly Gln Tyr Gly  Tyr Gly Pro
    2000                 2005                 2010

Gly Gln  Gln Gly Pro Tyr Gly  Pro Gly Ala Ser Gly  Gln Asn Gly
    2015                 2020                 2025

Pro Gly  Ser Gly Gln Tyr Gly  Pro Gly Gln Gln Gly  Pro Gly Gln
    2030                 2035                 2040

Ser Ala  Ala Ala Ala Ala Gly  Pro Gly Gln Gln Gly  Pro Tyr Gly
    2045                 2050                 2055

Pro Gly  Ala Ser Ala Ala Ala  Ala Ala Gly Gln Tyr  Gly Pro Gly
    2060                 2065                 2070

Gln Gln  Gly Pro Gly Gln Tyr  Gly Pro Gly Ser Ser  Gly Pro Gly
    2075                 2080                 2085

Gln Gln  Gly Pro Tyr Gly Pro  Gly Ser Ser Ala Ala  Ala Ala Ala
    2090                 2095                 2100

Gly Gln  Tyr Gly Pro Gly Gln  Gln Gly Pro Tyr Gly  Pro Gly Gln
    2105                 2110                 2115

Ser Ala  Ala Ala Ala Ala Gly  Gln Tyr Gln Gln Gly  Pro Gly Gln
    2120                 2125                 2130

Gln Gly  Pro Tyr Gly Pro Gly  Ala Ser Gly Pro Gly  Gln Gln Gly
    2135                 2140                 2145

Pro Tyr  Gly Pro Gly Ala Ser  Ala Ala Ala Ala Ala  Gly Pro Gly
    2150                 2155                 2160

Gln Tyr  Gly Pro Gly Gln Gln  Gly Pro Ser Ala Ser  Ala Ala Ala
    2165                 2170                 2175

Ala Ala  Gly Gln Tyr Gly Ser  Gly Pro Gly Gln Tyr  Gly Pro Tyr
    2180                 2185                 2190

Gly Pro  Gly Gln Ser Gly Pro  Gly Ser Gly Gln Gln  Gly Gln Gly
    2195                 2200                 2205

Pro Tyr  Gly Pro Gly Ala Ser  Ala Ala Ala Ala Ala  Gly Gln Tyr
    2210                 2215                 2220

Gly Pro  Gly Gln Gln Gly Pro  Tyr Gly Pro Gly Gln  Ser Ala Ala
    2225                 2230                 2235

Ala Ala  Ala Gly Pro Gly Ser  Gly Gln Tyr Gly Pro  Gly Ala Ser
    2240                 2245                 2250

Gly Gln  Asn Gly Pro Gly Ser  Gly Gln Tyr Gly Pro  Gly Gln Gln
    2255                 2260                 2265

Gly Pro  Gly Gln Ser Ala Ala  Ala Ala Ala Gly Gln  Tyr Gln Gln
    2270                 2275                 2280

Gly Pro  Gly Gln Gln Gly Pro  Tyr Gly Pro Gly Ala  Ser Ala Ala
    2285                 2290                 2295

Ala Ala  Ala Gly Gln Tyr Gly  Ser Gly Pro Gly Gln  Gln Gly Pro
    2300                 2305                 2310

Tyr Gly  Pro Gly Gln Ser Gly  Ser Gly Gln Gln Gly  Pro Gly Gln
    2315                 2320                 2325

Gln Gly  Pro Tyr Ala Ser Ala  Ala Ala Ala Ala Gly  Pro Gly Ser
    2330                 2335                 2340

Gly Gln  Gln Gly Ser Ser Val  Asp Lys Leu Ala Ala  Ala Leu Glu
    2345                 2350                 2355

His His  His His His His
    2360
```

```
<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Ala Gly Gly Tyr Gly Pro Gly Gly Gln Gly
        35                  40                  45

Pro Gly Gln Gln Gly Pro Gly Ser Ser Ala Ala Ala Ala Ala Gly Pro
    50                  55                  60

Gly Gly Tyr Gly Pro Gly Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Ala Gly Gly Tyr Gly Ser Gly
        115                 120                 125

Pro Gly Gln Gln Gly Pro Tyr Gly Ser Ala Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Ala Gly Pro Gly Gly Tyr Gly Pro Gly Gly Gln Gly Pro
                165                 170                 175

Ser Ala Ser Ala Ala Ala Ala Ala Gly Ser Gly Gln Gln Gly Pro Gly
            180                 185                 190

Gly Tyr Gly Pro Tyr Ala Ser Ala Ala Ala Ala Ala Gly Gly Tyr Gly
        195                 200                 205

Ser Gly Pro Gly Gln Gln Gly Pro Tyr Gly Pro Gly Gly Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gly Gln Gly Pro Tyr Gly
                245                 250                 255

Pro Gly Ser Ser Ala Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala Ala
        275                 280                 285

Gly Gly Asn Gly Pro Gly Ser Gly Gly Tyr Gly Pro Gly Gln Gln Gly
    290                 295                 300

Pro Gly Gly Ser Ala Ala Ala Ala Ala Gly Pro Gly Gly Gln Gly Pro
305                 310                 315                 320

Tyr Gly Pro Gly Ala Ser Ala Ala Ala Ala Ala Gly Gly Tyr Gly Pro
                325                 330                 335

Gly Gly Gln Gly Pro Gly Gly Tyr Gly Pro Gly Ser Ser Ala Ala Ala
            340                 345                 350

Ala Ala Gly Pro Gly Gly Gln Gly Pro Tyr Gly Pro Gly Ser Ser Ala
        355                 360                 365

Ala Ala Ala Ala Gly Gly Tyr Gly Pro Gly Gln Gln Gly Pro Tyr Gly
```

```
    370                 375                 380

Pro Gly Gly Ser Ala Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala Ala
                405                 410                 415

Gly Pro Gly Gly Gln Gly Pro Tyr Gly Pro Gly Ala Ser Ala Ala Ala
            420                 425                 430

Ala Ala Gly Pro Gly Gly Tyr Gly Pro Gly Gly Gln Gly Pro Ser Ala
        435                 440                 445

Ser Ala Ala Ala Ala Ala Gly Gly Tyr Gly Ser Gly Pro Gly Gly Tyr
    450                 455                 460

Gly Pro Tyr Gly Pro Gly Gly Ser Ala Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Ala Gly Pro Gly Ser Gly Gly Tyr Gly
        515                 520                 525

Pro Gly Ala Ser Ala Ala Ala Ala Ala Gly Gly Asn Gly Pro Gly Ser
    530                 535                 540

Gly Gly Tyr Gly Pro Gly Gln Gln Gly Pro Gly Gly Ser Ala Ala Ala
545                 550                 555                 560

Ala Ala Gly Gly Tyr Gln Gln Gly Pro Gly Gly Gln Gly Pro Tyr Gly
                565                 570                 575

Pro Gly Ala Ser Ala Ala Ala Ala Ala Gly Pro Gly Ser Gly Gln Gln
            580                 585                 590

Gly Pro Gly Ala Ser
        595


<210> SEQ ID NO 11
<211> LENGTH: 12
<212> TYPE: PRT
<213> ORGANISM: Artificial Sequence
<220> FEATURE:
<223> OTHER INFORMATION: HisTag

<400> SEQUENCE: 11

Met His His His His His His Ser Ser Gly Ser Ser
1               5                   10


<210> SEQ ID NO 12
<211> LENGTH: 608
<212> TYPE: PRT
<213> ORGANISM: Artificial Sequence
<220> FEATURE:
<223> OTHER INFORMATION: PRT380

<400> SEQUENCE: 12

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Ala Ala Ala
        35                  40                  45

Ala Ala Gly Gln Tyr Gly Pro Gly Gln Gln Gly Pro Gly Gln Gln Gly
    50                  55                  60
```

-continued

```
Pro Gly Ser Ser Ala Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Ala Gly Gln
            100                 105                 110

Tyr Gly Pro Gly Gln Gln Gly Pro Gly Gln Gln Gly Pro Gly Ser Ser
        115                 120                 125

Ala Ala Ala Ala Ala Gly Gln Tyr Gly Ser Gly Pro Gly Gln Gln Gly
    130                 135                 140

Pro Tyr Gly Ser Ala Ala Ala Ala Ala Gly Pro Gly Ser Gly Gln Tyr
145                 150                 155                 160

Gly Gln Gly Pro Tyr Gly Pro Gly Ala Ser Ala Ala Ala Ala Ala Gly
                165                 170                 175

Pro Gly Gln Tyr Gly Pro Gly Gln Gln Gly Pro Ser Ala Ser Ala Ala
            180                 185                 190

Ala Ala Ala Gly Ser Gly Gln Gln Gly Pro Gly Gln Tyr Gly Pro Tyr
        195                 200                 205

Ala Ser Ala Ala Ala Ala Ala Gly Gln Tyr Gly Ser Gly Pro Gly Gln
    210                 215                 220

Gln Gly Pro Tyr Gly Pro Gly Gln Ser Ala Ala Ala Ala Ala Gly Ser
225                 230                 235                 240

Gly Gln Gln Gly Pro Gly Gln Gln Gly Pro Tyr Ala Ser Ala Ala Ala
                245                 250                 255

Ala Ala Gly Pro Gly Gln Gln Gly Pro Tyr Gly Pro Gly Ser Ser Ala
            260                 265                 270

Ala Ala Ala Ala Gly Gln Tyr Gly Tyr Gly Pro Gly Gln Gln Gly Pro
        275                 280                 285

Tyr Gly Pro Gly Ala Ser Ala Ala Ala Ala Ala Gly Gln Asn Gly Pro
    290                 295                 300

Gly Ser Gly Gln Tyr Gly Pro Gly Gln Gln Gly Pro Gly Gln Ser Ala
305                 310                 315                 320

Ala Ala Ala Ala Gly Pro Gly Gln Gln Gly Pro Tyr Gly Pro Gly Ala
                325                 330                 335

Ser Ala Ala Ala Ala Ala Gly Gln Tyr Gly Pro Gly Gln Gln Gly Pro
            340                 345                 350

Gly Gln Tyr Gly Pro Gly Ser Ser Ala Ala Ala Ala Ala Gly Pro Gly
        355                 360                 365

Gln Gln Gly Pro Tyr Gly Pro Gly Ser Ser Ala Ala Ala Ala Ala Gly
    370                 375                 380

Gln Tyr Gly Pro Gly Gln Gln Gly Pro Tyr Gly Pro Gly Gln Ser Ala
385                 390                 395                 400

Ala Ala Ala Ala Gly Gln Tyr Gln Gln Gly Pro Gly Gln Gln Gly Pro
                405                 410                 415

Tyr Gly Pro Gly Ala Ser Ala Ala Ala Ala Ala Gly Pro Gly Gln Gln
            420                 425                 430

Gly Pro Tyr Gly Pro Gly Ala Ser Ala Ala Ala Ala Ala Gly Pro Gly
        435                 440                 445

Gln Tyr Gly Pro Gly Gln Gln Gly Pro Ser Ala Ser Ala Ala Ala Ala
    450                 455                 460

Ala Gly Gln Tyr Gly Ser Gly Pro Gly Gln Tyr Gly Pro Tyr Gly Pro
465                 470                 475                 480

Gly Gln Ser Ala Ala Ala Ala Ala Gly Pro Gly Ser Gly Gln Gln Gly
```

```
                485                 490                 495

Gln Gly Pro Tyr Gly Pro Gly Ala Ser Ala Ala Ala Ala Ala Gly Gln
            500                 505                 510

Tyr Gly Pro Gly Gln Gln Gly Pro Tyr Gly Pro Gly Gln Ser Ala Ala
        515                 520                 525

Ala Ala Ala Gly Pro Gly Ser Gly Gln Tyr Gly Pro Gly Ala Ser Ala
    530                 535                 540

Ala Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Ala Gly Gln Tyr
                565                 570                 575

Gln Gln Gly Pro Gly Gln Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
        595                 600                 605


<210> SEQ ID NO 13
<211> LENGTH: 601
<212> TYPE: PRT
<213> ORGANISM: Artificial Sequence
<220> FEATURE:
<223> OTHER INFORMATION: PRT410

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Ala Gly Gln Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Ala Gly Pro
225                 230                 235                 240

Gly Gln Gln Gly Pro Tyr Gly Pro Gly Ser Ser Ala Ala Ala Ala Ala
```

-continued

```
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Ala Gly Pro Gly Gln Gln
    290                 295                 300

Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Ala Gly Pro Gly Gln Tyr Gly
                405                 410                 415

Pro Gly Gln Gln Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
        515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590

Ser Gly Gln Gln Gly Pro Gly Ala Ser
        595                 600


<210> SEQ ID NO 14
<211> LENGTH: 576
<212> TYPE: PRT
<213> ORGANISM: Artificial Sequence
<220> FEATURE:
<223> OTHER INFORMATION: PRT525

<400> SEQUENCE: 14

Met His His His His His His Ser Ser Gly Ser Ser Gly Pro Gly Gln
```

-continued

```
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Ala Ala Gly Ser Tyr Gly Ser Gly Pro Gly Gln Gln Gly Pro Tyr
    130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala Ala
            180                 185                 190

Gly Ser Gly Gln Gln Gly Pro Gly Gln Tyr Gly Pro Tyr Ala Ser Ala
        195                 200                 205

Ala Ala Ala Ala Ala Ala Gly Ser Tyr Gly Ser Gly Pro Gly Gln Gln
    210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Ala Gly Pro
                245                 250                 255

Gly Gln Gln Gly Pro Tyr Gly Pro Gly Ser Ser Ala Ala Ala Ala Ala
            260                 265                 270

Ala Ala Gly Ser Tyr Gly Tyr Gly Pro Gly Gln Gln Gly Pro Tyr Gly
        275                 280                 285

Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Ala Ala Gly
305                 310                 315                 320

Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
        355                 360                 365

Ser Ser Ala Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
            420                 425                 430
```

```
Ala Ala Ala Ala Ala Ala Gly Pro Gly Gln Tyr Gly Pro Gly Gln Gln
        435                 440                 445

Gly Pro Ser Ala Ser Ala Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
                485                 490                 495

Ala Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575


<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Ala Gly Gln Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220
```

-continued

```
Pro Gly Gln Gln Gly Pro Tyr Ala Ser Ala Ala Ala Ala Ala Gly Pro
225                 230                 235                 240

Gly Gln Gln Gly Pro Tyr Gly Pro Gly Ser Ser Ala Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Ala Gly Pro Gly Gln Gln
    290                 295                 300

Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Ala Gly Pro Gly Gln Tyr Gly
                405                 410                 415

Pro Gly Gln Gln Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
        515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590

Ser Gly Gln Gln Gly Pro Gly Ala Ser Gly Gln Gln Gly Pro Tyr Gly
        595                 600                 605

Pro Gly Ala Ser Ala Ala Ala Ala Ala Gly Gln Asn Gly Pro Gly Ser
    610                 615                 620

Gly Gln Gln Gly Pro Gly Gln Ser Gly Gln Tyr Gly Pro Gly Gln Gln
625                 630                 635                 640
```

-continued

```
Gly Pro Gly Gln Gln Gly Pro Gly Ser Ser Ala Ala Ala Ala Ala Gly
                645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
        675                 680                 685

Gln Tyr Gly Pro Gly Gln Gln Gly Pro Gly Gln Gln Gly Pro Gly Ser
    690                 695                 700

Ser Ala Ala Ala Ala Ala Gly Gln Tyr Gly Ser Gly Pro Gly Gln Gln
705                 710                 715                 720

Gly Pro Tyr Gly Ser Ala Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Ala Gly
        755                 760                 765

Ser Gly Gln Gln Gly Pro Gly Gln Tyr Gly Pro Tyr Ala Ser Ala Ala
    770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Ala Gly Pro Gly Gln Gln Gly Pro
            820                 825                 830

Tyr Gly Pro Gly Ser Ser Ala Ala Ala Ala Ala Gly Gln Tyr Gly Tyr
        835                 840                 845

Gly Pro Gly Gln Gln Gly Pro Tyr Gly Pro Gly Ala Ser Gly Gln Asn
    850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gly Gln Gln Gly Pro Tyr Gly Pro
                885                 890                 895

Gly Ala Ser Ala Ala Ala Ala Ala Gly Gln Tyr Gly Pro Gly Gln Gln
            900                 905                 910

Gly Pro Gly Gln Tyr Gly Pro Gly Ser Ser Gly Pro Gly Gln Gln Gly
        915                 920                 925

Pro Tyr Gly Pro Gly Ser Ser Ala Ala Ala Ala Ala Gly Gln Tyr Gly
    930                 935                 940

Pro Gly Gln Gln Gly Pro Tyr Gly Pro Gly Gln Ser Ala Ala Ala Ala
945                 950                 955                 960

Ala Gly Gln Tyr Gln Gln Gly Pro Gly Gln Gln Gly Pro Tyr Gly Pro
                965                 970                 975

Gly Ala Ser Gly Pro Gly Gln Gln Gly Pro Tyr Gly Pro Gly Ala Ser
            980                 985                 990

Ala Ala Ala Ala Ala Gly Pro Gly  Gln Tyr Gly Pro Gly  Gln Gln Gly
        995                 1000                1005

Pro Ser  Ala Ser Ala Ala Ala  Ala Ala Gly Gln Tyr  Gly Ser Gly
    1010                 1015                 1020

Pro Gly  Gln Tyr Gly Pro Tyr  Gly Pro Gly Gln Ser  Gly Pro Gly
    1025                 1030                 1035

Ser Gly  Gln Gln Gly Gln Gly  Pro Tyr Gly Pro Gly  Ala Ser Ala
    1040                 1045                 1050

Ala Ala  Ala Ala Gly Gln Tyr  Gly Pro Gly Gln Gln  Gly Pro Tyr
```

-continued

```
    1055                1060                1065

Gly Pro  Gly Gln Ser Ala Ala  Ala Ala Ala Gly Pro  Gly Ser Gly
    1070                1075                1080

Gln Tyr  Gly Pro Gly Ala Ser  Gly Gln Asn Gly Pro  Gly Ser Gly
    1085                1090                1095

Gln Tyr  Gly Pro Gly Gln Gln  Gly Pro Gly Gln Ser  Ala Ala Ala
    1100                1105                1110

Ala Ala  Gly Gln Tyr Gln Gln  Gly Pro Gly Gln Gln  Gly Pro Tyr
    1115                1120                1125

Gly Pro  Gly Ala Ser Ala Ala  Ala Ala Ala Gly Gln  Tyr Gly Ser
    1130                1135                1140

Gly Pro  Gly Gln Gln Gly Pro  Tyr Gly Pro Gly Gln  Ser Gly Ser
    1145                1150                1155

Gly Gln  Gln Gly Pro Gly Gln  Gln Gly Pro Tyr Ala  Ser Ala Ala
    1160                1165                1170

Ala Ala  Ala Gly Pro Gly Ser  Gly Gln Gln Gly Pro  Gly Ala Ser
    1175                1180                1185

Gly Gln  Gln Gly Pro Tyr Gly  Pro Gly Ala Ser Ala  Ala Ala Ala
    1190                1195                1200

Ala Gly  Gln Asn Gly Pro Gly  Ser Gly Gln Gln Gly  Pro Gly Gln
    1205                1210                1215

Ser Gly  Gln Tyr Gly Pro Gly  Gln Gln Gly Pro Gly  Gln Gln Gly
    1220                1225                1230

Pro Gly  Ser Ser Ala Ala Ala  Ala Ala Gly Pro Gly  Gln Tyr Gly
    1235                1240                1245

Pro Gly  Gln Gln Gly Pro Ser  Ala Ser Ala Ala Ala  Ala Ala Gly
    1250                1255                1260

Pro Gly  Ser Gly Gln Gln Gly  Pro Gly Ala Ser Gly  Gln Tyr Gly
    1265                1270                1275

Pro Gly  Gln Gln Gly Pro Gly  Gln Gln Gly Pro Gly  Ser Ser Ala
    1280                1285                1290

Ala Ala  Ala Ala Gly Gln Tyr  Gly Ser Gly Pro Gly  Gln Gln Gly
    1295                1300                1305

Pro Tyr  Gly Ser Ala Ala Ala  Ala Ala Gly Pro Gly  Ser Gly Gln
    1310                1315                1320

Tyr Gly  Gln Gly Pro Tyr Gly  Pro Gly Ala Ser Gly  Pro Gly Gln
    1325                1330                1335

Tyr Gly  Pro Gly Gln Gln Gly  Pro Ser Ala Ser Ala  Ala Ala Ala
    1340                1345                1350

Ala Gly  Ser Gly Gln Gln Gly  Pro Gly Gln Tyr Gly  Pro Tyr Ala
    1355                1360                1365

Ser Ala  Ala Ala Ala Ala Gly  Gln Tyr Gly Ser Gly  Pro Gly Gln
    1370                1375                1380

Gln Gly  Pro Tyr Gly Pro Gly  Gln Ser Gly Ser Gly  Gln Gln Gly
    1385                1390                1395

Pro Gly  Gln Gln Gly Pro Tyr  Ala Ser Ala Ala Ala  Ala Ala Gly
    1400                1405                1410

Pro Gly  Gln Gln Gly Pro Tyr  Gly Pro Gly Ser Ser  Ala Ala Ala
    1415                1420                1425

Ala Ala  Gly Gln Tyr Gly Tyr  Gly Pro Gly Gln Gln  Gly Pro Tyr
    1430                1435                1440

Gly Pro  Gly Ala Ser Gly Gln  Asn Gly Pro Gly Ser  Gly Gln Tyr
    1445                1450                1455
```

```
Gly Pro  Gly Gln Gln Gly Pro  Gly Gln Ser Ala Ala  Ala Ala Ala
    1460                 1465                 1470

Gly Pro  Gly Gln Gln Gly Pro  Tyr Gly Pro Gly Ala  Ser Ala Ala
    1475                 1480                 1485

Ala Ala  Ala Gly Gln Tyr Gly  Pro Gly Gln Gln Gly  Pro Gly Gln
    1490                 1495                 1500

Tyr Gly  Pro Gly Ser Ser Gly  Pro Gly Gln Gln Gly  Pro Tyr Gly
    1505                 1510                 1515

Pro Gly  Ser Ser Ala Ala Ala  Ala Ala Gly Gln Tyr  Gly Pro Gly
    1520                 1525                 1530

Gln Gln  Gly Pro Tyr Gly Pro  Gly Gln Ser Ala Ala  Ala Ala Ala
    1535                 1540                 1545

Gly Gln  Tyr Gln Gln Gly Pro  Gly Gln Gln Gly Pro  Tyr Gly Pro
    1550                 1555                 1560

Gly Ala  Ser Gly Pro Gly Gln  Gln Gly Pro Tyr Gly  Pro Gly Ala
    1565                 1570                 1575

Ser Ala  Ala Ala Ala Ala Gly  Pro Gly Gln Tyr Gly  Pro Gly Gln
    1580                 1585                 1590

Gln Gly  Pro Ser Ala Ser Ala  Ala Ala Ala Ala Gly  Gln Tyr Gly
    1595                 1600                 1605

Ser Gly  Pro Gly Gln Tyr Gly  Pro Tyr Gly Pro Gly  Gln Ser Gly
    1610                 1615                 1620

Pro Gly  Ser Gly Gln Gln Gly  Gln Gly Pro Tyr Gly  Pro Gly Ala
    1625                 1630                 1635

Ser Ala  Ala Ala Ala Ala Gly  Gln Tyr Gly Pro Gly  Gln Gln Gly
    1640                 1645                 1650

Pro Tyr  Gly Pro Gly Gln Ser  Ala Ala Ala Ala Ala  Gly Pro Gly
    1655                 1660                 1665

Ser Gly  Gln Tyr Gly Pro Gly  Ala Ser Gly Gln Asn  Gly Pro Gly
    1670                 1675                 1680

Ser Gly  Gln Tyr Gly Pro Gly  Gln Gln Gly Pro Gly  Gln Ser Ala
    1685                 1690                 1695

Ala Ala  Ala Ala Gly Gln Tyr  Gln Gln Gly Pro Gly  Gln Gln Gly
    1700                 1705                 1710

Pro Tyr  Gly Pro Gly Ala Ser  Ala Ala Ala Ala Ala  Gly Gln Tyr
    1715                 1720                 1725

Gly Ser  Gly Pro Gly Gln Gln  Gly Pro Tyr Gly Pro  Gly Gln Ser
    1730                 1735                 1740

Gly Ser  Gly Gln Gln Gly Pro  Gly Gln Gln Gly Pro  Tyr Ala Ser
    1745                 1750                 1755

Ala Ala  Ala Ala Ala Gly Pro  Gly Ser Gly Gln Gln  Gly Pro Gly
    1760                 1765                 1770

Ala Ser  Gly Gln Gln Gly Pro  Tyr Gly Pro Gly Ala  Ser Ala Ala
    1775                 1780                 1785

Ala Ala  Ala Gly Gln Asn Gly  Pro Gly Ser Gly Gln  Gln Gly Pro
    1790                 1795                 1800

Gly Gln  Ser Gly Gln Tyr Gly  Pro Gly Gln Gln Gly  Pro Gly Gln
    1805                 1810                 1815

Gln Gly  Pro Gly Ser Ser Ala  Ala Ala Ala Ala Gly  Pro Gly Gln
    1820                 1825                 1830

Tyr Gly  Pro Gly Gln Gln Gly  Pro Ser Ala Ser Ala  Ala Ala Ala
    1835                 1840                 1845
```

-continued

```
Ala Gly Pro Gly Ser Gly Gln Gln Gly Pro Gly Ala Ser Gly Gln
    1850                1855                1860

Tyr Gly Pro Gly Gln Gln Gly Pro Gly Gln Gln Gly Pro Gly Ser
    1865                1870                1875

Ser Ala Ala Ala Ala Ala Gly Gln Tyr Gly Ser Gly Pro Gly Gln
    1880                1885                1890

Gln Gly Pro Tyr Gly Ser Ala Ala Ala Ala Ala Gly Pro Gly Ser
    1895                1900                1905

Gly Gln Tyr Gly Gln Gly Pro Tyr Gly Pro Gly Ala Ser Gly Pro
    1910                1915                1920

Gly Gln Tyr Gly Pro Gly Gln Gln Gly Pro Ser Ala Ser Ala Ala
    1925                1930                1935

Ala Ala Ala Gly Ser Gly Gln Gln Gly Pro Gly Gln Tyr Gly Pro
    1940                1945                1950

Tyr Ala Ser Ala Ala Ala Ala Ala Gly Gln Tyr Gly Ser Gly Pro
    1955                1960                1965

Gly Gln Gln Gly Pro Tyr Gly Pro Gly Gln Ser Gly Ser Gly Gln
    1970                1975                1980

Gln Gly Pro Gly Gln Gln Gly Pro Tyr Ala Ser Ala Ala Ala Ala
    1985                1990                1995

Ala Gly Pro Gly Gln Gln Gly Pro Tyr Gly Pro Gly Ser Ser Ala
    2000                2005                2010

Ala Ala Ala Ala Gly Gln Tyr Gly Tyr Gly Pro Gly Gln Gln Gly
    2015                2020                2025

Pro Tyr Gly Pro Gly Ala Ser Gly Gln Asn Gly Pro Gly Ser Gly
    2030                2035                2040

Gln Tyr Gly Pro Gly Gln Gln Gly Pro Gly Gln Ser Ala Ala Ala
    2045                2050                2055

Ala Ala Gly Pro Gly Gln Gln Gly Pro Tyr Gly Pro Gly Ala Ser
    2060                2065                2070

Ala Ala Ala Ala Ala Gly Gln Tyr Gly Pro Gly Gln Gln Gly Pro
    2075                2080                2085

Gly Gln Tyr Gly Pro Gly Ser Ser Gly Pro Gly Gln Gln Gly Pro
    2090                2095                2100

Tyr Gly Pro Gly Ser Ser Ala Ala Ala Ala Ala Gly Gln Tyr Gly
    2105                2110                2115

Pro Gly Gln Gln Gly Pro Tyr Gly Pro Gly Gln Ser Ala Ala Ala
    2120                2125                2130

Ala Ala Gly Gln Tyr Gln Gln Gly Pro Gly Gln Gln Gly Pro Tyr
    2135                2140                2145

Gly Pro Gly Ala Ser Gly Pro Gly Gln Gln Gly Pro Tyr Gly Pro
    2150                2155                2160

Gly Ala Ser Ala Ala Ala Ala Ala Gly Pro Gly Gln Tyr Gly Pro
    2165                2170                2175

Gly Gln Gln Gly Pro Ser Ala Ser Ala Ala Ala Ala Ala Gly Gln
    2180                2185                2190

Tyr Gly Ser Gly Pro Gly Gln Tyr Gly Pro Tyr Gly Pro Gly Gln
    2195                2200                2205

Ser Gly Pro Gly Ser Gly Gln Gln Gly Gln Gly Pro Tyr Gly Pro
    2210                2215                2220

Gly Ala Ser Ala Ala Ala Ala Ala Gly Gln Tyr Gly Pro Gly Gln
    2225                2230                2235

Gln Gly Pro Tyr Gly Pro Gly Gln Ser Ala Ala Ala Ala Ala Gly
```

```
    2240                2245                2250

Pro Gly  Ser Gly Gln Tyr Gly  Pro Gly Ala Ser Gly  Gln Asn Gly
    2255                2260                2265

Pro Gly  Ser Gly Gln Tyr Gly  Pro Gly Gln Gln Gly  Pro Gly Gln
    2270                2275                2280

Ser Ala  Ala Ala Ala Ala Gly  Gln Tyr Gln Gln Gly  Pro Gly Gln
    2285                2290                2295

Gln Gly  Pro Tyr Gly Pro Gly  Ala Ser Ala Ala Ala  Ala Ala Gly
    2300                2305                2310

Gln Tyr  Gly Ser Gly Pro Gly  Gln Gln Gly Pro Tyr  Gly Pro Gly
    2315                2320                2325

Gln Ser  Gly Ser Gly Gln Gln  Gly Pro Gly Gln Gln  Gly Pro Tyr
    2330                2335                2340

Ala Ser  Ala Ala Ala Ala Ala  Gly Pro Gly Ser Gly  Gln Gln Gly
    2345                2350                2355

Ser Ser  Val Asp Lys Leu Ala  Ala Ala Leu Glu His  His His His
    2360                2365                2370

His His
    2375


<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His His Ser Ser Gly Ser Ser Gly Pro Gly Gly
1               5                   10                  15

Gln Gly Pro Tyr Gly Pro Gly Ala Ser Ala Ala Ala Ala Ala Gly Gly
            20                  25                  30

Asn Gly Pro Gly Ser Gly Gln Gln Gly Pro Gly Gly Ser Ala Ala Ala
        35                  40                  45

Ala Ala Gly Gly Tyr Gly Pro Gly Gly Gln Gly Pro Gly Gln Gln Gly
    50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Ala Gly Pro Gly
                85                  90                  95

Ser Gly Gln Gln Gly Pro Gly Ala Ser Ala Ala Ala Ala Ala Gly Gly
            100                 105                 110

Tyr Gly Pro Gly Gly Gln Gly Pro Gly Gln Gln Gly Pro Gly Ser Ser
        115                 120                 125

Ala Ala Ala Ala Ala Gly Gly Tyr Gly Ser Gly Pro Gly Gln Gln Gly
    130                 135                 140

Pro Tyr Gly Ser Ala Ala Ala Ala Ala Gly Pro Gly Ser Gly Gly Tyr
145                 150                 155                 160

Gly Gln Gly Pro Tyr Gly Pro Gly Ala Ser Ala Ala Ala Ala Ala Gly
                165                 170                 175

Pro Gly Gly Tyr Gly Pro Gly Gly Gln Gly Pro Ser Ala Ser Ala Ala
            180                 185                 190

Ala Ala Ala Gly Ser Gly Gln Gln Gly Pro Gly Gly Tyr Gly Pro Tyr
        195                 200                 205

Ala Ser Ala Ala Ala Ala Ala Gly Gly Tyr Gly Ser Gly Pro Gly Gln
```

-continued

```
    210                 215                 220

Gln Gly Pro Tyr Gly Pro Gly Gly Ser Ala Ala Ala Ala Ala Gly Ser
225                 230                 235                 240

Gly Gln Gln Gly Pro Gly Gln Gln Gly Pro Tyr Ala Ser Ala Ala Ala
                245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
        275                 280                 285

Tyr Gly Pro Gly Ala Ser Ala Ala Ala Ala Ala Gly Gly Asn Gly Pro
    290                 295                 300

Gly Ser Gly Gly Tyr Gly Pro Gly Gln Gln Gly Pro Gly Gly Ser Ala
305                 310                 315                 320

Ala Ala Ala Ala Gly Pro Gly Gly Gln Gly Pro Tyr Gly Pro Gly Ala
                325                 330                 335

Ser Ala Ala Ala Ala Ala Gly Gly Tyr Gly Pro Gly Gly Gln Gly Pro
            340                 345                 350

Gly Gly Tyr Gly Pro Gly Ser Ser Ala Ala Ala Ala Ala Gly Pro Gly
        355                 360                 365

Gly Gln Gly Pro Tyr Gly Pro Gly Ser Ser Ala Ala Ala Ala Ala Gly
    370                 375                 380

Gly Tyr Gly Pro Gly Gln Gln Gly Pro Tyr Gly Pro Gly Gly Ser Ala
385                 390                 395                 400

Ala Ala Ala Ala Gly Gly Tyr Gln Gln Gly Pro Gly Gly Gln Gly Pro
                405                 410                 415

Tyr Gly Pro Gly Ala Ser Ala Ala Ala Ala Ala Gly Pro Gly Gly Gln
            420                 425                 430

Gly Pro Tyr Gly Pro Gly Ala Ser Ala Ala Ala Ala Ala Gly Pro Gly
        435                 440                 445

Gly Tyr Gly Pro Gly Gly Gln Gly Pro Ser Ala Ser Ala Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Ala Gly Pro Gly Ser Gly Gln Gln Gly
                485                 490                 495

Gln Gly Pro Tyr Gly Pro Gly Ala Ser Ala Ala Ala Ala Ala Gly Gly
            500                 505                 510

Tyr Gly Pro Gly Gln Gln Gly Pro Tyr Gly Pro Gly Gly Ser Ala Ala
        515                 520                 525

Ala Ala Ala Gly Pro Gly Ser Gly Gly Tyr Gly Pro Gly Ala Ser Ala
    530                 535                 540

Ala Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Ala Gly Gly Tyr
                565                 570                 575

Gln Gln Gly Pro Gly Gly Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
        595                 600                 605
```

<210> SEQ ID NO 17
<211> LENGTH: 590
<212> TYPE: PRT
<213> ORGANISM: Artificial Sequence -continued
<220> FEATURE:
<223> OTHER INFORMATION: Met-PRT399

<400> SEQUENCE: 17

```
Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gly Gln Gly Pro Gly Gln Gln Gly
        35                  40                  45

Pro Gly Ser Ser Ala Ala Ala Ala Ala Gly Pro Gly Gly Tyr Gly Pro
    50                  55                  60

Gly Gly Gln Gly Pro Ser Ala Ser Ala Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala Ala
            100                 105                 110

Gly Gly Tyr Gly Ser Gly Pro Gly Gln Gln Gly Pro Tyr Gly Ser Ala
        115                 120                 125

Ala Ala Ala Ala Gly Pro Gly Ser Gly Gly Tyr Gly Gln Gly Pro Tyr
    130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Ala Gly Ser Gly Gln Gln Gly Pro
                165                 170                 175

Gly Gly Tyr Gly Pro Tyr Ala Ser Ala Ala Ala Ala Ala Gly Gly Tyr
            180                 185                 190

Gly Ser Gly Pro Gly Gln Gln Gly Pro Tyr Gly Pro Gly Gly Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gly Gln Gly Pro Tyr Gly Pro Gly Ser Ser
225                 230                 235                 240

Ala Ala Ala Ala Ala Gly Gly Tyr Gly Tyr Gly Pro Gly Gly Gln Gly
                245                 250                 255

Pro Tyr Gly Pro Gly Ala Ser Gly Gly Asn Gly Pro Gly Ser Gly Gly
            260                 265                 270

Tyr Gly Pro Gly Gln Gln Gly Pro Gly Gly Ser Ala Ala Ala Ala Ala
        275                 280                 285

Gly Pro Gly Gly Gln Gly Pro Tyr Gly Pro Gly Ala Ser Ala Ala Ala
    290                 295                 300

Ala Ala Gly Gly Tyr Gly Pro Gly Gly Gln Gly Pro Gly Gly Tyr Gly
305                 310                 315                 320

Pro Gly Ser Ser Gly Pro Gly Gly Gln Gly Pro Tyr Gly Pro Gly Ser
                325                 330                 335

Ser Ala Ala Ala Ala Ala Gly Gly Tyr Gly Pro Gly Gln Gln Gly Pro
            340                 345                 350

Tyr Gly Pro Gly Gly Ser Ala Ala Ala Ala Ala Gly Gly Tyr Gln Gln
        355                 360                 365

Gly Pro Gly Gly Gln Gly Pro Tyr Gly Pro Gly Ala Ser Gly Pro Gly
    370                 375                 380

Gly Gln Gly Pro Tyr Gly Pro Gly Ala Ser Ala Ala Ala Ala Ala Gly
385                 390                 395                 400
```

-continued

```
Pro Gly Gly Tyr Gly Pro Gly Gly Gln Gly Pro Ser Ala Ser Ala Ala
                405                 410                 415

Ala Ala Ala Gly Gly Tyr Gly Ser Gly Pro Gly Gly Tyr Gly Pro Tyr
            420                 425                 430

Gly Pro Gly Gly Ser Gly Pro Gly Ser Gly Gln Gln Gly Gln Gly Pro
        435                 440                 445

Tyr Gly Pro Gly Ala Ser Ala Ala Ala Ala Ala Gly Gly Tyr Gly Pro
    450                 455                 460

Gly Gln Gln Gly Pro Tyr Gly Pro Gly Gly Ser Ala Ala Ala Ala Ala
465                 470                 475                 480

Gly Pro Gly Ser Gly Gly Tyr Gly Pro Gly Ala Ser Gly Gly Asn Gly
                485                 490                 495

Pro Gly Ser Gly Gly Tyr Gly Pro Gly Gln Gln Gly Pro Gly Gly Ser
            500                 505                 510

Ala Ala Ala Ala Ala Gly Gly Tyr Gln Gln Gly Pro Gly Gly Gln Gly
        515                 520                 525

Pro Tyr Gly Pro Gly Ala Ser Ala Ala Ala Ala Ala Gly Gly Tyr Gly
    530                 535                 540

Ser Gly Pro Gly Gln Gln Gly Pro Tyr Gly Pro Gly Gly Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590
```

<210> SEQ ID NO 18
<211> LENGTH: 601
<212> TYPE: PRT
<213> ORGANISM: Artificial Sequence
<220> FEATURE:
<223> OTHER INFORMATION: PRT399

<400> SEQUENCE: 18

```
Met His His His His His His Ser Ser Gly Ser Ser Gly Pro Gly Gly
1               5                   10                  15

Gln Gly Pro Tyr Gly Pro Gly Ala Ser Ala Ala Ala Ala Ala Gly Gly
            20                  25                  30

Asn Gly Pro Gly Ser Gly Gln Gln Gly Pro Gly Gly Ser Gly Gly Tyr
        35                  40                  45

Gly Pro Gly Gly Gln Gly Pro Gly Gln Gln Gly Pro Gly Ser Ser Ala
    50                  55                  60

Ala Ala Ala Ala Gly Pro Gly Gly Tyr Gly Pro Gly Gly Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gly Tyr Gly Pro Gly Gly Gln Gly Pro Gly Gln
            100                 105                 110

Gln Gly Pro Gly Ser Ser Ala Ala Ala Ala Ala Gly Gly Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser Ala
                165                 170                 175
```

-continued

```
Ala Ala Ala Ala Gly Ser Gly Gln Gln Gly Pro Gly Gly Tyr Gly Pro
            180                 185                 190

Tyr Ala Ser Ala Ala Ala Ala Ala Gly Gly Tyr Gly Ser Gly Pro Gly
        195                 200                 205

Gln Gln Gly Pro Tyr Gly Pro Gly Gly Ser Gly Ser Gly Gln Gln Gly
    210                 215                 220

Pro Gly Gln Gln Gly Pro Tyr Ala Ser Ala Ala Ala Ala Ala Gly Pro
225                 230                 235                 240

Gly Gly Gln Gly Pro Tyr Gly Pro Gly Ser Ser Ala Ala Ala Ala Ala
                245                 250                 255

Gly Gly Tyr Gly Tyr Gly Pro Gly Gly Gln Gly Pro Tyr Gly Pro Gly
            260                 265                 270

Ala Ser Gly Gly Asn Gly Pro Gly Ser Gly Gly Tyr Gly Pro Gly Gln
        275                 280                 285

Gln Gly Pro Gly Gly Ser Ala Ala Ala Ala Ala Gly Pro Gly Gly Gln
    290                 295                 300

Gly Pro Tyr Gly Pro Gly Ala Ser Ala Ala Ala Ala Ala Gly Gly Tyr
305                 310                 315                 320

Gly Pro Gly Gly Gln Gly Pro Gly Gly Tyr Gly Pro Gly Ser Ser Gly
                325                 330                 335

Pro Gly Gly Gln Gly Pro Tyr Gly Pro Gly Ser Ser Ala Ala Ala Ala
            340                 345                 350

Ala Gly Gly Tyr Gly Pro Gly Gln Gln Gly Pro Tyr Gly Pro Gly Gly
        355                 360                 365

Ser Ala Ala Ala Ala Ala Gly Gly Tyr Gln Gln Gly Pro Gly Gly Gln
    370                 375                 380

Gly Pro Tyr Gly Pro Gly Ala Ser Gly Pro Gly Gly Gln Gly Pro Tyr
385                 390                 395                 400

Gly Pro Gly Ala Ser Ala Ala Ala Ala Ala Gly Pro Gly Gly Tyr Gly
                405                 410                 415

Pro Gly Gly Gln Gly Pro Ser Ala Ser Ala Ala Ala Ala Ala Gly Gly
            420                 425                 430

Tyr Gly Ser Gly Pro Gly Gly Tyr Gly Pro Tyr Gly Pro Gly Gly Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gly Tyr Gly Pro Gly Gln Gln Gly Pro
465                 470                 475                 480

Tyr Gly Pro Gly Gly Ser Ala Ala Ala Ala Ala Gly Pro Gly Ser Gly
                485                 490                 495

Gly Tyr Gly Pro Gly Ala Ser Gly Gly Asn Gly Pro Gly Ser Gly Gly
            500                 505                 510

Tyr Gly Pro Gly Gln Gln Gly Pro Gly Gly Ser Ala Ala Ala Ala Ala
        515                 520                 525

Gly Gly Tyr Gln Gln Gly Pro Gly Gly Gln Gly Pro Tyr Gly Pro Gly
    530                 535                 540

Ala Ser Ala Ala Ala Ala Ala Gly Gly Tyr Gly Ser Gly Pro Gly Gln
545                 550                 555                 560

Gln Gly Pro Tyr Gly Pro Gly Gly Ser Gly Ser Gly Gln Gln Gly Pro
                565                 570                 575

Gly Gln Gln Gly Pro Tyr Ala Ser Ala Ala Ala Ala Ala Gly Pro Gly
            580                 585                 590
```

```
Ser Gly Gln Gln Gly Pro Gly Ala Ser
        595                 600


<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Gly Ser Tyr Gly Ser Val Leu Ile Gly Pro
        115                 120                 125

Gly Gln Gln Val Leu Ile Gly Pro Tyr Gly Ser Ala Ala Ala Ala Ala
    130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
                165                 170                 175

Ala Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Ala Gly
        195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gln Gly Pro Tyr Ala Ser
225                 230                 235                 240

Ala Ala Ala Ala Ala Gly Pro Gly Gln Gln Val Leu Ile Gly Pro Tyr
                245                 250                 255

Val Leu Ile Gly Pro Gly Ser Ser Ala Ala Ala Ala Ala Gly Gln Tyr
            260                 265                 270

Gly Tyr Gly Pro Gly Gln Gln Gly Pro Tyr Gly Pro Gly Ala Ser Gly
        275                 280                 285

Gln Asn Gly Pro Gly Ser Gly Gln Tyr Gly Pro Gly Gln Gln Gly Pro
    290                 295                 300

Gly Gln Ser Ala Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala Ala
                325                 330                 335

Gly Gln Tyr Gly Pro Gly Gln Gln Gly Pro Gly Gln Tyr Gly Pro Gly
            340                 345                 350
```

-continued

```
Ser Ser Gly Pro Gly Gln Gln Gly Pro Tyr Gly Pro Gly Ser Ser Ala
        355                 360                 365

Ala Ala Ala Ala Gly Ser Tyr Gly Pro Gly Gln Gln Val Leu Ile Gly
    370                 375                 380

Pro Tyr Val Leu Ile Gly Pro Gly Pro Ser Ala Ala Ala Ala Ala Gly
385                 390                 395                 400

Gln Tyr Gln Gln Gly Pro Gly Gln Gln Gly Pro Tyr Gly Pro Gly Ala
                405                 410                 415

Ser Gly Pro Gly Gln Gln Gly Pro Tyr Gly Pro Gly Ala Ser Ala Ala
            420                 425                 430

Ala Ala Ala Gly Pro Gly Gln Tyr Val Leu Ile Gly Pro Gly Gln Gln
        435                 440                 445

Val Leu Ile Gly Pro Ser Ala Ser Ala Ala Ala Ala Ala Gly Gln Tyr
    450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
                485                 490                 495

Ala Ala Ala Ala Ala Gly Ser Tyr Gly Pro Gly Gln Gln Val Leu Ile
            500                 505                 510

Gly Pro Tyr Val Leu Ile Gly Pro Gly Pro Ser Ala Ala Ala Ala Ala
        515                 520                 525

Gly Pro Gly Ser Gly Gln Tyr Gly Pro Gly Ala Ser Gly Gln Asn Gly
    530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
                565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
        595                 600                 605

Ser Val Leu Ile
    610
```

<210> SEQ ID NO 20
<211> LENGTH: 592
<212> TYPE: PRT
<213> ORGANISM: Artificial Sequence
<220> FEATURE:
<223> OTHER INFORMATION: Met-PRT665

<400> SEQUENCE: 20

```
Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Val Leu Ile Gly Pro Gly Gln Gln Gly Pro Ser Ala Ser Ala
65                  70                  75                  80

Ala Ala Ala Ala Ala Ala Gly Pro Gly Ser Gly Gln Gln Gly Pro Gly
                85                  90                  95
```

```
Ala Ser Gly Gln Tyr Gly Pro Gly Gln Gln Gly Pro Gly Gln Gln Gly
            100                 105                 110

Pro Gly Ser Ser Ala Ala Ala Ala Ala Ala Ala Gly Ser Tyr Gly Ser
        115                 120                 125

Val Leu Ile Gly Pro Gly Gln Gln Gly Pro Tyr Gly Ser Ala Ala Ala
    130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Ala Ala Gly Ser Gly Gln Gln
            180                 185                 190

Val Leu Ile Gly Pro Gly Gln Tyr Gly Pro Tyr Ala Ser Ala Ala Ala
        195                 200                 205

Ala Ala Ala Ala Gly Ser Tyr Gly Ser Gly Pro Gly Gln Gln Gly Pro
    210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Ala Gly Pro Gly Gln
                245                 250                 255

Gln Val Leu Ile Gly Pro Tyr Gly Pro Gly Ser Ser Ala Ala Ala Ala
            260                 265                 270

Ala Ala Ala Gly Ser Tyr Gly Tyr Gly Pro Gly Gln Gln Gly Pro Tyr
        275                 280                 285

Gly Pro Gly Ala Ser Gly Gln Asn Gly Pro Gly Ser Gly Gln Tyr Gly
    290                 295                 300

Pro Gly Gln Gln Gly Pro Gly Pro Ser Ala Ala Ala Ala Ala Ala Ala
305                 310                 315                 320

Gly Pro Gly Gln Gln Val Leu Ile Gly Pro Tyr Gly Pro Gly Ala Ser
                325                 330                 335

Ala Ala Ala Ala Ala Ala Ala Gly Ser Tyr Gly Pro Gly Gln Gln Gly
            340                 345                 350

Pro Gly Gln Tyr Gly Pro Gly Ser Ser Gly Pro Gly Gln Gln Gly Pro
        355                 360                 365

Tyr Gly Pro Gly Ser Ser Ala Ala Ala Ala Ala Ala Ala Gly Ser Tyr
    370                 375                 380

Gly Pro Gly Gln Gln Val Leu Ile Gly Pro Tyr Gly Pro Gly Pro Ser
385                 390                 395                 400

Ala Ala Ala Ala Ala Ala Ala Gly Ser Tyr Gln Gln Gly Pro Gly Gln
                405                 410                 415

Gln Gly Pro Tyr Gly Pro Gly Ala Ser Gly Pro Gly Gln Gln Gly Pro
            420                 425                 430

Tyr Gly Pro Gly Ala Ser Ala Ala Ala Ala Ala Ala Ala Gly Pro Gly
        435                 440                 445

Gln Tyr Val Leu Ile Gly Pro Gly Gln Gln Gly Pro Ser Ala Ser Ala
    450                 455                 460

Ala Ala Ala Ala Ala Ala Gly Ser Tyr Gly Ser Gly Pro Gly Gln Tyr
465                 470                 475                 480

Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala Ala
            500                 505                 510

Gly Ser Tyr Gly Pro Gly Gln Gln Val Leu Ile Gly Pro Tyr Gly Pro
```

```
        515                 520                 525

Gly Pro Ser Ala Ala Ala Ala Ala Ala Ala Gly Pro Gly Ser Gly Gln
    530                 535                 540

Tyr Gly Pro Gly Ala Ser Gly Gln Asn Gly Pro Gly Ser Gly Gln Tyr
545                 550                 555                 560

Gly Pro Gly Gln Gln Gly Pro Gly Pro Ser Ala Ala Ala Ala Ala Ala
                565                 570                 575

Ala Gly Pro Gly Ser Gly Gln Gln Gly Pro Gly Ala Ser Val Leu Ile
            580                 585                 590


<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Ala Gly Pro Gly
    50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
            100                 105                 110

Gln Gln Gly Pro Gly Ser Ser Ala Ala Ala Ala Ala Ala Ala Gly Ser
        115                 120                 125

Tyr Gly Ser Val Leu Ile Gly Pro Gly Gln Gln Val Leu Ile Gly Pro
    130                 135                 140

Tyr Gly Ser Ala Ala Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
                165                 170                 175

Gly Pro Gly Gln Gln Gly Pro Ser Ala Ser Ala Ala Ala Ala Ala Ala
            180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Ala Ala Gly Ser Tyr
    210                 215                 220

Gly Ser Gly Pro Gly Gln Gln Gly Pro Tyr Gly Pro Gly Gln Ser Gly
225                 230                 235                 240

Ser Gly Gln Gln Gly Pro Gly Gln Gln Gly Pro Tyr Ala Ser Ala Ala
                245                 250                 255

Ala Ala Ala Ala Ala Gly Pro Gly Gln Gln Val Leu Ile Gly Pro Tyr
            260                 265                 270

Val Leu Ile Gly Pro Gly Ser Ser Ala Ala Ala Ala Ala Ala Ala Gly
        275                 280                 285

Ser Tyr Gly Tyr Gly Pro Gly Gln Gln Gly Pro Tyr Gly Pro Gly Ala
```

```
    290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Ala Gly Pro Gly Gln
                325                 330                 335

Gln Val Leu Ile Gly Pro Tyr Val Leu Ile Gly Pro Gly Ala Ser Ala
            340                 345                 350

Ala Ala Ala Ala Ala Ala Gly Ser Tyr Gly Pro Gly Gln Gln Gly Pro
        355                 360                 365

Gly Gln Tyr Gly Pro Gly Ser Ser Gly Pro Gly Gln Gln Gly Pro Tyr
    370                 375                 380

Gly Pro Gly Ser Ser Ala Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
                405                 410                 415

Pro Ser Ala Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
        435                 440                 445

Gly Pro Tyr Gly Pro Gly Ala Ser Ala Ala Ala Ala Ala Ala Ala Gly
    450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Ala Ala Gly Ser Tyr Gly Ser
                485                 490                 495

Gly Pro Gly Gln Tyr Gly Pro Tyr Gly Pro Gly Gln Ser Gly Pro Gly
            500                 505                 510

Ser Gly Gln Gln Gly Gln Gly Pro Tyr Gly Pro Gly Ala Ser Ala Ala
        515                 520                 525

Ala Ala Ala Ala Ala Gly Ser Tyr Gly Pro Gly Gln Gln Val Leu Ile
    530                 535                 540

Gly Pro Tyr Val Leu Ile Gly Pro Gly Pro Ser Ala Ala Ala Ala Ala
545                 550                 555                 560

Ala Ala Gly Pro Gly Ser Gly Gln Tyr Gly Pro Gly Ala Ser Gly Gln
                565                 570                 575

Asn Gly Pro Gly Ser Gly Gln Tyr Gly Pro Gly Gln Gln Gly Pro Gly
            580                 585                 590

Pro Ser Ala Ala Ala Ala Ala Ala Ala Gly Pro Gly Ser Gly Gln Gln
        595                 600                 605

Val Leu Ile Gly Pro Gly Ala Ser Val Leu Ile
    610                 615


<210> SEQ ID NO 22
<211> LENGTH: 623
<212> TYPE: PRT
<213> ORGANISM: Artificial Sequence
<220> FEATURE:
<223> OTHER INFORMATION: PRT720

<400> SEQUENCE: 22

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
```

-continued

```
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
    130                 135                 140

Ile Gly Pro Tyr Gly Ser Ala Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
                165                 170                 175

Tyr Gly Pro Gly Gln Gln Gly Pro Ser Ala Ser Ala Ala Ala Ala Ala
            180                 185                 190

Gly Ser Gly Gln Gln Val Leu Ile Gly Pro Gly Gln Tyr Val Leu Ile
        195                 200                 205

Gly Pro Tyr Ala Ser Ala Ala Ala Ala Ala Gly Gln Tyr Gly Ser Gly
    210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala Ala
                245                 250                 255

Gly Pro Gly Gln Gln Val Leu Ile Gly Pro Tyr Val Leu Ile Gly Pro
            260                 265                 270

Gly Ser Ser Ala Ala Ala Ala Ala Gly Gln Tyr Gly Tyr Gly Pro Gly
        275                 280                 285

Gln Gln Gly Pro Tyr Gly Pro Gly Ala Ser Gly Gln Asn Gly Pro Gly
    290                 295                 300

Ser Gly Gln Tyr Gly Pro Gly Gln Gln Gly Pro Gly Gln Ser Ala Ala
305                 310                 315                 320

Ala Ala Ala Gly Pro Gly Gln Gln Val Leu Ile Gly Pro Tyr Val Leu
                325                 330                 335

Ile Gly Pro Gly Ala Ser Ala Ala Ala Ala Ala Gly Gln Tyr Gly Pro
            340                 345                 350

Gly Gln Gln Gly Pro Gly Gln Tyr Gly Pro Gly Ser Ser Gly Pro Gly
        355                 360                 365

Gln Gln Gly Pro Tyr Gly Pro Gly Ser Ser Ala Ala Ala Ala Ala Gly
    370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Ala Gly Gln Tyr Gln Gln Gly
                405                 410                 415

Pro Gly Gln Gln Gly Pro Tyr Gly Pro Gly Ala Ser Gly Pro Gly Gln
            420                 425                 430

Gln Gly Pro Tyr Gly Pro Gly Ala Ser Ala Ala Ala Ala Ala Gly Pro
        435                 440                 445

Gly Gln Tyr Val Leu Ile Gly Pro Gly Gln Gln Val Leu Ile Gly Pro
    450                 455                 460
```

```
Ser Ala Ser Ala Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
                485                 490                 495

Gln Gly Gln Gly Pro Tyr Gly Pro Gly Ala Ser Ala Ala Ala Ala Ala
            500                 505                 510

Gly Ser Tyr Gly Pro Gly Gln Gln Val Leu Ile Gly Pro Tyr Val Leu
        515                 520                 525

Ile Gly Pro Gly Pro Ser Ala Ala Ala Ala Ala Gly Pro Gly Ser Gly
    530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala Ala
                565                 570                 575

Gly Gln Tyr Gln Gln Val Leu Ile Gly Pro Gly Gln Gln Gly Pro Tyr
            580                 585                 590

Val Leu Ile Gly Pro Gly Ala Ser Ala Ala Ala Ala Ala Gly Pro Gly
        595                 600                 605

Ser Gly Gln Gln Val Leu Ile Gly Pro Gly Ala Ser Val Leu Ile
    610                 615                 620


<210> SEQ ID NO 23
<211> LENGTH: 603
<212> TYPE: PRT
<213> ORGANISM: Artificial Sequence
<220> FEATURE:
<223> OTHER INFORMATION: PRT665

<400> SEQUENCE: 23

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala Ala
                85                  90                  95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
        115                 120                 125

Ala Ala Ala Ala Ala Ala Gly Ser Tyr Gly Ser Val Leu Ile Gly Pro
    130                 135                 140

Gly Gln Gln Gly Pro Tyr Gly Ser Ala Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
            180                 185                 190

Ala Ala Ala Ala Ala Ala Gly Ser Gly Gln Gln Val Leu Ile Gly Pro
        195                 200                 205
```

```
Gly Gln Tyr Gly Pro Tyr Ala Ser Ala Ala Ala Ala Ala Ala Ala Gly
    210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
                245                 250                 255

Ala Ala Ala Ala Ala Ala Ala Gly Pro Gly Gln Gln Val Leu Ile Gly
            260                 265                 270

Pro Tyr Gly Pro Gly Ser Ser Ala Ala Ala Ala Ala Ala Ala Gly Ser
        275                 280                 285

Tyr Gly Tyr Gly Pro Gly Gln Gln Gly Pro Tyr Gly Pro Gly Ala Ser
    290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Ala Gly Pro Gly Gln Gln
                325                 330                 335

Val Leu Ile Gly Pro Tyr Gly Pro Gly Ala Ser Ala Ala Ala Ala Ala
            340                 345                 350

Ala Ala Gly Ser Tyr Gly Pro Gly Gln Gln Gly Pro Gly Gln Tyr Gly
        355                 360                 365

Pro Gly Ser Ser Gly Pro Gly Gln Gln Gly Pro Tyr Gly Pro Gly Ser
    370                 375                 380

Ser Ala Ala Ala Ala Ala Ala Ala Gly Ser Tyr Gly Pro Gly Gln Gln
385                 390                 395                 400

Val Leu Ile Gly Pro Tyr Gly Pro Gly Pro Ser Ala Ala Ala Ala Ala
                405                 410                 415

Ala Ala Gly Ser Tyr Gln Gln Gly Pro Gly Gln Gln Gly Pro Tyr Gly
            420                 425                 430

Pro Gly Ala Ser Gly Pro Gly Gln Gln Gly Pro Tyr Gly Pro Gly Ala
        435                 440                 445

Ser Ala Ala Ala Ala Ala Ala Ala Gly Pro Gly Gln Tyr Val Leu Ile
    450                 455                 460

Gly Pro Gly Gln Gln Gly Pro Ser Ala Ser Ala Ala Ala Ala Ala Ala
465                 470                 475                 480

Ala Gly Ser Tyr Gly Ser Gly Pro Gly Gln Tyr Gly Pro Tyr Gly Pro
                485                 490                 495

Gly Gln Ser Gly Pro Gly Ser Gly Gln Gln Gly Gln Gly Pro Tyr Gly
            500                 505                 510

Pro Gly Ala Ser Ala Ala Ala Ala Ala Ala Ala Gly Ser Tyr Gly Pro
        515                 520                 525

Gly Gln Gln Val Leu Ile Gly Pro Tyr Gly Pro Gly Pro Ser Ala Ala
    530                 535                 540

Ala Ala Ala Ala Ala Gly Pro Gly Ser Gly Gln Tyr Gly Pro Gly Ala
545                 550                 555                 560

Ser Gly Gln Asn Gly Pro Gly Ser Gly Gln Tyr Gly Pro Gly Gln Gln
                565                 570                 575

Gly Pro Gly Pro Ser Ala Ala Ala Ala Ala Ala Ala Gly Pro Gly Ser
            580                 585                 590

Gly Gln Gln Gly Pro Gly Ala Ser Val Leu Ile
        595                 600
```

<210> SEQ ID NO 24
<211> LENGTH: 630

```
<212> TYPE: PRT
<213> ORGANISM: Artificial Sequence
<220> FEATURE:
<223> OTHER INFORMATION: PRT666

<400> SEQUENCE: 24

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala Ala
                85                  90                  95

Ala Ala Ala Ala Gly Pro Gly Ser Gly Gln Gln Gly Pro Gly Ala Ser
            100                 105                 110

Gly Gln Tyr Gly Pro Gly Gln Gln Gly Pro Gly Gln Gln Gly Pro Gly
        115                 120                 125

Ser Ser Ala Ala Ala Ala Ala Ala Ala Gly Ser Tyr Gly Ser Val Leu
    130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gly Gln Gly Pro
                165                 170                 175

Tyr Gly Pro Gly Ala Ser Gly Pro Gly Gln Tyr Gly Pro Gly Gln Gln
            180                 185                 190

Gly Pro Ser Ala Ser Ala Ala Ala Ala Ala Ala Ala Gly Ser Gly Gln
        195                 200                 205

Gln Val Leu Ile Gly Pro Gly Gln Tyr Val Leu Ile Gly Pro Tyr Ala
    210                 215                 220

Ser Ala Ala Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
                245                 250                 255

Pro Gly Gln Gln Gly Pro Tyr Ala Ser Ala Ala Ala Ala Ala Ala Ala
            260                 265                 270

Gly Pro Gly Gln Gln Val Leu Ile Gly Pro Tyr Val Leu Ile Gly Pro
        275                 280                 285

Gly Ser Ser Ala Ala Ala Ala Ala Ala Ala Gly Ser Tyr Gly Tyr Gly
    290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
                325                 330                 335

Ala Ala Ala Ala Ala Ala Ala Gly Pro Gly Gln Gln Val Leu Ile Gly
            340                 345                 350

Pro Tyr Val Leu Ile Gly Pro Gly Ala Ser Ala Ala Ala Ala Ala Ala
        355                 360                 365

Ala Gly Ser Tyr Gly Pro Gly Gln Gln Gly Pro Gly Gln Tyr Gly Pro
    370                 375                 380
```

```
Gly Ser Ser Gly Pro Gly Gln Gln Gly Pro Tyr Gly Pro Gly Ser Ser
385                 390                 395                 400

Ala Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala Ala
            420                 425                 430

Ala Ala Ala Ala Gly Ser Tyr Gln Gln Gly Pro Gly Gln Gln Gly Pro
        435                 440                 445

Tyr Gly Pro Gly Ala Ser Gly Pro Gly Gln Gln Gly Pro Tyr Gly Pro
    450                 455                 460

Gly Ala Ser Ala Ala Ala Ala Ala Ala Ala Gly Pro Gly Gln Tyr Val
465                 470                 475                 480

Leu Ile Gly Pro Gly Gln Gln Val Leu Ile Gly Pro Ser Ala Ser Ala
                485                 490                 495

Ala Ala Ala Ala Ala Ala Gly Ser Tyr Gly Ser Gly Pro Gly Gln Tyr
            500                 505                 510

Gly Pro Tyr Gly Pro Gly Gln Ser Gly Pro Gly Ser Gly Gln Gln Gly
        515                 520                 525

Gln Gly Pro Tyr Gly Pro Gly Ala Ser Ala Ala Ala Ala Ala Ala Ala
    530                 535                 540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Ala Ala Gly Pro Gly
                565                 570                 575

Ser Gly Gln Tyr Gly Pro Gly Ala Ser Gly Gln Asn Gly Pro Gly Ser
            580                 585                 590

Gly Gln Tyr Gly Pro Gly Gln Gln Gly Pro Gly Pro Ser Ala Ala Ala
        595                 600                 605

Ala Ala Ala Ala Gly Pro Gly Ser Gly Gln Gln Val Leu Ile Gly Pro
    610                 615                 620

Gly Ala Ser Val Leu Ile
625                 630
```

<210> SEQ ID NO 25
<211> LENGTH: 593
<212> TYPE: PRT
<213> ORGANISM: Artificial Sequence
<220> FEATURE:
<223> OTHER INFORMATION: Met-PRT888

<400> SEQUENCE: 25

```
Met Gly Ser Ser Gly Pro Gly Val Leu Gly Pro Tyr Gly Pro Gly Ala
1               5                   10                  15

Ser Ala Ala Ala Ala Ala Gly Gln Asn Gly Pro Gly Ser Gly Val Leu
            20                  25                  30

Gly Pro Gly Gln Ser Gly Gln Tyr Gly Pro Gly Val Leu Gly Pro Gly
        35                  40                  45

Val Leu Gly Pro Gly Ser Ser Ala Ala Ala Ala Ala Gly Pro Gly Gln
    50                  55                  60

Tyr Gly Pro Gly Val Leu Gly Pro Ser Ala Ser Ala Ala Ala Ala Ala
65                  70                  75                  80

Gly Pro Gly Ser Gly Val Leu Gly Pro Gly Ala Ser Gly Gln Tyr Gly
                85                  90                  95

Pro Gly Val Leu Gly Pro Gly Val Leu Gly Pro Gly Ser Ser Ala Ala
            100                 105                 110
```

-continued

```
Ala Ala Ala Gly Gln Tyr Gly Ser Gly Pro Gly Val Leu Gly Pro Tyr
        115                 120                 125

Gly Ser Ala Ala Ala Ala Ala Gly Pro Gly Ser Gly Gln Tyr Gly Gln
    130                 135                 140

Gly Pro Tyr Gly Pro Gly Ala Ser Gly Pro Gly Gln Tyr Gly Pro Gly
145                 150                 155                 160

Val Leu Gly Pro Ser Ala Ser Ala Ala Ala Ala Ala Gly Ser Gly Val
                165                 170                 175

Leu Gly Pro Gly Gln Tyr Gly Pro Tyr Ala Ser Ala Ala Ala Ala Ala
            180                 185                 190

Gly Gln Tyr Gly Ser Gly Pro Gly Val Leu Gly Pro Tyr Gly Pro Gly
        195                 200                 205

Gln Ser Gly Ser Gly Val Leu Gly Pro Gly Val Leu Gly Pro Tyr Ala
    210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Ala Gly Gln Tyr Gly Tyr Gly Pro Gly
                245                 250                 255

Val Leu Gly Pro Tyr Gly Pro Gly Ala Ser Gly Gln Asn Gly Pro Gly
            260                 265                 270

Ser Gly Gln Tyr Gly Pro Gly Val Leu Gly Pro Gly Gln Ser Ala Ala
        275                 280                 285

Ala Ala Ala Gly Pro Gly Val Leu Gly Pro Tyr Gly Pro Gly Ala Ser
    290                 295                 300

Ala Ala Ala Ala Ala Gly Gln Tyr Gly Pro Gly Val Leu Gly Pro Gly
305                 310                 315                 320

Gln Tyr Gly Pro Gly Ser Ser Gly Pro Gly Val Leu Gly Pro Tyr Gly
                325                 330                 335

Pro Gly Ser Ser Ala Ala Ala Ala Ala Gly Gln Tyr Gly Pro Gly Val
            340                 345                 350

Leu Gly Pro Tyr Gly Pro Gly Gln Ser Ala Ala Ala Ala Ala Gly Gln
        355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Gln Tyr Gly Pro Gly Val Leu Gly Pro Ser Ala
                405                 410                 415

Ser Ala Ala Ala Ala Ala Gly Gln Tyr Gly Ser Gly Pro Gly Gln Tyr
            420                 425                 430

Gly Pro Tyr Gly Pro Gly Gln Ser Gly Pro Gly Ser Gly Val Leu Gly
        435                 440                 445

Gln Gly Pro Tyr Gly Pro Gly Ala Ser Ala Ala Ala Ala Ala Gly Gln
    450                 455                 460

Tyr Gly Pro Gly Val Leu Gly Pro Tyr Gly Pro Gly Gln Ser Ala Ala
465                 470                 475                 480

Ala Ala Ala Gly Pro Gly Ser Gly Gln Tyr Gly Pro Gly Ala Ser Gly
                485                 490                 495

Gln Asn Gly Pro Gly Ser Gly Gln Tyr Gly Pro Gly Val Leu Gly Pro
            500                 505                 510

Gly Gln Ser Ala Ala Ala Ala Ala Gly Gln Tyr Val Leu Gly Pro Gly
        515                 520                 525

Val Leu Gly Pro Tyr Gly Pro Gly Ala Ser Ala Ala Ala Ala Ala Gly
```

```
    530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Gly Val Leu Gly Pro Tyr Ala Ser
                565                 570                 575

Ala Ala Ala Ala Ala Gly Pro Gly Ser Gly Val Leu Gly Pro Gly Ala
            580                 585                 590

Ser


<210> SEQ ID NO 26
<211> LENGTH: 590
<212> TYPE: PRT
<213> ORGANISM: Artificial Sequence
<220> FEATURE:
<223> OTHER INFORMATION: Met-PRT965

<400> SEQUENCE: 26

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
        35                  40                  45

Pro Gly Ser Ser Ala Ala Ala Ala Ala Gly Pro Gly Ala Tyr Gly Pro
    50                  55                  60

Gly Thr Ser Gly Pro Ser Ala Ser Ala Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala Ala
            100                 105                 110

Gly Ala Tyr Gly Ser Gly Pro Gly Thr Ser Gly Pro Tyr Gly Ser Ala
        115                 120                 125

Ala Ala Ala Ala Gly Pro Gly Ser Gly Ala Tyr Gly Ala Gly Pro Tyr
    130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Ala Gly Ser Gly Thr Ser Gly Pro
                165                 170                 175

Gly Ala Tyr Gly Pro Tyr Ala Ser Ala Ala Ala Ala Ala Gly Ala Tyr
            180                 185                 190

Gly Ser Gly Pro Gly Thr Ser Gly Pro Tyr Gly Pro Gly Ala Ser Gly
        195                 200                 205

Ser Gly Thr Ser Gly Pro Gly Thr Ser Gly Pro Tyr Ala Ser Ala Ala
    210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
                245                 250                 255

Pro Tyr Gly Pro Gly Ala Ser Gly Ala Asn Gly Pro Gly Ser Gly Ala
            260                 265                 270

Tyr Gly Pro Gly Thr Ser Gly Pro Gly Ala Ser Ala Ala Ala Ala Ala
        275                 280                 285

Gly Pro Gly Thr Ser Gly Pro Tyr Gly Pro Gly Ala Ser Ala Ala Ala
    290                 295                 300
```

-continued

```
Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
                325                 330                 335

Ser Ala Ala Ala Ala Ala Gly Ala Tyr Gly Pro Gly Thr Ser Gly Pro
            340                 345                 350

Tyr Gly Pro Gly Ala Ser Ala Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380

Thr Ser Gly Pro Tyr Gly Pro Gly Ala Ser Ala Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
        435                 440                 445

Tyr Gly Pro Gly Ala Ser Ala Ala Ala Ala Ala Gly Ala Tyr Gly Pro
    450                 455                 460

Gly Thr Ser Gly Pro Tyr Gly Pro Gly Ala Ser Ala Ala Ala Ala Ala
465                 470                 475                 480

Gly Pro Gly Ser Gly Ala Tyr Gly Pro Gly Ala Ser Gly Ala Asn Gly
                485                 490                 495

Pro Gly Ser Gly Ala Tyr Gly Pro Gly Thr Ser Gly Pro Gly Ala Ser
            500                 505                 510

Ala Ala Ala Ala Ala Gly Ala Tyr Thr Ser Gly Pro Gly Thr Ser Gly
        515                 520                 525

Pro Tyr Gly Pro Gly Ala Ser Ala Ala Ala Ala Ala Gly Ala Tyr Gly
    530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
                565                 570                 575

Ala Ala Gly Pro Gly Ser Gly Thr Ser Gly Pro Gly Ala Ser
            580                 585                 590
```

<210> SEQ ID NO 27
<211> LENGTH: 593
<212> TYPE: PRT
<213> ORGANISM: Artificial Sequence
<220> FEATURE:
<223> OTHER INFORMATION: Met-PRT889

<400> SEQUENCE: 27

```
Met Gly Ser Ser Gly Pro Gly Val Leu Gly Pro Tyr Gly Pro Gly Ala
1               5                   10                  15

Ser Ala Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
        35                  40                  45

Val Leu Gly Pro Gly Ser Ser Ala Ala Ala Ala Ala Gly Pro Gly Ile
    50                  55                  60

Tyr Gly Pro Gly Val Leu Gly Pro Ser Ala Ser Ala Ala Ala Ala Ala
65                  70                  75                  80
```

-continued

```
Gly Pro Gly Ser Gly Val Leu Gly Pro Gly Ala Ser Gly Ile Tyr Gly
                85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
        115                 120                 125

Gly Ser Ala Ala Ala Ala Ala Gly Pro Gly Ser Gly Ile Tyr Gly Ile
    130                 135                 140

Gly Pro Tyr Gly Pro Gly Ala Ser Gly Pro Gly Ile Tyr Gly Pro Gly
145                 150                 155                 160

Val Leu Gly Pro Ser Ala Ser Ala Ala Ala Ala Ala Gly Ser Gly Val
                165                 170                 175

Leu Gly Pro Gly Ile Tyr Gly Pro Tyr Ala Ser Ala Ala Ala Ala Ala
            180                 185                 190

Gly Ile Tyr Gly Ser Gly Pro Gly Val Leu Gly Pro Tyr Gly Pro Gly
        195                 200                 205

Ile Ser Gly Ser Gly Val Leu Gly Pro Gly Val Leu Gly Pro Tyr Ala
    210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Ala Gly Ile Tyr Gly Tyr Gly Pro Gly
                245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
        275                 280                 285

Ala Ala Ala Gly Pro Gly Val Leu Gly Pro Tyr Gly Pro Gly Ala Ser
    290                 295                 300

Ala Ala Ala Ala Ala Gly Ile Tyr Gly Pro Gly Val Leu Gly Pro Gly
305                 310                 315                 320

Ile Tyr Gly Pro Gly Ser Ser Gly Pro Gly Val Leu Gly Pro Tyr Gly
                325                 330                 335

Pro Gly Ser Ser Ala Ala Ala Ala Ala Gly Ile Tyr Gly Pro Gly Val
            340                 345                 350

Leu Gly Pro Tyr Gly Pro Gly Ile Ser Ala Ala Ala Ala Ala Gly Ile
        355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Ile Tyr Gly Pro Gly Val Leu Gly Pro Ser Ala
                405                 410                 415

Ser Ala Ala Ala Ala Ala Gly Ile Tyr Gly Ser Gly Pro Gly Ile Tyr
            420                 425                 430

Gly Pro Tyr Gly Pro Gly Ile Ser Gly Pro Gly Ser Gly Val Leu Gly
        435                 440                 445

Ile Gly Pro Tyr Gly Pro Gly Ala Ser Ala Ala Ala Ala Ala Gly Ile
    450                 455                 460

Tyr Gly Pro Gly Val Leu Gly Pro Tyr Gly Pro Gly Ile Ser Ala Ala
465                 470                 475                 480

Ala Ala Ala Gly Pro Gly Ser Gly Ile Tyr Gly Pro Gly Ala Ser Gly
                485                 490                 495
```

Ile Asn Gly Pro Gly Ser Gly Ile Tyr Gly Pro Gly Val Leu Gly Pro
500 505 510

Gly Ile Ser Ala Ala Ala Ala Ala Gly Ile Tyr Val Leu Gly Pro Gly
515 520 525

Val Leu Gly Pro Tyr Gly Pro Gly Ala Ser Ala Ala Ala Ala Ala Gly
530 535 540

Ile Tyr Gly Ser Gly Pro Gly Val Leu Gly Pro Tyr Gly Pro Gly Ile
545 550 555 560

Ser Gly Ser Gly Val Leu Gly Pro Gly Val Leu Gly Pro Tyr Ala Ser
565 570 575

Ala Ala Ala Ala Ala Gly Pro Gly Ser Gly Val Leu Gly Pro Gly Ala
580 585 590

Ser

<210> SEQ ID NO 28
<211> LENGTH: 590
<212> TYPE: PRT
<213> ORGANISM: Artificial Sequence
<220> FEATURE:
<223> OTHER INFORMATION: Met-PRT916

<400> SEQUENCE: 28

Met Gly Pro Gly Val Ile Gly Pro Tyr Gly Pro Gly Ala Ser Ala Ala
1 5 10 15

Ala Ala Ala Gly Leu Asn Gly Pro Gly Ser Gly Val Ile Gly Pro Gly
20 25 30

Leu Ser Gly Leu Tyr Gly Pro Gly Val Ile Gly Pro Gly Val Ile Gly
35 40 45

Pro Gly Ser Ser Ala Ala Ala Ala Ala Gly Pro Gly Leu Tyr Gly Pro
50 55 60

Gly Val Ile Gly Pro Ser Ala Ser Ala Ala Ala Ala Ala Gly Pro Gly
65 70 75 80

Ser Gly Val Ile Gly Pro Gly Ala Ser Gly Leu Tyr Gly Pro Gly Val
85 90 95

Ile Gly Pro Gly Val Ile Gly Pro Gly Ser Ser Ala Ala Ala Ala Ala
100 105 110

Gly Leu Tyr Gly Ser Gly Pro Gly Val Ile Gly Pro Tyr Gly Ser Ala
115 120 125

Ala Ala Ala Ala Gly Pro Gly Ser Gly Leu Tyr Gly Leu Gly Pro Tyr
130 135 140

Gly Pro Gly Ala Ser Gly Pro Gly Leu Tyr Gly Pro Gly Val Ile Gly
145 150 155 160

Pro Ser Ala Ser Ala Ala Ala Ala Ala Gly Ser Gly Val Ile Gly Pro
165 170 175

Gly Leu Tyr Gly Pro Tyr Ala Ser Ala Ala Ala Ala Ala Gly Leu Tyr
180 185 190

Gly Ser Gly Pro Gly Val Ile Gly Pro Tyr Gly Pro Gly Leu Ser Gly
195 200 205

Ser Gly Val Ile Gly Pro Gly Val Ile Gly Pro Tyr Ala Ser Ala Ala
210 215 220

Ala Ala Ala Gly Pro Gly Val Ile Gly Pro Tyr Gly Pro Gly Ser Ser
225 230 235 240

Ala Ala Ala Ala Ala Gly Leu Tyr Gly Tyr Gly Pro Gly Val Ile Gly
245 250 255

Pro Tyr Gly Pro Gly Ala Ser Gly Leu Asn Gly Pro Gly Ser Gly Leu

```
            260                 265                 270

Tyr Gly Pro Gly Val Ile Gly Pro Gly Leu Ser Ala Ala Ala Ala Ala
        275                 280                 285

Gly Pro Gly Val Ile Gly Pro Tyr Gly Pro Gly Ala Ser Ala Ala Ala
    290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
                325                 330                 335

Ser Ala Ala Ala Ala Ala Gly Leu Tyr Gly Pro Gly Val Ile Gly Pro
            340                 345                 350

Tyr Gly Pro Gly Leu Ser Ala Ala Ala Ala Ala Gly Leu Tyr Val Ile
        355                 360                 365

Gly Pro Gly Val Ile Gly Pro Tyr Gly Pro Gly Ala Ser Gly Pro Gly
    370                 375                 380

Val Ile Gly Pro Tyr Gly Pro Gly Ala Ser Ala Ala Ala Ala Ala Gly
385                 390                 395                 400

Pro Gly Leu Tyr Gly Pro Gly Val Ile Gly Pro Ser Ala Ser Ala Ala
                405                 410                 415

Ala Ala Ala Gly Leu Tyr Gly Ser Gly Pro Gly Leu Tyr Gly Pro Tyr
            420                 425                 430

Gly Pro Gly Leu Ser Gly Pro Gly Ser Gly Val Ile Gly Leu Gly Pro
        435                 440                 445

Tyr Gly Pro Gly Ala Ser Ala Ala Ala Ala Ala Gly Leu Tyr Gly Pro
    450                 455                 460

Gly Val Ile Gly Pro Tyr Gly Pro Gly Leu Ser Ala Ala Ala Ala Ala
465                 470                 475                 480

Gly Pro Gly Ser Gly Leu Tyr Gly Pro Gly Ala Ser Gly Leu Asn Gly
                485                 490                 495

Pro Gly Ser Gly Leu Tyr Gly Pro Gly Val Ile Gly Pro Gly Leu Ser
            500                 505                 510

Ala Ala Ala Ala Ala Gly Leu Tyr Val Ile Gly Pro Gly Val Ile Gly
        515                 520                 525

Pro Tyr Gly Pro Gly Ala Ser Ala Ala Ala Ala Ala Gly Leu Tyr Gly
    530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
            580                 585                 590


<210> SEQ ID NO 29
<211> LENGTH: 590
<212> TYPE: PRT
<213> ORGANISM: Artificial Sequence
<220> FEATURE:
<223> OTHER INFORMATION: Met-PRT918

<400> SEQUENCE: 29

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
```

-continued

```
        35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
        115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
        195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
        275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
                325                 330                 335

Ser Ala Ala Ala Ala Ala Gly Ile Tyr Gly Pro Gly Val Phe Gly Pro
            340                 345                 350

Tyr Gly Pro Gly Ile Ser Ala Ala Ala Ala Ala Gly Ile Tyr Val Phe
        355                 360                 365

Gly Pro Gly Val Phe Gly Pro Tyr Gly Pro Gly Ala Ser Gly Pro Gly
    370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
        435                 440                 445

Tyr Gly Pro Gly Ala Ser Ala Ala Ala Ala Ala Gly Ile Tyr Gly Pro
    450                 455                 460
```

```
Gly Val Phe Gly Pro Tyr Gly Pro Gly Ile Ser Ala Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
        515                 520                 525

Pro Tyr Gly Pro Gly Ala Ser Ala Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590


<210> SEQ ID NO 30
<211> LENGTH: 565
<212> TYPE: PRT
<213> ORGANISM: Artificial Sequence
<220> FEATURE:
<223> OTHER INFORMATION: Met-PRT699

<400> SEQUENCE: 30

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Gln Ser Gly Gln Tyr Gly Pro Gly Val Leu Gly Pro Gly Val
        35                  40                  45

Leu Gly Pro Gly Ser Ser Ala Ala Ala Ala Ala Ala Ala Gly Pro Gly
    50                  55                  60

Gln Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Val Leu Gly Pro Ser Ala Ser Ala Ala
                165                 170                 175

Ala Ala Ala Ala Ala Gly Ser Gly Val Leu Gly Pro Gly Gln Tyr Gly
            180                 185                 190

Pro Tyr Ala Ser Ala Ala Ala Ala Ala Ala Ala Gly Ser Tyr Gly Ser
        195                 200                 205

Gly Pro Gly Val Leu Gly Pro Tyr Gly Pro Gly Gln Ser Gly Ser Gly
    210                 215                 220

Val Leu Gly Pro Gly Val Leu Gly Pro Tyr Ala Ser Ala Ala Ala Ala
225                 230                 235                 240
```

```
Ala Ala Ala Gly Pro Gly Val Leu Gly Pro Tyr Gly Pro Gly Ser Ser
                245                 250                 255

Ala Ala Ala Ala Ala Ala Ala Gly Ser Tyr Gly Tyr Gly Pro Gly Val
            260                 265                 270

Leu Gly Pro Tyr Gly Pro Gly Ala Ser Gly Gln Asn Gly Pro Gly Ser
        275                 280                 285

Gly Gln Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Ala Gly Ser Tyr Gly Pro Gly Val Leu
                325                 330                 335

Gly Pro Gly Gln Tyr Gly Pro Gly Ser Ser Gly Pro Gly Val Leu Gly
            340                 345                 350

Pro Tyr Gly Pro Gly Ser Ser Ala Ala Ala Ala Ala Ala Ala Gly Ser
        355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Ala Gly Pro Gly Gln Tyr
            420                 425                 430

Gly Pro Gly Val Leu Gly Pro Ser Ala Ser Ala Ala Ala Ala Ala Ala
        435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Ala Ala Gly Ser Tyr Gly Pro
                485                 490                 495

Gly Val Leu Gly Pro Tyr Gly Pro Gly Pro Ser Ala Ala Ala Ala Ala
            500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Val Leu Gly Pro Gly
    530                 535                 540

Pro Ser Ala Ala Ala Ala Ala Ala Ala Gly Pro Gly Ser Gly Val Leu
545                 550                 555                 560

Gly Pro Gly Ala Ser
                565
```

<210> SEQ ID NO 31
<211> LENGTH: 565
<212> TYPE: PRT
<213> ORGANISM: Artificial Sequence
<220> FEATURE:
<223> OTHER INFORMATION: Met-PRT698

<400> SEQUENCE: 31

```
Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30
```

-continued

```
Pro Gly Ile Ser Gly Ile Tyr Gly Pro Gly Val Leu Gly Pro Gly Val
        35                  40                  45

Leu Gly Pro Gly Ser Ser Ala Ala Ala Ala Ala Ala Ala Gly Pro Gly
    50                  55                  60

Ile Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
                85                  90                  95

Ile Tyr Gly Pro Gly Val Leu Gly Pro Gly Val Leu Gly Pro Gly Ser
            100                 105                 110

Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Ala Gly Pro
    130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
                165                 170                 175

Ala Ala Ala Ala Ala Gly Ser Gly Val Leu Gly Pro Gly Ile Tyr Gly
            180                 185                 190

Pro Tyr Ala Ser Ala Ala Ala Ala Ala Ala Ala Gly Ser Tyr Gly Ser
        195                 200                 205

Gly Pro Gly Val Leu Gly Pro Tyr Gly Pro Gly Ile Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
                245                 250                 255

Ala Ala Ala Ala Ala Ala Ala Gly Ser Tyr Gly Tyr Gly Pro Gly Val
            260                 265                 270

Leu Gly Pro Tyr Gly Pro Gly Ala Ser Gly Ile Asn Gly Pro Gly Ser
        275                 280                 285

Gly Ile Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Ala Gly Ser Tyr Gly Pro Gly Val Leu
                325                 330                 335

Gly Pro Gly Ile Tyr Gly Pro Gly Ser Ser Gly Pro Gly Val Leu Gly
            340                 345                 350

Pro Tyr Gly Pro Gly Ser Ser Ala Ala Ala Ala Ala Ala Ala Gly Ser
        355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Ala Gly Pro Gly Ile Tyr
            420                 425                 430

Gly Pro Gly Val Leu Gly Pro Ser Ala Ser Ala Ala Ala Ala Ala Ala
        435                 440                 445
```

```
Ala Gly Ser Tyr Gly Ser Gly Pro Gly Ile Tyr Gly Pro Tyr Gly Pro
    450                 455                 460

Gly Ile Ser Gly Pro Gly Ser Gly Val Leu Gly Ile Gly Pro Tyr Gly
465                 470                 475                 480

Pro Gly Ala Ser Ala Ala Ala Ala Ala Ala Ala Gly Ser Tyr Gly Pro
                485                 490                 495

Gly Val Leu Gly Pro Tyr Gly Pro Gly Pro Ser Ala Ala Ala Ala Ala
            500                 505                 510

Ala Ala Gly Pro Gly Ser Gly Ile Tyr Gly Pro Gly Ala Ser Gly Ile
        515                 520                 525

Asn Gly Pro Gly Ser Gly Ile Tyr Gly Pro Gly Val Leu Gly Pro Gly
    530                 535                 540

Pro Ser Ala Ala Ala Ala Ala Ala Ala Gly Pro Gly Ser Gly Val Leu
545                 550                 555                 560

Gly Pro Gly Ala Ser
                565


<210> SEQ ID NO 32
<211> LENGTH: 1179
<212> TYPE: PRT
<213> ORGANISM: Artificial Sequence
<220> FEATURE:
<223> OTHER INFORMATION: Met-PRT966

<400> SEQUENCE: 32

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
        115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
        195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240
```

-continued

```
Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
        275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
                325                 330                 335

Ser Ala Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
        355                 360                 365

Gly Pro Gly Val Phe Gly Pro Tyr Gly Pro Gly Ala Ser Gly Pro Gly
    370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
        435                 440                 445

Tyr Gly Pro Gly Ala Ser Ala Ala Ala Ala Ala Gly Ile Tyr Gly Pro
    450                 455                 460

Gly Val Phe Gly Pro Tyr Gly Pro Gly Ile Ser Ala Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
        515                 520                 525

Pro Tyr Gly Pro Gly Ala Ser Ala Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser Gly Pro
            580                 585                 590

Gly Val Phe Gly Pro Tyr Gly Pro Gly Ala Ser Ala Ala Ala Ala Ala
        595                 600                 605

Gly Ile Asn Gly Pro Gly Ser Gly Val Phe Gly Pro Gly Ile Ser Gly
    610                 615                 620

Ile Tyr Gly Pro Gly Val Phe Gly Pro Gly Val Phe Gly Pro Gly Ser
625                 630                 635                 640

Ser Ala Ala Ala Ala Ala Gly Pro Gly Ile Tyr Gly Pro Gly Val Phe
                645                 650                 655

Gly Pro Ser Ala Ser Ala Ala Ala Ala Ala Gly Pro Gly Ser Gly Val
```

```
            660                 665                 670

Phe Gly Pro Gly Ala Ser Gly Ile Tyr Gly Pro Gly Val Phe Gly Pro
        675                 680                 685

Gly Val Phe Gly Pro Gly Ser Ser Ala Ala Ala Ala Ala Gly Ile Tyr
    690                 695                 700

Gly Ser Gly Pro Gly Val Phe Gly Pro Tyr Gly Ser Ala Ala Ala Ala
705                 710                 715                 720

Ala Gly Pro Gly Ser Gly Ile Tyr Gly Ile Gly Pro Tyr Gly Pro Gly
                725                 730                 735

Ala Ser Gly Pro Gly Ile Tyr Gly Pro Gly Val Phe Gly Pro Ser Ala
            740                 745                 750

Ser Ala Ala Ala Ala Ala Gly Ser Gly Val Phe Gly Pro Gly Ile Tyr
        755                 760                 765

Gly Pro Tyr Ala Ser Ala Ala Ala Ala Ala Gly Ile Tyr Gly Ser Gly
    770                 775                 780

Pro Gly Val Phe Gly Pro Tyr Gly Pro Gly Ile Ser Gly Ser Gly Val
785                 790                 795                 800

Phe Gly Pro Gly Val Phe Gly Pro Tyr Ala Ser Ala Ala Ala Ala Ala
                805                 810                 815

Gly Pro Gly Val Phe Gly Pro Tyr Gly Pro Gly Ser Ser Ala Ala Ala
            820                 825                 830

Ala Ala Gly Ile Tyr Gly Tyr Gly Pro Gly Val Phe Gly Pro Tyr Gly
        835                 840                 845

Pro Gly Ala Ser Gly Ile Asn Gly Pro Gly Ser Gly Ile Tyr Gly Pro
    850                 855                 860

Gly Val Phe Gly Pro Gly Ile Ser Ala Ala Ala Ala Ala Gly Pro Gly
865                 870                 875                 880

Val Phe Gly Pro Tyr Gly Pro Gly Ala Ser Ala Ala Ala Ala Ala Gly
                885                 890                 895

Ile Tyr Gly Pro Gly Val Phe Gly Pro Gly Ile Tyr Gly Pro Gly Ser
            900                 905                 910

Ser Gly Pro Gly Val Phe Gly Pro Tyr Gly Pro Gly Ser Ser Ala Ala
        915                 920                 925

Ala Ala Ala Gly Ile Tyr Gly Pro Gly Val Phe Gly Pro Tyr Gly Pro
    930                 935                 940

Gly Ile Ser Ala Ala Ala Ala Ala Gly Ile Tyr Val Phe Gly Pro Gly
945                 950                 955                 960

Val Phe Gly Pro Tyr Gly Pro Gly Ala Ser Gly Pro Gly Val Phe Gly
                965                 970                 975

Pro Tyr Gly Pro Gly Ala Ser Ala Ala Ala Ala Ala Gly Pro Gly Ile
            980                 985                 990

Tyr Gly Pro Gly Val Phe Gly Pro  Ser Ala Ser Ala Ala  Ala Ala Ala
        995                 1000                1005

Gly Ile  Tyr Gly Ser Gly Pro  Gly Ile Tyr Gly Pro  Tyr Gly Pro
    1010                 1015                 1020

Gly Ile  Ser Gly Pro Gly Ser  Gly Val Phe Gly Ile  Gly Pro Tyr
    1025                 1030                 1035

Gly Pro  Gly Ala Ser Ala Ala  Ala Ala Ala Gly Ile  Tyr Gly Pro
    1040                 1045                 1050

Gly Val  Phe Gly Pro Tyr Gly  Pro Gly Ile Ser Ala  Ala Ala Ala
    1055                 1060                 1065

Ala Gly  Pro Gly Ser Gly Ile  Tyr Gly Pro Gly Ala  Ser Gly Ile
    1070                 1075                 1080
```

```
Asn Gly Pro Gly Ser Gly Ile Tyr Gly Pro Gly Val Phe Gly Pro
    1085                1090                1095

Gly Ile Ser Ala Ala Ala Ala Ala Gly Ile Tyr Val Phe Gly Pro
    1100                1105                1110

Gly Val Phe Gly Pro Tyr Gly Pro Gly Ala Ser Ala Ala Ala Ala
    1115                1120                1125

Ala Gly Ile Tyr Gly Ser Gly Pro Gly Val Phe Gly Pro Tyr Gly
    1130                1135                1140

Pro Gly Ile Ser Gly Ser Gly Val Phe Gly Pro Gly Val Phe Gly
    1145                1150                1155

Pro Tyr Ala Ser Ala Ala Ala Ala Ala Gly Pro Gly Ser Gly Val
    1160                1165                1170

Phe Gly Pro Gly Ala Ser
    1175


<210> SEQ ID NO 33
<211> LENGTH: 601
<212> TYPE: PRT
<213> ORGANISM: Artificial Sequence
<220> FEATURE:
<223> OTHER INFORMATION: PRT888

<400> SEQUENCE: 33

Met His His His His His His Ser Ser Gly Ser Ser Gly Pro Gly Val
1               5                   10                  15

Leu Gly Pro Tyr Gly Pro Gly Ala Ser Ala Ala Ala Ala Ala Gly Gln
            20                  25                  30

Asn Gly Pro Gly Ser Gly Val Leu Gly Pro Gly Gln Ser Gly Gln Tyr
        35                  40                  45

Gly Pro Gly Val Leu Gly Pro Gly Val Leu Gly Pro Gly Ser Ser Ala
    50                  55                  60

Ala Ala Ala Ala Gly Pro Gly Gln Tyr Gly Pro Gly Val Leu Gly Pro
65                  70                  75                  80

Ser Ala Ser Ala Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
            100                 105                 110

Leu Gly Pro Gly Ser Ser Ala Ala Ala Ala Ala Gly Gln Tyr Gly Ser
        115                 120                 125

Gly Pro Gly Val Leu Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Ala Gly Ser Gly Val Leu Gly Pro Gly Gln Tyr Gly Pro
            180                 185                 190

Tyr Ala Ser Ala Ala Ala Ala Ala Gly Gln Tyr Gly Ser Gly Pro Gly
        195                 200                 205

Val Leu Gly Pro Tyr Gly Pro Gly Gln Ser Gly Ser Gly Val Leu Gly
    210                 215                 220

Pro Gly Val Leu Gly Pro Tyr Ala Ser Ala Ala Ala Ala Ala Gly Pro
225                 230                 235                 240

Gly Val Leu Gly Pro Tyr Gly Pro Gly Ser Ser Ala Ala Ala Ala Ala
                245                 250                 255
```

```
Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Ala Gly Pro Gly Val Leu
    290                 295                 300

Gly Pro Tyr Gly Pro Gly Ala Ser Ala Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala Ala
            340                 345                 350

Ala Gly Gln Tyr Gly Pro Gly Val Leu Gly Pro Tyr Gly Pro Gly Gln
        355                 360                 365

Ser Ala Ala Ala Ala Ala Gly Gln Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Ala Gly Pro Gly Gln Tyr Gly
                405                 410                 415

Pro Gly Val Leu Gly Pro Ser Ala Ser Ala Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
    450                 455                 460

Ser Ala Ala Ala Ala Ala Gly Gln Tyr Gly Pro Gly Val Leu Gly Pro
465                 470                 475                 480

Tyr Gly Pro Gly Gln Ser Ala Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Val Leu Gly Pro Gly Gln Ser Ala Ala Ala Ala Ala
        515                 520                 525

Gly Gln Tyr Val Leu Gly Pro Gly Val Leu Gly Pro Tyr Gly Pro Gly
    530                 535                 540

Ala Ser Ala Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
                565                 570                 575

Gly Val Leu Gly Pro Tyr Ala Ser Ala Ala Ala Ala Ala Gly Pro Gly
            580                 585                 590

Ser Gly Val Leu Gly Pro Gly Ala Ser
        595                 600
```

<210> SEQ ID NO 34
<211> LENGTH: 601
<212> TYPE: PRT
<213> ORGANISM: Artificial Sequence
<220> FEATURE:
<223> OTHER INFORMATION: PRT965

<400> SEQUENCE: 34

```
Met His His His His His His Ser Ser Gly Ser Ser Gly Pro Gly Thr
1               5                   10                  15
```

-continued

```
Ser Gly Pro Tyr Gly Pro Gly Ala Ser Ala Ala Ala Ala Ala Gly Ala
            20                  25                  30

Asn Gly Pro Gly Ser Gly Thr Ser Gly Pro Gly Ala Ser Gly Ala Tyr
        35                  40                  45

Gly Pro Gly Thr Ser Gly Pro Gly Thr Ser Gly Pro Gly Ser Ser Ala
    50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Ala Gly Pro Gly Ser Gly Thr Ser Gly
                85                  90                  95

Pro Gly Ala Ser Gly Ala Tyr Gly Pro Gly Thr Ser Gly Pro Gly Thr
            100                 105                 110

Ser Gly Pro Gly Ser Ser Ala Ala Ala Ala Ala Gly Ala Tyr Gly Ser
        115                 120                 125

Gly Pro Gly Thr Ser Gly Pro Tyr Gly Ser Ala Ala Ala Ala Ala Gly
    130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
                165                 170                 175

Ala Ala Ala Ala Gly Ser Gly Thr Ser Gly Pro Gly Ala Tyr Gly Pro
            180                 185                 190

Tyr Ala Ser Ala Ala Ala Ala Ala Gly Ala Tyr Gly Ser Gly Pro Gly
        195                 200                 205

Thr Ser Gly Pro Tyr Gly Pro Gly Ala Ser Gly Ser Gly Thr Ser Gly
    210                 215                 220

Pro Gly Thr Ser Gly Pro Tyr Ala Ser Ala Ala Ala Ala Ala Gly Pro
225                 230                 235                 240

Gly Thr Ser Gly Pro Tyr Gly Pro Gly Ser Ser Ala Ala Ala Ala Ala
                245                 250                 255

Gly Ala Tyr Gly Tyr Gly Pro Gly Thr Ser Gly Pro Tyr Gly Pro Gly
            260                 265                 270

Ala Ser Gly Ala Asn Gly Pro Gly Ser Gly Ala Tyr Gly Pro Gly Thr
        275                 280                 285

Ser Gly Pro Gly Ala Ser Ala Ala Ala Ala Ala Gly Pro Gly Thr Ser
    290                 295                 300

Gly Pro Tyr Gly Pro Gly Ala Ser Ala Ala Ala Ala Ala Gly Ala Tyr
305                 310                 315                 320

Gly Pro Gly Thr Ser Gly Pro Gly Ala Tyr Gly Pro Gly Ser Ser Gly
                325                 330                 335

Pro Gly Thr Ser Gly Pro Tyr Gly Pro Gly Ser Ser Ala Ala Ala Ala
            340                 345                 350

Ala Gly Ala Tyr Gly Pro Gly Thr Ser Gly Pro Tyr Gly Pro Gly Ala
        355                 360                 365

Ser Ala Ala Ala Ala Ala Gly Ala Tyr Thr Ser Gly Pro Gly Thr Ser
    370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Ala Gly Pro Gly Ala Tyr Gly
                405                 410                 415

Pro Gly Thr Ser Gly Pro Ser Ala Ser Ala Ala Ala Ala Ala Gly Ala
            420                 425                 430
```

Tyr Gly Ser Gly Pro Gly Ala Tyr Gly Pro Tyr Gly Pro Gly Ala Ser
        435                 440                 445

Gly Pro Gly Ser Gly Thr Ser Gly Ala Gly Pro Tyr Gly Pro Gly Ala
    450                 455                 460

Ser Ala Ala Ala Ala Ala Gly Ala Tyr Gly Pro Gly Thr Ser Gly Pro
465                 470                 475                 480

Tyr Gly Pro Gly Ala Ser Ala Ala Ala Ala Ala Gly Pro Gly Ser Gly
            485                 490                 495

Ala Tyr Gly Pro Gly Ala Ser Gly Ala Asn Gly Pro Gly Ser Gly Ala
            500                 505                 510

Tyr Gly Pro Gly Thr Ser Gly Pro Gly Ala Ser Ala Ala Ala Ala Ala
        515                 520                 525

Gly Ala Tyr Thr Ser Gly Pro Gly Thr Ser Gly Pro Tyr Gly Pro Gly
    530                 535                 540

Ala Ser Ala Ala Ala Ala Ala Gly Ala Tyr Gly Ser Gly Pro Gly Thr
545                 550                 555                 560

Ser Gly Pro Tyr Gly Pro Gly Ala Ser Gly Ser Gly Thr Ser Gly Pro
            565                 570                 575

Gly Thr Ser Gly Pro Tyr Ala Ser Ala Ala Ala Ala Ala Gly Pro Gly
            580                 585                 590

Ser Gly Thr Ser Gly Pro Gly Ala Ser
        595                 600

<210> SEQ ID NO 35
<211> LENGTH: 601
<212> TYPE: PRT
<213> ORGANISM: Artificial Sequence
<220> FEATURE:
<223> OTHER INFORMATION: PRT889

<400> SEQUENCE: 35

Met His His His His His His Ser Ser Gly Ser Ser Gly Pro Gly Val
1               5                   10                  15

Leu Gly Pro Tyr Gly Pro Gly Ala Ser Ala Ala Ala Ala Ala Gly Ile
            20                  25                  30

Asn Gly Pro Gly Ser Gly Val Leu Gly Pro Gly Ile Ser Gly Ile Tyr
        35                  40                  45

Gly Pro Gly Val Leu Gly Pro Gly Val Leu Gly Pro Gly Ser Ser Ala
    50                  55                  60

Ala Ala Ala Ala Gly Pro Gly Ile Tyr Gly Pro Gly Val Leu Gly Pro
65                  70                  75                  80

Ser Ala Ser Ala Ala Ala Ala Ala Gly Pro Gly Ser Gly Val Leu Gly
            85                  90                  95

Pro Gly Ala Ser Gly Ile Tyr Gly Pro Gly Val Leu Gly Pro Gly Val
            100                 105                 110

Leu Gly Pro Gly Ser Ser Ala Ala Ala Ala Ala Gly Ile Tyr Gly Ser
        115                 120                 125

Gly Pro Gly Val Leu Gly Pro Tyr Gly Ser Ala Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Leu Gly Pro Ser Ala Ser Ala
            165                 170                 175

Ala Ala Ala Ala Gly Ser Gly Val Leu Gly Pro Gly Ile Tyr Gly Pro
            180                 185                 190

-continued

```
Tyr Ala Ser Ala Ala Ala Ala Ala Gly Ile Tyr Gly Ser Gly Pro Gly
        195                 200                 205

Val Leu Gly Pro Tyr Gly Pro Gly Ile Ser Gly Ser Gly Val Leu Gly
    210                 215                 220

Pro Gly Val Leu Gly Pro Tyr Ala Ser Ala Ala Ala Ala Ala Gly Pro
225                 230                 235                 240

Gly Val Leu Gly Pro Tyr Gly Pro Gly Ser Ser Ala Ala Ala Ala Ala
                245                 250                 255

Gly Ile Tyr Gly Tyr Gly Pro Gly Val Leu Gly Pro Tyr Gly Pro Gly
            260                 265                 270

Ala Ser Gly Ile Asn Gly Pro Gly Ser Gly Ile Tyr Gly Pro Gly Val
        275                 280                 285

Leu Gly Pro Gly Ile Ser Ala Ala Ala Ala Ala Gly Pro Gly Val Leu
    290                 295                 300

Gly Pro Tyr Gly Pro Gly Ala Ser Ala Ala Ala Ala Ala Gly Ile Tyr
305                 310                 315                 320

Gly Pro Gly Val Leu Gly Pro Gly Ile Tyr Gly Pro Gly Ser Ser Gly
                325                 330                 335

Pro Gly Val Leu Gly Pro Tyr Gly Pro Gly Ser Ser Ala Ala Ala Ala
            340                 345                 350

Ala Gly Ile Tyr Gly Pro Gly Val Leu Gly Pro Tyr Gly Pro Gly Ile
        355                 360                 365

Ser Ala Ala Ala Ala Ala Gly Ile Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Leu Gly Pro Ser Ala Ser Ala Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Leu Gly Ile Gly Pro Tyr Gly Pro Gly Ala
    450                 455                 460

Ser Ala Ala Ala Ala Ala Gly Ile Tyr Gly Pro Gly Val Leu Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Leu Gly Pro Gly Ile Ser Ala Ala Ala Ala Ala
        515                 520                 525

Gly Ile Tyr Val Leu Gly Pro Gly Val Leu Gly Pro Tyr Gly Pro Gly
    530                 535                 540

Ala Ser Ala Ala Ala Ala Ala Gly Ile Tyr Gly Ser Gly Pro Gly Val
545                 550                 555                 560

Leu Gly Pro Tyr Gly Pro Gly Ile Ser Gly Ser Gly Val Leu Gly Pro
                565                 570                 575

Gly Val Leu Gly Pro Tyr Ala Ser Ala Ala Ala Ala Ala Gly Pro Gly
            580                 585                 590

Ser Gly Val Leu Gly Pro Gly Ala Ser
        595                 600
```

<210> SEQ ID NO 36
<211> LENGTH: 601
<212> TYPE: PRT
<213> ORGANISM: Artificial Sequence
<220> FEATURE:
<223> OTHER INFORMATION: PRT916

<400> SEQUENCE: 36

```
Met His His His His His His Ser Ser Gly Ser Ser Gly Pro Gly Val
1               5                   10                  15

Ile Gly Pro Tyr Gly Pro Gly Ala Ser Ala Ala Ala Ala Ala Gly Leu
            20                  25                  30

Asn Gly Pro Gly Ser Gly Val Ile Gly Pro Gly Leu Ser Gly Leu Tyr
        35                  40                  45

Gly Pro Gly Val Ile Gly Pro Gly Val Ile Gly Pro Gly Ser Ser Ala
    50                  55                  60

Ala Ala Ala Ala Gly Pro Gly Leu Tyr Gly Pro Gly Val Ile Gly Pro
65                  70                  75                  80

Ser Ala Ser Ala Ala Ala Ala Ala Gly Pro Gly Ser Gly Val Ile Gly
                85                  90                  95

Pro Gly Ala Ser Gly Leu Tyr Gly Pro Gly Val Ile Gly Pro Gly Val
            100                 105                 110

Ile Gly Pro Gly Ser Ser Ala Ala Ala Ala Ala Gly Leu Tyr Gly Ser
        115                 120                 125

Gly Pro Gly Val Ile Gly Pro Tyr Gly Ser Ala Ala Ala Ala Ala Gly
    130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
                165                 170                 175

Ala Ala Ala Ala Gly Ser Gly Val Ile Gly Pro Gly Leu Tyr Gly Pro
            180                 185                 190

Tyr Ala Ser Ala Ala Ala Ala Ala Gly Leu Tyr Gly Ser Gly Pro Gly
        195                 200                 205

Val Ile Gly Pro Tyr Gly Pro Gly Leu Ser Gly Ser Gly Val Ile Gly
    210                 215                 220

Pro Gly Val Ile Gly Pro Tyr Ala Ser Ala Ala Ala Ala Ala Gly Pro
225                 230                 235                 240

Gly Val Ile Gly Pro Tyr Gly Pro Gly Ser Ser Ala Ala Ala Ala Ala
                245                 250                 255

Gly Leu Tyr Gly Tyr Gly Pro Gly Val Ile Gly Pro Tyr Gly Pro Gly
            260                 265                 270

Ala Ser Gly Leu Asn Gly Pro Gly Ser Gly Leu Tyr Gly Pro Gly Val
        275                 280                 285

Ile Gly Pro Gly Leu Ser Ala Ala Ala Ala Ala Gly Pro Gly Val Ile
    290                 295                 300

Gly Pro Tyr Gly Pro Gly Ala Ser Ala Ala Ala Ala Ala Gly Leu Tyr
305                 310                 315                 320

Gly Pro Gly Val Ile Gly Pro Gly Leu Tyr Gly Pro Gly Ser Ser Gly
                325                 330                 335

Pro Gly Val Ile Gly Pro Tyr Gly Pro Gly Ser Ser Ala Ala Ala Ala
            340                 345                 350

Ala Gly Leu Tyr Gly Pro Gly Val Ile Gly Pro Tyr Gly Pro Gly Leu
        355                 360                 365

Ser Ala Ala Ala Ala Ala Gly Leu Tyr Val Ile Gly Pro Gly Val Ile
```

```
    370                 375                 380

Gly Pro Tyr Gly Pro Gly Ala Ser Gly Pro Gly Val Ile Gly Pro Tyr
385                 390                 395                 400

Gly Pro Gly Ala Ser Ala Ala Ala Ala Ala Gly Pro Gly Leu Tyr Gly
                405                 410                 415

Pro Gly Val Ile Gly Pro Ser Ala Ser Ala Ala Ala Ala Ala Gly Leu
            420                 425                 430

Tyr Gly Ser Gly Pro Gly Leu Tyr Gly Pro Tyr Gly Pro Gly Leu Ser
        435                 440                 445

Gly Pro Gly Ser Gly Val Ile Gly Leu Gly Pro Tyr Gly Pro Gly Ala
    450                 455                 460

Ser Ala Ala Ala Ala Ala Gly Leu Tyr Gly Pro Gly Val Ile Gly Pro
465                 470                 475                 480

Tyr Gly Pro Gly Leu Ser Ala Ala Ala Ala Ala Gly Pro Gly Ser Gly
                485                 490                 495

Leu Tyr Gly Pro Gly Ala Ser Gly Leu Asn Gly Pro Gly Ser Gly Leu
            500                 505                 510

Tyr Gly Pro Gly Val Ile Gly Pro Gly Leu Ser Ala Ala Ala Ala Ala
        515                 520                 525

Gly Leu Tyr Val Ile Gly Pro Gly Val Ile Gly Pro Tyr Gly Pro Gly
    530                 535                 540

Ala Ser Ala Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Ala Gly Pro Gly
            580                 585                 590

Ser Gly Val Ile Gly Pro Gly Ala Ser
        595                 600


<210> SEQ ID NO 37
<211> LENGTH: 601
<212> TYPE: PRT
<213> ORGANISM: Artificial Sequence
<220> FEATURE:
<223> OTHER INFORMATION: PRT918

<400> SEQUENCE: 37

Met His His His His His His Ser Ser Gly Ser Ser Gly Pro Gly Val
1               5                   10                  15

Phe Gly Pro Tyr Gly Pro Gly Ala Ser Ala Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Ala Gly Ile Tyr Gly Ser
        115                 120                 125

Gly Pro Gly Val Phe Gly Pro Tyr Gly Ser Ala Ala Ala Ala Ala Gly
```

```
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Ala Gly Ser Gly Val Phe Gly Pro Gly Ile Tyr Gly Pro
            180                 185                 190

Tyr Ala Ser Ala Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
    210                 215                 220

Pro Gly Val Phe Gly Pro Tyr Ala Ser Ala Ala Ala Ala Ala Gly Pro
225                 230                 235                 240

Gly Val Phe Gly Pro Tyr Gly Pro Gly Ser Ser Ala Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Ala Gly Pro Gly Val Phe
    290                 295                 300

Gly Pro Tyr Gly Pro Gly Ala Ser Ala Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Phe Gly Pro Ser Ala Ser Ala Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Phe Gly Pro Gly Ile Ser Ala Ala Ala Ala Ala
        515                 520                 525

Gly Ile Tyr Val Phe Gly Pro Gly Val Phe Gly Pro Tyr Gly Pro Gly
    530                 535                 540

Ala Ser Ala Ala Ala Ala Ala Gly Ile Tyr Gly Ser Gly Pro Gly Val
545                 550                 555                 560
```

```
Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Ala Gly Pro Gly
            580                 585                 590

Ser Gly Val Phe Gly Pro Gly Ala Ser
        595                 600


<210> SEQ ID NO 38
<211> LENGTH: 576
<212> TYPE: PRT
<213> ORGANISM: Artificial Sequence
<220> FEATURE:
<223> OTHER INFORMATION: PRT699

<400> SEQUENCE: 38

Met His His His His His His Ser Ser Gly Ser Ser Gly Pro Gly Val
1               5                   10                  15

Leu Gly Pro Tyr Gly Pro Gly Ala Ser Ala Ala Ala Ala Ala Ala Ala
            20                  25                  30

Gly Ser Asn Gly Pro Gly Ser Gly Val Leu Gly Pro Gly Gln Ser Gly
        35                  40                  45

Gln Tyr Gly Pro Gly Val Leu Gly Pro Gly Val Leu Gly Pro Gly Ser
    50                  55                  60

Ser Ala Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Ala Ala Gly Pro
                85                  90                  95

Gly Ser Gly Val Leu Gly Pro Gly Ala Ser Gly Gln Tyr Gly Pro Gly
            100                 105                 110

Val Leu Gly Pro Gly Val Leu Gly Pro Gly Ser Ser Ala Ala Ala Ala
        115                 120                 125

Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala Ala
            180                 185                 190

Gly Ser Gly Val Leu Gly Pro Gly Gln Tyr Gly Pro Tyr Ala Ser Ala
        195                 200                 205

Ala Ala Ala Ala Ala Ala Gly Ser Tyr Gly Ser Gly Pro Gly Val Leu
    210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Ala Gly Pro
                245                 250                 255

Gly Val Leu Gly Pro Tyr Gly Pro Gly Ser Ser Ala Ala Ala Ala Ala
            260                 265                 270

Ala Ala Gly Ser Tyr Gly Tyr Gly Pro Gly Val Leu Gly Pro Tyr Gly
        275                 280                 285

Pro Gly Ala Ser Gly Gln Asn Gly Pro Gly Ser Gly Gln Tyr Gly Pro
    290                 295                 300

Gly Val Leu Gly Pro Gly Pro Ser Ala Ala Ala Ala Ala Ala Ala Gly
305                 310                 315                 320
```

```
Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Gln Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
        435                 440                 445

Gly Pro Ser Ala Ser Ala Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
                485                 490                 495

Ala Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575
```

<210> SEQ ID NO 39
<211> LENGTH: 576
<212> TYPE: PRT
<213> ORGANISM: Artificial Sequence
<220> FEATURE:
<223> OTHER INFORMATION: PRT698

<400> SEQUENCE: 39

```
Met His His His His His His Ser Ser Gly Ser Ser Gly Pro Gly Val
1               5                   10                  15

Leu Gly Pro Tyr Gly Pro Gly Ala Ser Ala Ala Ala Ala Ala Ala Ala
            20                  25                  30

Gly Ser Asn Gly Pro Gly Ser Gly Val Leu Gly Pro Gly Ile Ser Gly
        35                  40                  45

Ile Tyr Gly Pro Gly Val Leu Gly Pro Gly Val Leu Gly Pro Gly Ser
    50                  55                  60

Ser Ala Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Ala Ala Gly Pro
                85                  90                  95

Gly Ser Gly Val Leu Gly Pro Gly Ala Ser Gly Ile Tyr Gly Pro Gly
            100                 105                 110
```

```
Val Leu Gly Pro Gly Val Leu Gly Pro Gly Ser Ser Ala Ala Ala Ala
        115                 120                 125

Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
                165                 170                 175

Pro Gly Val Leu Gly Pro Ser Ala Ser Ala Ala Ala Ala Ala Ala Ala
            180                 185                 190

Gly Ser Gly Val Leu Gly Pro Gly Ile Tyr Gly Pro Tyr Ala Ser Ala
        195                 200                 205

Ala Ala Ala Ala Ala Ala Gly Ser Tyr Gly Ser Gly Pro Gly Val Leu
    210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Ala Gly Pro
                245                 250                 255

Gly Val Leu Gly Pro Tyr Gly Pro Gly Ser Ser Ala Ala Ala Ala Ala
            260                 265                 270

Ala Ala Gly Ser Tyr Gly Tyr Gly Pro Gly Val Leu Gly Pro Tyr Gly
        275                 280                 285

Pro Gly Ala Ser Gly Ile Asn Gly Pro Gly Ser Gly Ile Tyr Gly Pro
    290                 295                 300

Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Ile Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Ile Tyr Gly Pro Gly Val Leu
        435                 440                 445

Gly Pro Ser Ala Ser Ala Ala Ala Ala Ala Ala Ala Gly Ser Tyr Gly
    450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
                485                 490                 495

Ala Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Ala Gly Pro Gly
        515                 520                 525
```

```
Ser Gly Ile Tyr Gly Pro Gly Ala Ser Gly Ile Asn Gly Pro Gly Ser
    530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575


<210> SEQ ID NO 40
<211> LENGTH: 1190
<212> TYPE: PRT
<213> ORGANISM: Artificial Sequence
<220> FEATURE:
<223> OTHER INFORMATION: PRT966

<400> SEQUENCE: 40

Met His His His His His His Ser Ser Gly Ser Ser Gly Pro Gly Val
1               5                   10                  15

Phe Gly Pro Tyr Gly Pro Gly Ala Ser Ala Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Ala Gly Ile Tyr Gly Ser
        115                 120                 125

Gly Pro Gly Val Phe Gly Pro Tyr Gly Ser Ala Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Ala Gly Ser Gly Val Phe Gly Pro Gly Ile Tyr Gly Pro
            180                 185                 190

Tyr Ala Ser Ala Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
    210                 215                 220

Pro Gly Val Phe Gly Pro Tyr Ala Ser Ala Ala Ala Ala Ala Gly Pro
225                 230                 235                 240

Gly Val Phe Gly Pro Tyr Gly Pro Gly Ser Ser Ala Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Ala Gly Pro Gly Val Phe
    290                 295                 300

Gly Pro Tyr Gly Pro Gly Ala Ser Ala Ala Ala Ala Ala Gly Ile Tyr
305                 310                 315                 320
```

-continued

```
Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Phe Gly Pro Ser Ala Ser Ala Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Phe Gly Pro Gly Ile Ser Ala Ala Ala Ala Ala
        515                 520                 525

Gly Ile Tyr Val Phe Gly Pro Gly Val Phe Gly Pro Tyr Gly Pro Gly
    530                 535                 540

Ala Ser Ala Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Ala Gly Pro Gly
            580                 585                 590

Ser Gly Val Phe Gly Pro Gly Ala Ser Gly Pro Gly Val Phe Gly Pro
        595                 600                 605

Tyr Gly Pro Gly Ala Ser Ala Ala Ala Ala Ala Gly Ile Asn Gly Pro
    610                 615                 620

Gly Ser Gly Val Phe Gly Pro Gly Ile Ser Gly Ile Tyr Gly Pro Gly
625                 630                 635                 640

Val Phe Gly Pro Gly Val Phe Gly Pro Gly Ser Ser Ala Ala Ala Ala
                645                 650                 655

Ala Gly Pro Gly Ile Tyr Gly Pro Gly Val Phe Gly Pro Ser Ala Ser
            660                 665                 670

Ala Ala Ala Ala Ala Gly Pro Gly Ser Gly Val Phe Gly Pro Gly Ala
        675                 680                 685

Ser Gly Ile Tyr Gly Pro Gly Val Phe Gly Pro Gly Val Phe Gly Pro
    690                 695                 700

Gly Ser Ser Ala Ala Ala Ala Ala Gly Ile Tyr Gly Ser Gly Pro Gly
705                 710                 715                 720

Val Phe Gly Pro Tyr Gly Ser Ala Ala Ala Ala Ala Gly Pro Gly Ser
                725                 730                 735

Gly Ile Tyr Gly Ile Gly Pro Tyr Gly Pro Gly Ala Ser Gly Pro Gly
```

-continued

```
            740                 745                 750

Ile Tyr Gly Pro Gly Val Phe Gly Pro Ser Ala Ser Ala Ala Ala Ala
        755                 760                 765

Ala Gly Ser Gly Val Phe Gly Pro Gly Ile Tyr Gly Pro Tyr Ala Ser
    770                 775                 780

Ala Ala Ala Ala Ala Gly Ile Tyr Gly Ser Gly Pro Gly Val Phe Gly
785                 790                 795                 800

Pro Tyr Gly Pro Gly Ile Ser Gly Ser Gly Val Phe Gly Pro Gly Val
            805                 810                 815

Phe Gly Pro Tyr Ala Ser Ala Ala Ala Ala Ala Gly Pro Gly Val Phe
            820                 825                 830

Gly Pro Tyr Gly Pro Gly Ser Ser Ala Ala Ala Ala Ala Gly Ile Tyr
        835                 840                 845

Gly Tyr Gly Pro Gly Val Phe Gly Pro Tyr Gly Pro Gly Ala Ser Gly
    850                 855                 860

Ile Asn Gly Pro Gly Ser Gly Ile Tyr Gly Pro Gly Val Phe Gly Pro
865                 870                 875                 880

Gly Ile Ser Ala Ala Ala Ala Ala Gly Pro Gly Val Phe Gly Pro Tyr
            885                 890                 895

Gly Pro Gly Ala Ser Ala Ala Ala Ala Ala Gly Ile Tyr Gly Pro Gly
            900                 905                 910

Val Phe Gly Pro Gly Ile Tyr Gly Pro Gly Ser Ser Gly Pro Gly Val
        915                 920                 925

Phe Gly Pro Tyr Gly Pro Gly Ser Ser Ala Ala Ala Ala Ala Gly Ile
    930                 935                 940

Tyr Gly Pro Gly Val Phe Gly Pro Tyr Gly Pro Gly Ile Ser Ala Ala
945                 950                 955                 960

Ala Ala Ala Gly Ile Tyr Val Phe Gly Pro Gly Val Phe Gly Pro Tyr
            965                 970                 975

Gly Pro Gly Ala Ser Gly Pro Gly Val Phe Gly Pro Tyr Gly Pro Gly
            980                 985                 990

Ala Ser Ala Ala Ala Ala Ala Gly  Pro Gly Ile Tyr Gly  Pro Gly Val
        995                 1000                1005

Phe Gly  Pro Ser Ala Ser Ala  Ala Ala Ala Ala Gly  Ile Tyr Gly
    1010                1015                1020

Ser Gly  Pro Gly Ile Tyr Gly  Pro Tyr Gly Pro Gly  Ile Ser Gly
    1025                1030                1035

Pro Gly  Ser Gly Val Phe Gly  Ile Gly Pro Tyr Gly  Pro Gly Ala
    1040                1045                1050

Ser Ala  Ala Ala Ala Ala Gly  Ile Tyr Gly Pro Gly  Val Phe Gly
    1055                1060                1065

Pro Tyr  Gly Pro Gly Ile Ser  Ala Ala Ala Ala Ala  Gly Pro Gly
    1070                1075                1080

Ser Gly  Ile Tyr Gly Pro Gly  Ala Ser Gly Ile Asn  Gly Pro Gly
    1085                1090                1095

Ser Gly  Ile Tyr Gly Pro Gly  Val Phe Gly Pro Gly  Ile Ser Ala
    1100                1105                1110

Ala Ala  Ala Ala Gly Ile Tyr  Val Phe Gly Pro Gly  Val Phe Gly
    1115                1120                1125

Pro Tyr  Gly Pro Gly Ala Ser  Ala Ala Ala Ala Ala  Gly Ile Tyr
    1130                1135                1140

Gly Ser  Gly Pro Gly Val Phe  Gly Pro Tyr Gly Pro  Gly Ile Ser
    1145                1150                1155
```

Gly Ser Gly Val Phe Gly Pro Gly Val Phe Gly Pro Tyr Ala Ser
1160 1165 1170

Ala Ala Ala Ala Ala Gly Pro Gly Ser Gly Val Phe Gly Pro Gly
1175 1180 1185

Ala Ser
1190

<210> SEQ ID NO 41
<211> LENGTH: 590
<212> TYPE: PRT
<213> ORGANISM: Artificial Sequence
<220> FEATURE:
<223> OTHER INFORMATION: Met-PRT917

<400> SEQUENCE: 41

Met Gly Pro Gly Leu Ile Gly Pro Tyr Gly Pro Gly Ala Ser Ala Ala
1 5 10 15

Ala Ala Ala Gly Val Asn Gly Pro Gly Ser Gly Leu Ile Gly Pro Gly
20 25 30

Val Ser Gly Val Tyr Gly Pro Gly Leu Ile Gly Pro Gly Leu Ile Gly
35 40 45

Pro Gly Ser Ser Ala Ala Ala Ala Ala Gly Pro Gly Val Tyr Gly Pro
50 55 60

Gly Leu Ile Gly Pro Ser Ala Ser Ala Ala Ala Ala Ala Gly Pro Gly
65 70 75 80

Ser Gly Leu Ile Gly Pro Gly Ala Ser Gly Val Tyr Gly Pro Gly Leu
85 90 95

Ile Gly Pro Gly Leu Ile Gly Pro Gly Ser Ser Ala Ala Ala Ala Ala
100 105 110

Gly Val Tyr Gly Ser Gly Pro Gly Leu Ile Gly Pro Tyr Gly Ser Ala
115 120 125

Ala Ala Ala Ala Gly Pro Gly Ser Gly Val Tyr Gly Val Gly Pro Tyr
130 135 140

Gly Pro Gly Ala Ser Gly Pro Gly Val Tyr Gly Pro Gly Leu Ile Gly
145 150 155 160

Pro Ser Ala Ser Ala Ala Ala Ala Ala Gly Ser Gly Leu Ile Gly Pro
165 170 175

Gly Val Tyr Gly Pro Tyr Ala Ser Ala Ala Ala Ala Ala Gly Val Tyr
180 185 190

Gly Ser Gly Pro Gly Leu Ile Gly Pro Tyr Gly Pro Gly Val Ser Gly
195 200 205

Ser Gly Leu Ile Gly Pro Gly Leu Ile Gly Pro Tyr Ala Ser Ala Ala
210 215 220

Ala Ala Ala Gly Pro Gly Leu Ile Gly Pro Tyr Gly Pro Gly Ser Ser
225 230 235 240

Ala Ala Ala Ala Ala Gly Val Tyr Gly Tyr Gly Pro Gly Leu Ile Gly
245 250 255

Pro Tyr Gly Pro Gly Ala Ser Gly Val Asn Gly Pro Gly Ser Gly Val
260 265 270

Tyr Gly Pro Gly Leu Ile Gly Pro Gly Val Ser Ala Ala Ala Ala Ala
275 280 285

Gly Pro Gly Leu Ile Gly Pro Tyr Gly Pro Gly Ala Ser Ala Ala Ala
290 295 300

Ala Ala Gly Val Tyr Gly Pro Gly Leu Ile Gly Pro Gly Val Tyr Gly
305 310 315 320

-continued

Pro Gly Ser Ser Gly Pro Gly Leu Ile Gly Pro Tyr Gly Pro Gly Ser
325 330 335

Ser Ala Ala Ala Ala Ala Gly Val Tyr Gly Pro Gly Leu Ile Gly Pro
340 345 350

Tyr Gly Pro Gly Val Ser Ala Ala Ala Ala Ala Gly Val Tyr Leu Ile
355 360 365

Gly Pro Gly Leu Ile Gly Pro Tyr Gly Pro Gly Ala Ser Gly Pro Gly
370 375 380

Leu Ile Gly Pro Tyr Gly Pro Gly Ala Ser Ala Ala Ala Ala Ala Gly
385 390 395 400

Pro Gly Val Tyr Gly Pro Gly Leu Ile Gly Pro Ser Ala Ser Ala Ala
405 410 415

Ala Ala Ala Gly Val Tyr Gly Ser Gly Pro Gly Val Tyr Gly Pro Tyr
420 425 430

Gly Pro Gly Val Ser Gly Pro Gly Ser Gly Leu Ile Gly Val Gly Pro
435 440 445

Tyr Gly Pro Gly Ala Ser Ala Ala Ala Ala Ala Gly Val Tyr Gly Pro
450 455 460

Gly Leu Ile Gly Pro Tyr Gly Pro Gly Val Ser Ala Ala Ala Ala Ala
465 470 475 480

Gly Pro Gly Ser Gly Val Tyr Gly Pro Gly Ala Ser Gly Val Asn Gly
485 490 495

Pro Gly Ser Gly Val Tyr Gly Pro Gly Leu Ile Gly Pro Gly Val Ser
500 505 510

Ala Ala Ala Ala Ala Gly Val Tyr Leu Ile Gly Pro Gly Leu Ile Gly
515 520 525

Pro Tyr Gly Pro Gly Ala Ser Ala Ala Ala Ala Ala Gly Val Tyr Gly
530 535 540

Ser Gly Pro Gly Leu Ile Gly Pro Tyr Gly Pro Gly Val Ser Gly Ser
545 550 555 560

Gly Leu Ile Gly Pro Gly Leu Ile Gly Pro Tyr Ala Ser Ala Ala Ala
565 570 575

Ala Ala Gly Pro Gly Ser Gly Leu Ile Gly Pro Gly Ala Ser
580 585 590

<210> SEQ ID NO 42
<211> LENGTH: 587
<212> TYPE: PRT
<213> ORGANISM: Artificial Sequence
<220> FEATURE:
<223> OTHER INFORMATION: Met-PRT1028

<400> SEQUENCE: 42

Met Gly Pro Gly Ile Phe Gly Pro Tyr Gly Pro Gly Ala Ser Ala Ala
1 5 10 15

Ala Ala Ala Gly Thr Gly Pro Gly Ser Gly Ile Phe Gly Pro Gly Thr
20 25 30

Ser Gly Thr Tyr Gly Pro Gly Ile Phe Gly Pro Gly Ile Phe Gly Pro
35 40 45

Gly Ser Ser Ala Ala Ala Ala Ala Gly Pro Gly Thr Tyr Gly Pro Gly
50 55 60

Ile Phe Gly Pro Ser Ala Ser Ala Ala Ala Ala Ala Gly Pro Gly Ser
65 70 75 80

Gly Ile Phe Gly Pro Gly Ala Ser Gly Thr Tyr Gly Pro Gly Ile Phe
85 90 95

```
Gly Pro Gly Ile Phe Gly Pro Gly Ser Ser Ala Ala Ala Ala Ala Gly
            100                 105                 110

Thr Tyr Gly Ser Gly Pro Gly Ile Phe Gly Pro Tyr Gly Ser Ala Ala
        115                 120                 125

Ala Ala Ala Gly Pro Gly Ser Gly Thr Tyr Gly Thr Gly Pro Tyr Gly
    130                 135                 140

Pro Gly Ala Ser Gly Pro Gly Thr Tyr Gly Pro Gly Ile Phe Gly Pro
145                 150                 155                 160

Ser Ala Ser Ala Ala Ala Ala Ala Gly Ser Gly Ile Phe Gly Pro Gly
                165                 170                 175

Thr Tyr Gly Pro Tyr Ala Ser Ala Ala Ala Ala Ala Gly Thr Tyr Gly
            180                 185                 190

Ser Gly Pro Gly Ile Phe Gly Pro Tyr Gly Pro Gly Thr Ser Gly Ser
        195                 200                 205

Gly Ile Phe Gly Pro Gly Ile Phe Gly Pro Tyr Ala Ser Ala Ala Ala
    210                 215                 220

Ala Ala Gly Pro Gly Ile Phe Gly Pro Tyr Gly Pro Gly Ser Ser Ala
225                 230                 235                 240

Ala Ala Ala Ala Gly Thr Tyr Gly Tyr Gly Pro Gly Ile Phe Gly Pro
                245                 250                 255

Tyr Gly Pro Gly Ala Ser Gly Thr Gly Pro Gly Ser Gly Thr Tyr Gly
            260                 265                 270

Pro Gly Ile Phe Gly Pro Gly Thr Ser Ala Ala Ala Ala Ala Gly Pro
        275                 280                 285

Gly Ile Phe Gly Pro Tyr Gly Pro Gly Ala Ser Ala Ala Ala Ala Ala
    290                 295                 300

Gly Thr Tyr Gly Pro Gly Ile Phe Gly Pro Gly Thr Tyr Gly Pro Gly
305                 310                 315                 320

Ser Ser Gly Pro Gly Ile Phe Gly Pro Tyr Gly Pro Gly Ser Ser Ala
                325                 330                 335

Ala Ala Ala Ala Gly Thr Tyr Gly Pro Gly Ile Phe Gly Pro Tyr Gly
            340                 345                 350

Pro Gly Thr Ser Ala Ala Ala Ala Ala Gly Thr Tyr Ile Phe Gly Pro
        355                 360                 365

Gly Ile Phe Gly Pro Tyr Gly Pro Gly Ala Ser Gly Pro Gly Ile Phe
    370                 375                 380

Gly Pro Tyr Gly Pro Gly Ala Ser Ala Ala Ala Ala Ala Gly Pro Gly
385                 390                 395                 400

Thr Tyr Gly Pro Gly Ile Phe Gly Pro Ser Ala Ser Ala Ala Ala Ala
                405                 410                 415

Ala Gly Thr Tyr Gly Ser Gly Pro Gly Thr Tyr Gly Pro Tyr Gly Pro
            420                 425                 430

Gly Thr Ser Gly Pro Gly Ser Gly Ile Phe Gly Thr Gly Pro Tyr Gly
        435                 440                 445

Pro Gly Ala Ser Ala Ala Ala Ala Ala Gly Thr Tyr Gly Pro Gly Ile
    450                 455                 460

Phe Gly Pro Tyr Gly Pro Gly Thr Ser Ala Ala Ala Ala Ala Gly Pro
465                 470                 475                 480

Gly Ser Gly Thr Tyr Gly Pro Gly Ala Ser Gly Thr Gly Pro Gly Ser
                485                 490                 495

Gly Thr Tyr Gly Pro Gly Ile Phe Gly Pro Gly Thr Ser Ala Ala Ala
            500                 505                 510
```

```
Ala Ala Gly Thr Tyr Ile Phe Gly Pro Gly Ile Phe Gly Pro Tyr Gly
        515                 520                 525

Pro Gly Ala Ser Ala Ala Ala Ala Ala Gly Thr Tyr Gly Ser Gly Pro
    530                 535                 540

Gly Ile Phe Gly Pro Tyr Gly Pro Gly Thr Ser Gly Ser Gly Ile Phe
545                 550                 555                 560

Gly Pro Gly Ile Phe Gly Pro Tyr Ala Ser Ala Ala Ala Ala Ala Gly
                565                 570                 575

Pro Gly Ser Gly Ile Phe Gly Pro Gly Ala Ser
            580                 585


<210> SEQ ID NO 43
<211> LENGTH: 601
<212> TYPE: PRT
<213> ORGANISM: Artificial Sequence
<220> FEATURE:
<223> OTHER INFORMATION: PRT917

<400> SEQUENCE: 43

Met His His His His His His Ser Ser Gly Ser Ser Gly Pro Gly Leu
1               5                   10                  15

Ile Gly Pro Tyr Gly Pro Gly Ala Ser Ala Ala Ala Ala Ala Gly Val
            20                  25                  30

Asn Gly Pro Gly Ser Gly Leu Ile Gly Pro Gly Val Ser Gly Val Tyr
        35                  40                  45

Gly Pro Gly Leu Ile Gly Pro Gly Leu Ile Gly Pro Gly Ser Ser Ala
    50                  55                  60

Ala Ala Ala Ala Gly Pro Gly Val Tyr Gly Pro Gly Leu Ile Gly Pro
65                  70                  75                  80

Ser Ala Ser Ala Ala Ala Ala Ala Gly Pro Gly Ser Gly Leu Ile Gly
                85                  90                  95

Pro Gly Ala Ser Gly Val Tyr Gly Pro Gly Leu Ile Gly Pro Gly Leu
            100                 105                 110

Ile Gly Pro Gly Ser Ser Ala Ala Ala Ala Ala Gly Val Tyr Gly Ser
        115                 120                 125

Gly Pro Gly Leu Ile Gly Pro Tyr Gly Ser Ala Ala Ala Ala Ala Gly
    130                 135                 140

Pro Gly Ser Gly Val Tyr Gly Val Gly Pro Tyr Gly Pro Gly Ala Ser
145                 150                 155                 160

Gly Pro Gly Val Tyr Gly Pro Gly Leu Ile Gly Pro Ser Ala Ser Ala
                165                 170                 175

Ala Ala Ala Ala Gly Ser Gly Leu Ile Gly Pro Gly Val Tyr Gly Pro
            180                 185                 190

Tyr Ala Ser Ala Ala Ala Ala Ala Gly Val Tyr Gly Ser Gly Pro Gly
        195                 200                 205

Leu Ile Gly Pro Tyr Gly Pro Gly Val Ser Gly Ser Gly Leu Ile Gly
    210                 215                 220

Pro Gly Leu Ile Gly Pro Tyr Ala Ser Ala Ala Ala Ala Ala Gly Pro
225                 230                 235                 240

Gly Leu Ile Gly Pro Tyr Gly Pro Gly Ser Ser Ala Ala Ala Ala Ala
                245                 250                 255

Gly Val Tyr Gly Tyr Gly Pro Gly Leu Ile Gly Pro Tyr Gly Pro Gly
            260                 265                 270

Ala Ser Gly Val Asn Gly Pro Gly Ser Gly Val Tyr Gly Pro Gly Leu
        275                 280                 285
```

```
Ile Gly Pro Gly Val Ser Ala Ala Ala Ala Ala Gly Pro Gly Leu Ile
    290                 295                 300

Gly Pro Tyr Gly Pro Gly Ala Ser Ala Ala Ala Ala Ala Gly Val Tyr
305                 310                 315                 320

Gly Pro Gly Leu Ile Gly Pro Gly Val Tyr Gly Pro Gly Ser Ser Gly
                325                 330                 335

Pro Gly Leu Ile Gly Pro Tyr Gly Pro Gly Ser Ser Ala Ala Ala Ala
            340                 345                 350

Ala Gly Val Tyr Gly Pro Gly Leu Ile Gly Pro Tyr Gly Pro Gly Val
        355                 360                 365

Ser Ala Ala Ala Ala Ala Gly Val Tyr Leu Ile Gly Pro Gly Leu Ile
    370                 375                 380

Gly Pro Tyr Gly Pro Gly Ala Ser Gly Pro Gly Leu Ile Gly Pro Tyr
385                 390                 395                 400

Gly Pro Gly Ala Ser Ala Ala Ala Ala Ala Gly Pro Gly Val Tyr Gly
                405                 410                 415

Pro Gly Leu Ile Gly Pro Ser Ala Ser Ala Ala Ala Ala Ala Gly Val
            420                 425                 430

Tyr Gly Ser Gly Pro Gly Val Tyr Gly Pro Tyr Gly Pro Gly Val Ser
        435                 440                 445

Gly Pro Gly Ser Gly Leu Ile Gly Val Gly Pro Tyr Gly Pro Gly Ala
    450                 455                 460

Ser Ala Ala Ala Ala Ala Gly Val Tyr Gly Pro Gly Leu Ile Gly Pro
465                 470                 475                 480

Tyr Gly Pro Gly Val Ser Ala Ala Ala Ala Ala Gly Pro Gly Ser Gly
                485                 490                 495

Val Tyr Gly Pro Gly Ala Ser Gly Val Asn Gly Pro Gly Ser Gly Val
            500                 505                 510

Tyr Gly Pro Gly Leu Ile Gly Pro Gly Val Ser Ala Ala Ala Ala Ala
        515                 520                 525

Gly Val Tyr Leu Ile Gly Pro Gly Leu Ile Gly Pro Tyr Gly Pro Gly
    530                 535                 540

Ala Ser Ala Ala Ala Ala Ala Gly Val Tyr Gly Ser Gly Pro Gly Leu
545                 550                 555                 560

Ile Gly Pro Tyr Gly Pro Gly Val Ser Gly Ser Gly Leu Ile Gly Pro
                565                 570                 575

Gly Leu Ile Gly Pro Tyr Ala Ser Ala Ala Ala Ala Ala Gly Pro Gly
            580                 585                 590

Ser Gly Leu Ile Gly Pro Gly Ala Ser
        595                 600
```

<210> SEQ ID NO 44
<211> LENGTH: 598
<212> TYPE: PRT
<213> ORGANISM: Artificial Sequence
<220> FEATURE:
<223> OTHER INFORMATION: PRT1028

<400> SEQUENCE: 44

```
Met His His His His His His Ser Ser Gly Ser Ser Gly Pro Gly Ile
1               5                   10                  15

Phe Gly Pro Tyr Gly Pro Gly Ala Ser Ala Ala Ala Ala Ala Gly Thr
            20                  25                  30

Gly Pro Gly Ser Gly Ile Phe Gly Pro Gly Thr Ser Gly Thr Tyr Gly
        35                  40                  45
```

-continued

```
Pro Gly Ile Phe Gly Pro Gly Ile Phe Gly Pro Gly Ser Ser Ala Ala
    50                  55                  60

Ala Ala Ala Gly Pro Gly Thr Tyr Gly Pro Gly Ile Phe Gly Pro Ser
65                  70                  75                  80

Ala Ser Ala Ala Ala Ala Ala Gly Pro Gly Ser Gly Ile Phe Gly Pro
                85                  90                  95

Gly Ala Ser Gly Thr Tyr Gly Pro Gly Ile Phe Gly Pro Gly Ile Phe
            100                 105                 110

Gly Pro Gly Ser Ser Ala Ala Ala Ala Ala Gly Thr Tyr Gly Ser Gly
        115                 120                 125

Pro Gly Ile Phe Gly Pro Tyr Gly Ser Ala Ala Ala Ala Ala Gly Pro
    130                 135                 140

Gly Ser Gly Thr Tyr Gly Thr Gly Pro Tyr Gly Pro Gly Ala Ser Gly
145                 150                 155                 160

Pro Gly Thr Tyr Gly Pro Gly Ile Phe Gly Pro Ser Ala Ser Ala Ala
                165                 170                 175

Ala Ala Ala Gly Ser Gly Ile Phe Gly Pro Gly Thr Tyr Gly Pro Tyr
            180                 185                 190

Ala Ser Ala Ala Ala Ala Ala Gly Thr Tyr Gly Ser Gly Pro Gly Ile
        195                 200                 205

Phe Gly Pro Tyr Gly Pro Gly Thr Ser Gly Ser Gly Ile Phe Gly Pro
    210                 215                 220

Gly Ile Phe Gly Pro Tyr Ala Ser Ala Ala Ala Ala Ala Gly Pro Gly
225                 230                 235                 240

Ile Phe Gly Pro Tyr Gly Pro Gly Ser Ser Ala Ala Ala Ala Ala Gly
                245                 250                 255

Thr Tyr Gly Tyr Gly Pro Gly Ile Phe Gly Pro Tyr Gly Pro Gly Ala
            260                 265                 270

Ser Gly Thr Gly Pro Gly Ser Gly Thr Tyr Gly Pro Gly Ile Phe Gly
        275                 280                 285

Pro Gly Thr Ser Ala Ala Ala Ala Ala Gly Pro Gly Ile Phe Gly Pro
    290                 295                 300

Tyr Gly Pro Gly Ala Ser Ala Ala Ala Ala Ala Gly Thr Tyr Gly Pro
305                 310                 315                 320

Gly Ile Phe Gly Pro Gly Thr Tyr Gly Pro Gly Ser Ser Gly Pro Gly
                325                 330                 335

Ile Phe Gly Pro Tyr Gly Pro Gly Ser Ser Ala Ala Ala Ala Ala Gly
            340                 345                 350

Thr Tyr Gly Pro Gly Ile Phe Gly Pro Tyr Gly Pro Gly Thr Ser Ala
        355                 360                 365

Ala Ala Ala Ala Gly Thr Tyr Ile Phe Gly Pro Gly Ile Phe Gly Pro
    370                 375                 380

Tyr Gly Pro Gly Ala Ser Gly Pro Gly Ile Phe Gly Pro Tyr Gly Pro
385                 390                 395                 400

Gly Ala Ser Ala Ala Ala Ala Ala Gly Pro Gly Thr Tyr Gly Pro Gly
                405                 410                 415

Ile Phe Gly Pro Ser Ala Ser Ala Ala Ala Ala Ala Gly Thr Tyr Gly
            420                 425                 430

Ser Gly Pro Gly Thr Tyr Gly Pro Tyr Gly Pro Gly Thr Ser Gly Pro
        435                 440                 445

Gly Ser Gly Ile Phe Gly Thr Gly Pro Tyr Gly Pro Gly Ala Ser Ala
    450                 455                 460

Ala Ala Ala Ala Gly Thr Tyr Gly Pro Gly Ile Phe Gly Pro Tyr Gly
```

-continued

```
465                 470                 475                 480

Pro Gly Thr Ser Ala Ala Ala Ala Ala Gly Pro Gly Ser Gly Thr Tyr
                485                 490                 495

Gly Pro Gly Ala Ser Gly Thr Gly Pro Gly Ser Gly Thr Tyr Gly Pro
            500                 505                 510

Gly Ile Phe Gly Pro Gly Thr Ser Ala Ala Ala Ala Ala Gly Thr Tyr
        515                 520                 525

Ile Phe Gly Pro Gly Ile Phe Gly Pro Tyr Gly Pro Gly Ala Ser Ala
    530                 535                 540

Ala Ala Ala Ala Gly Thr Tyr Gly Ser Gly Pro Gly Ile Phe Gly Pro
545                 550                 555                 560

Tyr Gly Pro Gly Thr Ser Gly Ser Gly Ile Phe Gly Pro Gly Ile Phe
                565                 570                 575

Gly Pro Tyr Ala Ser Ala Ala Ala Ala Ala Gly Pro Gly Ser Gly Ile
            580                 585                 590

Phe Gly Pro Gly Ala Ser
        595
```